(12) United States Patent
Leclerc et al.

(10) Patent No.: US 7,705,157 B2
(45) Date of Patent: Apr. 27, 2010

(54) PHENOL-HETEROCYCLIC LIGANDS, METAL COMPLEXES, AND THEIR USES AS CATALYSTS

(75) Inventors: Margarete K. Leclerc, Santa Clara, CA (US); Xiaohong Bei, Oak Park, CA (US); James Longmire, San Jose, CA (US); Gary M. Diamond, San Jose, CA (US); James A. W. Shoemaker, Gilroy, CA (US); Lily Ackerman, Fremont, CA (US); Pu Sun, San Jose, CA (US); Jessica Zhang, Milpitas, CA (US)

(73) Assignee: Symyx Solutions, Inc., Sunnyvale, CA (US)

( * ) Notice: Subject to any disclaimer, the term of this patent is extended or adjusted under 35 U.S.C. 154(b) by 260 days.

(21) Appl. No.: 11/305,426

(22) Filed: Dec. 16, 2005

(65) Prior Publication Data

US 2006/0135713 A1    Jun. 22, 2006

Related U.S. Application Data

(60) Provisional application No. 60/636,555, filed on Dec. 16, 2004.

(51) Int. Cl.
*C07F 19/00* (2006.01)
*C07F 7/00* (2006.01)
*C07F 11/00* (2006.01)

(52) U.S. Cl. .................. 548/101; 548/106; 556/51; 556/53; 556/57; 556/42; 526/172; 526/204; 526/205

(58) Field of Classification Search .................. 556/51, 556/42, 57, 101; 526/172, 161, 204, 205; 548/101
See application file for complete search history.

(56) References Cited

U.S. PATENT DOCUMENTS 4,297,465 A    10/1981    Smith (Continued)

FOREIGN PATENT DOCUMENTS

EP    0 277 004    8/1988

(Continued)

OTHER PUBLICATIONS

JP 2001-271063 (Oct. 2001) abstract and translation in English.*

(Continued)

*Primary Examiner*—James J. Seidleck
*Assistant Examiner*—Rip A. Lee
(74) *Attorney, Agent, or Firm*—Armstrong Teasdale LLP

(57) ABSTRACT

Ligands, compositions, and metal-ligand complexes that incorporate phenol-heterocyclic compounds are disclosed that are useful in the catalysis of transformations such as the polymerization of monomers into polymers. The catalysts have high performance characteristics, including high comonomer incorporation into ethylene/olefin copolymers, where such olefins are for example, 1-octene, propylene or styrene. The catalysts particularly polymerize styrene to form polystyrene.

10 Claims, 25 Drawing Sheets

U.S. PATENT DOCUMENTS

| | | | |
|---|---|---|---|
| 4,971,936 | A | 11/1990 | Wilson et al. |
| 5,064,802 | A | 11/1991 | Stevens et al. |
| 5,093,415 | A | 3/1992 | Brady, III et al. |
| 5,153,157 | A | 10/1992 | Hlatky et al. |
| 5,318,935 | A | 6/1994 | Canich et al. |
| 5,385,993 | A | 1/1995 | Fujita |
| 5,453,410 | A | 9/1995 | Kolthammer et al. |
| 5,599,761 | A | 2/1997 | Turner |
| 5,616,664 | A | 4/1997 | Timmers et al. |
| 5,637,660 | A | 6/1997 | Nagy et al. |
| 5,985,356 | A | 11/1999 | Schultz et al. |
| 6,030,917 | A | 2/2000 | Weinberg et al. |
| 6,175,409 | B1 | 1/2001 | Nielsen et al. |
| 6,214,939 | B1 | 4/2001 | Shinozaki et al. |
| 6,239,236 | B1 | 5/2001 | Morini et al. |
| 6,260,407 | B1 | 7/2001 | Petro et al. |
| 6,294,388 | B1 | 9/2001 | Petro |
| 6,306,658 | B1 | 10/2001 | Turner et al. |
| 6,309,997 | B1 | 10/2001 | Fujita et al. |
| 6,333,389 | B2 * | 12/2001 | Whiteker et al. ............ 526/161 |
| 6,358,634 | B1 * | 3/2002 | Igarashi et al. .............. 428/690 |
| 6,406,632 | B1 | 6/2002 | Safir et al. |
| 6,410,660 | B1 | 6/2002 | Johnson et al. |
| 6,436,292 | B1 | 8/2002 | Petro |
| 6,454,947 | B1 | 9/2002 | Safir et al. |
| 6,455,316 | B1 | 9/2002 | Turner et al. |
| 6,461,515 | B1 | 10/2002 | Safir |
| 6,475,391 | B2 | 11/2002 | Safir et al. |
| 6,489,168 | B1 | 12/2002 | Wang et al. |
| 6,491,816 | B2 | 12/2002 | Petro |
| 6,491,823 | B1 | 12/2002 | Safir et al. |
| 6,507,945 | B1 | 1/2003 | Rust et al. |
| 6,508,984 | B1 | 1/2003 | Turner |
| 6,620,759 | B2 | 9/2003 | Johnson et al. |
| 6,713,577 | B2 | 3/2004 | Boussie |
| 6,750,345 | B2 | 6/2004 | Boussie et al. |
| 6,759,014 | B2 | 7/2004 | Dales et al. |
| 6,794,514 | B2 * | 9/2004 | Brummer et al. ............ 548/146 |
| 6,933,355 | B2 * | 8/2005 | Brummer et al. ............ 526/161 |
| 6,965,004 | B2 * | 11/2005 | Brummer et al. ............ 526/346 |
| 7,074,870 | B2 * | 7/2006 | Brummer et al. ............ 526/346 |
| 7,259,219 | B2 * | 8/2007 | Rosen et al. ................. 526/346 |
| 2003/0161763 | A1 | 8/2003 | Erden et al. |
| 2003/0165711 | A1 * | 9/2003 | Kim et al. ................... 428/690 |
| 2003/0232717 | A1 | 12/2003 | Brummer et al. |
| 2004/0023061 | A1 * | 2/2004 | Kathirgamanathan et al. .... 428/690 |
| 2004/0121448 | A1 | 6/2004 | Goh et al. |
| 2005/0043497 | A1 * | 2/2005 | Gindelberger et al. ....... 526/219 |

FOREIGN PATENT DOCUMENTS

| | | | |
|---|---|---|---|
| EP | 0 292 134 | | 11/1988 |
| EP | 0 622 380 | | 11/1994 |
| EP | 1 080 435 | | 2/2002 |
| EP | 0 874 005 | | 7/2003 |
| EP | 1 175 645 | | 7/2003 |
| EP | 0 950 667 | | 8/2005 |
| JP | 9-111234 | * | 4/1997 |
| JP | 2000-030864 | | 1/2000 |
| JP | 2000-30864 | A * | 1/2000 |
| JP | 2000-252067 | A * | 9/2000 |
| JP | 2001-40346 | * | 2/2001 |
| JP | 2001-131162 | A * | 5/2001 |
| JP | 2001-271063 | * | 10/2001 |
| JP | 2002-338957 | A * | 11/2002 |
| WO | WO 98/03521 | | 1/1998 |
| WO | WO 99/05186 | | 2/1999 |
| WO | WO 99/06413 | | 2/1999 |
| WO | WO 99/42467 | | 8/1999 |
| WO | WO 00/09255 | | 2/2000 |
| WO | WO 00/37512 | | 6/2000 |
| WO | WO 01/98371 | | 12/2001 |
| WO | WO 02/06358 | | 1/2002 |
| WO | WO 02/38628 | | 5/2002 |
| WO | WO 03/040201 | | 5/2002 |
| WO | WO 02/46250 | | 6/2002 |
| WO | WO 03/087178 | A1 * | 10/2003 |
| WO | WO 03/091262 | | 11/2003 |
| WO | WO 2004/060550 | | 7/2004 |
| WO | WO 2004/078765 | | 9/2004 |
| WO | WO 2006/036748 | | 4/2006 |

OTHER PUBLICATIONS

JP 9-111234 (Apr. 1997) abstract and translation in English.*
JP 2001-40346 (Feb. 2001) abstract and translation in English.*
Barron, "Alkylalumoxanes, Synthesis, Structure and Reactivity", Metallocene-Based Polyolefins: Preparation, Properties and Technology, Schiers and W. Kaminsky (eds.), 2000, pp. 33-67, Wiley Series in Polymer Science, John Wiley & Sons, Ltd., Chichester, England.
Blaser et al., "Enantioselective Synthesis", Applied Homogeneous Catalysis with Organometallic Compounds, Cornils & Herrmann (eds.), vol. 3, 2nd Ed., 2002, pp. 1131-1149, Wiley-VCH, Weinheim, Germany.
Bochmann et al., "Base-Free Cationic Zirconium Benzyl Complexes as Highly Active Polymerization Catalysts", Organometallics, vol. 12, 1993, pp. 633-640.
Bott et al., "Group 4 Salicyloxazolines are Potent Polymerization Catalysts", Dalton Trans., 2005, pp. 3611-3613.
Brintzinger et al., "Stereospecific Olefin Polymerization with Chiral Metallocene Catalysts", Angew Chem Int Ed Engl., vol. 34, 1995, pp. 1143-1170.
Coates, "Precise Control of Polyolefin Stereochemistry Using Single-Site Metal Catalysts", Chem Rev., vol. 100, 2000, pp. 1223-1252.
Coates et al., "Gel Permeation Chromatography as a Combinatorial Screening Method: Identification of Highly Active Heteroligated Phenoxyimine Polymerization Catalysts", J Am Chem Soc., vol. 126, 2004, pp. 10798-10799.
Emslie et al., "2,2'-Diborabiphenyl; A Lewis Acid Analogue of 2,2'-Bipyridine", Angew Chem Int Ed., vol. 42, 2003, pp. 1251-1255, (printed from www.chemistry.mcmaster.ca/emslie on Nov. 14, 2005).
Fink et al., "Propene Polymerization with Silica-Supported Metallocene/MAO Catalysts", Chem Rev., vol. 100, 2000, pp. 1377-1390.
Gibson et al., "The Search for New-Generation Olefin Polymerization Catalysts: Life Beyond Metallocenes", Angew Chem Int Ed., vol. 38, 1999, pp. 428-447.
Gibson et al., "Advances in Non-Metallocene Olefin Polymerization Catalysis", Chem Rev., 2003, vol. 103, pp. 283-315.
Grassi et al., "Olefin Polymerization Promoted by a Stereorigid Bridged Diiminobis(phenolate) Zirconium Complex", Macromolecules, 2004, vol. 37, pp. 7469-7476.
Harwood et al., "75-MHz 13C NMR Studies on Polystyrene and Epimerized Isotactic Polystyrenes", Chap. 13, pp. 197-222, NMR and Macromolecules—Sequence, Dynamic, and Domain Structure, Randall et al (Eds.), ACS Symposium Series 247, 1984.
Hlatky, "Heterogeneous Single-Site Catalysts for Olefin Polymerization", Chem Rev., 2000, vol. 100, pp. 1347-1376.
Katritzky (Ed.), Handbook of Heterocyclic Chemistry, 1985, Pergammon Press.
Katritzky et al. (Eds.), Comprehensive Heterocyclic Chemistry—The Structure, Reactions, Synthesis and Uses of Heterocyclic Compounds, 1984, 1st Ed., Elsevier, New York.
Katritzky et al. (Eds.), Comprehensive Heterocyclic Chemistry II—A Review of the Literature 1982-1995, 1996, 1st Ed., Elsevier.
Kim et al., "Synthesis of Chlorotitanium(IV) Schiff-Base Complexes and their Application to Styrene Polymerization", Macromol Rapid Commun., 2004, vol. 25, pp. 1319-1323.

Lancaster et al., "Hybrid Catalysts: the Synthesis, Structure and Ethene Polymerisation Activity of (Salicylaldiminato)(Pyrrolylaldiminato) Titanium Complexes", Chem Commun., 2005, vol. 25, pp. 3150-3152.

LaPointe et al., "New Family of Weakly Coordinating Atoms", J Am Chem Soc., 2000, vol. 122, pp. 9560-9561.

Liu et al., "A Particularly Convenient Preparation of Benzohydroximinoyl Chlorides (Nitrile Oxide Precursors)", J Org Chem., 1980, vol. 45, pp. 3916-3918.

Luongo, "Infrared Study of Polypropylene", J Applied Polymer Science, 1960, vol. 3, pp. 302-309.

March (Ed.), Advanced Organic Chemistry—Reactions, Mechanisms, and Structure, 1992, 4th Ed., Wiley, New York.

Marks et al., "Cocatalysts for Metal-Catalyzed Olefin Polymerization: Activators, Activation Processes, and Structure-Activity Relationships", Chem Rev., 2000, vol. 100, pp. 1391-1434.

Ojima (Ed.), Catalytic Asymmetric Synthesis, 1993, VCH Publishers, Inc., New York.

Okuda et al., "Stereospecific Post-Metallocene Polymerization Catalysts: the Example of Isospecific Styrene Polymerization", J Organometallic Chem., 2004, vol. 689, pp. 4636-4641.

Okuda et al., "Living Isospecific Styrene Polymerization by Chiral Benzyl Titanium Complexes That Contain a Tetradentate [OSSO]-Type Bis(phenolato) Ligand", Organometallics, 2005, vol. 224, pp. 2971-2982.

Pellecchia et al., "Synthesis, Crystal Structure, and Olefin Polymerization of a Zwitterionic n(sup)6 (sup)-Arene Zirconium Tris(hydrocarbyl)", J Am Chem Soc., 1993, vol. 115, pp. 1160-1162.

Pellecchia et al., "A Novel n(sup)7(sup) Coordination Mode of a Benzyl Ligand in a Cationic Zirconium Complex", Organometallics, 1993, vol. 13, pp. 3773-3775.

Pellecchia et al., "Single Insertion of a-Olefins into the Cationic Complex (Zr(CH(sub)2(sub)Ph)(sub)3(sub)]+ Affording Isolable . . . ", Organometallics, 1994, vol. 13, pp. 298-302.

Piers et al., "New Bifunctional Perfluoroaryl Boranes: Synthesis and Reactivity of the Ortho-Phenylene-Bridged Diboranes . . . ", J Am Chem Soc., 1999, vol. 121, pp. 3244-3245.

Piers et al., "A New Chelating Anilido-Imine Donor Related to Beta-Diketiminato Ligands for Stabilization of Organoyttrium Cations", Organometallics, 2003, vol. 22, pp. 1577-1579.

Piers et al., "Organo-Scandium and -Yttrium Complexes Supported by a Salicylaldiminato Ligand", J Chem Soc., Dalton Trans., 2002, pp. 293-294.

Proto et al., "ZrCl(4) as Catalyst for Olefins and Styrene Polymerization: Effect of Ethereal Donors on the Activity and Stereospecificity", Macromolecules, 2003, vol. 36, pp. 5942-5946.

Repo et al., "Ethylenebis(salicylideneiminato)Zirconium Dichloride: Crystal Structure and Use as a Heterogeneous Catalyst in the Polymerization of Ethylene", Macromolecules, 1997, vol. 30, pp. 171-175.

Resconi et al., "Selectivity in Propene Polymerization with Metallocene Catalysts", Chem Rev., 2000, vol. 100, pp. 1253-1345.

Severn et al., "Bound but Not Gagged—Immobilizing Single-Site (alpha)-Olefin Polymerization Catalysts", Chem Rev., 2005, vol. 105, pp. 4073-4147.

Schrock et al., "Synthesis of Titanium, Zirconium, and Hafnium Complexes That Contain Diamido Donor Ligands of the Type . . . ", Organometallics, 1999, vol. 18, pp. 3649-3670.

Sundell et al., "Isotacticity Determination of Polypropylene Using FT-Raman Spectroscopy", Polymer, 1996, vol. 37, pp. 3227-3231.

Anthony et al., "Solid-State Fluorescent Photophysics of Some 2-Substituted Benzothiazoles", J. Chem. Soc., Perkins Trans. II, 1984, pp. 2111-2117.

Bach et al., "Synthesis of 2-(o-hydroxyaryl)-4-arylthiazoles by Regioselective Pd(0)-catalyzed Cross-Coupling", Tetrahedron Letters, vol. 41, 2000, pp. 1707-1710.

Beger et al., "O- und N-alkylsubstituierte 2-(2'-Hydroxyphenyl)-benzimidazole und -1,3,4-oxadiazole als Komplexbildner und Extraktioinsmittel fur Kupfer-II-ionen", Journal f. prakt. Chemie. Band, vol. 325, No. 5, 1983, pp. 708-718.

Benisvy et al., "A Phenol-Imidazole Pro-Ligand That Can Exist as a Phenoxyl Radical, Alone and When Complexed to Copper(II) and Zinc(II)", Dalton Trans., 2003, pp. 1975-1985.

Calhorda et al., "Bis(n-cyclopentadienyl)-molybdenum (and -tungsten or -titanium) Complexes with Chelate Imidazole Derivatives and Related Ligands", J. Chem. Soc., Dalton Trans., 1980, pp. 1443-1447.

Carvalho et al., "Excited-State Acidity of Bifunctional Compounds", J. Chem. Soc., Faraday Trans., vol. 93, No. 18, 1997, pp. 3325-3329.

Cook et al., "Experiments in the Triazine and the Glyoxaline Series", J. Chem. Soc., 1941, pp. 278-282.

Cousin et al., "Sur Les Nitriles Salicycliques", Bulletin de la Societe Chimique de France, vol. 4, No. 15, 1914, pp. 414-421.

Cozzi et al., "Bis(hydroxyphenyloxazolinato)-titanium(IV) and -zirconium(IV) triflates as Novel Transition Metal-Based Lewis Acids", J. Chem. Soc., Perkins Trans. I, 1995, pp. 2557-2563.

Cozzi et al.,"(Hydroxyphenyl)oxazoline: A Novel and Remarkably Facile Entry into the Area of Chiral Cationic Alkylzirconium Complexes Which Serve as Polymerization Catalysts", Organometallics, vol. 14, 1995, pp. 4994-4996.

Cozzi et al., "Oxazoline Early Transition Metal Complexes: Functionalizable Achiral Titanium (IV), Titanium(III), Zirconium(IV), Vanadium(III), and Chiral Zirconium(IV) Bis(oxazoline) Complexes", Inorg. Chem., vol. 34, 1995, pp. 2921-2930.

Deliwala et al., "Chemotherapy of Tuberculosis", Proceedings of the Indian Academy of Sciences, Section A, vol. 31, 1950, pp. 107-116.

Fukata et al., "Cyclodienones. 9. Reaction of 4-Halo-2,4,6-Tri-Tert-Butyl-2,5-Cyclohexadien-1-Ones with Pyrazoles and Preparation of 1-(2-Hydroxyphenyl)- and 1-(4-Hydroxyphenyl)Pyrazoles", Heterocycles, vol. 19, No. 8, 1982, pp. 1487-1495.

Maurya et al., "Oxo, Dioxo and Oxoperoxo Complexes of Molybdenum and Tungsten with 2-(2'-Hydroxyphenyl)benzimidazole", J. Chem. Research (S), 1996, vol. 390-391.

Mishra et al., "Rare Earth Complexes with N, O-Donor Ligands. Part-I. Nitrato-Complexes of Terpositive Yttrium and Lighter Lanthanides with 2-(2'Hydroxyphenyl)benzimidazole", Journal of the Indian Chemical Society, vol. 57, No. 3, Mar. 1980, pp. 249-251.

Mishra et al., "Rare Earth Complexes with N, O-Donor Ligands. Part-II. Complexes of Gd(III), Tb(III, Dy(III) and Ho(III) with 2-(2'-Hydroxyphenyl)benzimidazole", Journal of the Indian Chemical Society, vol. 58, No. 12, Dec. 1981, pp. 1197-1198.

Pla-Dalmau, 2-(2'-Hydroxyphenyl)benzothiazoles, -benzoxazoles, and -benzimidazoles for Plastic Scintillation Applications, J. Org. Chem., vol. 60, 1995, pp. 5468-5473.

Ryabukhin et al., "Synthesis of Bis(o-hydroxyphenyl)-1,3,5-triazines, 1,2,4-triazoles, and Oxadiazole by Recyclization of the o-hydroxyphenyl-4-oxo-1,3-benzoxazinium cation", Chemistry of Heterocyclic Compounds, vol. 19, No. 3, 1983, pp. 332-336.

Ryabukhin et al., "Synthesis and Study of the Structure of o-Hydroxyaryl-1,2,4-oxadiazoles", Chemistry of Heterocyclic Compounds, vol. 28, No. 4, 1992, pp. 454-463.

Weidner-Wells et al., "Amidino Benzimidazole Inhibitors of Bacterial Two-Component Systems", Bioorganic & Medicinal Chemistry Letters, vol. 11, No. 12, Jun. 18, 2001, pp. 1545-1548.

Beckerle et al., "Living Isospecific Styrene Polymerization by Chiral Benzyl Titanium Complexes that Contain a Tetradentate [OSSO]-Type Bis(phenolato) Ligand," Organometallics, vol. 25, No. 12, (2006), pp. 3019-3026.

Capacchione et al., "Isospecific Styrene Polymerization by Chiral Benzyl Titanium Complexes that Contain a Tetradentate [OSSO]-Type Bis(phenolato) Ligand," Organometallics, vol. 24, No. 12, (2005), pp. 2971-2982.

* cited by examiner

A1

A2

A3

A4

A5

A6

A7

A8

A9

A10

A11

A16

A12

A17

A13

A18

A14

A19

A15

A20

A21

A22

A23

A24

A25

A26

A27

A28

A29

A30

A31

A36

A32

A37

A33

A38

A34

A39

A35

A40

A41

A46

A42

A47

A43

A48

A44

A49

A45

A50

B1

B6

B2

B7

B3

B8

B4

B9

B5

B10

B11

B12

B13

C1

C6

C2

C7

C3

C8

C4

C9

C5

C10

C11

C16

C12

C17

C13

C18

C14

C19

C15

C20

C21

C26

C22

C27

C23

C28

C24

C29

C25

C30

C31

C36

C32

C37

C33

C38

C34

C39

C35

C40

C41

C42

D1

D2

D3

D4

D5

E11

E16

E12

E17

E13

E18

E14

E19

E15

E20

E21

E22

E23

E24

E25

E26

F11

F12

G1

G2

G3

G4

M7

M8

M9

M10

M11

M12

M13

M14

M15

M16

M17

M18

M19

M21

M23

M20

M22

M24

M25

M28

M26

M29

M27

M30

PHENOL-HETEROCYCLIC LIGANDS, METAL COMPLEXES, AND THEIR USES AS CATALYSTS

This application claims the benefit of U.S. Provisional Application No. 60/636,555, filed Dec. 16, 2004, which is incorporated herein by reference for all purposes.

TECHNICAL FIELD

The present invention relates to ligands, ligand-metal compositions, complexes, and catalysts useful in the polymerization of olefins and other transformations.

BACKGROUND OF THE INVENTION

Ancillary (or spectator) ligand-metal coordination complexes (including organometallic complexes) and compositions are useful as catalysts, additives, stoichiometric reagents, solid-state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, Diels-Alder reactions and other transformations.

One example of the use of these types of ancillary ligand-metal complexes and compositions is in the field of polymerization catalysis. In connection with single site catalysis, the ancillary ligand typically offers opportunities to modify the electronic and/or steric environment surrounding an active metal center. This allows the ancillary ligand to assist in the creation of possibly different polymers. Group 4 metallocene based single site catalysts are generally known for polymerization reactions. See, generally, "Chemistry of Cationic Dicyclopentadienyl Group 4 Metal-Alkyl Complexes", Jordan, Adv. Organometallic Chem. 1991, 32,325-153, and the references therein, all of which is incorporated herein by reference.

One application for metallocene catalysts is producing isotactic polypropylene. An extensive body of scientific literature examines catalyst structures, mechanism and polymers prepared by metallocene catalysts. See, e.g., Resconi et al., "Selectivity in Propene Polymerization with Metallocene Catalysts," Chem. Rev. 2000, 100, 1253-1345 and G. W. Coates, "Precise Control of Polyolefin Stereochemistry Using Single-Site Metal Catalysts," Chem. Rev. 2000, 100, 1223-1252 and the references cited in these review articles. Isotactic polypropylene has historically been produced with heterogeneous catalysts that may be described as a catalyst on a solid support (e.g., titanium tetrachloride and aluminum alkyls and additional modifiers or "donors" on magnesium dichloride). This process typically uses hydrogen to control the molecular weight and electron-donor compounds to control the isotacticity. See also EP 0 622 380, EP 0 292 134 and U.S. Pat. Nos. 4,971,936, 5,093,415, 4,297,465, 5,385,993 and 6,239,236.

Given the extensive research activities with respect to metallocene catalysts, there is continued interested in the next generation of non-cyclopentadienyl ligands for olefin polymerization catalysts providing attractive alternatives. See, e.g., "The Search for New-Generation Olefin Polymerization Catalysts: Life beyond Metallocenes", Gibson, et al., Angew. Chem. Int. Ed. 1999, 38, 428-447; Organometallics 1999, 18, 3649-3670 and "Advances in Non-Metallocene Olefin Polymerization Catalysts", Gibson, et al., Chem Rev. 2003, 103, 283-315. See also U.S. Pat. No. 6,750,345 and International Application No. WO 02/38628. Recently, for isotactic polypropylene, bis-amide catalysts have been disclosed in U.S. Pat. No. 5,318,935 and amidinate catalysts have been disclosed in WO 99/05186. See also U.S. Pat. Nos. 6,214,939 and 6,713,577, and International Application Nos. WO 03/040201 WO 03/091262 for non-metallocene isotactic polypropylene catalysts.

The polymerization of vinylidene aromatic monomers, especially styrene, has proven difficult to accomplish using non-metallocene catalysts. Recently, Okuda and other researchers have reported the results of their investigations, See, Okuda et al., *J. Organometallic Chem.*, 689 (2004) 46364641, Okuda et al., *Organometallics*, 224, 2971-2982 (2005), WO 2004/078765, Kim, et al., *Macromol. Rapid Commun.* 2004, 25, 1319-1323, and Proto et al., *Macromolecules* 2003, 36, 5942-5946. In general, the known processes have been limited to the use of relatively low reaction temperatures and the production of undifferentiated polymers.

Despite the efforts of many workers in the field, a need remains for commercially suitable catalyst systems for the polymerization of monomers, and in particular for the homopolymerization or copolymerization of vinylidene aromatic monomers, especially styrene or substituted styrenes, for the production of polymers having molecular weights high enough for general commercial use, and variable tacticities, at high reaction temperatures. In particular, what is needed is a catalyst or family of catalysts capable of making a range of vinylidene aromatic polymers with differing degrees of stereoregularity that can be controlled by the appropriate choice of catalyst and conditions. A range of product opportunities could then exist, including polymers uniquely suited for preparation via high temperature solution polymerization processes.

Therefore, a need remains for new polyolefin catalysts in general.

BRIEF SUMMARY OF THE INVENTION

The invention features ligands, compositions and metal complexes that are useful in catalysts for olefin polymerization and other transformations, as well as methods for preparing the ligands and for using the compositions or complexes in catalytic transformations such as olefin polymerization. In general, the ligands have a phenol-heterocyclic structure, as will be discussed in more detail below. Catalysts according to the invention can be provided by compositions including a ligand, a metal precursor, and optionally an activator, combination of activators, or an activator technique. Alternatively, catalysts can be provided by metal-ligand complexes and optionally may additionally include an activator, combination of activators or activator technique.

In general, in one aspect, the invention provides compositions of matter, including ligands, compositions and metal-ligand complexes, that include a compound characterized by the formula (I):

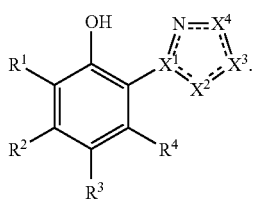

R$^1$, R$^2$, R$^3$, R$^4$, R$^5$, R$^6$ and R$^7$ are the same or different and are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the exception that R$^1$ may not be hydrogen, optionally two or more of R$^1$, R$^2$, R$^3$ and R$^4$ may be joined to form a fused ring system having up to 50 atoms, not counting hydrogen atoms, and optionally two or more of R$^5$, R$^6$ and R$^7$ may be joined to form a fused ring system having up to 50 atoms, not counting hydrogen atoms.

For compounds of formula (I), X$^1$ is N or C, X$^2$ is O, S, N(R$^5$)$_{n'}$, or CR$^5$, X$^3$ is O, S, N(R$^6$)$_{n''}$ or CR$^6$, X$^4$ is O, S, N(R$^7$)$_{n'''}$ or CR$^7$, wherein each n', n'', and n''' are each independently 0 or 1, provided that the heteroatom containing ring system is heteroaromatic, provided combinations of X$^1$, X$^2$; X$^1$, X$^3$; and X$^1$, X$^4$ are not both N and X$^1$, X$^2$ and X$^3$ are not all N. Additional compounds that are not included are those where X$^1$, X$^3$, X$^4$ are each N, X$^2$ is C, R$^5$ is H and R$^1$ is selected from the group consisting of t-butyl, —CMe$_2$Et, —C(Et)$_3$, —CMe$_2$Ph, —C(Ph)$_3$, —Si(Et)$_3$, and —Si(Ph)$_3$, and when R$^1$ is F, R$^3$ is F, X$^1$, X$^2$, X$^3$ are all C, X$^4$ is N, R$^5$, R$^6$ are each H and R$^7$ is t-butyl.

In one aspect for compounds of formula (I), R$^1$ is selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl.

In another aspect for compounds of formula (I), R$^7$ is selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl and in particular, R$^1$ is selected from the group consisting of t-butyl, naphthyl, substituted naphthyl, carbazolyl, substituted carbazolyl, phenyl and substituted phenyl and R$^7$ is selected from the group consisting of substituted phenyl and anthracenyl.

In a first embodiment for compounds having formula (I), X$^1$ is C, X$^2$ is O, X$^3$ is N and X$^4$ is CR$^7$ and are referred to as formulae (Ia). In certain aspects of formula (Ia), R$^1$ is an alkyl, substituted alkyl, aryl or a substituted aryl. In other aspects of formula (Ia), R$^3$ is an alkyl or a substituted alkyl. In still other aspects of formula (Ia), R$^7$ is an aryl or a substituted aryl.

In a second embodiment for compounds having formula (I), X$^1$ is C, X$^2$ is N, X$^3$ is O and X$^4$ is CR$^7$ and are referred to as formulae (Ib). In particular embodiments of formula (Ib), R$^1$ is an alkyl or a substituted alkyl. In other embodiments of (Ib), R$^3$ is an alkyl or a substituted alkyl. In still other embodiments of formula (Ib), R$^7$ is an aryl or a substituted aryl.

In third embodiment for compounds of formula (I), X$^1$ is C, X$^2$ is NR$^5$, X$^3$ is CR$^6$ and X$^4$ is CR$^7$ and are referred to as formulae (Ic). In particular aspects of formula (Ic), R$^1$ is an alkyl, substituted alkyl, aryl, or a substituted aryl. In other aspects of formula (Ic), R$^3$ is an alkyl or a substituted alkyl. In still other aspects of formula (Ic), R$^5$ is an alkyl or a substituted alkyl. In another aspect of formula (Ic), R$^6$ is an aryl or a substituted aryl. In still yet another aspect of formula (Ic), R$^7$ is an aryl or a substituted aryl.

In a fourth embodiment for compounds having formula (I), X$^1$ is C, X$^2$ is S, X$^3$ is CR$^6$ and X$^4$ is CR$^7$ and are referred to as formulae (Id). In one embodiment of formula (Id), R$^1$ is an aryl, substituted aryl, alkyl or a substituted alkyl. In another embodiment of formula (Id), R$^3$ is an alkyl or a substituted alkyl. In still another embodiment of formula (Id), R$^6$ is a hydrogen. In still yet another embodiment of formula (Id), R$^7$ is bromide, phenyl, substituted phenyl, naphthyl, substituted naphthyl, anthracenyl, substituted anthracenyl, or a hydrogen.

In a fifth embodiment for compounds having formula (I), X$^1$ is C, X$^2$ is CR$^5$, X$^3$ is S and X$^4$ is CR$^7$ and are referred to as formulae (Ie). In one aspect of formula (Ie), R$^1$ is an aryl or a substituted aryl. In another aspect of formula (Ie), R$^3$ is a hydrogen, an alkyl or a substituted alkyl. In still another aspect of formula (Ie), R$^5$ is a hydrogen. In still yet another aspect of formula (Ie), R$^7$ is an aryl or a substituted aryl.

In a sixth embodiment for compounds having formula (1), X$^1$ is N, X$^2$ is CR$^5$, X$^3$ is CR$^6$ and X$^4$ is CR$^7$ and are referred to as formulae (If). In one embodiment of formula (If), R$^1$ is an aryl or substituted aryl. In another embodiment of formula (If), R$^3$ is an alkyl or substituted alkyl. In still another embodiment of formula (If), R$^5$ is a hydrogen. In still another embodiment of formula (If), R$^6$ is a hydrogen. In still yet another embodiment of formula (If), R$^7$ is an alkyl or phenyl.

In an seventh embodiment for compounds having formula (I), X$^1$ is C, X$^2$ is CR$^5$, X$^3$ is CR$^6$ and X$^4$ is NR$^7$ and are referred to as formulae (Ig). In one aspect of formula (Ig), R$^1$ is a halogen. In another aspect of formula (Ig), R$^2$ is a hydrogen or methyl. In still another aspect of formula (Ig), R$^3$ is a halogen. In still yet another aspect of formula (Ig), R$^5$ is a hydrogen. In still another aspect of formula (Ig), R$^6$ is a hydrogen. In still yet another aspect of formula (Ig), R$^7$ is a hydrogen, an alkyl or a substituted alkyl. In one aspect for a compound having formula (Ig), R$^1$ and R$^3$ are not both F and R$^7$ is not t-butyl.

In an additional embodiment for compounds having formula (I), X$^1$ is C, X$^2$ is CR$^5$, X$^3$ is NR$^6$ and X$^4$ is CR$^7$ and are referred to as formulae (Ih). In an additional embodiment for compounds having formula (I), X$^1$ is C, X$^2$ is O, X$^3$ is CR$^6$ and X$^4$ is CR$^7$ and are referred to as formulae (Ii). In an additional embodiment for compounds having formula (I), X$^1$ is C, X$^2$ is CR$^5$, X$^3$ is O and X$^4$ is CR$^7$ and are referred to as formulae (Ij). Preferred R groups for these additional embodiments are chosen from those disclosed for formula (I) through (Ig).

In general, in one aspect, the invention provides compositions of matter, including ligands, compositions and metal-ligand complexes, that include a compound characterized by the formula (II):

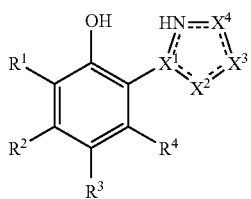

(II)

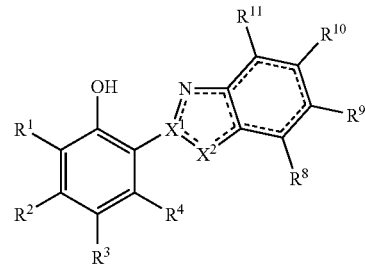

(III)

where $R^1, R^2, R^3, R^4, R^5, R^6, R^7$, are the same or different and are each independent of one another and are as described above.

For compounds of formula (II), $X^1$ is N or C, $X^2$ is N or $CR^5$, $X^3$ is N or $CR^6$, $X^4$ is N or $CR^7$, provided that the heteroatom containing ring system is heteroaromatic, provided that compounds when $X^1, X^2, X^3$ and $X^4$ are each C, $R^5$, $R^6$ and $R^7$ are each H and $R^1$ is selected from the group consisting of t-butyl, —$CMe_2Et$, —$C(Et)_3$, —$CMe_2Ph$, —$C(Ph)_3$, —$Si(Et)_3$, and —$Si(Ph)_3$, are not included.

In one aspect for compounds of formula (II), $R^1$ is selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl.

In another aspect for compounds of formula (II), $R^7$ is selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl In still another aspect for compounds having formula (II), $R^1$ is selected from the group consisting of t-butyl, naphthyl, substituted naphthyl, carbazolyl, substituted carbazolyl, phenyl and substituted phenyl and $R^7$ is selected from the group consisting of substituted phenyl and anthracenyl.

In a first embodiment for compounds having formula (II), $X^1$ is C, $X^2$ is N, $X^3$ is $CR^6$ and $X^4$ is $CR^7$ and are referred to as formulae (IIa). In one aspect of formula (IIa), $R^1$ is an alkyl, substituted alkyl, aryl, or a substituted aryl. In another aspect of formula (IIa), $R^3$ is a hydrogen, an alkyl or a substituted alkyl. In still another aspect of formula (IIa), $R^6$ is an aryl or a substituted aryl. In still yet another aspect of formula (IIa), $R^7$ is an aryl or a substituted aryl.

In certain aspects for compounds of formulae (I) through (Ig), (II) and (IIa), $R^7$ is a disubstituted phenyl group, and in particular, a 2,6 disubstituted phenyl group.

In general, in one aspect, the invention provides compositions of matter, including ligands, compositions and metal-ligand complexes, that include a compound characterized by the formula (III):

$R^1, R^2, R^3, R^4, R^5, R^8, R^9, R^{10}$, and $R^{11}$ are the same or different and are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the exception that $R^1$ may not be hydrogen, optionally two or more of $R^1, R^2, R^3$ and $R^4$ may be joined to form a fused ring system having up to 50 atoms, not counting hydrogen atoms, and optionally two or more of $R^8$, $R^9, R^{10}$ and $R^{11}$ may be joined to form a fused ring system having up to 50 atoms, not counting hydrogen atoms.

For compounds of formula (III), $X^1$ is N or C, $X^2$ is O, S, $N(R^5)_{n'}$ or $CR^5$, wherein n' is 0 or 1, provided that the heteroatom containing ring system is heteroaromatic, provided $X^1$ and $X^2$ are not both N.

In one aspect for compounds of formula (III), $R^1$ is selected from the group consisting of t-butyl, naphthyl, substituted naphthyl, carbazolyl, substituted carbazolyl, phenyl and substituted phenyl.

In a first embodiment for compounds having formula (III), $X^1$ is C, $X^2$ is $NR^5$ and are referred to as formulae (IIIa). In one aspect of formula (IIIa), $R^1$ is an alkyl, substituted alkyl, aryl or a substituted aryl. In another aspect of formula (IIIa), $R^3$ is a hydrogen, alkyl or substituted alkyl. In still another aspect of formula (IIIa), $R^5$ is an alkyl or substituted alkyl.

In a second embodiment for compounds having formula (III), $X^1$ is C and $X^2$ is S and are referred to as formulae (IIIb). In one embodiment of formula (IIIb), $R^1$ is an alkyl or a substituted alkyl. In another embodiment of formula (IIIb), $R^3$ is a hydrogen, an alkyl or a substituted alkyl.

In a third embodiment for compounds having formula (III), $X^1$ is C and $X^2$ is O and are referred to as formulae (IIIc).

In a fourth embodiment for compounds having formula (III), $X^1$ is N and $X^2$ is $CR^5$ and are referred to as formulae (IIId). In one aspect of formula (IIId), $R^1$ is an alkyl or substituted alkyl. In another aspect of formula (IIId), $R^3$ is an alkyl or substituted alkyl.

In general, in one aspect, the invention provides compositions of matter, including ligands, compositions and metal-ligand complexes, that include a compound characterized by the formula (IV):

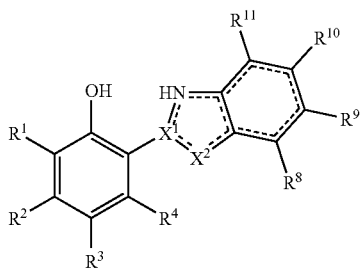

where $R^1, R^2, R^3, R^4, R^5, R^8, R^9, R^{10}$, and $R^{11}$ are the same or different and are each independent of each other and are as described above.

For compounds of formula (IV), $X^1$ is C, $X^2$ is N or $CR^5$, provided that the heteroatom containing ring system is heteroaromatic.

In one aspect for compounds having formula (IV), $R^1$ is selected from the group consisting of t-butyl, naphthyl, substituted naphthyl, carbazolyl, substituted carbazolyl, phenyl and substituted phenyl.

In a first embodiment for compounds having formula (IV), $X^1$ is C and $X^2$ is N and are referred to as formulae (IVa). In one aspect of formula (IVa), $R^1$ is an alkyl, substituted alkyl, aryl or substituted aryl. In another aspect of formula (IVa), $R^3$ is a hydrogen, an alkyl or a substituted alkyl. In yet another aspect of formula (IVa), $R^9$ is a hydrogen, halogen, alkyl, substituted alkyl, or an alkoxy. In still another aspect of formula (IVa), $R^{10}$ is a hydrogen, halogen, alkyl, or a substituted alkyl.

In general, in another aspect, the invention provides compositions of matter, including ligands, compositions and metal-ligand complexes, that include a compound characterized by the formula (V):

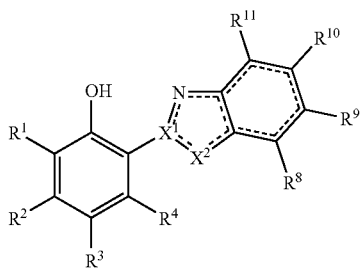

where $R^1, R^2, R^3, R^4, R^5, R^8, R^9, R^{10}$, and $R^{11}$ are the same or different and are each independent of each other and are as described above.

For compounds of formula (V), $X^1$ is N or C, $X^2$ is O, S, $N(R^5)_{n'}$ or $CR^5$, wherein n' is 0 or 1, provided that the heteroatom containing ring system is heteroaromatic, provided when $X^1$ and $X^2$ are both N, then:

$R^1$ is t-butyl, $R^2$ is H, $R^3$ is Me, $R^4$ is H, $R^8, R^9, R^{11}$ are each H and $R^{10}$ is Cl;

$R^1$ is i-propyl, $R^2$ is H, $R^3$ is t-butyl, $R^4, R^8, R^9, R^{10}$ and $R^{11}$ are each H;

$R^1$ is t-butyl, $R^2$ is H, $R^3$ is t-butyl, $R^4$ is H, $R^8, R^9, R^{11}$ are each H and $R^{10}$ is Cl;

$R^1$ is 1,1-dimethylpropyl, $R^2$ is H, $R^3$ is 1,1-dimethylpropyl, $R^4, R^8, R^9, R^{10}$ and $R^{11}$ are each H;

$R^1$ is isopropylbenzyl, $R^2$ is H, $R^3$ is isopropylbenzyl, $R^4$ is H, $R^8, R^9, R^{11}$ are each H and $R^{10}$ is Cl;

$R^1$ is t-butyl, $R^2$ is H, $R^3$ is t-butyl, $R^4$ is H, $R^8, R^9, R^{11}$ are each H and $R^{10}$ is F;

$R^1$ is t-butyl, $R^2$ is H, $R^3$ is t-butyl, $R^4$ is H, $R^8, R^{11}$ are each H, $R^9$ and $R^{10}$ are each F;

$R^1$ is t-butyl, $R^2$ is H, $R^3$ is t-butyl, $R^4$ is H, $R^8, R^{11}$ are each H, $R^9$ and $R^{10}$ are each Cl;

$R^1$ is t-butyl, $R^2$ is H, $R^3$ is t-butyl, $R^4$ is H, $R^8, R^9, R^{11}$ are each H and $R^{10}$ is —$CF_3$;

$R^1$ is t-butyl, $R^2$ is H, $R^3$ is t-butyl, $R^4$ is H, $R^8, R^9, R^{11}$ are each H and $R^{10}$ is —OMe;

$R^1$ is t-butyl, $R^2$ is H, $R^3$ is t-butyl, $R^4$ is H, $R^8, R^{11}$ are each H, $R^9$ and $R^{10}$ is are each Me;

$R^1$ is t-butyl, $R^2$ is H, $R^3$ is —OMe, $R^4$ is H, $R^8, R^9, R^{11}$ are each H and $R^{10}$ is Cl;

$R^1$ is phenyl, $R^2$ is H, $R^3$ is t-butyl, $R^4$ is H, $R^8, R^9, R^{11}$ are each H and $R^{10}$ is Cl;

$R^1$ is t-butyl, $R^2$ is H, $R^3$ is -Me, $R^4$ is H, $R^8, R^9, R^{11}$ are each H and $R^{10}$ is Cl;

$R^1$ is 2,4,6-trimethylphenyl, $R^2$ is H, $R^3$ is -Me, $R^4$ is H, $R^8, R^9, R^{11}$ are each H and $R^{10}$ is Cl;

$R^1$ is 1-naphthyl, $R^2$ is H, $R^3$ is -Me, $R^4$ is H, $R^8, R^9, R^{11}$ are each H and $R^{10}$ is Cl;

$R^1$ is 9-anthracenyl, $R^2$ is H, $R^3$ is -Me, $R^4$ is H, $R^8, R^9, R^{11}$ are each H and $R^{10}$ is Cl;

$R^1$ is 3,5-difluorophenyl, $R^2$ is H, $R^3$ is -Me, $R^4$ is H, $R^8, R^9, R^{11}$ are each H and $R^{10}$ is Cl;

$R^1$ is an alkyldiarylsilyl or dialkylarylsilyl, $R^2$ is H, $R^3$ is -Me, $R^4$ is H, $R^8, R^9, R^{11}$ are each H and $R^{10}$ is Cl;

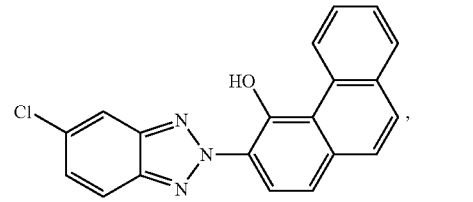

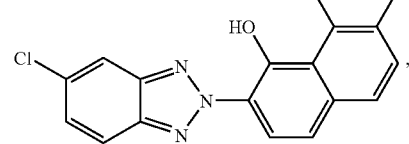

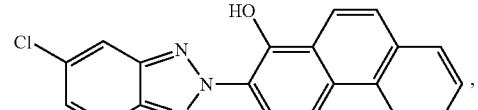

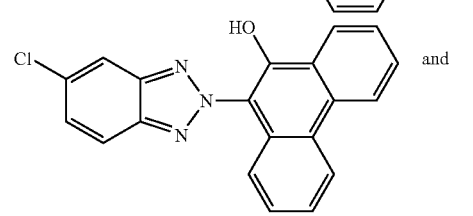

-continued

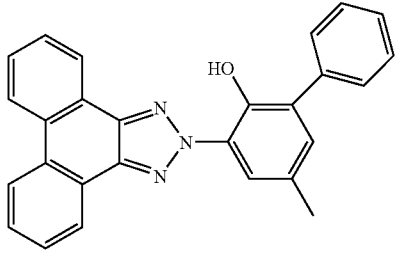

are not included.

In one aspect of compounds having formula (V), $R^1$ is selected from the group consisting of t-butyl, naphthyl, substituted naphthyl, carbazolyl, substituted carbazolyl, phenyl and substituted phenyl.

In any of the preceding aspects, compositions according to the invention can include a metal precursor or activated metal precursor including a metal selected from groups 3-6 and the lanthanide series of the periodic table of elements, and one or more optional activators. In particular embodiments, the metal precursor can be a compound characterized by the general formula $M(L)_m$, where M is a metal selected from the group consisting of groups 3-6 and lanthanides of the periodic table of elements, and each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups can be joined into a ring structure, Optionally, one or more of the ligands L can be ionically bonded to the metal M. m is 1, 2, 3, 4, 5, or 6. In more particular embodiments, M can be Ti, Zr, and Hf.

In general, in another aspect, the invention features metal-ligand complexes characterized by the formula (VI):

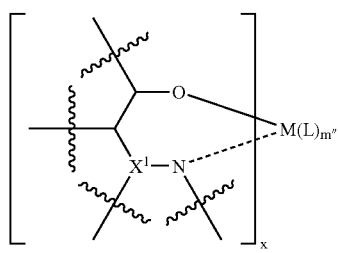

(VI)

where M, L and $X^1$ are as described above with the broken bonds representing the compounds having formulae (I) through (Ig), (III) through (IIId) and (V) as described above, x is 1, 2, 3, or 4 and m" is 0, 1, 2, 3 or 4. Alternatively, formulae (VI) includes those compounds having formulae (II), (IIa) and (IV) as described above, the nitrogen includes a hydrogen, and m' and x are as described above. The dashed bond shown between the nitrogen atom with M depicted in formula (VI) can be dative, nonexistent, or covalent. In many aspects herein, the phrase the bond between the heteroaromatic nitrogen (N) and the metal (M) is dative or absent is used to indicate additionally that the bond may attach or detach such that the bond fluxuates between dative and absent. This depiction and understanding is used throughout this specification. In an alternative embodiment, the complex may include more than one metal (M) and one or more ligands, each independent of one another, and the ligand to metal ratio may be fractional.

Particular embodiments can include one or more of the following features. In particular embodiments, the complex can be characterized by the formula (VII):

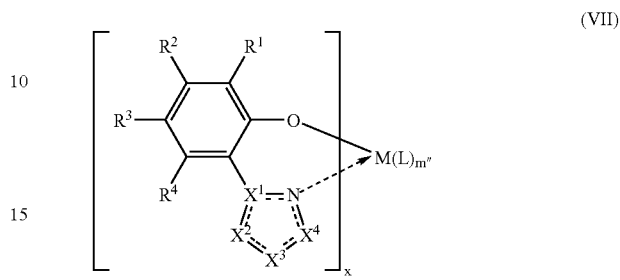

(VII)

where $R^1$, $R^2$, $R^3$, $R^4$, $R^5$, $R^6$, $R^7$, $X^1$, $X^2$, $X^3$ and $X^4$ are as described above for compounds of formulae (I) through formulae (Ig); M and L are as described above, x is 1, 2, 3, or 4, m" is 0, 1, 2, 3, or 4 and the bond between the heteroaromatic nitrogen (N) and the metal (M) is dative or absent.

In general, in yet another aspect, the invention features metal-ligand complexes characterized by the formula (VIII):

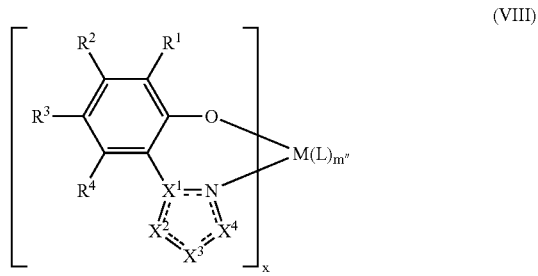

(VIII)

where $R^1$, $R^2$, $R^3$, $R^4$, $R^5$, $R^6$, $R^7$, $X^1$, $X^2$, $X^3$ and $X^4$ are as described above for compounds of formulae (II) and (IIa), M and L are as described above, x is 1 or 2 and m" is 0, 1, 2, 3, or 4.

In certain aspects for complexes of formulae (VII) through (VIIg), (VIII) and (VIIIa), $R^7$ is a disubstituted phenyl group, and in particular, a 2,6 disubstituted phenyl group.

In general, in still another aspect, the invention features metal-ligand complexes characterized by the formula (IX):

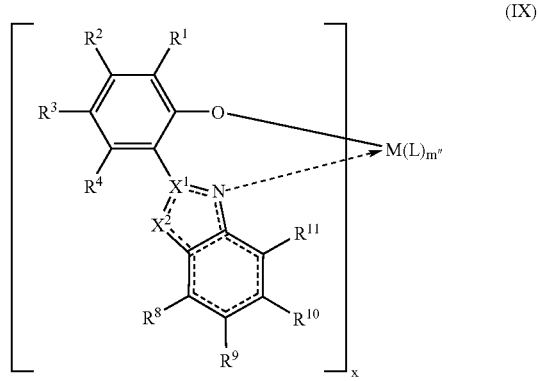

(IX)

where $R^1$, $R^2$, $R^3$, $R^4$, $R^5$, $R^8$, $R^9$, $R^{10}$, $R^{11}$, $X^1$ and $X^2$ are as described above for compounds of formulae (III) through formulae (IIId), M and L are as described above, x is 1, 2, 3, or 4 and m'' is 0, 1, 2, 3, or 4 and the bond between the heteroaromatic nitrogen (N) and the metal (M) is dative or absent.

In general, in still another aspect, the invention features metal-ligand complexes characterized by the formula (X):

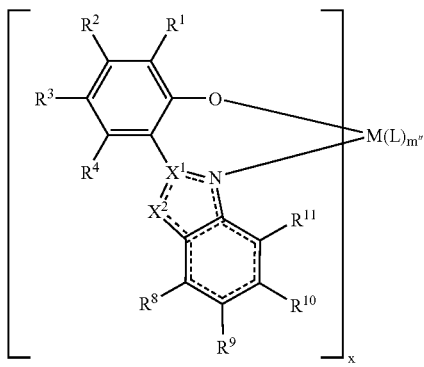

(X)

where $R^1$, $R^2$, $R^3$, $R^4$, $R^5$, $R^8$, $R^9$, $R^{10}$, $R^{11}$, $X^1$ and $X^2$ are as described above for compounds of formulae (IV) and (IVa), M and L are as described above, x is 1 or 2 and m'' is 0, 1, 2, 3, or 4.

In general, in still yet another aspect, the invention features metal-ligand complexes characterized by the formula (XI):

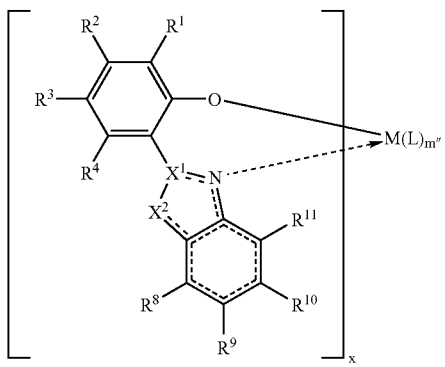

(XI)

where $R^1$, $R^2$, $R^3$, $R^4$, $R^5$, $R^8$, $R^9$, $R^{10}$, $R^{11}$, $X^1$ and $X^2$ are as described above for compounds of formulae (V), M and L are as described above, x is 1, 2, 3, or 4 and m'' is 0, 1, 2, 3, or 4 and the bond between the heteroaromatic nitrogen (N) and the metal (M) is dative or absent.

In particular, for the compounds and complexes described throughout the specification, $R^1$ and $R^7$ can be thiophenyl, substituted thiophenyl, carbazole, substituted carbazoles, indoles and substituted indoles.

In general, in another aspect, the invention provides bis-ligand complexes, as well as compositions where the ratio of metal to ligand is about one to two. In some embodiments, these bis-ligand systems are those where x is 2 in any of the above metal complex formulae, and in other embodiments, the bis-ligand systems have one ancillary ligand as described in the above formulae and a second ancillary ligand that can generally be within the definition of L. For example, a bis-ligand complex can be characterized by the general formula:

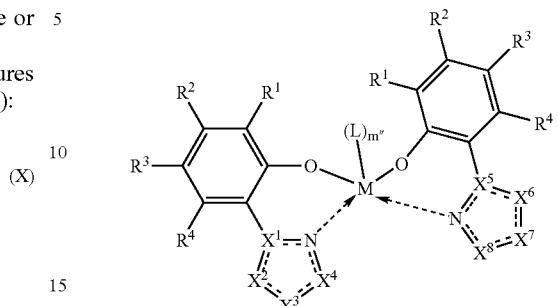

wherein each $R^1$, $R^2$, $R^3$; $R^4$, $R^5$, $R^6$, $R^7$ are the same or different and are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the exception that $R^1$ may not be hydrogen, optionally two or more of $R^1$, $R^2$, $R^3$ and $R^4$ on the same ring in the formula may be joined to form a fused ring system having up to 50 atoms, not counting hydrogen atoms, and optionally two or more of $R^5$, $R^6$ and $R^7$ on the same ring in the formula may be joined to form a fused ring system having up to 50 atoms, not counting hydrogen atoms; $X^1$ is N or C, $X^2$ is O, S, $N(R^5)_{n'}$ or $CR^5$, $X^3$ is O, S, $N(R^6)_{n''}$ or $CR^6$, $X^4$ is O, S, $N(R^7)_{n'''}$ or $CR^7$, wherein each n', n'', and n''' are each independently 0 or 1, provided that the heteroatom containing ring system is heteroaromatic; $X^5$ is N or C, $X^6$ is O, S, $N(R^5)_{n'}$ or $CR^5$, $X^7$ is O, S, $N(R^6)_{n''}$ or $CR^6$, $X^8$ is O, S, $N(R^7)_{n'''}$ or $CR^7$, wherein each n', n'', and n''' are each independently 0 or 1, provided that the heteroatom containing ring system is heteroaromatic; and further provided that in the selection of the C, N, O or S atom, at least, either $X^1$ and $X^5$ are different or $X^2$ and $X^6$ are different or $X^3$ and $X^7$ are different or $X^4$ and $X^8$ are different; wherein M is a metal selected from the group consisting of groups 3 through 6 of the periodic table elements and lanthanides; wherein each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof; m'' is 0, 1, 2, or 3; and the bond between the heteroaromatic nitrogens (N) and the metal (M) is dative or absent.

In general, in still another aspect, the invention provides arrays of materials. The arrays include a substrate having at least 8 members associated with regions of the substrate. Each array member is different from the other members of the array. Each array member includes a compound, composition or complex according to one of the aspects described above.

In general, in another aspect, the invention provides catalytic methods. In the methods, one or more reagents is reacted in the presence of a catalyst comprising a composition or complex as described above, and optionally one or more activators, under conditions sufficient to yield one or more reaction products.

In general, in another aspect, the invention provides polymerization processes that employ the composition or complexes of the invention, optionally in the presence of at least one activator. In particular embodiments, the activator can include an ion forming activator and, optionally, a group 13 reagent. The activator can include an alumoxane.

In general, in another aspect, the invention provides a process for the polymerization of an alpha-olefin. According to the process, at least one alpha-olefin is polymerized in the presence of a catalyst formed from a composition or complex of the invention, optionally in the presence of one or more activators, under polymerization conditions sufficient to form a substantially stereoregular polymer.

In general, in another aspect, the invention provides a process for polymerizing ethylene and at least one alpha-olefin. According to the process, ethylene is polymerized in the presence of at least one alpha-olefin in the presence of a catalyst formed from a composition or complex of the invention, optionally in the presence of one or more activators.

Particular embodiments can include one or more of the following features. The at least one alpha-olefin can include propylene, 1-butene, 1-hexene, 1-octene, 1-decene, styrene or substituted styrene. The process can be a solution process, and can be operated under polymerization conditions that include a temperature of at least 100° C., or at least 125° C.

In general, in another aspect, the invention provides a process for polymerizing at least one monomer. The process includes providing a reactor with reactor contents including at least one polymerizable monomer and a composition or complex of the invention, and subjecting the reactor contents to polymerization conditions. In particular embodiments, the at least one polymerizable monomer can include ethylene and propylene, ethylene and 1-hexene, ethylene and 1-butene, 1-octene, 1-decene, ethylene and styrene, ethylene and a cyclic alkene, ethylene and a diene, or ethylene, propylene, and a diene selected from the group consisting of ethylidenenorbornene, dicyclopentadiene, and 1,4-hexadiene.

In general, in another aspect, the invention provides a process for the polymerization of a polymerizable monomer. According to the process, a composition or complex of the invention is provided, the composition or complex is optionally activated, and at least one polymerizable monomer is polymerized in the presence of the activated composition or complex to produce a distribution of product polymers that is at least bimodal by one or more of molecular weight or composition.

The invention can be implemented to provide one or more of the following advantages. The ligands, compositions, complexes and polymerization methods of the invention can be used to provide catalysts exhibiting enhanced activity. Catalysts incorporating the ligands, compositions and/or complexes can be used to catalyze a variety of transformations, such as olefin oligomerization (specifically dimerization, trimerization and tetramerization) or polymerization. By selecting an appropriate ligand and metal, compositions and/or complexes can be obtained to provide for desired properties in the resulting product. Thus, polymers produced using the ligands, compositions, complexes, and methods of the invention can exhibit higher (or lower) melting points, higher (or lower) molecular weights, and/or higher (or lower) polydispersities, than polymers produced using prior known catalysts. In some embodiments, polymer products having bi- or multi-modal distributions of product composition and/or molecular weight can be obtained by selecting a single catalyst precursor and activating it under certain conditions. Catalysts incorporating the ligands, compositions and/or complexes can be used according to the polymerization methods of the invention to produce polymers under commercially desirable polymerization conditions. Catalysts incorporating the ligands, compositions and complexes of the invention can exhibit catalytic activity at higher temperatures than prior known catalysts. Copolymerization processes (e.g., ethylene/α-olefin copolymerizations) using the ligands, compositions and complexes of the invention can exhibit higher (or lower) comonomer incorporation than processes involving prior known catalysts. Chiral compositions and/or complexes according to the invention can be used to catalyze stereoselective, enantioselective or diastereoselective transformations.

DETAILED DESCRIPTION

Figure 1:
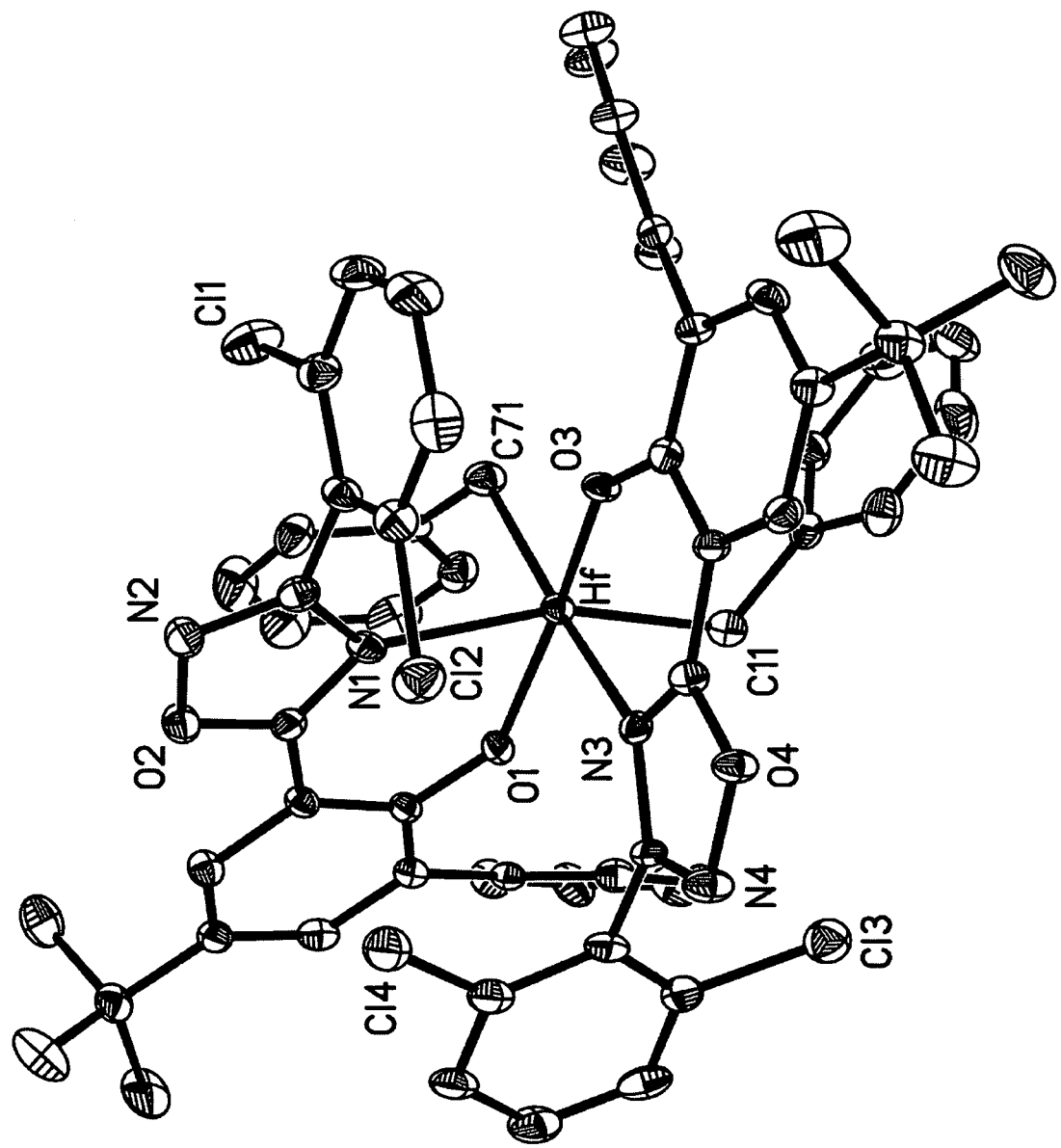
FIG. 1 is an X-ray structure determination of complex M1 of the invention.

The invention provides ligands, compositions and complexes that are useful as catalysts for a variety of transformations, including olefin polymerization reactions.

As used herein, the phrase "characterized by the formula" is not intended to be limiting and is used in the same way that "comprising" is commonly used. The term "independently selected" is used herein to indicate that the groups in question—e.g., $R^1$, $R^2$, $R^3$, $R^4$, $R^5$, etc.—can be identical or different (e.g., $R^1$, $R^2$, $R^3$, $R^4$, $R^5$, etc. may all be substituted alkyls, or $R^1$ and $R^2$ may be a substituted alkyl and $R^3$ may be an aryl, etc.). When two or more specific R groups appear in a formula, they can also be the same or different from each other; for example, if $R^1$ appears twice in a formula (e.g., formula XX), then each occurance of $R^1$ can be the same or different from the other occurances. Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where the event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "substituted" as in "substituted hydrocarbyl," "substituted aryl," "substituted alkyl," and the like, means that in the group in question (i.e., the hydrocarbyl, alkyl, aryl or other moiety that follows the term), at least one hydrogen atom bound to a carbon atom is replaced with one or more substituent groups such as hydroxy, alkoxy, alkylthio, phosphino, amino, halo, silyl, and the like. When the term "substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, napthyl, pyrrolyl, furyl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "hydrocarbyl" refers to hydrocarbyl radicals containing 1 to about 50 carbon atoms, specifically 1 to about 24 carbon atoms, most specifically 1 to about 16 carbon atoms, including branched or unbranched, cyclic or acyclic, saturated or unsaturated species, such as alkyl groups, alkenyl groups, aryl groups, and the like.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "alkenyl" as used herein refers to a branched or unbranched, cyclic or acyclic hydrocarbon group typically although not necessarily containing 2 to about 50 carbon atoms and at least one double bond, such as ethenyl, n-propenyl, isopropenyl, n-butenyl, isobutenyl, octenyl, decenyl, and the like. Generally, although again not necessarily, alkenyl groups herein contain 2 to about 20 carbon atoms.

The term "alkynyl" as used herein refers to a branched or unbranched, cyclic or acyclic hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 20 carbon atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl or 9-phenanthrenyl.

The term "alkoxy" as used herein intends an alkyl group bound through a single, terminal ether linkage; that is, an "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyrrolidine, pyrroline, furan, tetrahydrofuran, thiophene, imidazole, oxazole, thiazole, indole, and the like, including any isomers of these. Additional heterocycles are described, for example, in Alan R. Katritzky, *Handbook of Heterocyclic Chemistry*, Pergammon Press, 1985, and in *Comprehensive Heterocyclic Chemistry*, A. R. Katritzky et al., eds, Elsevier, 2d. ed., 1996. The term "metallocycle" refers to a heterocycle in which one or more of the heteroatoms in the ring or rings is a metal.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene, benzimidiazole, benzthiazole, benzoxazoles, indazole and the like and isomers thereof, e.g., reverse isomers.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds.

As used herein the term "silyl" refers to the —$SiZ^1Z^2Z^3$ radical, where each of $Z^1$, $Z^2$, and $Z^3$ is independently selected from the group consisting of hydrogen and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the —$BZ^1Z^2$ group, where each of $Z^1$ and $Z^2$ is as defined above. As used herein, the term "phosphino" refers to the group —$PZ^1Z^2$, where each of $Z^1$ and $Z^2$ is as defied above. As used herein, the term "phosphine" refers to the group :$PZ^1Z^2Z^3$, where each of $Z^1$, $Z^3$ and $Z^2$ is as defined above. The term "amino" is used herein to refer to the group —$NZ^1Z^2$, where each of $Z^1$ and $Z^2$ is as defined above. The term "amine" is used herein to refer to the group :NZ$^1$Z$^2$Z$^3$, where each of Z$^1$, Z$^2$ and Z$^3$ is as defined above.

In this specification, ligand binding is sometimes referred to as (2,1) complexation or (2,2) complexation, with the first number representing the number of coordinating atoms and second number representing the number of anionic sites on the phenol-heterocycle ligand, when the metal-ligand bonding is considered from an ionic bonding model perspective, with the metal considered to be cationic and the ligand considered to be anionic. From a covalent bonding model perspective, a (2,1) complex may be considered to be a complex in which the phenol-heterocycle ligand is bound to the metal center via one covalent bond and one dative bond, while a (2,2) complex may be considered to be a complex in which the phenol-heterocycle ligand is bound to the metal center via two covalent bonds. Examples of (2,1) complexation include the complex examples labeled M1 through M30 as listed below. Additionally, in certain embodiments, a covalent bond or dative bond may be formed from R$^1$, R$^7$ or R$^{11}$ to the metal, to form a (3,2) complex, or (3,1) complex respectively. For example, where R$^1$, R$^7$ or R$^{11}$ is an aryl or heteroaryl, C—H activation may occur to form a (3,2) complex, or where R$^1$, R$^7$ or R$^{11}$ is a heteroatom-containing group, a dative bond may be found from heteroatom to metal to give a (3,1) complex.

It should be noted that the complexes can include "mono" ligand and "bis" ligand complexes. Examples of "mono" ligand complexes, where a single phenol-heterocycle ligand is complexed to the metal atom include M7 and M8. Examples of "bis" ligand complexes include, M1 through M6 and M9 through M30. FIG. 1 depicts "bis" ligand complex M1. It should also be understood that "bis" ligands can include two different phenol-heterocycle ligands. Examples of bis-liagnd complexes of two different phenol-heterocycle ligands include M13, M15, M17, M19, M21 and M23.

Other abbreviations used herein include: "Cbz" to refer to N-carbazole; "'Pr" to refer to isopropyl; "'Bu" to refer to tert-butyl; "Me" to refer to methyl; "Et" to refer to ethyl; "Ph" to refer to phenyl; "Mes" to refer to mesityl (2,4,6-trimethyl phenyl); "TFA" to refer to trifluoroacetate and "THF" to refer to tetrahydrofuran.

The ligands according to the invention can be characterized broadly as monoanionic ligands having a phenol and a heterocyclic or substituted heterocyclic group. Preferred ligand substituents for some particular monomers are described in more detail below. In some embodiments, the ligands of the invention can be characterized by the following (I):

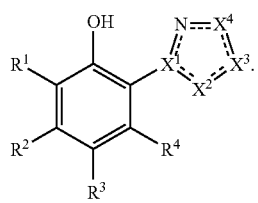

(I)

R$^1$, R$^2$, R$^3$, R$^4$, R$^5$, R$^6$, R$^7$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the exception that R$^1$ may not be hydrogen, optionally two or more of R$^1$, R$^2$, R$^3$ and R$^4$ may be joined to form a fused ring system having up to 50 atoms, not counting hydrogen atoms, and optionally two or more of R$^5$, R$^6$ and R$^7$ may be joined to form a fused ring system having up to 50 atoms, not counting hydrogen atoms.

For compounds of formula (I), X$^1$ is N or C, X$^2$ is O, S, N(R$^5$)$_{n'}$ or CR$^5$, X$^3$ is O, S, N(R$^6$)$_{n''}$ or CR$^6$, X$^4$ is O, S, N(R$^7$)$_{n'''}$ or CR$^7$, wherein each n', n'', and n''' are each independently 0 or 1, provided that the heteroatom containing ring system is heteroaromatic, provided combinations of X$^1$, X$^2$; X$^1$, X$^3$; and X$^1$, X$^4$ are not both N and X$^1$, X$^2$ and X$^3$ are not all N. Additional compounds that are not included are those where X$^1$, X$^3$, X$^4$ are each N, X$^2$ is C, R$^5$ is H and R$^1$ is selected from the group consisting of t-butyl, —CMe$_2$Et, —C(Et)$_3$, —CMe$_2$Ph, —C(Ph)$_3$, —Si(Et)$_3$, and —Si(Ph)$_3$, and when R$^1$ is F, R$^3$ is F, X$^1$, X$^2$, X$^3$ are all C, X$^4$ is N, R$^5$, R$^6$ are each H and R$^7$ is t-butyl.

Additionally, the compounds and complexes disclosed in U.S. Pat. No. 6,333,389, issued to Whiteker et al. on Dec. 25, 2001 and US Patent Publication No. US 2003/0232717 A1 to Brummer et al, published Dec. 18, 2003 are excluded from the present invention.

In formulae presented throughout this specification, the presence of one solid line and one dashed line between any pair of atoms is intended to indicate that the bond in question may be a single bond or a double bond, or a bond with bond order intermediate between single and double, such as the delocalized bonding in an aromatic ring.

In one aspect for compounds of formula (I) and the below formulas, R$^1$ is selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl.

In another aspect for compounds of formula (I), R$^7$ is selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl and in particular, R$^1$ is selected from the group consisting of t-butyl, naphthyl, substituted naphthyl, carbazolyl, substituted carbazolyl, phenyl and substituted phenyl and R$^7$ is selected from the group consisting of substituted phenyl and anthracenyl.

In a first embodiment for compounds having formula (I), X$^1$ is C, X$^2$ is O, X$^3$ is N and X$^4$ is CR$^7$ and are referred to as formulae (Ia):

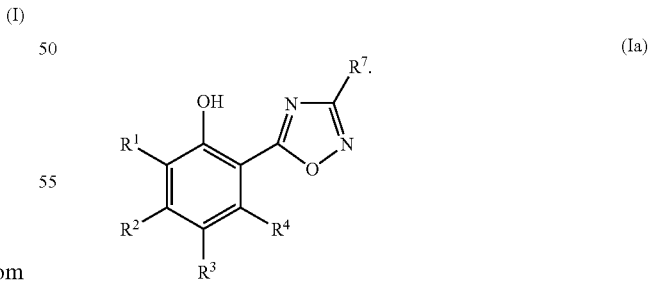

(Ia)

In certain aspects of formula (Ia), R$^1$ is an alkyl, substituted alkyl, aryl, substituted aryl, heteroaryl or substituted heteroaryl. In other aspects of formula (Ia), R$^3$ is an alkyl or a substituted alkyl. In still other aspects of formula (Ia), R$^7$ is an aryl or a substituted aryl. Specific examples of ligands within the scope of formula (Ia) include those set out in FIG. 2 as "A" ligands.

In a second embodiment for compounds having formula (I), $X^1$ is C, $X^2$ is N, $X^3$ is O and $X^4$ is $CR^7$ and are referred to as formulae (Ib):

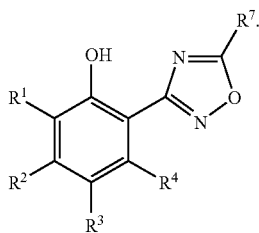

(Ib)

In particular embodiments of formula (Ib), $R^1$ is an alkyl or a substituted alkyl. In other embodiments of (Ib), $R^3$ is an alkyl or a substituted alkyl. In still other embodiments of formula (Ib), $R^7$ is an aryl or a substituted aryl. Specific examples of ligands within the scope of formula (Ib) includes those set out in FIG. 2 as "B" ligands.

In third embodiment for compounds of formula (I), $X^1$ is C, $X^2$ is $NR^5$, $X^3$ is $CR^6$ and $X^4$ is $CR^7$ and are referred to as formulae (Ic):

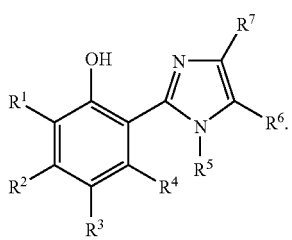

(Ic)

In particular aspects of formula (Ic), $R^1$ is an alkyl, substituted alkyl, aryl, substituted aryl, heteroaryl or a substituted heteroaryl. In other aspects of formula (Ic), $R^3$ is an alkyl or a substituted alkyl. In still other aspects of formula (Ic), $R^5$ is an alkyl or a substituted alkyl. In another aspect of formula (Ic), $R^6$ is an aryl or a substituted aryl. In still yet another aspect of formula (Ic), $R^7$ is an aryl or a substituted aryl. Suitable examples of ligands within the scope of formula (Ic) include those set out in FIG. 2 as "F" ligands.

In a fourth embodiment for compounds having formula (I), $X^1$ is C, $X^2$ is S, $X^3$ is $CR^6$ and $X^4$ is $CR^7$ and are referred to as formulae (Id):

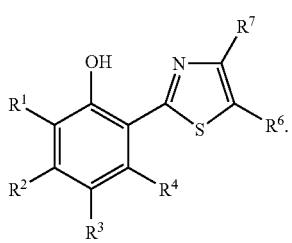

(Id)

In one embodiment of formula (Id), $R^1$ is an aryl, substituted aryl, alkyl, substituted alkyl, heteroaryl or a substituted heteroaryl. In another embodiment of formula (Id), $R^3$ is an alkyl or a substituted alkyl. In still another embodiment of formula (Id), $R^6$ is a hydrogen. In still yet another embodiment of formula (Id), $R^7$ is a halide, phenyl, substituted phenyl, naphthyl, substituted naphthyl, anthracenyl, substituted anthracenyl, or a hydrogen. Specific examples of ligands within the scope of formula (Id) include those set out in FIG. 5 as "C" ligands.

In a fifth embodiment for compounds having formula (I), $X^1$ is C, $X^2$ is $CR^5$, $X^3$ is S and $X^4$ is $CR^7$ and are referred to as formulae (Ie):

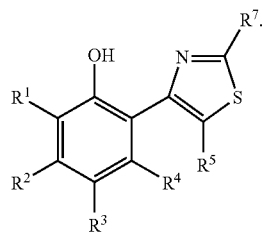

(Ie)

Figure 2:
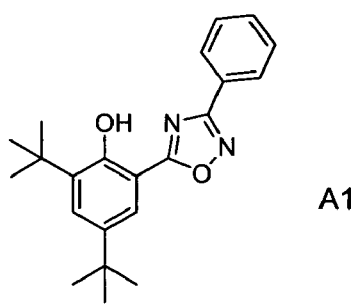
FIG. 2 is a list of certain ligands that comprise Tables 1-7, in accord with the invention herein.
Figure 2:
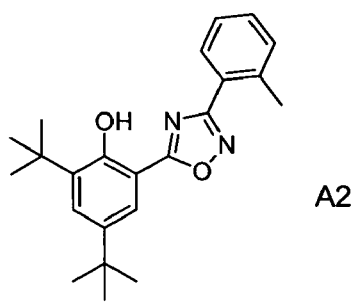
Figure 2:
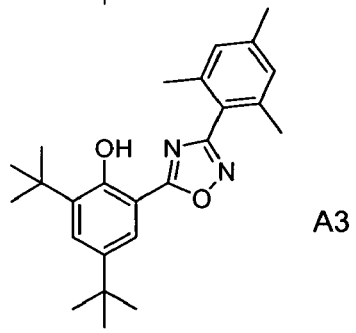
Figure 2:
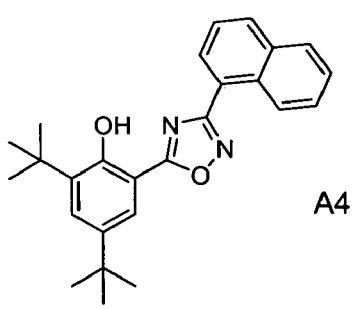
Figure 2:
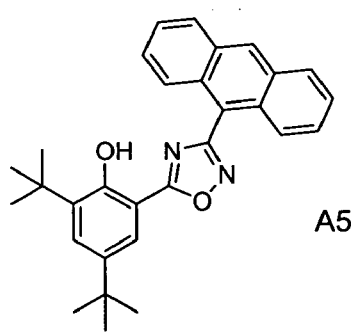
Figure 2:
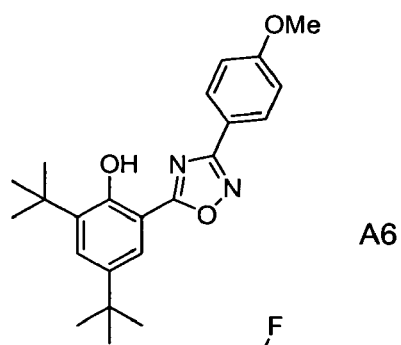
Figure 2:
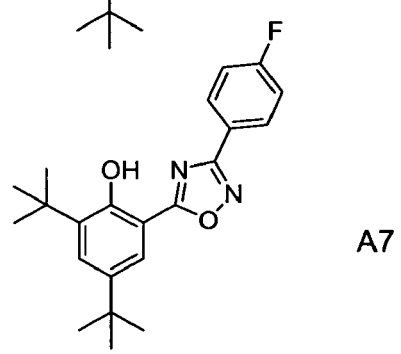
Figure 2:
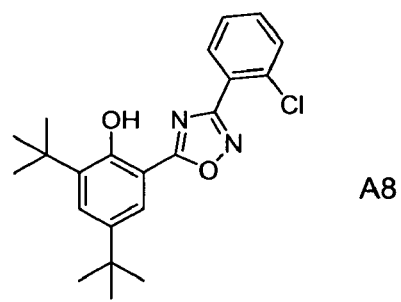
Figure 2:
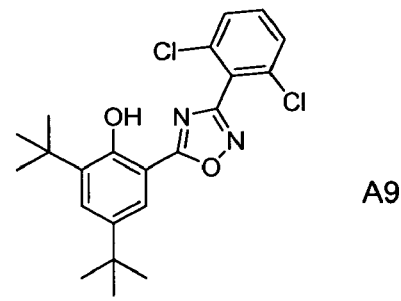
Figure 2:
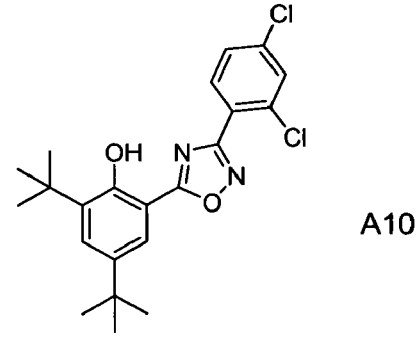
Figure 2:
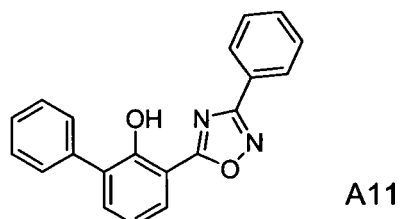
Figure 2:
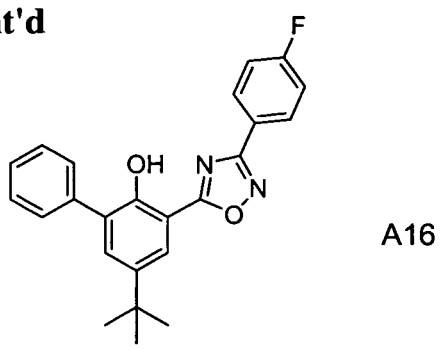
Figure 2:
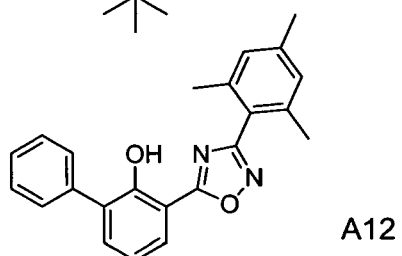
Figure 2:
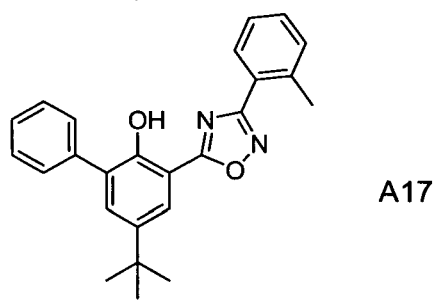
Figure 2:
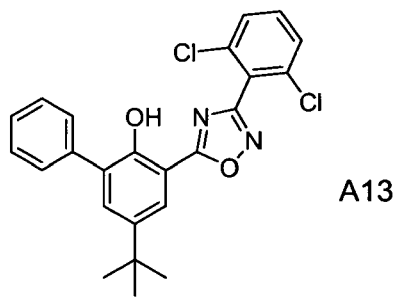
Figure 2:
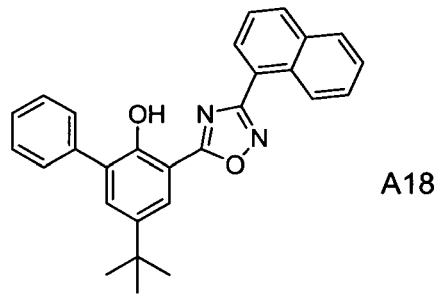
Figure 2:
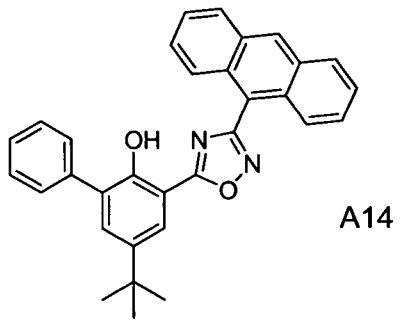
Figure 2:
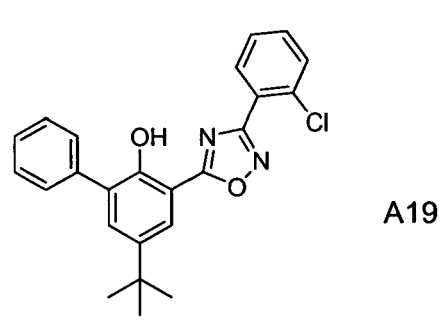
Figure 2:
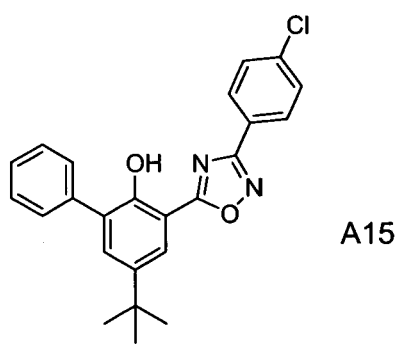
Figure 2:
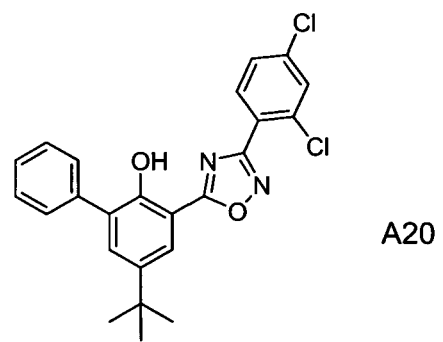
Figure 2:
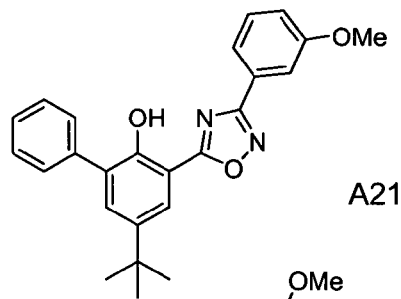
Figure 2:
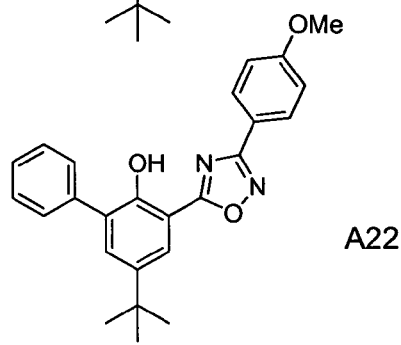
Figure 2:
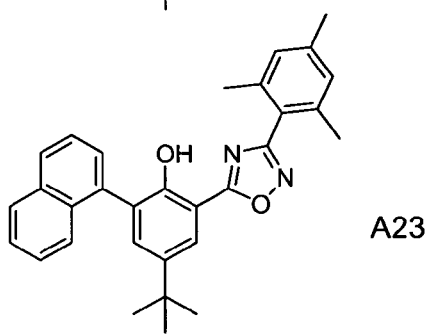
Figure 2:
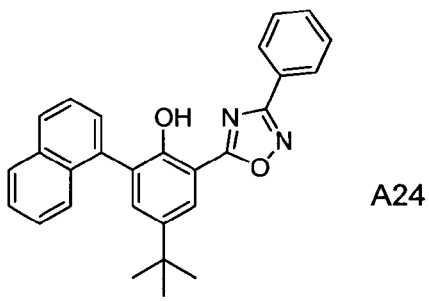
Figure 2:
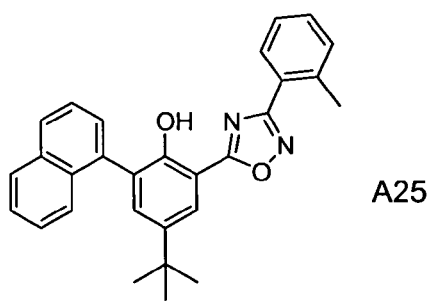
Figure 2:
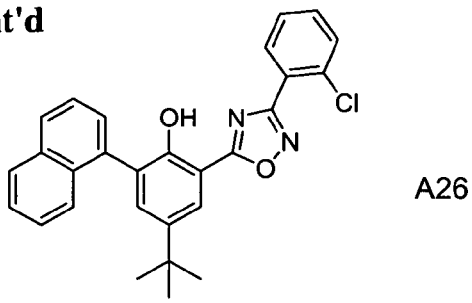
Figure 2:
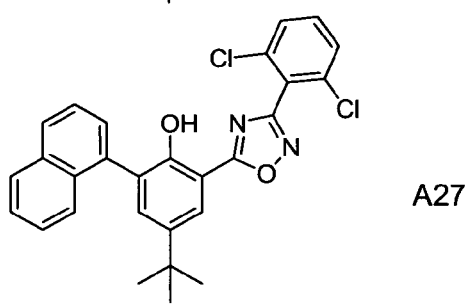
Figure 2:
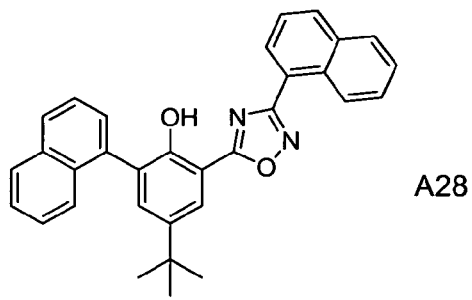
Figure 2:
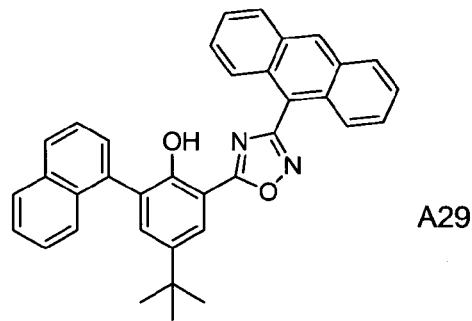
Figure 2:
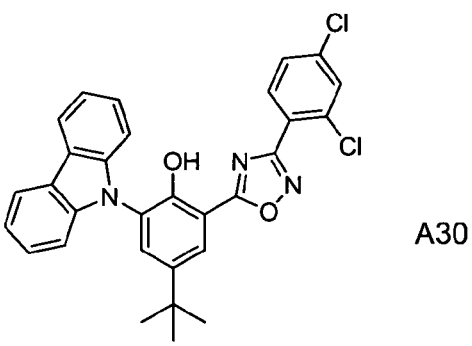
Figure 2:
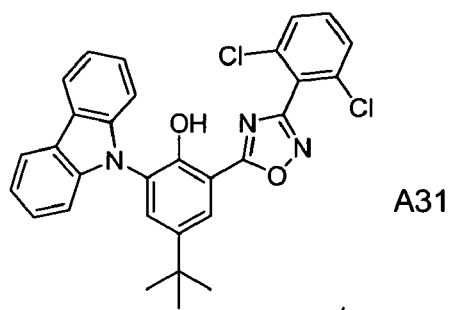
Figure 2:
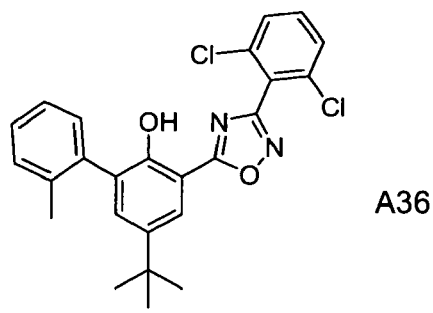
Figure 2:
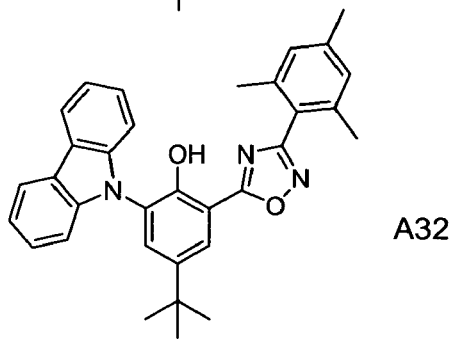
Figure 2:
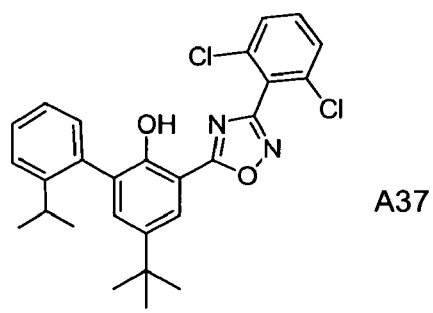
Figure 2:
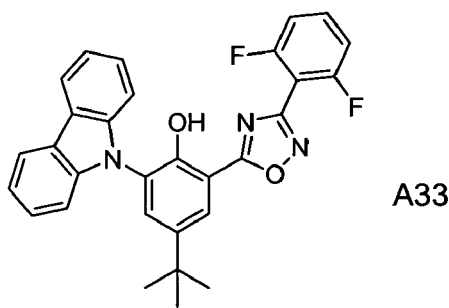
Figure 2:
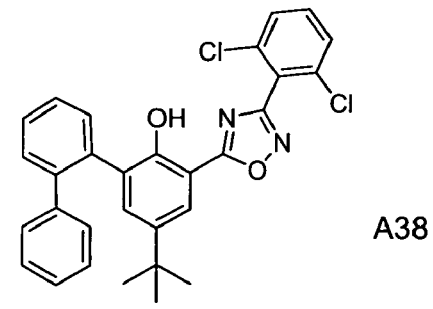
Figure 2:
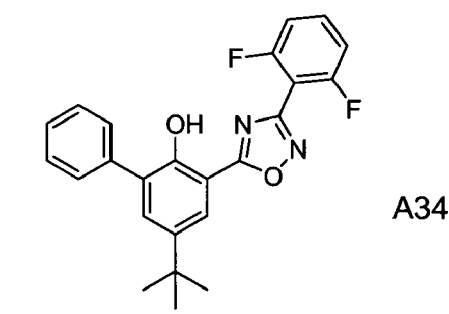
Figure 2:
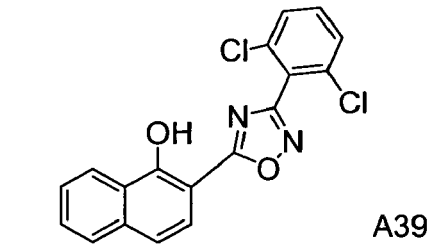
Figure 2:
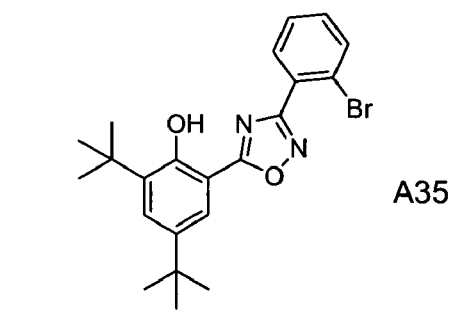
Figure 2:
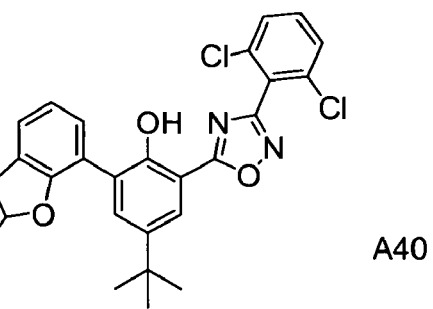
Figure 2:
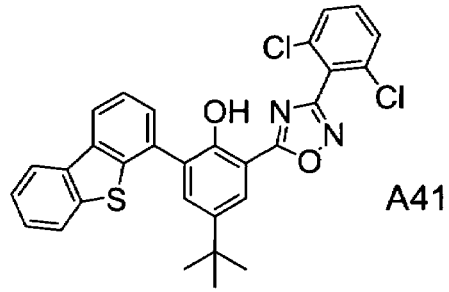
Figure 2:
Figure 2:
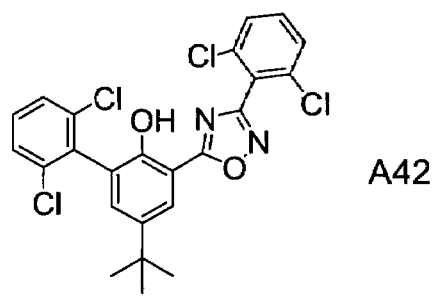
Figure 2:
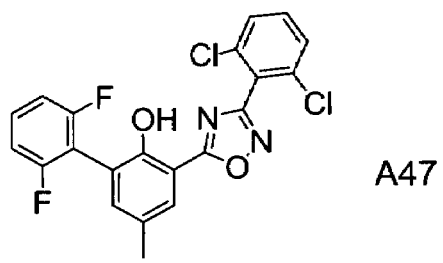
Figure 2:
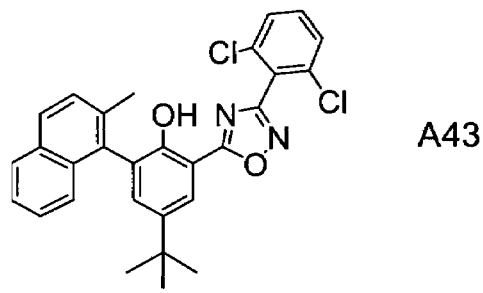
Figure 2:
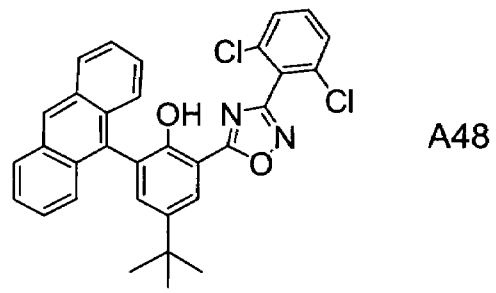
Figure 2:
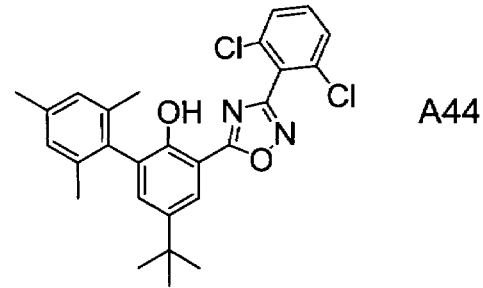
Figure 2:
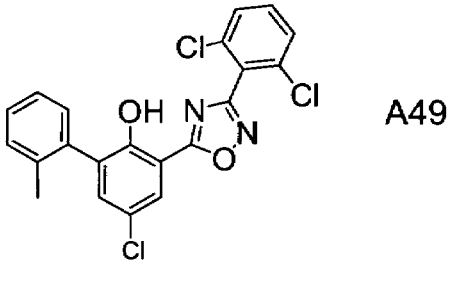
Figure 2:
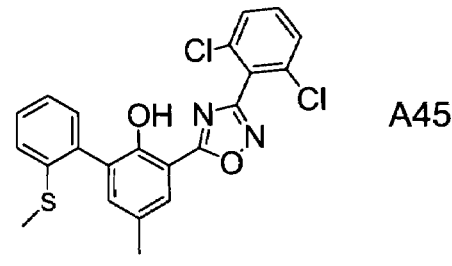
Figure 2:
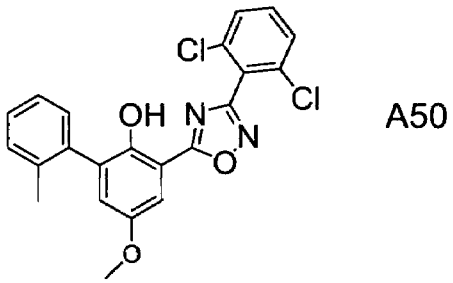
Figure 2:
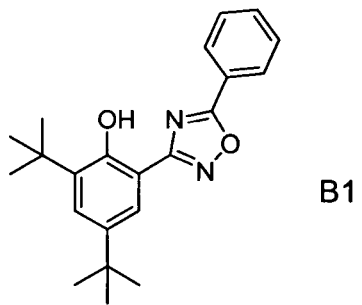
Figure 2:
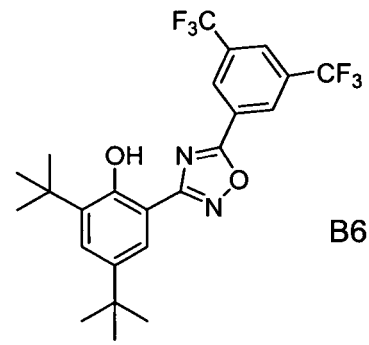
Figure 2:
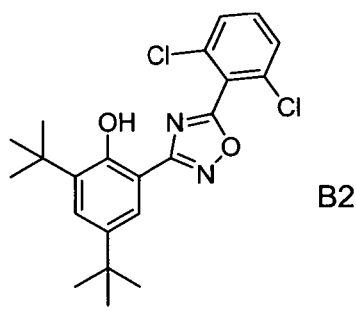
Figure 2:
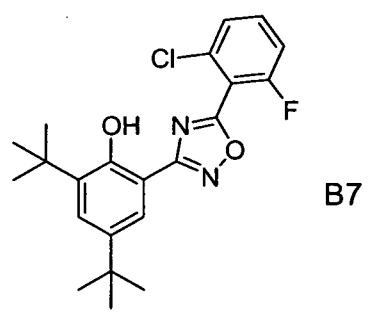
Figure 2:
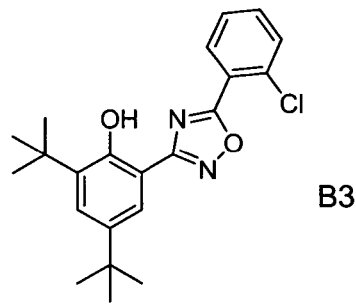
Figure 2:
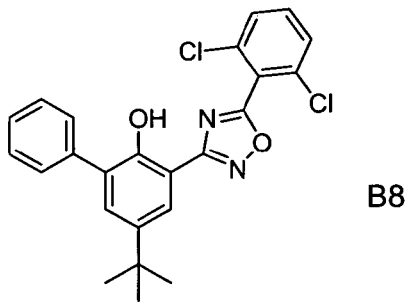
Figure 2:
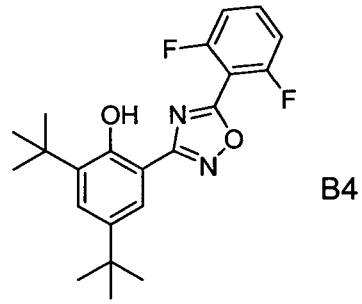
Figure 2:
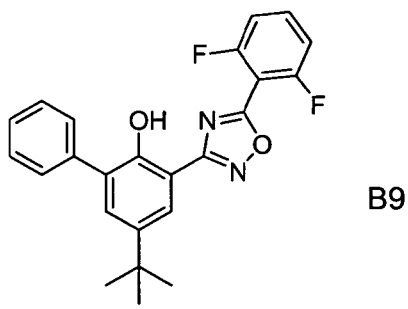
Figure 2:
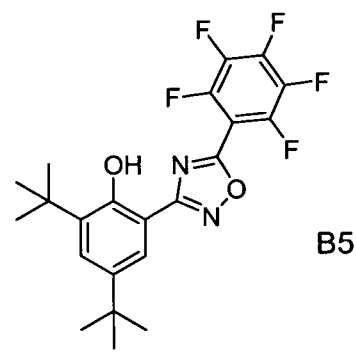
Figure 2:
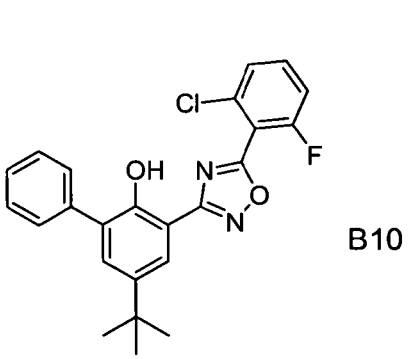
Figure 2:
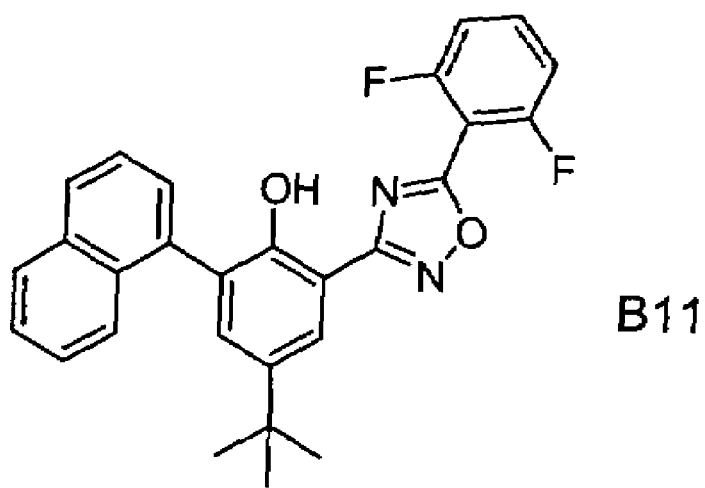
Figure 2:
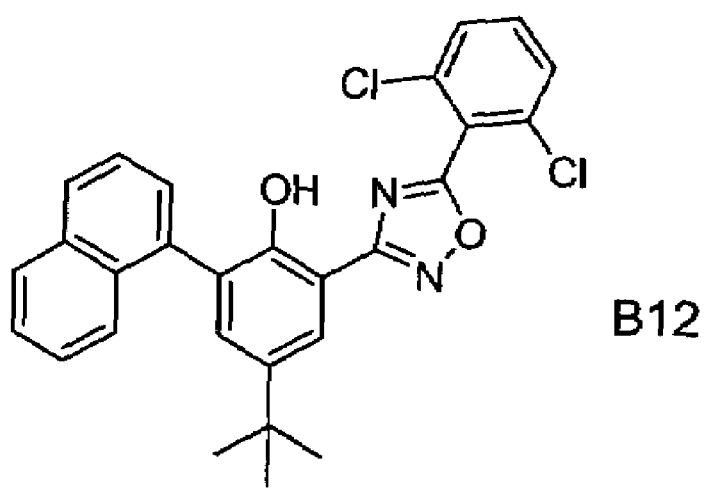
Figure 2:
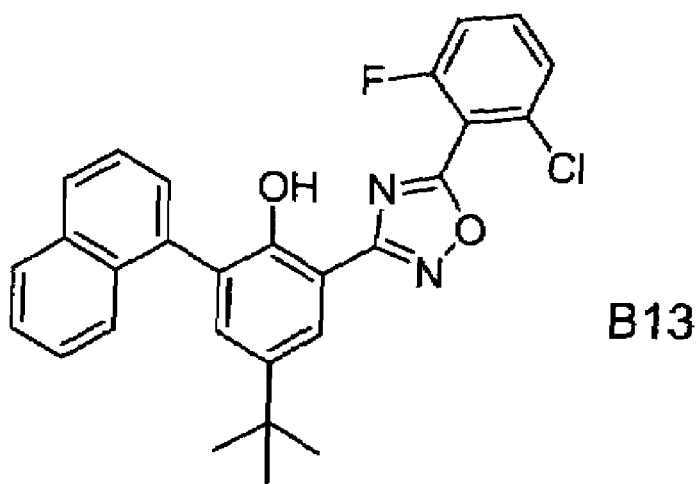
Figure 2:
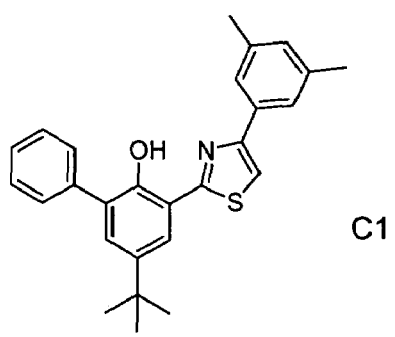
Figure 2:
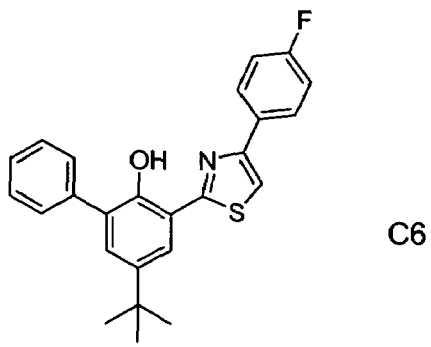
Figure 2:
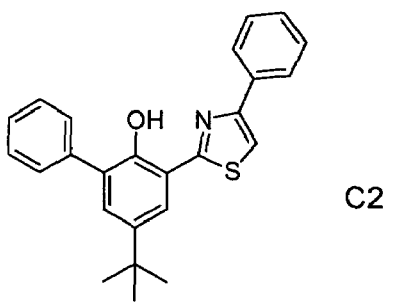
Figure 2:
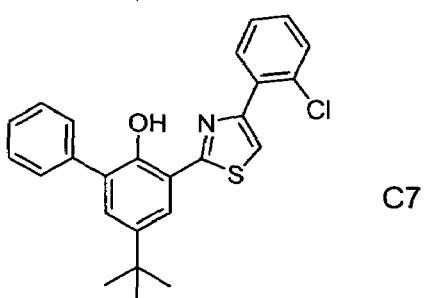
Figure 2:
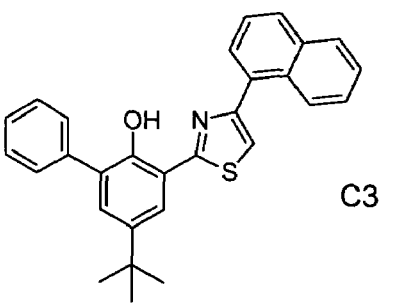
Figure 2:
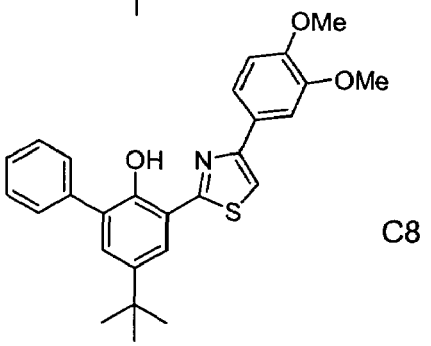
Figure 2:
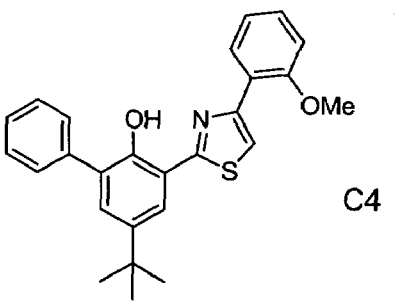
Figure 2:
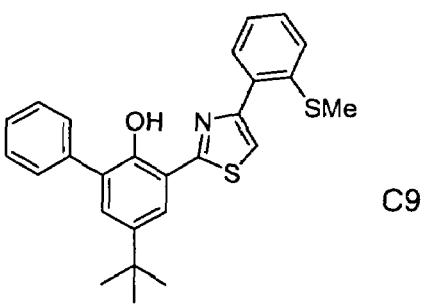
Figure 2:
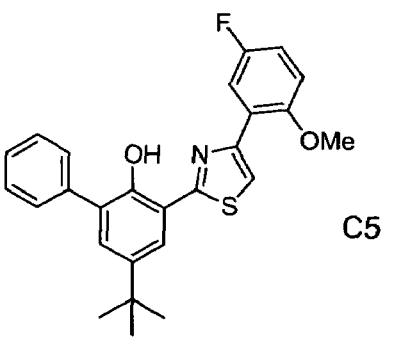
Figure 2:
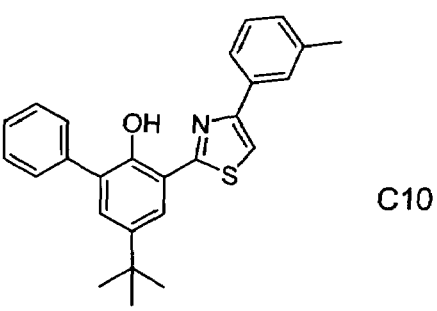
Figure 2:
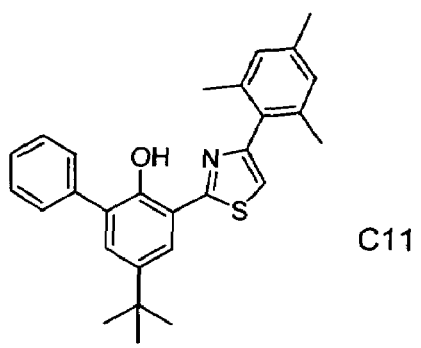
Figure 2:
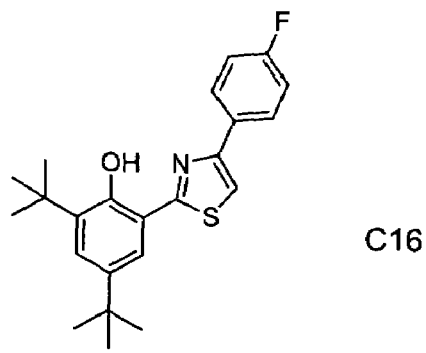
Figure 2:
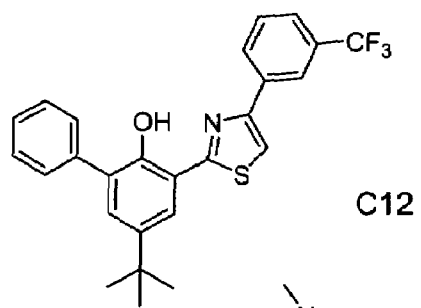
Figure 2:
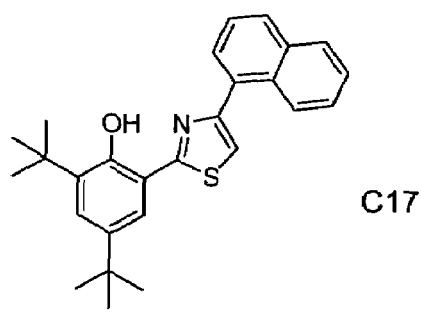
Figure 2:
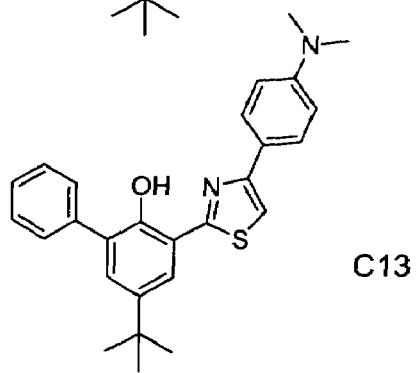
Figure 2:
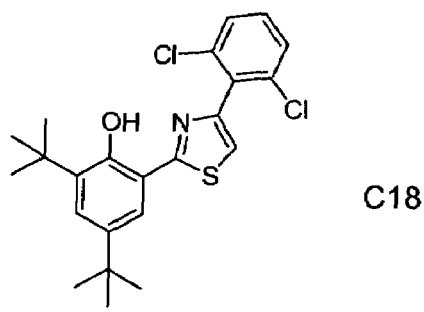
Figure 2:
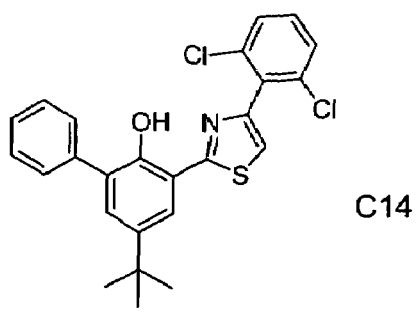
Figure 2:
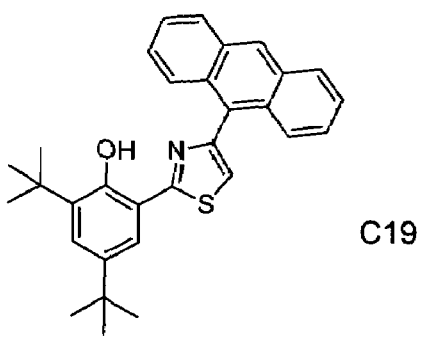
Figure 2:
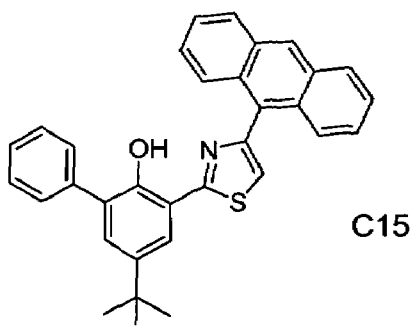
Figure 2:
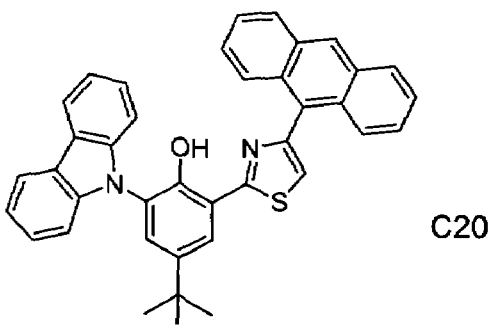
Figure 2:
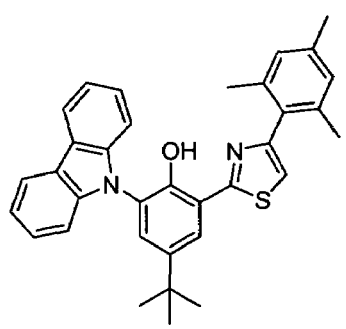
Figure 2:
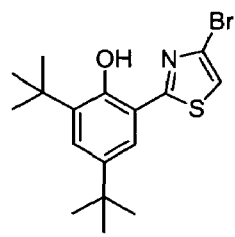
Figure 2:
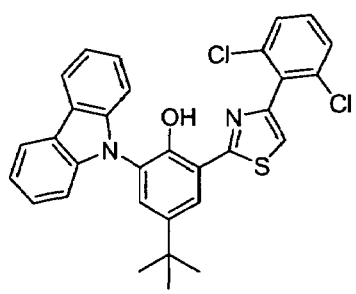
Figure 2:
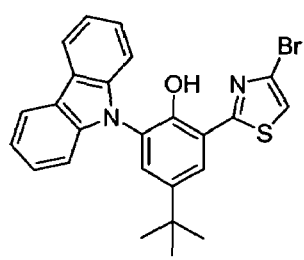
Figure 2:
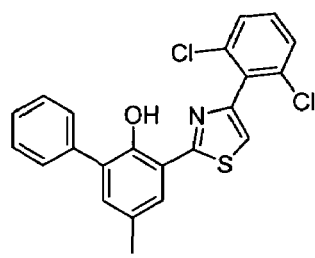
Figure 2:
Figure 2:
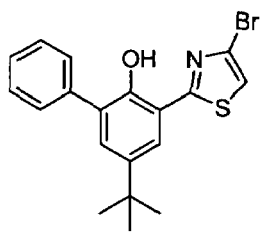
Figure 2:
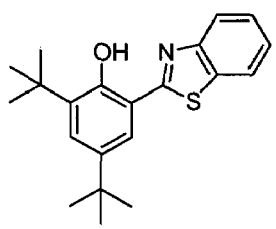
Figure 2:
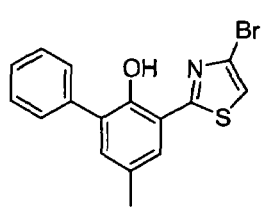
Figure 2:
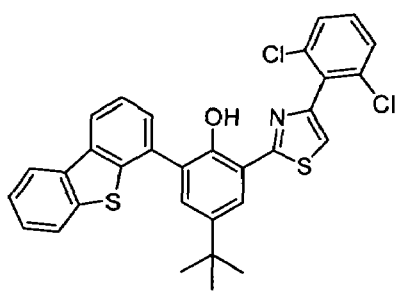
Figure 2:
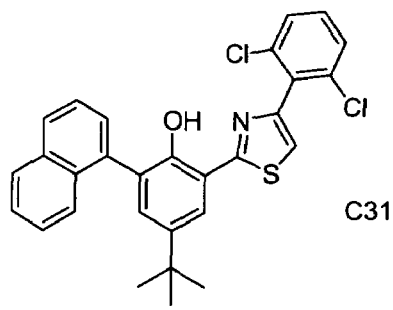
Figure 2:
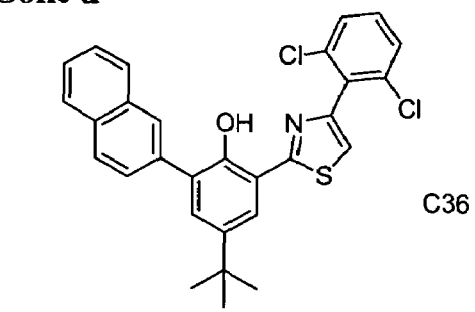
Figure 2:
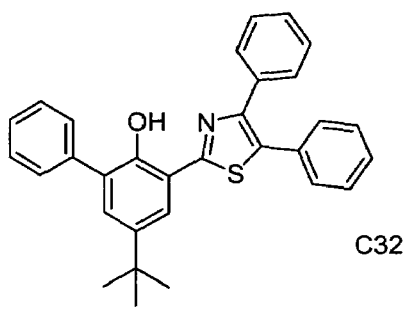
Figure 2:
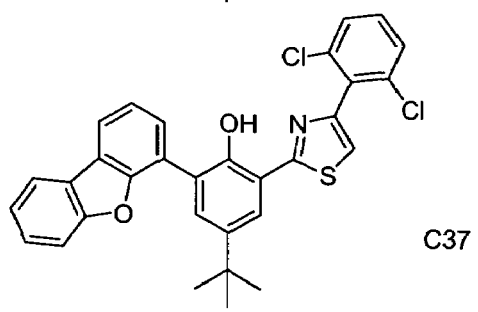
Figure 2:
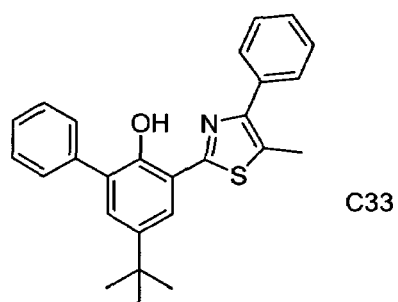
Figure 2:
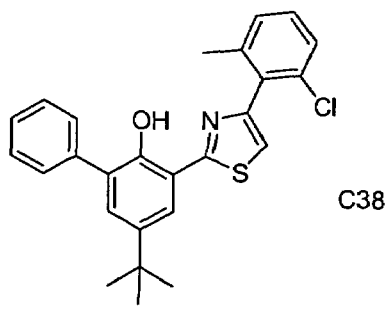
Figure 2:
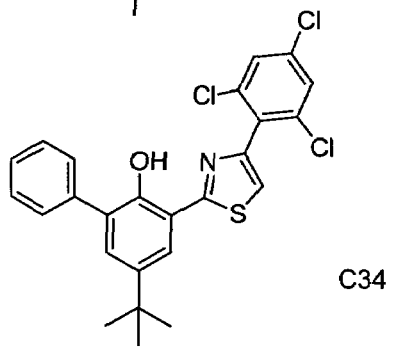
Figure 2:
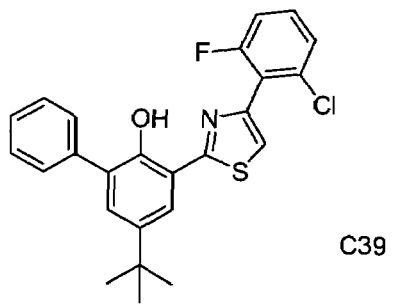
Figure 2:
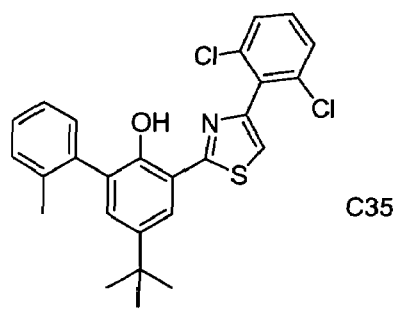
Figure 2:
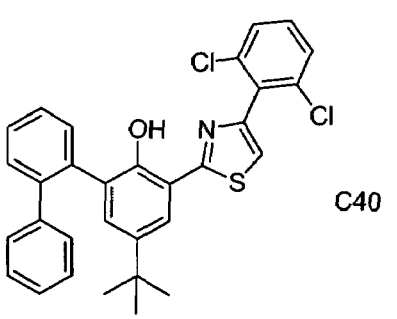
Figure 2:
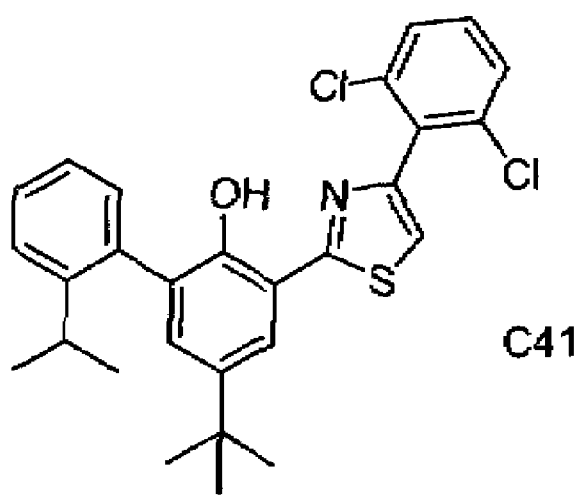
Figure 2:
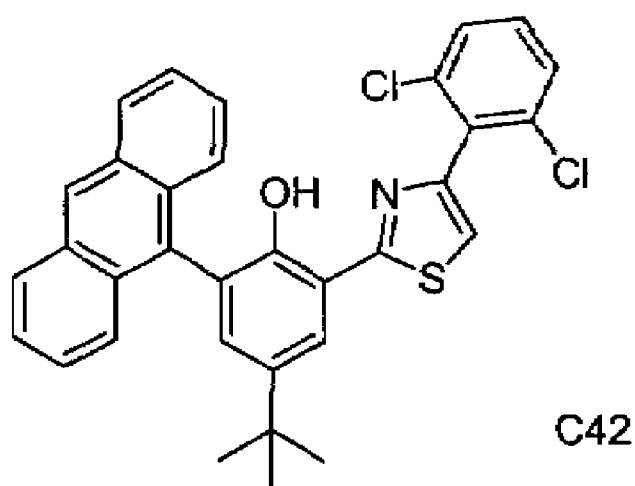
Figure 2:
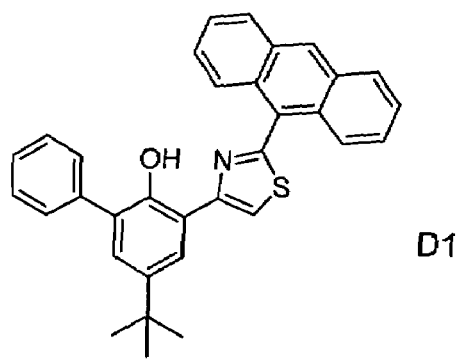
Figure 2:
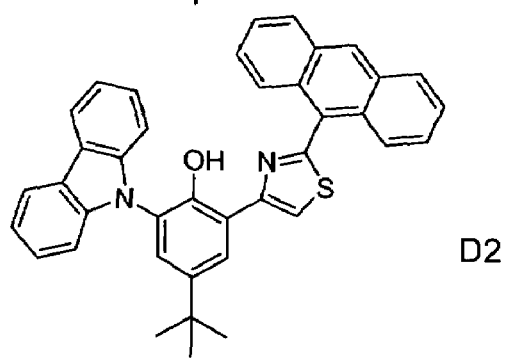
Figure 2:
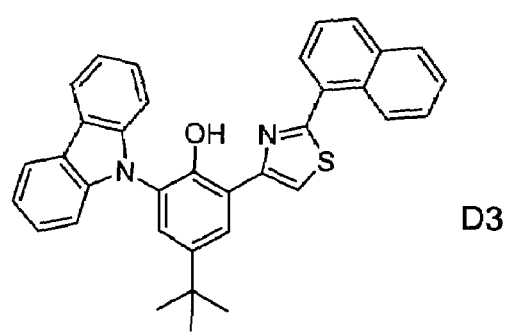
Figure 2:
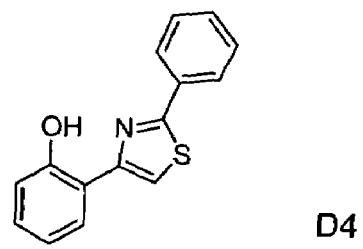
Figure 2:
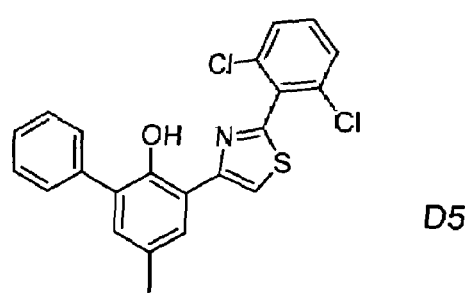
Figure 2:
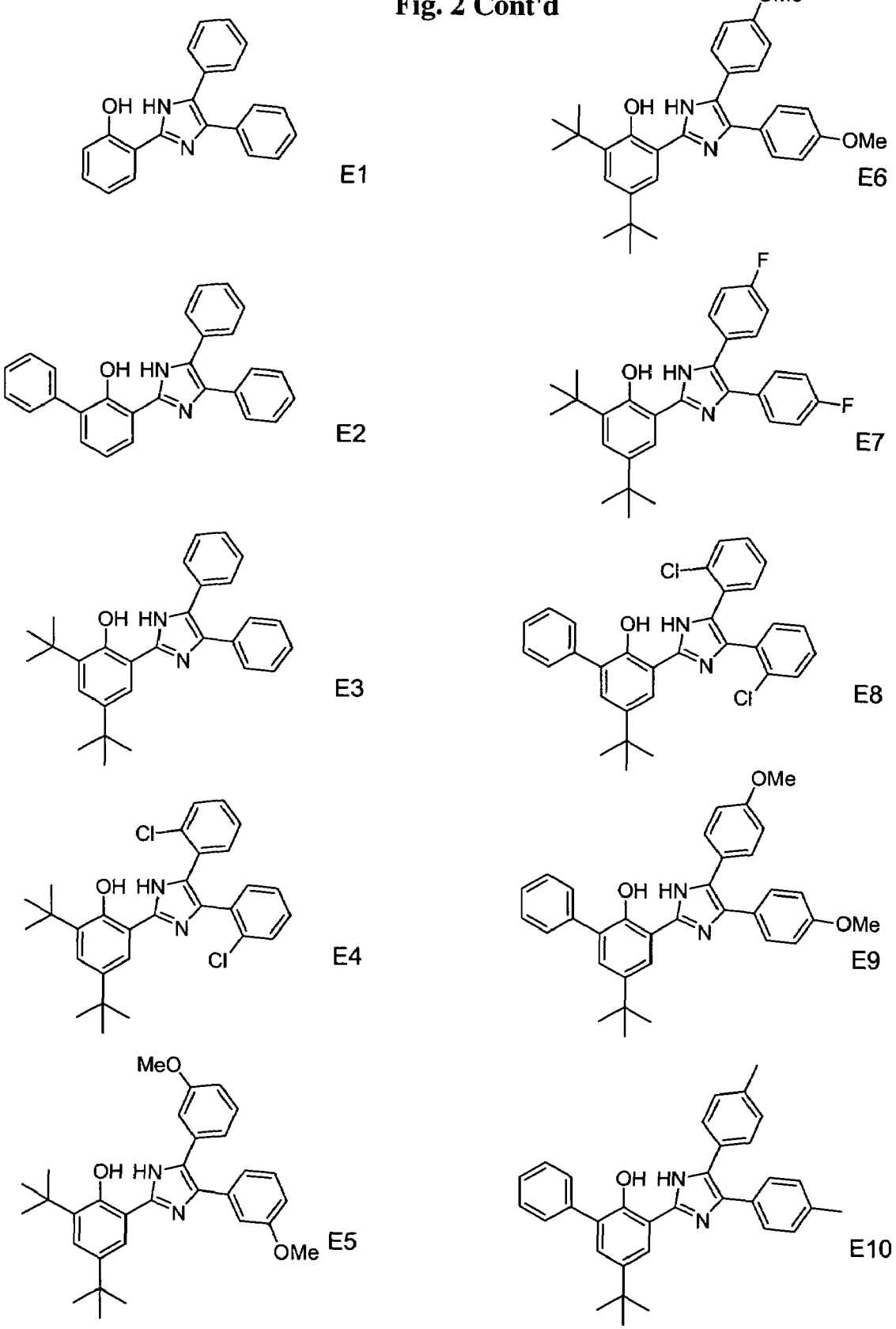
Figure 2:
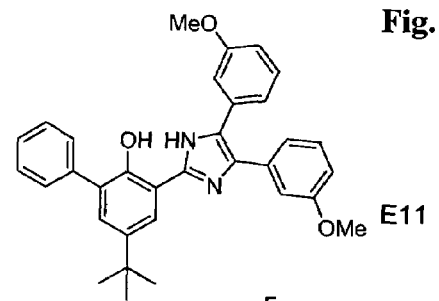
Figure 2:
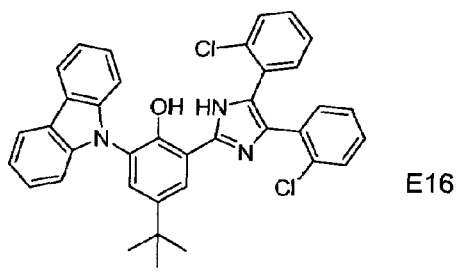
Figure 2:
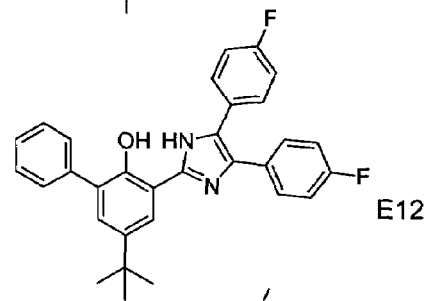
Figure 2:
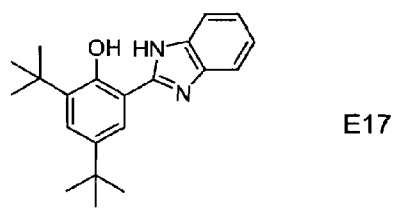
Figure 2:
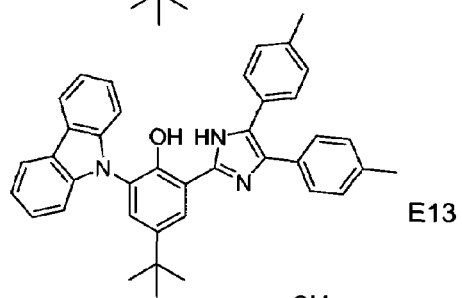
Figure 2:
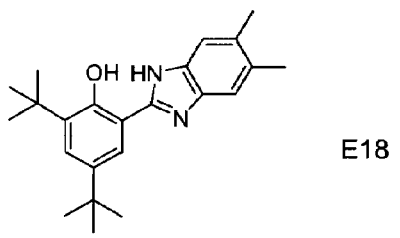
Figure 2:
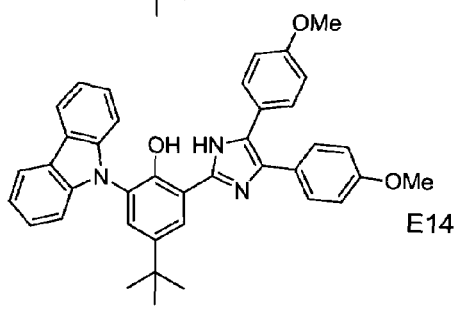
Figure 2:
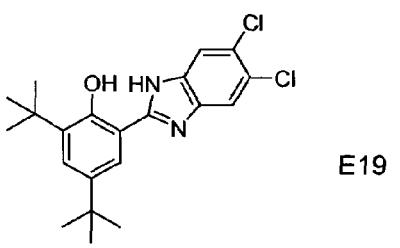
Figure 2:
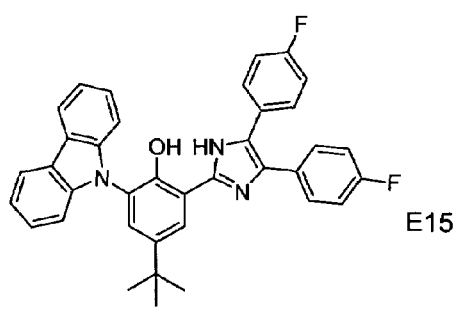
Figure 2:
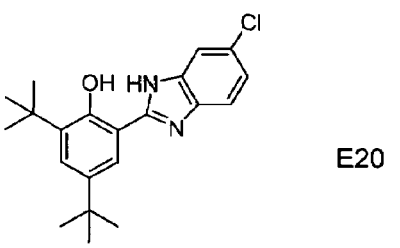
Figure 2:
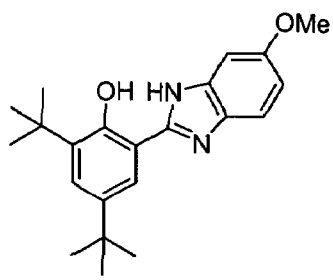
Figure 2:
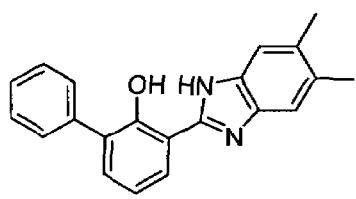
Figure 2:
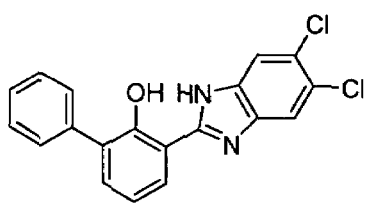
Figure 2:
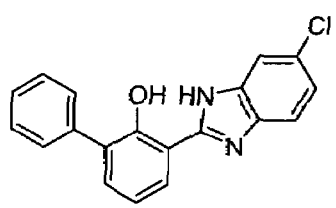
Figure 2:
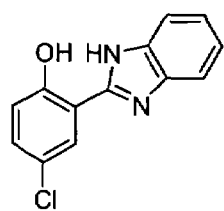
Figure 2:
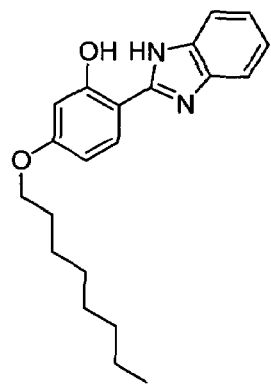
Figure 2:
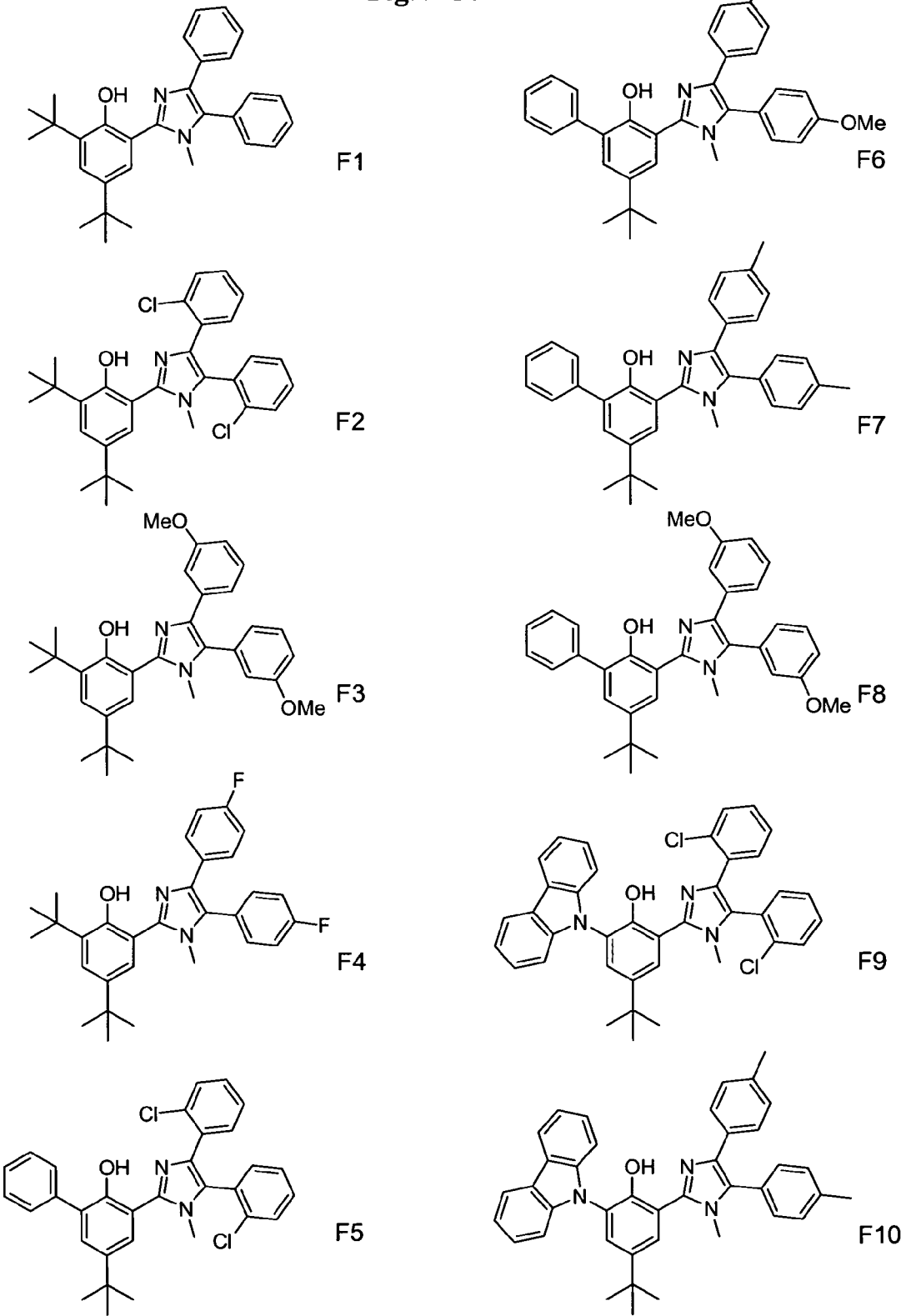
Figure 2:
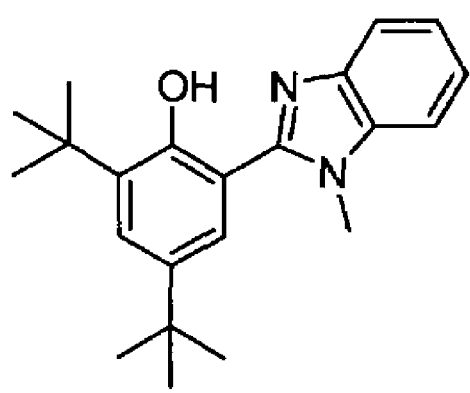
Figure 2:
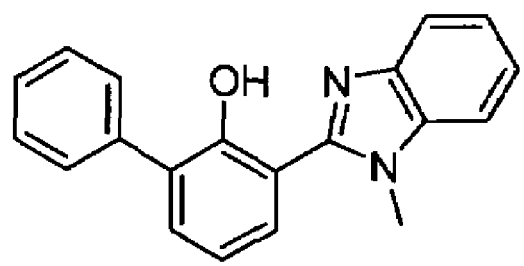
Figure 2:
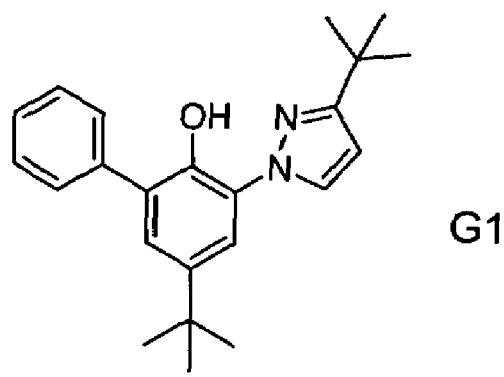
Figure 2:
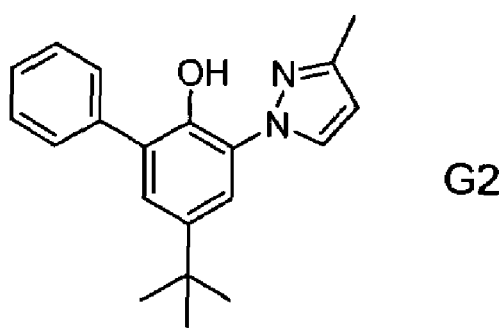
Figure 2:
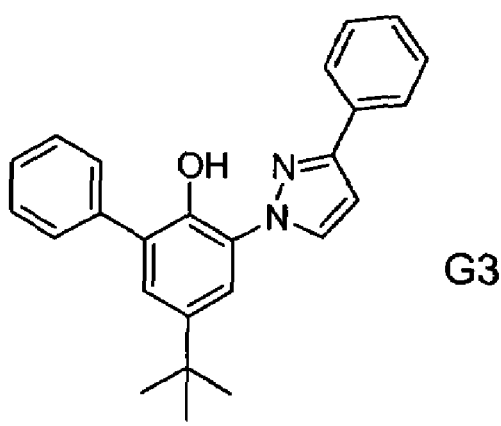
Figure 2:
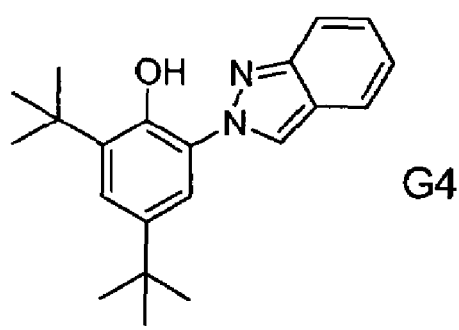
Figure 3:
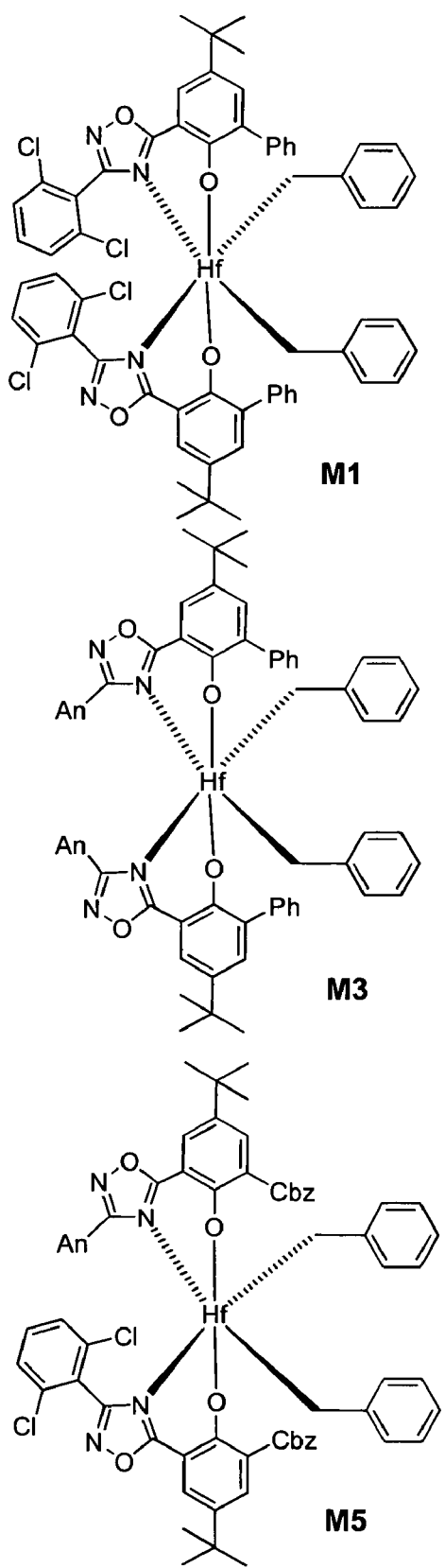
FIG. 3 is a list of certain metal-ligand complexes in accord with the inventions herein.
Figure 3:
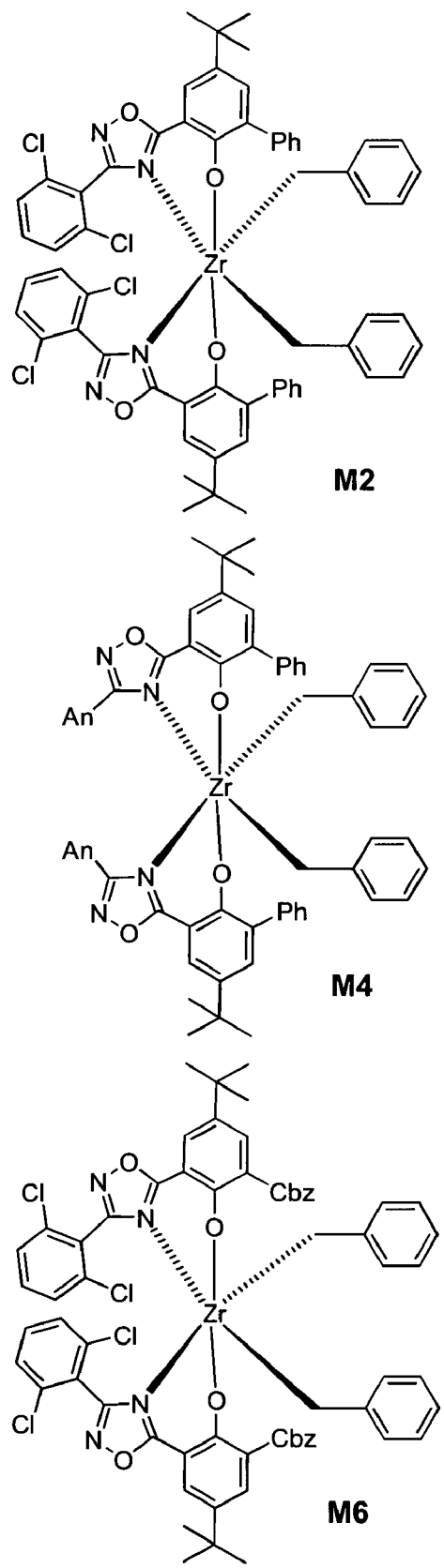
Figure 3:
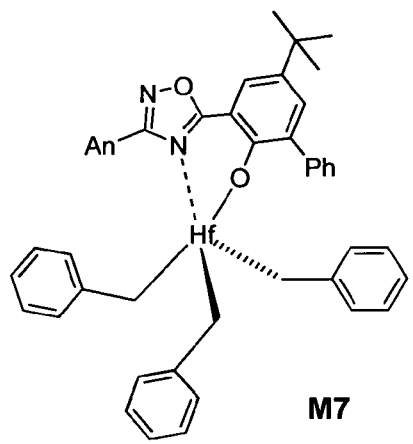
Figure 3:
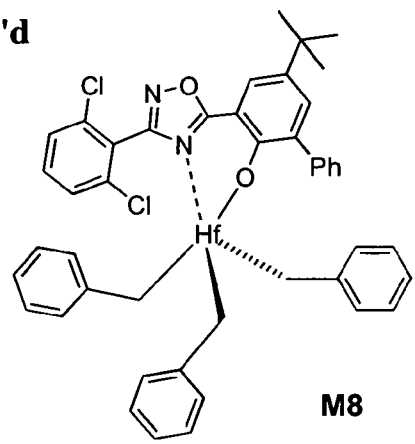
Figure 3:
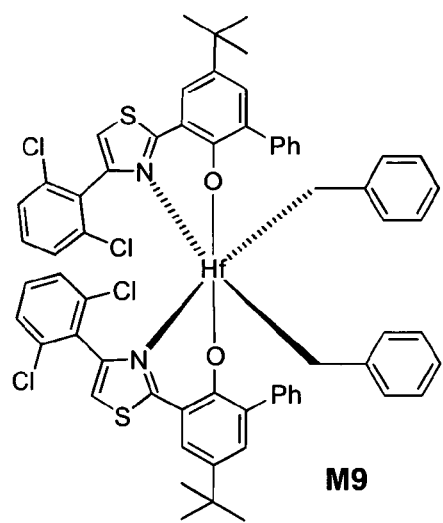
Figure 3:
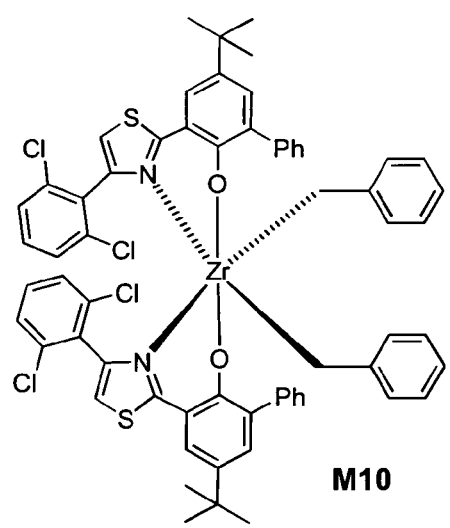
Figure 3:
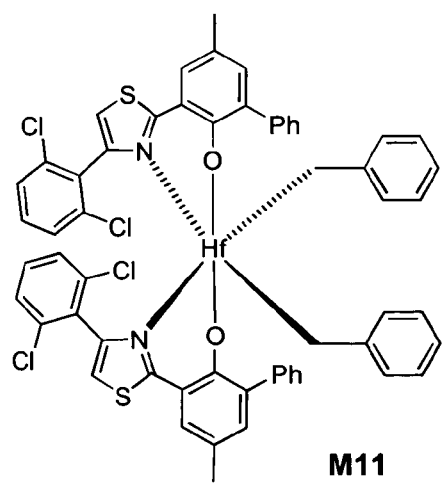
Figure 3:
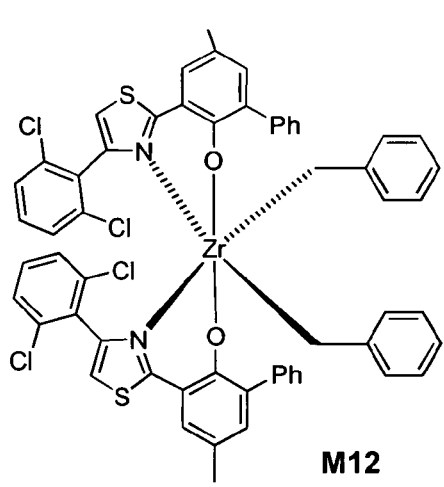
Figure 3:
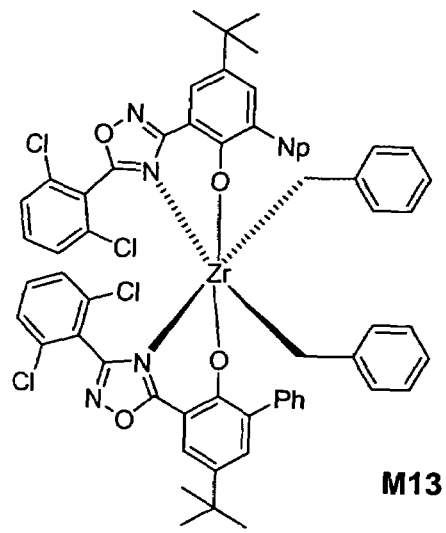
Figure 3:
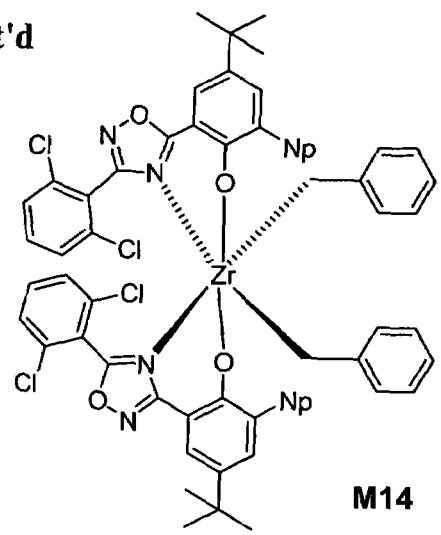
Figure 3:
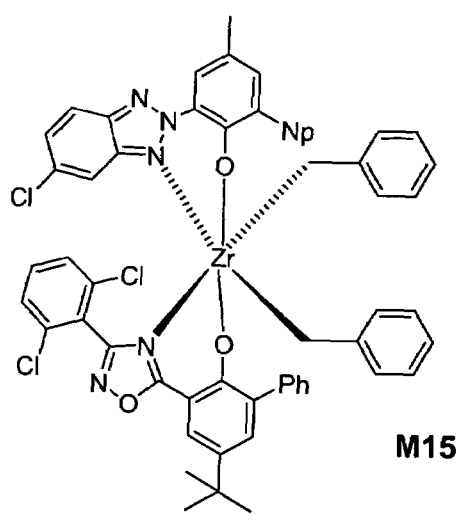
Figure 3:
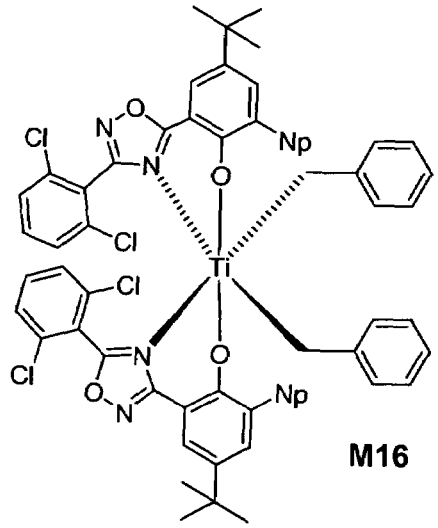
Figure 3:
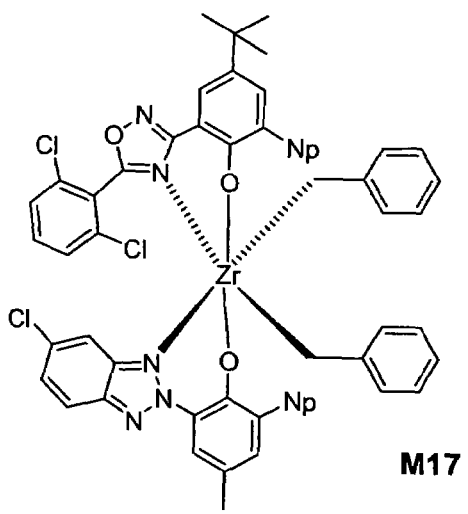
Figure 3:
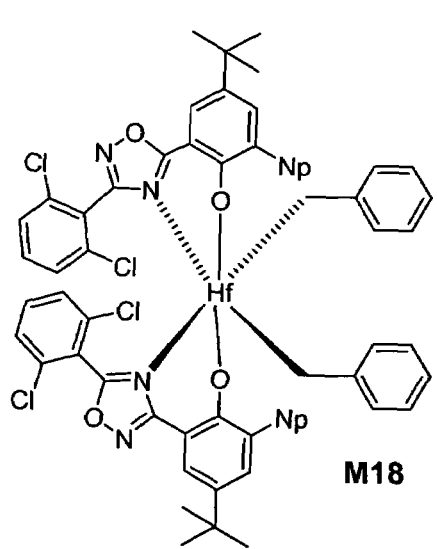
Figure 3:
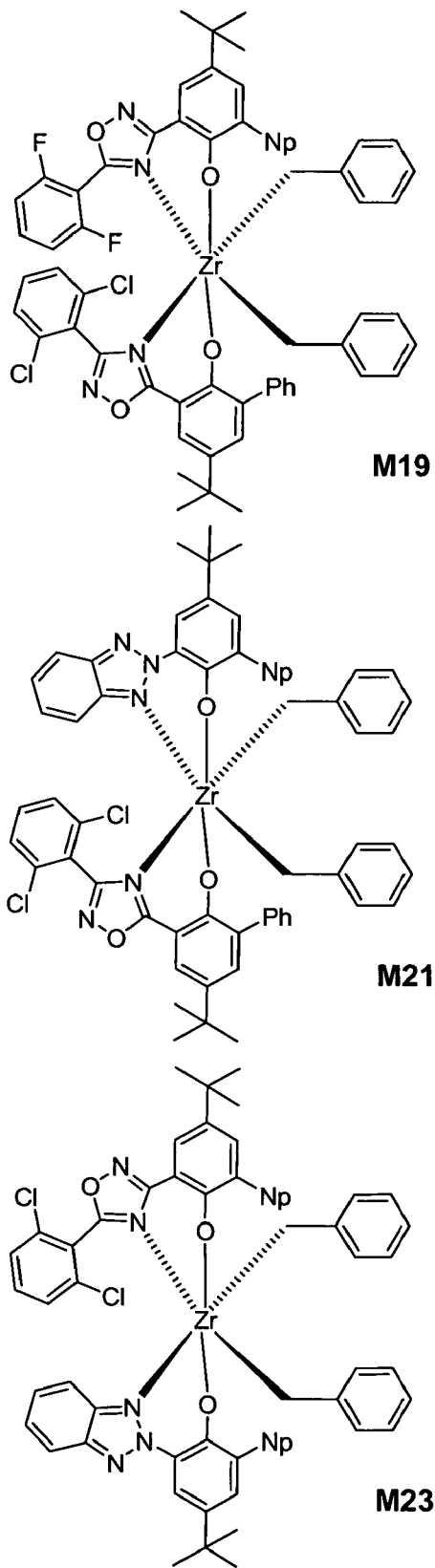
Figure 3:
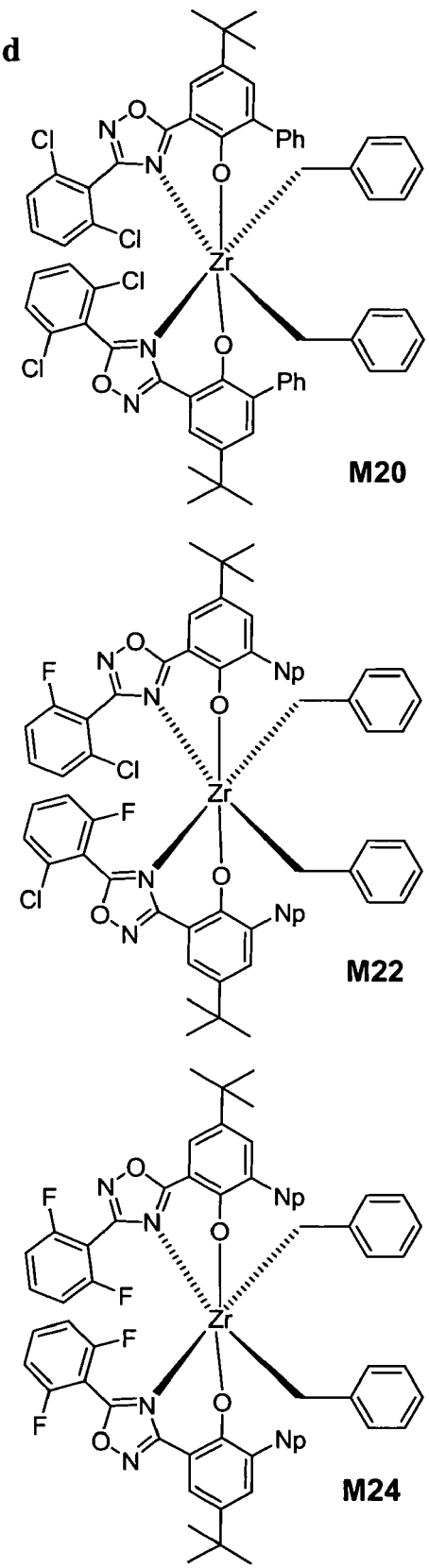
Figure 3:
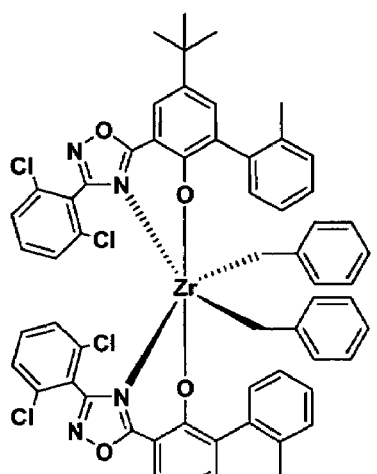
Figure 3:
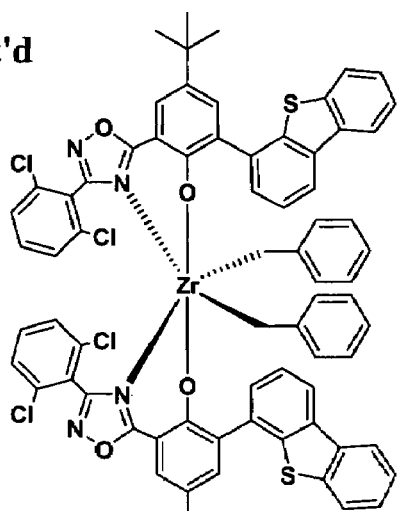
Figure 3:
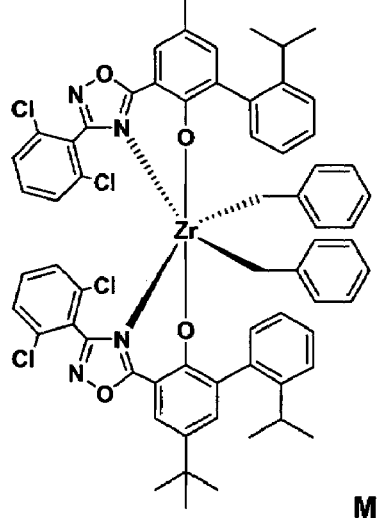
Figure 3:
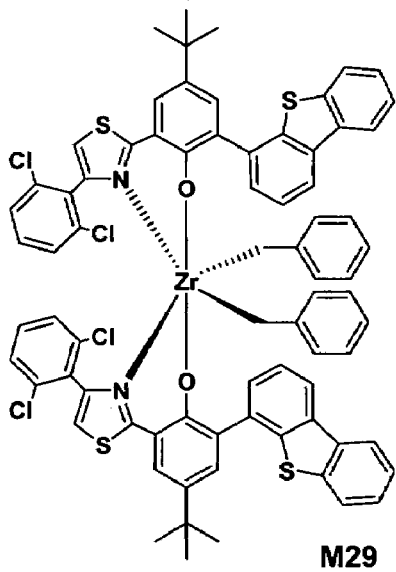
Figure 3:
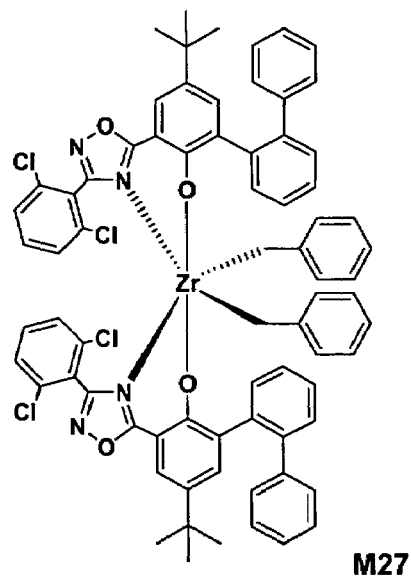
Figure 3:
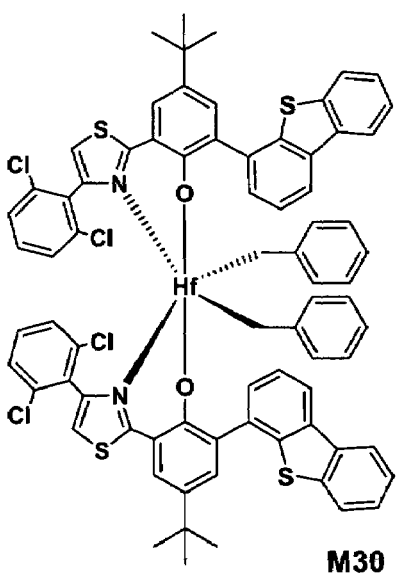

Specific examples of ligands within the scope of formula (Ie) includes those set out in FIG. 2 as "D" ligands.

In one aspect of formula (Ie), $R^1$ is an aryl, substituted aryl, hetroaryl or substituted heteroaryl. In another aspect of formula (Ie), $R^3$ is an alkyl or a substituted alkyl. In still another aspect of formula (Ie), $R^5$ is a hydrogen. In still yet another aspect of formula (Ie), $R^7$ is an aryl or a substituted aryl.

In a sixth embodiment for compounds having formula (I), $X^1$ is N, $X^2$ is $CR^5$, $X^3$ is $CR^6$ and $X^4$ is $CR^7$ and are referred to as formulae (If):

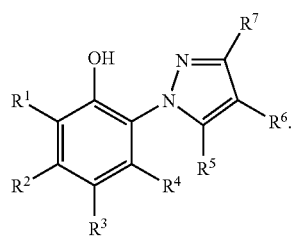

(If)

In one embodiment of formula (If), $R^1$ is an aryl or substituted aryl. In another embodiment of formula (If), $R^3$ is an alkyl or substituted alkyl. In still another embodiment of formula (If), $R^5$ is a hydrogen. In still another embodiment of formula (If), $R^6$ is a hydrogen. In still yet another embodiment of formula (If), $R^7$ is an alkyl, substituted alkyl, phenyl or substituted phenyl. Suitable examples of ligands within the scope of formula (If) include those set out in FIG. 2 as "G" ligands.

In a seventh embodiment for compounds having formula (I), $X^1$ is C, $X^2$ is $CR^5$, $X^3$ is $CR^6$ and $X^4$ is $NR^7$ and are referred to as formulae (Ig):

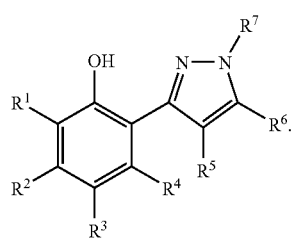

(Ig)

In one aspect of formula (Ig), $R^1$ is a halogen. In another aspect of formula (Ig), $R^2$ is a hydrogen or methyl. In still another aspect of formula (Ig), $R^3$ is a halogen. In still yet another aspect of formula (Ig), $R^5$ is a hydrogen. In still another aspect of formula (Ig), $R^6$ is a hydrogen. In still yet another aspect of formula (Ig), $R^7$ is a hydrogen, an alkyl or a substituted alkyl. In certain embodiments, formulae (Ig) do not include the compounds where R¹ and R³ are fluorine and R⁷ is a t-butyl.

In further embodiments for compounds having formula (I), X¹ is C, X² is CR⁵, X³ is NR⁶ and X⁴ is CR⁷ and are referred to as formulae (Ih). In an additional embodiment for compounds having formula (I), X¹ is C, X² is O, X³ is CR⁶ and X⁴ is CR⁷ and are referred to as formulae (Ii). In an additional embodiment for compounds having formula (I), X¹ is C, X² is CR⁵, X³ is O and X⁴ is CR⁷ and are referred to as formulae (Ij). These embodiments are drawn as:

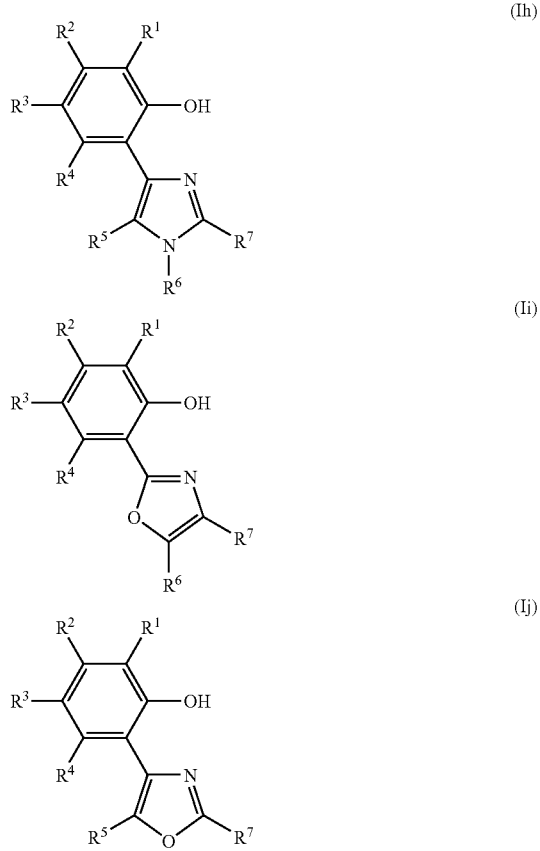

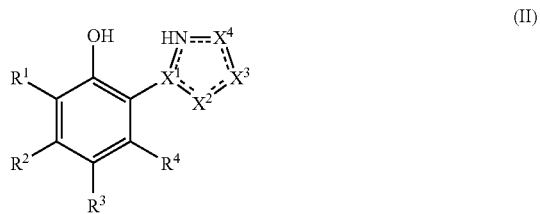

Preferred R groups for these additional embodiments are chosed from those disclosed for formula (I) through (Ig).

In some embodiments, the invention provides compositions of matter, including ligands, compositions and metal-ligand complexes, that include a compound characterized by the formula (II):

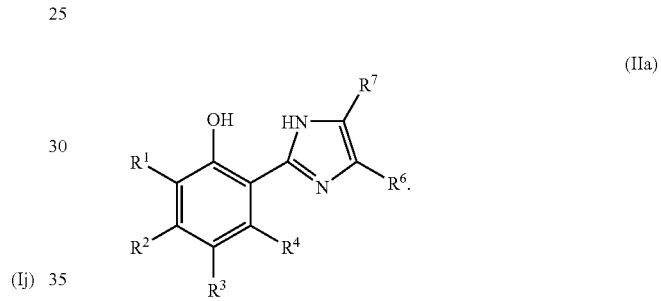

where R¹, R², R³, R⁴, R⁵, R⁶, R⁷, are each independent of one another and are as described above.

For compounds of formula (II), X¹ is N or C, X² is N or CR⁵, X³ is N or CR⁶, X⁴ is N or CR⁷, provided that the heteroatom containing ring system is heteroaromatic, provided that compounds when X¹, X², X³ and X⁴ are each C, R⁵, R⁶ and R⁷ are each H and R¹ is selected from the group consisting of t-butyl, —CMe₂Et, —C(Et)₃, —CMe₂Ph, —C(Ph)₃, —Si(Et)₃, and —Si(Ph)₃, are not included.

In one aspect for compounds of formula (II), R¹ is selected from the group consisting of alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl.

In another aspect for compounds of formula (II), R⁷ is selected from the group consisting of alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl In still another aspect for compounds having formula (II), R¹ is selected from the group consisting of t-butyl, naphthyl, substituted naphthyl, carbazolyl, substituted carbazolyl, phenyl and substituted phenyl and R⁷ is selected from the group consisting of substituted phenyl and anthracenyl.

In a first embodiment for compounds having formula (II), X¹ is C, X² is N, X³ is CR⁶ and X⁴ is CR⁷ and are referred to as formulae (IIa):

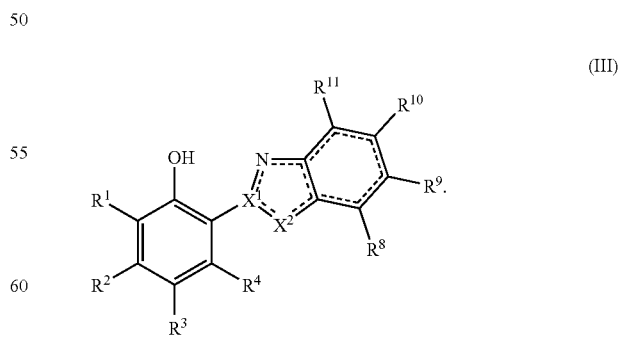

In one aspect of formula (IIa), R¹ is an alkyl, substituted alkyl, aryl, substituted aryl, heteroaryl or a substituted heteroaryl. In another aspect of formula (IIa), R³ is a hydrogen, an alkyl or a substituted alkyl. In still another aspect of formula (IIa), R⁶ is an aryl or a substituted aryl. In still yet another aspect of formula (IIa), R⁷ is an aryl or a substituted aryl. Suitable examples of ligands within the scope of formula (IIa) include those set out in FIG. 2 as "E" ligands.

In general, in one aspect, the invention provides compositions of matter, including ligands, compositions and metal-ligand complexes, that include a compound characterized by the formula (III):

R¹, R², R³, R⁴, R⁵, R⁸, R⁹, R¹⁰, and R¹¹ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the exception that $R^1$ may not be hydrogen, optionally two or more of $R^1$, $R^2$, $R^3$ and $R^4$ may be joined to form a fused ring system having up to 50 atoms, not counting hydrogen atoms, and optionally two or more of $R^8$, $R^9$, $R^{10}$ and $R^{11}$ may be joined to form a fused ring system having up to 50 atoms, not counting hydrogen atoms.

For compounds of formula (III), $X^1$ is N or C, $X^2$ is O, S, $N(R^5)_{n'}$ or $CR^5$, wherein n' is 0 or 1, provided that the heteroatom containing ring system is heteroaromatic, provided $X^1$ and $X^2$ are not both N.

In one aspect for compounds of formula (III), $R^1$ is selected from the group consisting of t-butyl, naphthyl, substituted naphthyl, carbazolyl, substituted carbazolyl, phenyl and substituted phenyl.

In a first embodiment for compounds having formula (III), $X^1$ is C, $X^2$ is $NR^5$ and are referred to as formulae (IIIa):

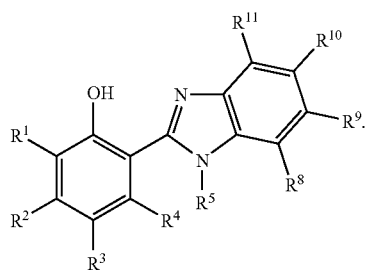

(IIIa)

In one aspect of formula (IIIa), $R^1$ is an alkyl, substituted alkyl, aryl or a substituted aryl. In another aspect of formula (IIIa), $R^3$ is a hydrogen, alkyl or substituted alkyl. In still another aspect of formula (IIIa), $R^5$ is an alkyl or substituted alkyl. Suitable examples of ligands within the scope of formula (IIIa) include F11 and F12 set forth in FIG. 2.

In a second embodiment for compounds having formula (III), $X^1$ is C and $X^2$ is S and are referred to as formulae (IIIb):

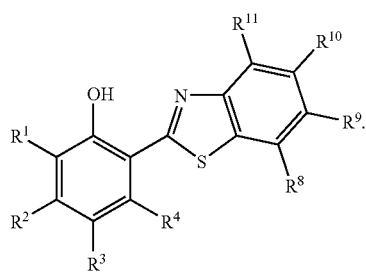

(IIIb)

In one embodiment of formula (IIIb), $R^1$ is an alkyl or a substituted alkyl. In another embodiment of formula (IIIb), $R^3$ is a hydrogen, an alkyl or a substituted alkyl. Suitable examples of ligands within the scope of formula (IIIb) include C29 those set forth in FIG. 2.

In a third embodiment for compounds having formula (III), $X^1$ is C and $X^2$ is O and are referred to as formulae (IIIc):

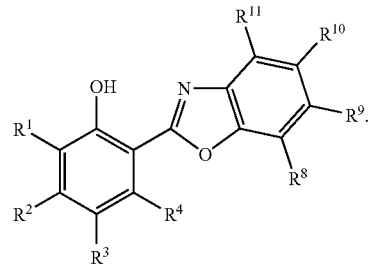

(IIIc)

In a fourth embodiment for compounds having formula (III), $X^1$ is N and $X^2$ is $CR^5$ and are referred to as formulae (IIId):

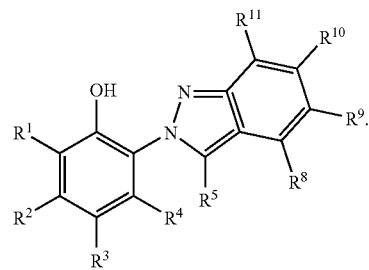

(IIId)

In one aspect of formula (IIId), $R^1$ is an alkyl or substituted alkyl. In another aspect of formula (IIId), $R^3$ is an alkyl or substituted alkyl. Suitable example of a ligand within the scope of formula (IIId) includes G4 set out in FIG. 2.

In general, in one aspect, the invention provides compositions of matter, including ligands, compositions and metal-ligand complexes, that include a compound characterized by the formula (IV):

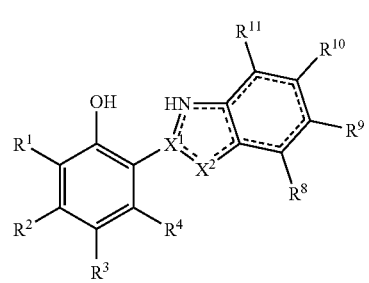

(IV)

where $R^1$, $R^2$, $R^3$, $R^4$, $R^5$, $R^8$, $R^9$, $R^{10}$, and $R^{11}$ are each independent of each other and are as described above.

For compounds of formula (IV), $X^1$ C, $X^2$ N or $CR^5$, provided that the heteroatom containing ring system is heteroaromatic.

In one aspect for compounds having formula (IV), $R^1$ is selected from the group consisting of t-butyl, naphthyl, substituted naphthyl, carbazolyl, substituted carbazolyl, phenyl and substituted phenyl.

In a first embodiment for compounds having formula (IV), $X^1$ is C and $X^2$ is N and are referred to as formulae (IVa)

(IVa)

In one aspect of formula (IVa), $R^1$ is an alkyl, substituted alkyl, aryl or substituted aryl. In another aspect of formula (IVa), $R^3$ is a hydrogen, an alkyl or a substituted alkyl. In yet another aspect of formula (IVa), $R^9$ is a hydrogen, halogen, alkyl, substituted alkyl, or an alkoxy. In still another aspect of formula (IVa), $R^{10}$ is a hydrogen, halogen, alkyl, or a substituted alkyl.

Specific examples of ligands within the scope of formula (IVa) include those set forth in Table 10, shown in FIG. 7.

In general, in another aspect, the invention provides compositions of matter, including ligands, compositions and metal-ligand complexes, that include a compound characterized by the formula (V):

(V)

where $R^1$, $R^2$, $R^3$, $R^4$, $R^5$, $R^8$, $R^9$, $R^{10}$, and $R^{11}$ are each independent of each other and are as described above.

For compounds of formula (V), $X^1$ is N or C, $X^2$ is O, S, $N(R^5)_{n'}$ or $CR^5$, wherein n' is 0 or 1, provided that the heteroatom containing ring system is heteroaromatic, provided when $X^1$ and $X^2$ are both N, then:

$R^1$ is t-butyl, $R^2$ is H, $R^3$ is Me, $R^4$ is H, $R^8$, $R^9$, $R^{11}$ are each H and $R^{10}$ is Cl;

$R^1$ is i-propyl, $R^2$ is H, $R^3$ is t-butyl, $R^4$, $R^8$, $R^9$, $R^{10}$ and $R^{11}$ are each H;

$R^1$ is t-butyl, $R^2$ is H, $R^3$ is t-butyl, $R^4$ is H, $R^8$, $R^9$, $R^{11}$ are each H and $R^{10}$ is Cl;

$R^1$ is 1,1-dimethylpropyl, $R^2$ is H, $R^3$ is 1,1-dimethylpropyl, $R^4$, $R^8$, $R^9$, $R^{10}$ and $R^{11}$ are each H;

$R^1$ is isopropylbenzyl, $R^2$ is H, $R^3$ is isopropylbenzyl, $R^4$ is H, $R^8$, $R^9$, $R^{11}$ are each H and $R^{10}$ is Cl;

$R^1$ is t-butyl, $R^2$ is H, $R^3$ is t-butyl, $R^4$ is H, $R^8$, $R^9$, $R^{11}$ are each H and $R^{10}$ is F;

$R^1$ is t-butyl, $R^2$ is H, $R^3$ is t-butyl, $R^4$ is H, $R^8$, $R^{11}$ are each H, $R^9$ and $R^{10}$ are each F;

$R^1$ is t-butyl, $R^2$ is H, $R^3$ is t-butyl, $R^4$ is H, $R^8$, $R^{11}$ are each H, $R^9$ and $R^{10}$ are each Cl;

$R^1$ is t-butyl, $R^2$ is H, $R^3$ is t-butyl, $R^4$ is H, $R^8$, $R^9$, $R^{11}$ are each H and $R^{10}$ is —$CF_3$;

$R^1$ is t-butyl, $R^2$ is H, $R^3$ is t-butyl, $R^4$ is H, $R^8$, $R^9$, $R^{11}$ are each H and $R^{10}$ is —OMe;

$R^1$ is t-butyl, $R^2$ is H, $R^3$ is t-butyl, $R^4$ is H, $R^8$, $R^{11}$ are each H, $R^9$ and $R^{10}$ is are each Me;

$R^1$ is t-butyl, $R^2$ is H, $R^3$ is —OMe, $R^4$ is H, $R^8$, $R^9$, $R^{11}$ are each H and $R^{10}$ is Cl;

$R^1$ is phenyl, $R^2$ is H, $R^3$ is t-butyl, $R^4$ is H, $R^8$, $R^9$, $R^{11}$ are each H and $R^{10}$ is Cl;

$R^1$ is t-butyl, $R^2$ is H, $R^3$ is -Me, $R^4$ is H, $R^8$, $R^9$, $R^{11}$ are each H and $R^{10}$ is Cl;

$R^1$ is 2,4,6-trimethylphenyl, $R^2$ is H, $R^3$ is -Me, $R^4$ is H, $R^8$, $R^9$, $R^{11}$ are each H and $R^{10}$ is Cl;

$R^1$ is 1-naphthyl, $R^2$ is H, $R^3$ is -Me, $R^4$ is H, $R^8$, $R^9$, $R^{11}$ are each H and $R^{10}$ is Cl;

$R^1$ is 9-anthracenyl, $R^2$ is H, $R^3$ is -Me, $R^4$ is H, $R^8$, $R^9$, $R^{11}$ are each H and $R^{10}$ is Cl;

$R^1$ is 3,5-difluorophenyl, $R^2$ is H, $R^3$ is -Me, $R^4$ is H, $R^8$, $R^9$, $R^{11}$ are each H and $R^{10}$ is Cl;

$R^1$ is an alkyldiarylsilyl or dialkylarylsilyl, $R^2$ is H, $R^3$ is -Me, $R^4$ is H, $R^8$, $R^9$, $R^{11}$ are each H and $R^{10}$ is Cl; but are not included.

In one aspect of compounds having formula (V), $R^1$ is selected from the group consisting of t-butyl, naphthyl, substituted naphthyl, carbazolyl, substituted carbazolyl, phenyl and substituted phenyl.

It should be understood that in the compounds identified as (Ia) through (Ij), (IIa), (IIIa) through (IIId), (IVa), etc. and complexes thereof, that the substituent $R^1$ through $R^{11}$, if present in the molecule, and not specifically identified, are as defined throughout the specification.

More specifically, for compounds (Ia) through (Ij) and (Ia), $R^1$ is selected from the group consisting of optionally substituted alkyl, heteroalkyl, aryl and heteroaryl. In other embodiments, $R^1$ can be selected from the group consisting of alkyl, substituted alkyl, naphthyl, substituted naphthyl, N-carbazolyl, substituted N-carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl.

Additionally, for compounds of formulae (Ia) through (Ij) and (IIa), $R^7$ is selected from the group consisting of optionally substituted alkyl, heteroalkyl, aryl and heteroaryl; more specifically, selected from the group consisting of alkyl, substituted alkyl, naphthyl, substituted naphthyl, carbazolyl, substituted carbazolyl, phenyl, substituted phenyl, indolyl, substituted indolyl, adamantyl, substituted adamantyl, thiophenyl, substituted thiophenyl, benzofuranyl, substituted benzofuranyl, benzothiophenyl and substituted benzothiophenyl.

The choice of particular heterocyclic ligand can have a strong influence on the catalysis of particular transformations. Thus, the choice of substituent in the ligands of the invention when incorporated in a polymerization catalyst can affect catalyst activity, thermal stability, molecular weight of the product polymer, or the degree and/or kind of stereo- or regioerrors, as well as other factors known to be significant in the production of various polymers.

Specific ligands, metal precursors and activation techniques that are used for the production of polypropylene are specified in Tables 2C, 3A and 3B. Additionally, specific ligands, metal precursors and activation techniques that are used for the production of low molecular weight polypropylene waxes are specified in Table 3A, examples PP3-PP7, and Table 3B. Specific ligands, metal precursors and activation techniques that are used for the production of ethlyene-1-octene copolymersare specified in Tables 3C and 3D. Specific ligands, metal precursors and activation techniques that are used for the production of polystyene are specified in Tables 3E.

The ligands of the invention can be prepared using known procedures, such as those described, for example, in March, Advanced Organic Chemistry, Wiley, New York 1992 (4$^{th}$ Ed.), and in Katritzky et al., Comprehensive Heterocyclic Chemistry, Elsevier, New York 1984 (1$^{st}$ Ed.) & 1996 (2$^{nd}$ Ed.). Specifically, in some embodiments the ligands of the invention can be prepared according to the general procedures that follow.

Once the desired ligand is formed, it can be combined with a metal atom, ion, compound or other metal precursor compound, and in some embodiments the present invention encompasses compositions that include any of the above-mentioned ligands in combination with an appropriate metal precursor and an optional activator. For example, in some embodiments, the metal precursor can be an activated metal precursor, which refers to a metal precursor (described below) that has been combined or reacted with an activator (described below) prior to combination or reaction with the ancillary ligand. As noted above, in one aspect the invention provides compositions that include such combinations of ligand and metal atom, ion, compound or precursor. In some applications, the ligands are combined with a metal compound or precursor and the product of such combination is not determined, if a product forms. For example, the ligand may be added to a reaction vessel at the same time as the metal or metal precursor compound along with the reactants, activators, scavengers, etc. Additionally, the ligand can be modified prior to addition to or after the addition of the metal precursor, e.g. through a deprotonation reaction or some other modification.

In general, the metal precursor compounds can be characterized by the general formula $M(L)_m$ where M is a metal selected from the group consisting of groups 3-6 and lanthanides of the periodic table of elements and m is 1, 2, 3, 4, 5, or 6. Thus, in particular embodiments M can be selected from scandium, yttrium, titanium, zirconium, hafnium, vanadium, niobium, tantalum, chromium, molybdenum, tungsten, lanthanum, cerium, praseodymium, neodymium, samarium, europium, gadolinium, terbium, dysprosium, holmium, erbium, thulium, ytterbium, and lutetium. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof. Optionally, two or more L groups are joined into a ring structure. One or more of the ligands L may be ionically bonded to the metal M and, for example, L may be a non-coordinated or loosely coordinated or weakly coordinated anion (e.g., L may be selected from the group consisting of those anions described below in the conjunction with the activators). (See Marks et al., Chem. Rev. 2000, 100, 1391-1434, for a detailed discussion of these weak interactions.) The metal precursors may be monomeric, dimeric or higher orders thereof. In particular embodiments, the metal precursor includes a metal selected from Ti, Zr, or Hf. In more specific embodiments, the metal precursor includes a metal selected from Zr and Hf.

Specific examples of suitable titanium, hafnium and zirconium precursors include, but are not limited to $TiCl_4$, $Ti(CH_2Ph)_4$, $Ti(CH_2CMe_3)_4$, $Ti(CH_2Sile_3)_4$, $Ti(CH_2Ph)_3Cl$, $Ti(CH_2CMe_3)_3Cl$, $Ti(CH_2SiMe_3)_3Cl$, $Ti(CH_2Ph)_2Cl_2$, $Ti(CH_2CMe_3)_2Cl_2$, $Ti(CH_2SiNe_3)_2Cl_2$, $Ti(NMe_2)_4$, $Ti(NEt_2)_4$, $Ti(O-^iPr)_4$, and $Ti(N(SiNe_3)_2)_2Cl_2$; $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$, $Hf(N(SiMe_3)CH_2CH_2CH_2N(SiMe_3))Cl_2$, $Hf(N(Ph)CH_2CH_2CH_2N(Ph))Cl_2$, $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, $Zr(N(SiMe_3)_2)_2Cl_2$, $Zr(N(SiMe_3)CH_2 CH_2CH_2N(SiMe_3))Cl_2$, and $Zr(N(Ph)CH_2CH_2CH_2N(Ph))Cl_2$. Lewis base adducts of these examples are also suitable as metal precursors, for example, ethers, amines, thioethers, phosphines and the like are suitable as Lewis bases. Specific examples include $HfCl_4(THF)_2$, $HfCl_4(SMe_2)_2$ and $Hf(CH_2Ph)_2Cl_2(OEt_2)$. Activated metal precursors may be ionic or zwitterionic compounds, such as $[M(CH_2Ph)_3^+][B(C_6F_5)_4^-]$ or $[M(CH_2Ph)_3^+][PhCH_2B(C_6F_5)_3^-]$ where M is Zr or Hf. Activated metal precursors or such ionic compounds can be prepared in the manner shown in Pellecchia et al., Organometallics 1994, 13, 298-302; Pellecchia et al., J. Am. Chem. Soc. 1993, 115, 1160-1162; Pellecchia et al., Organometallics 1993, 13, 3773-3775 and Bochmann et al., Organometallics 1993, 12, 633-640, each of which is incorporated herein by reference.

The ligand to metal precursor compound ratio is typically in the range of about 0.01:1 to about 100:1, more specifically in the range of about 0.1:1 to about 10:1 and even more specifically about 1:1, 2:1 or 3:1.

As noted above, in another aspect, this invention relates to compositions of one or more ligands and a metal precursor compound, where the compositions include two equivalents of ligand to metal precursor compound, referred to herein as the bis-ligand embodiment. The other aspects, there is also a bis-ligand complex embodiment, specifically, those embodiments where x is 2 in the below complexation formulae. The bis-ligand composition embodiment can include two equivalents of the same phenol-heterocycle ligand or one equivalent of a first phenol-heterocycle ligand and one equivalent of a second phenol-heterocycle ligand, wherein the first and second phenol-heterocycle ligands are different from each other. In other embodiments, the ratio of first phenol-heterocycle ligand to second phenol-heterocycle ligand is not one to one, but ranging from 1 to 99 parts to 99 to 1 parts. In some embodiments, in addition, the first phenol-heterocycle ligand is a ligand of this invention and the second phenol-heterocycle ligand is otherwise known. For example in some embodiments, the second phenol-heterocycle ligand can be a triazole ligand, such as those disclosed in U.S. Pat. No. 6,933,355, incorporated herein by reference. Triazole ligands that may be used as second phenol-heterocycle ligands in bis-ligand compositions (and complexes) include those characterized by the general formula:

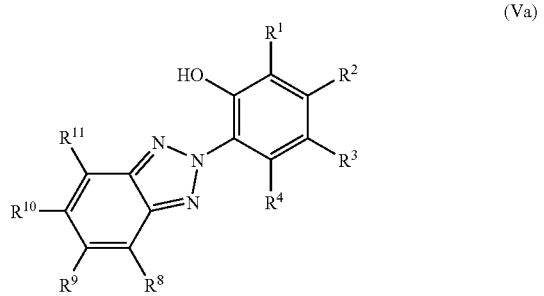

(Va)

wherein $R^8$, $R^9$, $R^{10}$ and $R^{11}$ are selected from the same groups as $R^1$, $R^2$, $R^3$, and $R^4$, defined in the various embodiments above. Specific examples of ligands that may be preferably used as second phenol-heterocycle ligands in bis-ligand are shown in the various examples and figures herein. See the following for general mixed ligand systems: *J. Am. Chem. Soc.* 2004, 126, 10798-10799; *Chem. Common.* 2005, 25, 3150-3152; and *Dalton Trans.* 2005, 3611-3613, each of which is incorporated herein by reference.

As also noted above, in another aspect the invention relates to metal-ligand complexes. Generally, the ligand (or optionally a modified ligand as discussed above) is mixed with a suitable metal precursor (and optionally other components, such as activators) prior to or simultaneously with allowing the mixture to be contacted with the reactants (e.g., monomers). When the ligand is mixed with the metal precursor compound, a metal-ligand complex may be formed, which may itself be an active catalyst or may be transformed into a catalyst upon activation.

The invention features metal-ligand complexes characterized by the formula (VI):

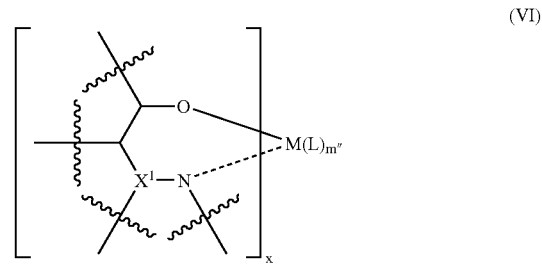

(VI)

where M, L and $X^1$ are as described above with the broken bonds representing the compounds having formulae (I) through (Ig), (III) through (IIId) and (V) as described above, x is 1, 2, 3, or 4 and m″ is 0, 1, 2, 3, or 4. Alternatively, formulae (VI) includes those compounds having formulae (II), (IIa) and (IV) as described above, the nitrogen includes a hydrogen, and m' and x are as described above. The dashed bond shown between the nitrogen atom with M depicted in formula (VI) can be dative, nonexistent, or covalent. When the bond is intended to be a dative bond, it is shown as a dashed arrow. The bond between the nitrogen atom and the metal (M) may come on and off again, giving it fluxional behavior, and thus any of the formula here can be drawn without that bond. Again, when x is 2 or higher, compounds may include those of formula (Va) as one of the bis-ligand compounds. This depiction is used throughout, herein. In an alternative embodiment, the complex may include more than one metal (M) and one or more ligands, each independent of one another, and the ligand to metal ratio may be fractional.

Particular embodiments can include one or more of the following features. In particular embodiments, the complex can be characterized by the formula (VII):

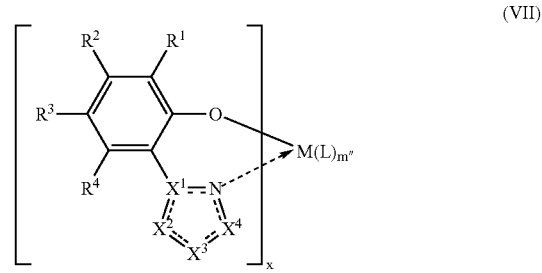

(VII)

where $R^1$, $R^2$, $R^3$, $R^4$, $R^5$, $R^6$, $R^7$, $X^1$, $X^2$, $X^3$ and $X^4$ are as described above for compounds of formulae (I) through formulae (Ig); M and L are as described above, x is 1, 2, 3, or 4, m″ is 0, 1, 2, 3, or 4 and the bond between the heteroaromatic nitrogen (N) and the metal (M) is dative or absent.

For example, in a first embodiment for complexes having formula (VII), $X^1$ is C, $X^2$ is O, $X^3$ is N and $X^4$ is $CR^7$ and are referred to as formulae (VIIa):

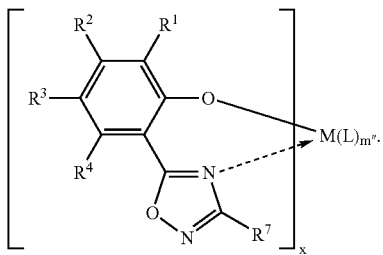

(VIIa)

In certain aspects of formula (VIIa), $R^1$ is an alkyl, substituted alkyl, aryl or a substituted aryl. In other aspects of formula (VIIa), $R^3$ is an alkyl or a substituted alkyl. In still other aspects of formula (VIIa), $R^7$ is an aryl or a substituted aryl.

Specific examples of ligands within the scope of formula (VIIa) include those set out in Table 1.

In a second embodiment for complexes having formula (VII), $X^1$ is C, $X^2$ is N, $X^3$ is O and $X^4$ is $CR^7$ and are referred to as formulae (VIIb):

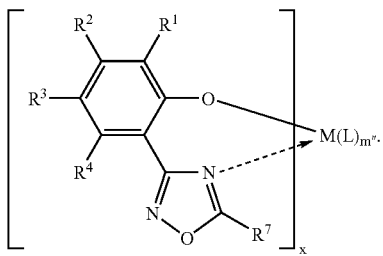

(VIIb)

In particular embodiments of formula (VIIb), $R^1$ is an alkyl or a substituted alkyl. In other embodiments of (VIIb), $R^3$ is an alkyl or a substituted alkyl. In still other embodiments of formula (VIIb), $R^7$ is an aryl or a substituted aryl.

Specific examples of ligands within the scope of formula (VIIb) includes those set out in Table 2.

In third embodiment for complexes of formula (VII), $X^1$ is C, $X^2$ is $NR^5$, $X^3$ is $CR^6$ and $X^4$ is $CR^7$ and are referred to as formulae (VIIc):

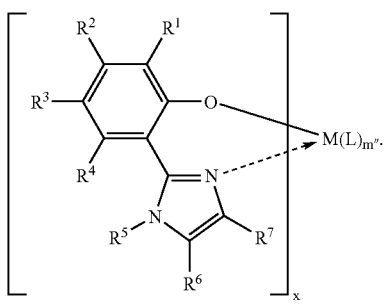

(VIIc)

In particular aspects of formula (VIIc), $R^1$ is an alkyl, substituted alkyl, aryl, or a substituted aryl. In other aspects of formula (VIIc), $R^3$ is an alkyl or a substituted alkyl. In still other aspects of formula (VIIc), $R^5$ is an alkyl or a substituted alkyl. In another aspect of formula (VIIc), $R^6$ is an aryl or a substituted aryl. In still yet another aspect of formula (VIIc), $R^7$ is an aryl or a substituted aryl.

Suitable examples of ligands within the scope of formula (VIIc) include those set out in Table 3.

In a fourth embodiment for complexes having formula (VII), $X^1$ is C, $X^2$ is S, $X^3$ is $CR^6$ and $X^4$ is $CR^7$ and are referred to as formulae (VIId):

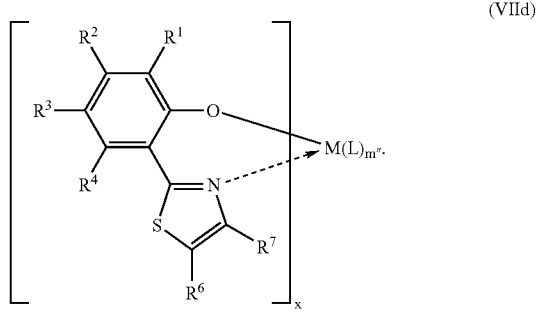

(VIId)

In one embodiment of formula (VIId), $R^1$ is an aryl, substituted aryl, alkyl or a substituted alkyl. In another embodiment of formula (VIId), $R^3$ is an alkyl or a substituted alkyl. In still another embodiment of formula (VIId), $R^6$ is a hydrogen. In still yet another embodiment of formula (VIId), $R^7$ is bromide, phenyl, substituted phenyl, naphthyl, substituted naphthyl, anthracenyl, substituted anthracenyl, or a hydrogen.

Specific examples of ligands within the scope of formula (VIId) include those set out in Table 5.

In a fifth embodiment for complexes having formula (VII), $X^1$ is C, $X^2$ is $CR^5$, $X^3$ is S and $X^4$ is $CR^7$ and are referred to as formulae (VIIe):

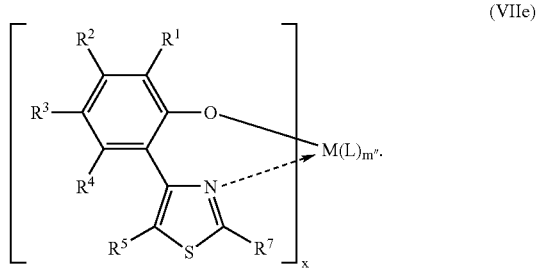

(VIIe)

In one aspect of formula (VIIe), $R^1$ is an aryl or a substituted aryl. In another aspect of formula (VIIe), $R^3$ is a hydrogen, an alkyl or a substituted alkyl. In still another aspect of formula (VIIe), $R^5$ is a hydrogen. In still yet another aspect of formula (VIIe), $R^7$ is an aryl or a substituted aryl.

Specific examples of ligands within the scope of formula (VIIe) includes those set out in Table 6.

In a sixth embodiment for complexes having formula (VII), $X^1$ is N, $X^2$ is $CR^5$, $X^3$ is $CR^6$ and $X^4$ is $CR^7$ and are referred to as formulae (VIIf):

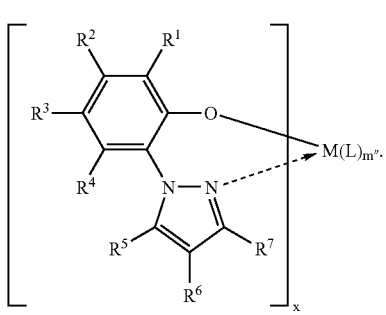

(VIIf)

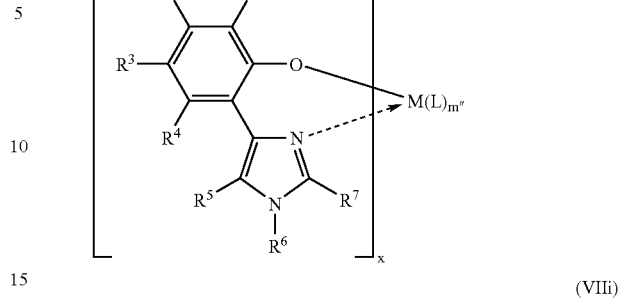

(VIIh)

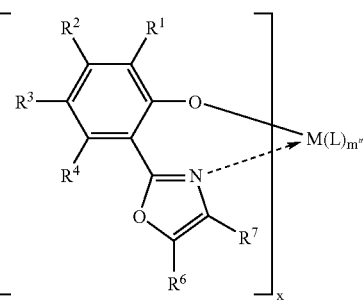

(VIIi)

In one embodiment of formula (VIIf), $R^1$ is an aryl or substituted aryl. In another embodiment of formula (VIIf), $R^3$ is an alkyl or substituted alkyl. In still another embodiment of formula (VIIf), $R^5$ is a hydrogen. In still another embodiment of formula (VIIf), $R^6$ is a hydrogen. In still yet another embodiment of formula (VIIf), $R^7$ is an alkyl or phenyl.

Suitable examples of ligands within the scope of formula (VIIf) include those set out in Table 7.

In an seventh embodiment for complexes having formula (VII), $X^1$ is C, $X^2$ is $CR^5$, $X^3$ is $CR^6$ and $X^4$ is $NR^7$ and are referred to as formulae (VIIg):

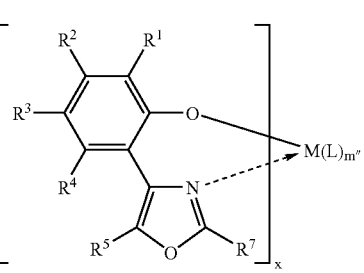

(VIIj)

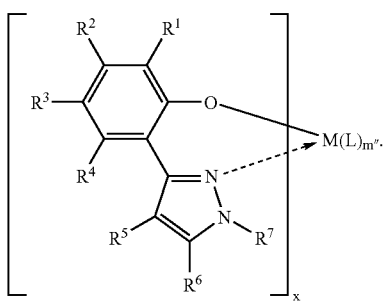

(VIIg)

The preferred R groups for these aspects are shown herein for formulae (I) through (Ij).

In general, in yet another aspect, the invention features metal-ligand complexes characterized by the formula (VIII):

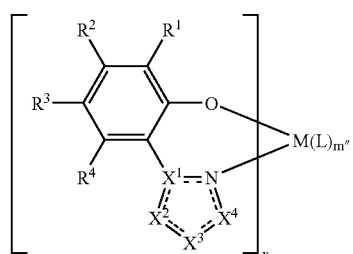

(VIII)

In one aspect of formula (VIIg), $R^1$ is a halogen. In another aspect of formula (VIIg), $R^2$ is a hydrogen or methyl. In still another aspect of formula (VIIg), $R^3$ is a halogen. In still yet another aspect of formula (VIIg), $R^5$ is a hydrogen. In still another aspect of formula (VIIg), $R^6$ is a hydrogen. In still yet another aspect of formula (VIIg), $R^7$ is a hydrogen, an alkyl or a substituted alkyl. In certain embodiments, formulae (VIIg) do not include the compounds where $R^1$ and $R^3$ are fluorine and $R^7$ is a t-butyl.

In a further aspect for compounds having formula (VII), $X^1$ is C, $X^2$ is $CR^5$, $X^3$ is $NR^6$ and $X^4$ is $CR^7$ and are referred to as formulae (VIIh). In an additional aspect for compounds having formula (VII), $X^1$ is C, $X^2$ is O, $X^3$ is $CR^6$ and $X^4$ is $CR^7$ and are referred to as formulae (VIIi). In another aspect for compounds having formula (VII), $X^1$ is C, $X^2$ is $CR^5$, $X^3$ is O and $X^4$ is $CR^7$ and are referred to as formulae (VIIj). These aspects are drawn as wherein $R^1$, $R^2$, $R^3$, $R^4$, $R^5$, $R^6$, $R^7$, $X^1$, $X^2$, $X^3$ and $X^4$ are as described above for compounds of formulae (II) and (IIa), M and L are as described above, x is 1 or 2 and m″ is 0, 1, 2, 3, or 4.

In a first embodiment for compounds having formula (VIII), $X^1$ is C, $X^2$ is N, $X^3$ is $CR^6$ and $X^4$ is $CR^7$ and are referred to as formulae (VIIIa):

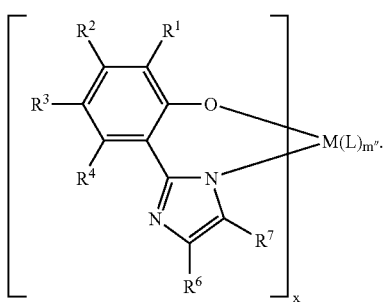

(VIIIa)

In one aspect of formula (VIIIa), $R^1$ is an alkyl, substituted alkyl, aryl, or a substituted aryl. In another aspect of formula (VIIIa), $R^3$ is a hydrogen, an alkyl or a substituted alkyl. In still another aspect of formula (VIIIa), $R^6$ is an aryl or a substituted aryl. In still yet another aspect of formula (VIIIa), $R^7$ is an aryl or a substituted aryl.

Suitable examples of ligands within the scope of formula (VIIIa) include those set out in Table 4.

In general, in still another aspect, the invention features metal-ligand complexes characterized by the formula (IX):

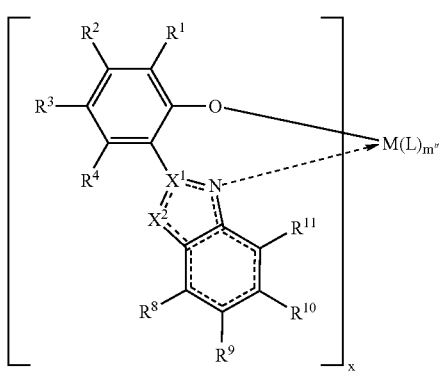

(IX)

where $R^1$, $R^2$, $R^3$, $R^4$, $R^5$, $R^8$, $R^9$, $R^{10}$, $R^{11}$, $X^1$ and $X^2$ are as described above for compounds of formulae (III) through formulae (IIId), M and L are as described above, x is 1, 2, 3, or 4 and m'' is 0, 1, 2, 3, or 4 and the bond between N and the metal (M) is dative or absent.

In a first embodiment for complexes having formula (IX), $X^1$ is C, $X^2$ is $NR^5$ and are referred to as formulae (IXa):

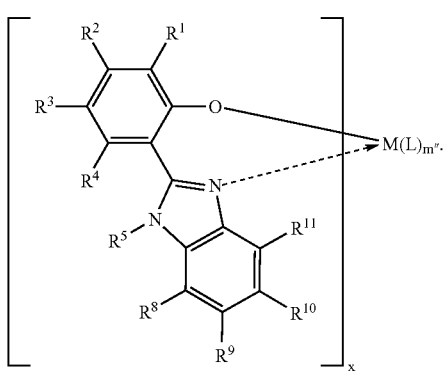

(IXa)

In one aspect of formula (IXa), $R^1$ is an alkyl, substituted alkyl, aryl or a substituted aryl. In another aspect of formula (IXa), $R^3$ is a hydrogen, alkyl or substituted alkyl. In still another aspect of formula (IXa), $R^5$ is an alkyl or substituted alkyl.

Suitable examples of ligands within the scope of formula (IXa) include those set forth in Table 9.

In a second embodiment for complexes having formula (IX), $X^1$ is C and $X^2$ is S and are referred to as formulae (IXb):

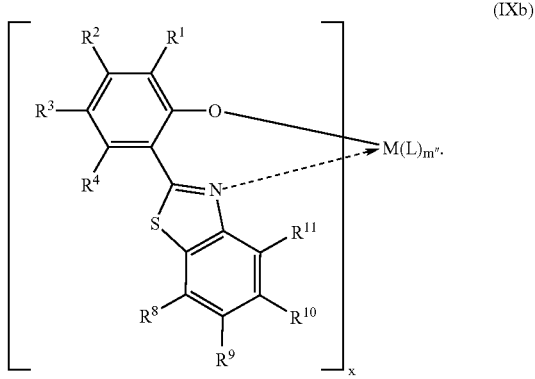

(IXb)

In one embodiment of formula (IXb), $R^1$ is an alkyl or a substituted alkyl. In another embodiment of formula (IXb), $R^3$ is a hydrogen, an alkyl or a substituted alkyl.

Suitable examples of ligands within the scope of formula (IXb) include those set forth in Table 11.

In a third embodiment for complexes having formula (IX), $X^1$ is C and $X^2$ is O and are referred to as formulae (IXc):

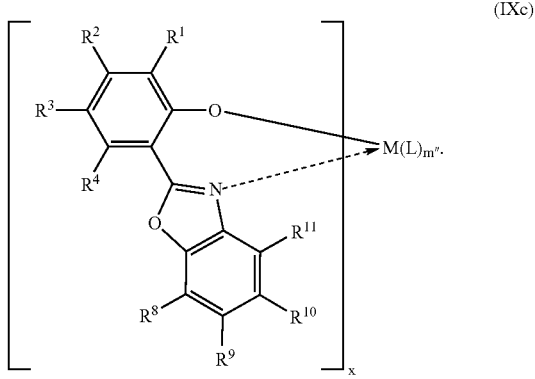

(IXc)

In a fourth embodiment for complexes having formula (IX), $X^1$ is N and $X^2$ is $CR^5$ and are referred to as formulae (IXd):

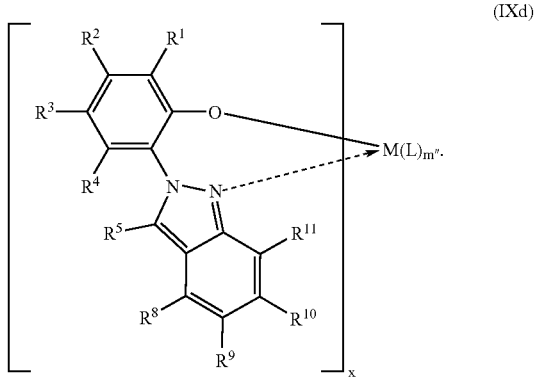

(IXd)

In one aspect of formula (IXd), $R^1$ is an alkyl or substituted alkyl. In another aspect of formula (IXd), $R^3$ is an alkyl or substituted alkyl.

Suitable examples of ligands within the scope of formula (IXd) include those set out in Table 13.

In general, in still another aspect, the invention features metal-ligand complexes characterized by the formula:

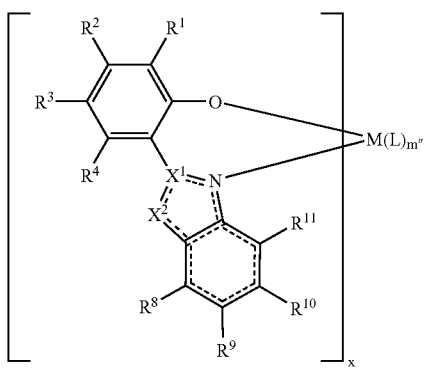

(X)

where $R^1, R^2, R^3, R^4, R^5, R^8, R^9, R^{10}, R^{11}, X^1$ and $X^2$ are as described above for compounds of formulae (IV) and (IVa), M and are as described above, x is 1 or 2 and m" is 0, 1, 2, 3, or 4.

In a first embodiment for complexes having formula (X), $X^1$ is C and $X^2$ is N and are referred to as formulae (Xa)

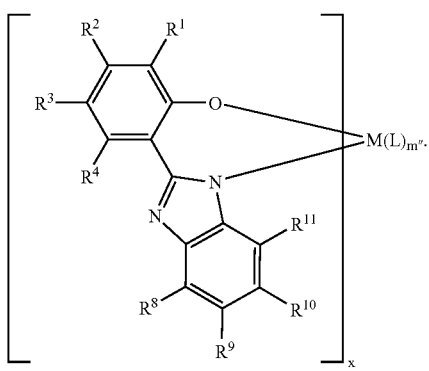

(Xa)

In one aspect of formula (Xa), $R^1$ is an alkyl, substituted alkyl, aryl or substituted aryl. In another aspect of formula (Xa), $R^3$ is a hydrogen, an alkyl or a substituted alkyl. In yet another aspect of formula (Xa), $R^9$ is a hydrogen, halogen, alkyl, substituted alkyl, or an alkoxy. In still another aspect of formula (Xa), $R^{10}$ is a hydrogen, halogen, alkyl, or a substituted alkyl.

Specific examples of ligands within the scope of formula (Xa) include those set forth in Table 10.

In general, in still yet another aspect, the invention features metal-ligand complexes characterized by the formula (XI):

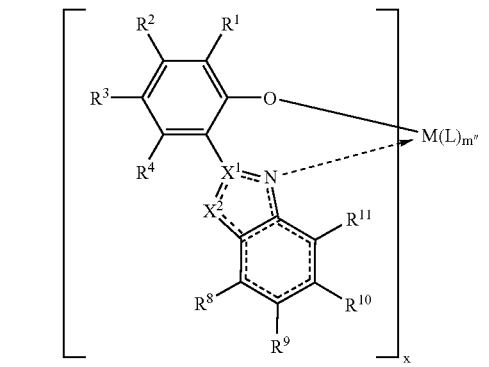

(XI)

where $R^1, R^2, R^3, R^4, R^5, R^8, R^9, R^{10}, R^{11}, X^1$ and $X^2$ are as described above for compounds of formulae (V), M and L are as described above, x is 1, 2, 3, or 4 and m" is 0, 1, 2, 3, or 4 and the bond between N and the metal (M) is dative or absent.

The ligands, complexes or catalysts may be supported on organic or inorganic supports. Suitable supports include silicas, aluminas, clays, zeolites, magnesium chloride, polystyrenes, substituted polystyrenes and the like. Polymeric supports may be cross-linked or not. Similarly, the ligands, complexes or catalysts may be supported on supports known to those of skill in the art. See for example, Severn et al. *Chem. Rev.* 2005, 105, 4073-4147, particularly pages 4115-4117; Hlatky, *Chem. Rev.* 2000, 100, 1347-1376 and Fink et al., *Chem. Rev.* 2000, 100, 1377-1390, each of which is incorporated herein by reference, including the references cited therein. The compositions, complexes and/or catalysts may be contacted with an activator (described below) before or after contact with the support; alternatively, the support may be contacted with the activator prior to contact with the composition, complex or catalyst. In addition, the catalysts of this invention may be combined with other catalysts in a single reactor and/or employed in a series of reactors (parallel or serial) in order to form blends of polymer products.

The other aspects, there is also a bis-ligand complex embodiment of this invention. In one aspect, x is 2 in any of formulae (VII), (VIIa), (VIIb), (VIIc), (VIId), (VIIe), (VIIf), (VIIg), (VIIh), (VIIi), (VIIj), (VIII), (VIIIa), (IX), (IXa), (IXb), (IXc), (IXd), (X), (Xa), and/or (XI). The bis-ligand complex embodiments include two equivalents of the same phenol-heterocycle ligand or one equivalent of a first phenol-heterocycle ligand and one equivalent of a second phenol-heterocycle ligand, wherein the first and second phenol-heterocycle ligands are different from each other. In some embodiments of the bis-ligand complex, the first phenol-heterocycle ligand is a ligand in accord with this invention and the second phenol-heterocycle ligand is otherwise known. For example in some embodiments, the second phenol-heterocycle ligand can be a triazole ligand, such as those disclosed in U.S. Pat. No. 6,933,355, incorporated herein by reference. For example, use of a triazole ligand as the second phenol-heterocycle ligand in a bis-ligand complexes in accord with formula (VII) is characterized by the general formula:

(IXX)

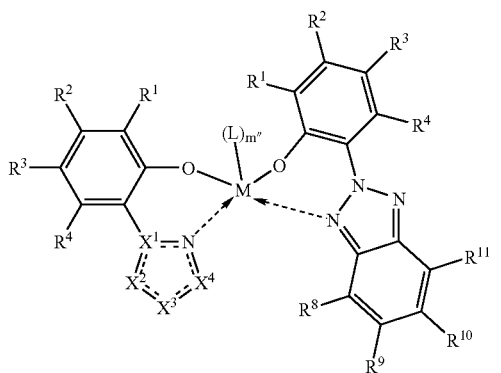

where the variables are defined in various embodiments above.

Also for example, a bis-ligand complex can be characterized by the general formula:

(XX)

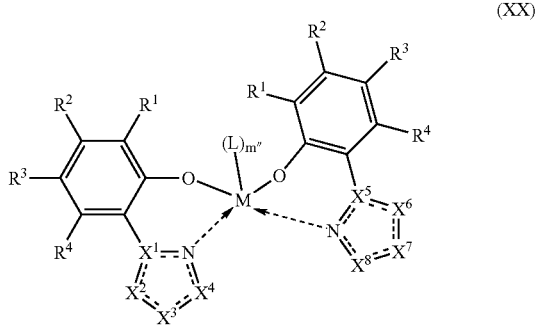

wherein each $R^1$, $R^2$, $R^3$, $R^4$, $R^5$, $R^6$, $R^7$ are the same or different and are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the exception that $R^1$ may not be hydrogen, optionally two or more of $R^1$, $R^2$, $R^3$ and $R^4$ on the same ring in the formula may be joined to form a fused ring system having up to 50 atoms, not counting hydrogen atoms, and optionally two or more of $R^5$, $R^6$ and $R^7$ on the same ring in the formula may be joined to form a fused ring system having up to 50 atoms, not counting hydrogen atoms. It is meant that the R groups on any one particular ring do not bridge to the R groups of another ring when forming a fused ring system, which is the meaning of the "on the same ring" language above.

In formula (XX) the heterocyclic rings are different from each other in that the atoms in the ring are different from each other. $X^1$ is N or C, $X^2$ is O, S, $N(R^5)_{n'}$ or $CR^5$, $X^3$ is O, S, $N(R^6)_{n''}$ or $CR^6$, $X^4$ is O, S, $N(R^7)_{n'''}$ or $CR^7$, wherein each n', n'', and n''' are each independently 0 or 1, provided that the heteroatom containing ring system is heteroaromatic; $X^5$ is N or C, $X^6$ is O, S, $N(R^5)_{n'}$ or $CR^5$, $X^7$ is O, S, $N(R^6)_{n''}$ or $CR^6$, $X^8$ is O, S, $N(R^7)_{n'''}$ or $CR^7$, wherein each n', n'', and n''' are each independently 0 or 1 provided that the heteroatom containing ring system is heteroaromatic. To make the atoms in the ring different from each other, it is further provided that the atoms in the $X^1$, $X^2$, $X^3$, $X^4$, N ring are different from the atoms in the $X^5$, $X^6$, $X^7$, $X^8$, N ring in the selection of the C, N, O or S atom, such that at least, either $X^1$ and $X^5$ are different or $X^2$ and $X^6$ are different or $X^3$ and $X^7$ are different or $X^4$ and $X^8$ are different. Of course more than these particular X groups might be different from each other. Certain embodiments include, triazoles, where combinations of $X^5$, $X^6$; $X^5$, $X^7$; or $X^5$, $X^8$ are both N (meaning that the atom in the ring is N, but the R groups are as specified herein); 2-benzotriazoles, where $X^5$ and $X^6$ are both N; $X^7$, $X^8$ are carbon atoms of benzo-ring fused to triazole; 1-benzotriazoles, $X^5$ and $X^8$ are both N, $X^6$, $X^7$ are carbon atoms of benzo-ring fused to triazole); and tetrazoles, where $X^5$ is N, and 2 of $X^6$; $X^7$; or $X^8$ are N.

Also in conjunction with formula (XX), M is a metal selected from the group consisting of groups 3 through 6 of the periodic table elements and lanthanides; wherein each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof; m" is 0, 1, 2, or 3; and the bond between the heteroaromatic nitrogens (N) and the metal (M) is dative or absent.

Within formula (XX), more specific embodiments of the bis-ligand complexes can be characterized by a general formula selected from the group consisting of:

(XXa)

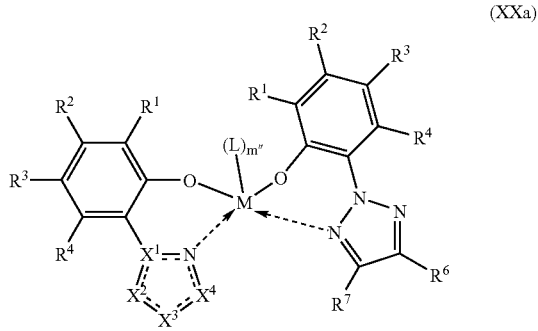

(XXb)

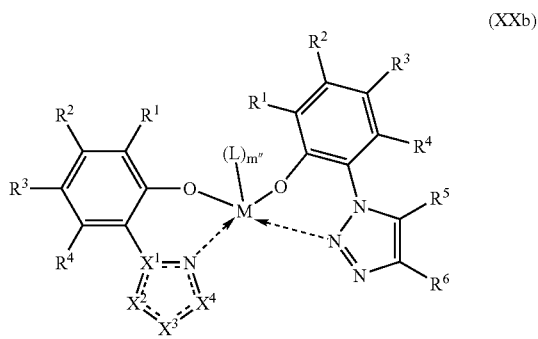

-continued

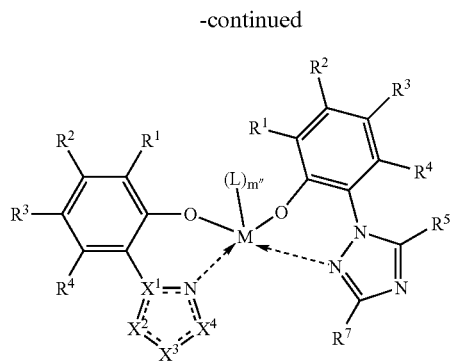 (XXc)

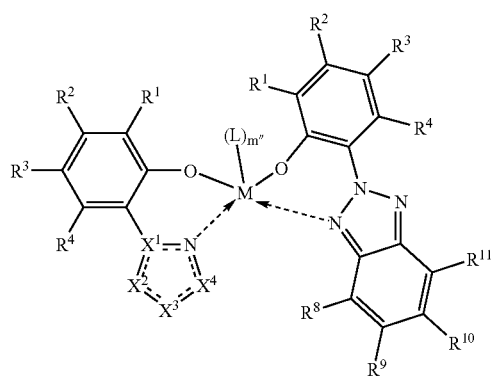 (XXd)

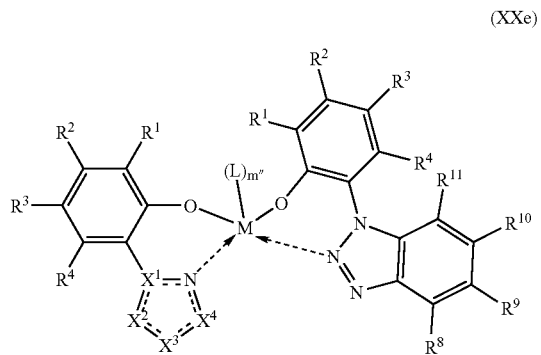 (XXe)

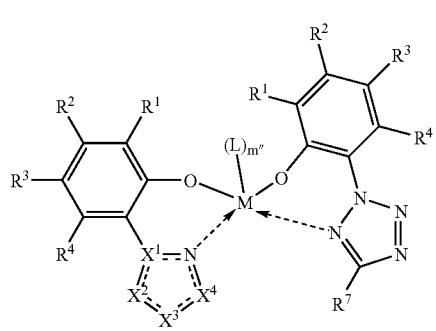 (XXf)

-continued

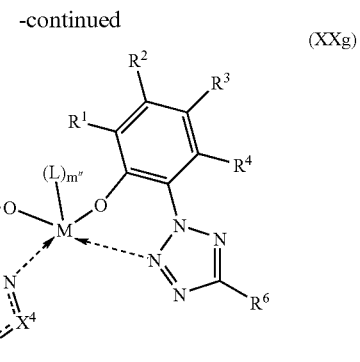 (XXg)

Within each of formulae (XXa-g) the variables are as defined herein.

The metal-ligand complexes and compositions described herein are active catalysts typically in combination with a suitable activator, combination of activators, activating technique or activating technique, although some of the ligand-metal complexes may be active without an activator or activating technique depending on the ligand-metal complex and on the process being catalyzed. Broadly, the activator(s) may comprise alumoxanes, Lewis acids, Bronsted acids, compatible non-interfering activators and combinations of the foregoing. These types of activators have been taught for use with different compositions or metal complexes in the following references, which are hereby incorporated by reference in their entirety: U.S. Pat. Nos. 5,599,761, 5,616,664, 5,453,410, 5,153,157, 5,064,802, EP-A-277,004 and Marks et al., Chem. Rev. 2000, 100, 1391-1434. In some embodiments, ionic or ion forming activators are preferred. In other embodiments, alumoxane activators are preferred.

Suitable ion forming compounds useful as an activator in one embodiment comprise a cation that is a Bronsted acid capable of donating a proton, and an inert, compatible, non-interfering, anion, $A^-$. Suitable anions include, but are not limited to, those containing a single coordination complex comprising a charge-bearing metal or metalloid core. Mechanistically, the anion should be sufficiently labile to be displaced by olefinic, diolefinic and unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions that comprise coordination complexes containing a single metal or metalloid atom are well known and many, particularly such compounds containing a single boron atom in the anion portion, are available commercially.

Specifically, such activators may be represented by the following general formula:

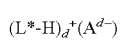

wherein L* is a neutral Lewis base; (L*-H)$^+$ is a Bronsted acid; $A^{d-}$ is a non-interfering, compatible anion having a charge of d−, and d is an integer from 1 to 3. More specifically $A^{d-}$ corresponds to the formula: $(M'^{3+}Q_h)^{d-}$ wherein h is an integer from 4 to 6; h−3=d; M' is an element selected from group 13 of the periodic table; and Q is independently selected from the group consisting of hydrogen, dialkylamido, halogen, alkoxy, aryloxy, hydrocarbyl, and substituted-hydrocarbyl radicals (including halogen substituted hydrocarbyl, such as perhalogenated hydrocarbyl radicals), said Q having up to 20 carbons. In a more specific embodiment, d is one, i.e., the counter ion has a single negative charge and corresponds to the formula A⁻.

Activators comprising boron or aluminum can be represented by the following general formula:

$$(L^*-H)^+(M''Q_4)^-$$

wherein: L* is as previously defined; M" is boron or aluminum; and Q is a fluorinated $C_{1-20}$ hydrocarbyl group. Most specifically, Q is independently selected from the group consisting of fluorinated aryl group, such as a pentafluorophenyl group (i.e., a $C_6F_5$ group) or a 3,5-bis$(CF_3)_2C_6H_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl) borate, tripropylammonium tetrakis(pentafluorophenyl) borate, tri (n-butyl)ammonium tetrakis(pentafluorophenyl) borate, tri (secbutyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-(2,3,4,6-tetrafluorophenyl)borate and N,N-dimethylanilinium tetrakis-(2,3,4,6-tetrafluorophenyl) borate; dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphospnonium tetrakis(pentafluorophenyl) borate, tri (o-tolyl)phosphonium tetrakis(pentafluorophenyl) borate, and tri(2,6-dimethylphenyl)phosphonium tetrakis(pentafluorophenyl) borate; N,N-dimethylanilinium tetrakis(3,5-bis (trifluoromethyl)phenyl)borate; $HNMe(C_{18}H_{37})_2^+B(C_6F_5)_4^-$; $HNPh(C_{18}H_{37})_2^+B(C_6F_5)_4^-$ and $((4-nBu-Ph)NH(n-hexyl)_2)^+B(C_6F_5)_4^-$ and $((4-nBu-Ph)NH(n-decyl)_2)^+B(C_6F_5)_4^-$. Specific (L*-H)⁺ cations are N,N-dialkylanilinium cations, such as $HNMe_2Ph^+$, substituted N,N-dialkylanilinium cations, such as $(4-nBu-C_6H_4)NH(n-C_6H_{13})_2^+$ and $(4-nBu-C_6H_4)NH(n-C_{10}H_{21})_2^+$ and $HNMe(C_{18}H_{37})_2^+$. Specific examples of anions are tetrakis(3,5-bis(trifluoromethyl) phenyl)borate and tetrakis(pentafluorophenyl)borate. In some embodiments, the specific activator is $PhNMe_2H^+B(C_6F_5)_4^-$.

Other suitable ion forming activators comprise a salt of a cationic oxidizing agent and a non-interfering, compatible anion represented by the formula:

$$(Ox^{e+})_d(A^{d-})_e$$

wherein: $Ox^{e+}$ is a cationic oxidizing agent having a charge of e+; e is an integer from 1 to 3; and $A^{d-}$, and d are as previously defined. Examples of cationic oxidizing agents include: ferrocenium, hydrocarbyl-substituted ferrocenium, Ag⁺, or Pb⁺². Specific embodiments of $A^{d-}$ are those anions previously defined with respect to the Bronsted acid containing activating cocatalysts, especially tetrakis(pentafluorophenyl) borate.

Another suitable ion forming, activating cocatalyst comprises a compound that is a salt of a carbenium ion or silyl cation and a non-interfering, compatible anion represented by the formula:

$$©^+A^-$$

wherein: ©⁺ is a $C_{1-100}$ carbenium ion or silyl cation; and A⁻ is as previously defined. A preferred carbenium ion is the trityl cation, i.e. triphenylcarbenium. The silyl cation may be characterized by the formula $Z^4Z^5Z^6Si^+$ cation, where each of $Z^4$, $Z^5$, and $Z^6$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio, arylthio, and combinations thereof. In some embodiments, a specified activator is $Ph_3C^+B(C_6F_5)_4^-$.

Other suitable activating cocatalysts comprise a compound that is a salt, which is represented by the formula $(A^{*+a})_b(Z^*J^*_j)^{-c}_d$ wherein A* is a cation of charge +a; Z* is an anion group of from 1 to 50, specifically 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that a×b is equal to c×d. See WO 99/42467, which is incorporated herein by reference. In other embodiments, the anion portion of these activating cocatalysts may be characterized by the formula $(((C_6F_5)_3M''''-LN-M''''(C_6F_5)_3)^-$ where M''''is boron or aluminum and LN is a linking group, which is specifically selected from the group consisting of cyanide, azide, dicyanamide and imidazolide. The cation portion is specifically a quaternary amine. See, e.g., LaPointe, et al., *J. Am. Chem. Soc.* 2000, 122, 9560-9561, which is incorporated herein by reference.

In addition, suitable activators include Lewis acids, such as those selected from the group consisting of tris(aryl)boranes, tris(substituted aryl)boranes, tris(aryl)alanes, tris(substituted aryl)alanes, including activators such as tris(pentafluorophenyl)borane. Other useful ion forming Lewis acids include those having two or more Lewis acidic sites, such as those described in WO 99/06413 or Piers, et al., *J. Am. Chem. Soc.*, 1999, 121, 3244-3245, both of which are incorporated herein by reference. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a group 13 reagent that may be characterized by the formula $G^{13}R^{50}_{3-p}D_p$ where $G^{13}$ is selected from the group consisting of B, Al, Ga, In and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof. In other embodiments, the group 13 activator is an oligomeric or polymeric alumoxane compound, such as methylalumoxane and the known modifications thereof. See, for example, Barron, "*Alkylalumoxanes, Synthesis, Structure and Reactivity*", pp. 33-67 in *Metallocene-Based Polyolefins: Preparation, Properties and Technology*, J. Schiers and W. Kaminsky (eds.), Wiley Series in Polymer Science, John Wiley & Sons Ltd., Chichester, England, 2000, and references cited therein. In other embodiments, a divalent metal reagent may be used that is defined by the general formula $M'R^{50}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd and combinations thereof. In still other embodiments, an alkali metal reagent may be used that is defined by the general formula $M^{iv}R^{50}$ and in this embodiment $R^{50}$ is as defined above. $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defied above, with the proviso that there is at least one D that is a hydrogen.

The molar ratio of metal:activator (whether a composition or complex is employed as a catalyst) employed specifically ranges from 1:10,000 to 100:1, more specifically from 1:5000 to 10:1, most specifically from 1:10 to 1:1. In one embodiment of the invention mixtures of the above compounds are used, particularly a combination of a group 13 reagent and an ion-forming activator. The molar ratio of group 13 reagent to ion-forming activator is specifically from 1:10,000 to 1000:1, more specifically from 1:5000 to 100:1, most specifically from 1:100 to 10:1. In another embodiment, the ion forming activators are combined with a group 13 reagent. Another embodiment is a combination of the above compounds having about 1 equivalent of an optionally substituted N,N-dialkylanilinium tetrakis(pentafluorophenyl) borate, and 5-30 equivalents of a group 13 reagent. In some embodiments from about 30 to 2000 equivalents of an oligomeric or polymeric alumoxane activator, such as a modified alumoxane (e.g., alkylalumoxane), can be used.

In some embodiments, the ligand or bis-ligand combination will be mixed with a suitable metal precursor compound prior to or simultaneous with allowing the mixture to be contacted to the reactants. When the ligand is mixed with the metal precursor compound, a metal-ligand complex may be formed, which may be a catalyst. Also, the ligand or ligand composition can be combined with an activated metal precursor, as described herein. In other aspects, the catalysts of the invention may be combeined with other catalysts to make bi-modal polymer products; and here the catalysts may be combined together in solution and/or on a solid support.

The ligands, compositions, complexes and/or catalysts of the invention can be used to catalyze a variety of transformations, including, for example, oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, Diels-Alder reactions, Baeyer-Villiger reactions, and other transformations. Some compositions, complexes and/or catalysts according to the invention are particularly effective at polymerizing ethylene or α-olefins (such as propylene, 1-butene, 1-pentene, 1-hexene, 1-heptene, 1-octene, 1-decene and styrene), copolymerizing ethylene with α-olefins (such as propylene, 1-butene, 1-pentene, 1-hexene, 1-heptene, 1-octene, and styrene), copolymerizing ethylene with 1,1-disubstituted olefins (such as isobutylene), or copolymerizing ethylene, propylene and a diene monomer suitable for production of EPDM (Ethylene-Propylene-Diene Monomer) synthetic rubbers. Thus, for example, in some embodiments, metal-ligand compositions and complexes containing zirconium or hafnium may be useful in the polymerization of propylene to form isotactic polypropylene or in the copolymerization of ethylene and one or more α-olefins, as noted above. In other embodiments, vanadium and chromium compositions and/or complexes according to the invention may be useful in, for example, the polymerization of ethylene. The compositions, complexes and/or catalysts according to the invention may also polymerize monomers that have polar functionalities in homopolymerizations or copolymerizations and/or homopolymerize 1,1- and 1,2-disubstituted olefins. Also, diolefins in combination with ethylene and/or α-olefins or 1,1- and 1,2-disubstituted olefins may be copolymerized. In some embodiments, catalysts incorporating the ligands, compositions and/or complexes of the present invention exhibit high catalytic activity in the polymerization of such α-olefins, including at high temperatures.

In general monomers useful herein may be olefinically unsaturated monomers having from 2 to 20 carbon atoms either alone or in combination. Generally, monomers may include olefins (including cyclic olefins), diolefins and unsaturated monomers including ethylene and $C_3$ to $C_{20}$ α-olefins such as propylene, 1-butene, 1-hexene, 1-octene, 4-methyl-1-pentene, 1-norbornene, styrene and mixtures thereof; additionally, 1,1-disubstituted olefins, such as isobutylene, 2-methyl-1-butene, 2-methyl-1-pentene, 2-ethyl-1-pentene, 2-methyl-1-hexene, 3-trimethylsilyl-2-methyl-1-propene, α-methyl-styrene, either alone or with other monomers such as ethylene or $C_3$ to $C_{20}$ α-olefins and/or diolefins; additionally 1,2-substituted olefins, such as 2-butene. The α-olefins listed above may be polymerized in a stereospecific manner—for example, as in the generation of isotactic or syndiotactic or hemiisotactic polypropylene. Additionally the α-olefins may be polymerized to produce a polymer with differing tacticity sequences within the polymer chain, such as polypropylene containing atactic and isotactic sequences within the same polymer chain. Diolefins generally comprise 1,3-dienes such as (butadiene), substituted 1,3-dienes (such as isoprene) and other substituted 1,3-dienes, with the term substituted referring to the same types of substituents referred to above in the definition section. Diolefins also comprise 1,5-dienes and other non-conjugated dienes, such as ethylidene-norbornene, 1,4-hexadiene, dicyclopentadiene and other dienes used in the manufacture of EPDM synthetic rubbers. The styrene monomers may be unsubstituted or substituted at one or more positions on the aryl ring. The use of diolefins in this invention is typically in conjunction with another monomer that is not a diolefin. In some embodiments, acetylenically unsaturated monomers may be employed.

More specifically, the catalysts of the present invention are active for certain monomers, particularly ethylene and/or styrene. Thus, the catalysts of the present invention may provide lower comonomer incorporation in the presence of a comonomer, making these catalysts particularly useful for certain polymerization reactions where low co-monomer incorporation is desired. Also particular catalysts of the present invention co-polymerize ethylene and styrene (or substituted styrenes), forming ethylene-styrene copolymers. Also the catalysts of this invention are useful to polymerize a vinylidene aromatic monomer in a solution polymerization process conducted at a temperature greater than or equal to 100° C.

Polymers that can be prepared according to the present invention include ethylene copolymers with at least one $C_3$-$C_{20}$ α-olefin, particularly propylene, 1-butene, 1-hexene, 4-methyl-1-pentene and 1-octene. The copolymers of ethylene with at least one $C_3$-$C_{20}$ α-olefin comprise from about 0.1 mol. % α-olefin to about 50 mol. % α-olefin, more specifically from about 0.2 mol. % α-olefin to about 50 mol. % α-olefin and still more specifically from about 2 mol. % α-olefin to about 30 mol. % higher olefin. For certain embodiments of this invention, product copolymers may include those of ethylene and a comonomer selected from the group consisting of propylene, 1-butene, 1-hexene, and 1-octene comprise from about 0.2 to about 30 mol. % comonomer, more specifically from about 1 to about 20 mol. % comonomer. In particular, in some embodiments ethylene copolymers with at least one $C_3$-$C_{20}$ α-olefin can be produced having a high molecular weight (e.g., greater than about 50,000, more specifically greater than about 150,000) in a solution process at a temperature of greater than about 100° C., more specifically greater than about 130° C. In certain embodiments, ethylene copolymers with at least one $C_3$-$C_{20}$ α-olefin can be produced with a low molecular weight (e.g., less than about 50,000, more specifically, less than about 40,000, and even more specifically less than about 30,000).

The ligands, compositions, complexes, and/or catalysts of the invention may also be used to catalyze other (i.e., non-polymerization) transformations. Examples of asymmetric or enantioselective reactions catalyzed by chiral Group 4 catalysts include olefin hydrogenation, olefin epoxidation, olefin isomerization, olefin-pyridine coupling, imine hydrogenation, aldol reactions, imino aldol reactions, epoxidation of allylic alcohols, alkylation of aldehydes, alkylation of imines, Diels-Alder reactions, Baeyer-Villiger reactions, hydroamination/cyclization of amino-alkenes, pinacol coupling of aldehydes, and hydrosilation of imines, ketones, and olefins. In some embodiments, the complexes and catalysts of the invention may be chiral. For example, in some instances, substantially diastereomerically pure or substantially enantiomerically pure complexes may be useful for stereoselective, asymmetric, enantioselective, or diastereoselective reactions or transformations. Thus, in some embodiments substantially enantiomerically- or diastereomerically-pure complexes, ligand-metal compositions, and catalysts according to the invention may be used as asymmetric catalysts for a range of reactions, including polymerization reactions and other (non-polymerization) reactions, including many reactions useful in organic synthesis. In some embodiments, catalysts incorporating the compositions and complexes of the invention may be used to catalyze the asymmetric production of reaction products with enantiomeric excess (ee) or diastereomeric excess (de) of greater than 90% or greater than 99%. The asymmetric synthesis of chiral organic molecules is an important field, and is critical in the synthesis of many pharmaceuticals and other products. Single enantiomers of a chiral product can be prepared by a variety of techniques, including the resolution of racemates, or the use of substantially enantiomerically pure starting materials from the chiral pool of natural products, but for large scale synthesis the use of enantioselective catalysis is often the most attractive, and most economical, choice. See, e.g., Blaser et al., "Enantioselective Synthesis", pp. 1131-1149, in *Applied Homogeneous Catalysis with Organometallic Compounds*, Vol. 3, Comils, B., & Herrmann, W. (eds.), 2nd Edition, Wiley-VCH, Weinheim, Germany, 2002, and *Catalytic Asymmetric Synthesis*, Ojima (ed.), VCH Publishers, Inc., New York, 1993, and the references cited therein.

In some embodiments, novel products, such as polymers, copolymers or interpolymers, may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, bottles, containers, foams, coatings, insulating devices and household items. Also, such functionalized polymers are useful as solid supports for organometallic or chemical synthesis processes.

The α-olefins listed above may be polymerized in a stereoselective manner to produce a substantially stereoregular polymer product (that is, a polymer product that is detectably enriched in m or r dyads (as determined, e.g., by $^{13}$C NMR) as compared to a corresponding atactic material), as in the generation of isotactic, syndiotactic or hemiisotactic poly-α-olefins. For example, in some embodiments 1-butene may be polymerized into isotactic poly-1-butene. Additionally, the α-olefins may be polymerized to produce a polymer with differing tacticity sequences within the polymer chain, such as polypropylene containing atactic and isotactic sequences within the same polymer chain. The stereoregularity may be interrupted by stereoerrors, in particular isolated stereoerrors, which is an indication of enantiomorphic side control. Also, in some embodiments the isotactic polypropylene may include regioerrors as described in the literature (see, e.g., Resconi et al., Chem. Rev. 2000, 100, 1253-1345).

More specifically, it has been found that particular catalysts of the present invention polymerize propylene to isotactic or crystalline polypropylene, forming polymers with novel properties. In particular, in some embodiments isotactic polypropylene can be produced having a narrow polydispersity (e.g., less than about 3.0 and more specifically less than 2.5) combined with a high molecular weight (e.g., greater than about 50,000, more specifically greater than about 100,000, even more specifically greater than about 150,000, and even more specifically greater than about 500,000) in a solution polymerization process at a temperature of greater than about 100° C. In certain embodiments, isotactic polypropylene can be produced with a low molecular weight (e.g., less than about 30,000, more specifically less than about 15,000, and even more specifically less than about 5,000). In some embodiments, broader polydispersities can be obtained for the isotactic polypropylene or other polymers (e.g., copolymers of ethylene and α-olefins as discussed in more detail below) produced according to the invention.

The polymerization conditions are described herein, producing isotactic polypropylene with a crystallinity index of between about 0.35 and about 0.95, more specifically between about 0.65 and 0.95. The crystallinity index is determined using FTIR as is known to those of skill in the art and calibrated based on a relative scale. In one embodiment, the crystallinity index value can be determined using commercially available FTIR equipment (such as a Bruker Equinox 55 with an IR Scope II in reflection mode using Pike MappIR software). The crystallinity index is obtained from the ratio of band heights at 995 $cm^{-1}$ and 972 $cm^{-1}$. Atactic polypropylene has a ratio of band heights or crystallinity index of 0.2. Greater than 98% isotactic polypropylene has a crystallinity index ratio of greater than 0.95. Generally, the amount of error in crystallinity index measurements is ±0.05. Polymer blends of various compositions show a linear relationship between % isotacticity and crystallinity index. See, for example, J. P.

Luongo, J. Appl. Polym. Sci. 1960, 3, 302-309 and T. Sundell, et al., Polymer 1996, 37, 3227-3231, each of which is incorporated herein by reference.

As those of skill in the art will recognize, isotacticity can also be represented by percent pentads (% mmmm) as determined by $^{13}C$ NMR spectroscopy. Proton decoupled $^{13}C$ NMR spectroscopy can be performed using commercially available equipment (such as a Bruker 300 MHz at 100° C. probe temperature) to determine the degree of tacticity as % mmmm pentads (for assignment of $^{13}C$ signals see the review H. H. Brintzinger et al., Angew. Chem. Int. Ed. Eng. 1995, 34, 1143, which is incorporated herein by reference; and Resconi, Chem. Rev. 2000, 100, 1253-1345 and Gibson et al., Chem Rev. 2003, 103, 283-315). For example, a 15-30 mg polymer sample is dissolved in a 1:1 mixture of $C_2D_2Cl_4$ and $C_2Cl_4$ by heating the sample to ca. 100° C. The % mmmm is determined by the ratio of peak integral from 23.5 to 21.5 ppm and peak integral 23.5 to 19 ppm (in the absence of significant chain end regio-irregularity signals in this region). Proton decoupled $^{13}C$ NMR spectroscopy can be also performed to determine the frequency of and nature of stereoerrors and regioerrors.

In addition, the melting point of the crystalline polypropylene is generally in the range of from about 115° C. to about 165° C., more specifically between about 120° C. and 155° C., and in some embodiments specifically above about 150° C. Melting points are determined by differential scanning calorimetry, as is known in the art (see also the example section, herein).

The FTIR method used for determining mol % total styrene in product is as described in U.S. Pat. No. 6,794,514, the contents of which are incorporated herein in their entirety. FTIR was performed on a Bruker Equinox 55+IR Scope II in reflection mode using a Pike MappIR accessory with 16 scans. The ratio of total styrene to ethylene was obtained from the ratio of band heights at 4330 $cm^{-1}$ and 1602 $cm^{-1}$. This method was calibrated using a set of ethylene-styrene copolymers with a range of known styrene content.

The total styrene content of the polymer products (mol % total styrene), includes both the styrene incorporated in the ethylene-styrene copolymer and any background homopolystyrene (PS) in the product sample. Tacticity determination for polystyrene samples are determined using $^{13}C$ NMR. High temperature NMR spectra are recorded on a Bruker 300 MHz spectrometer. $^{13}C$ chemical shifts (75.47 MHz) are referenced relative to tetrachloro-ethane-$d_2$ solvent peaks. Polymer sample concentrations are 100-200 mg/ml. Acquisition parameters are 8196-16392 scans; 30° pulse width; acquisition time=1 second; d1=3 seconds; 70-90° C. probe temperature. Tacticity of styrene polymers is determined using the 144-147 ppm region of the $^{13}C$ NMR spectrum (phenyl C(1)), see *NMR and Macromolecules*, Randall Ed., Harwood et al. Ch. 13: Polystyrene and Epimerized Isotactic Polystyrenes (1983).

The ratio of 1-octene to ethylene incorporated in the ethylene-octene copolymer products was determined by FTIR. FTIR was performed on a Bruker Equinox 55+IR Scope II in reflection mode using a Pike MappIR accessory with 16 scans. The ratio of 1-octene to ethylene incorporation was represented as the weight % (wt. %) of 1-octene incorporated in the polymer (wt. % 1-octene). Wt. % 1-octene was obtained from ratio of band heights at 1378 $cm^{-1}$ and 4335 $cm^{-1}$. This method was calibrated using a set of ethylene/1-octene copolymers with a range of known wt. % 1-octene content.

Novel polymers, copolymers or interpolymers may be formed having unique physical and/or melt flow properties. Polymers that can be prepared according to the present invention include copolymers of ethylene and one or more α-olefins, such as copolymers of ethylene with at least one $C_4$-$C_{20}$ α-olefin, such as 1-butene, 1-hexene, 4-methyl-1-pentene, 1-octene or styrene. Similarly, the techniques described herein can be used to prepare propylene copolymers with at least one $C_4$-$C_{20}$ α-olefin. In some embodiments, the copolymers of ethylene or propylene with at least one $C_4$-$C_{20}$ α-olefin comprise from about 0.01 mol. % higher olefin to about 50 mol. % higher olefin, more specifically from about 0.1 mol. % higher olefin to about 50 mol. % higher olefin and still more specifically from about 1 mol. % higher olefin to about 30 mol. % higher olefin. For certain embodiments of this invention, crystalline copolymers include those of ethylene or propylene and a comonomer selected from the group consisting of ethylene, 1-butene, 1-hexene, 1-octene and styrene comprise from about 0.1 to about 50 mol. % comonomer, more specifically from about 1 to about 20 mol. % comonomer, even more specifically from about 2 to about 15 mol. % comonomer and most specifically from about 5 to about 12 mol. % comonomer.

The novel polymers disclosed herein can be employed alone or with other natural or synthetic polymers in a blend. Such other natural or synthetic polymers can be polyethylene (including linear low density polyethylene, low density polyethylene, high density polyethylene, etc.), atactic polypropylene, nylon, EPDM, ethylene-propylene elastomer copolymers, polystyrene (including syndiotactic polystyrene), ethylene-styrene copolymers and terpolymers of ethylene-styrene and other $C_3$-$C_{20}$ olefins (such as propylene).

Polymerization is carried out under polymerization conditions, including temperatures of from –100° C. to 300° C. and pressures from atmospheric to 3000 atmospheres. Suspension, solution, slurry, gas phase or high-pressure polymerization processes may be employed with the catalysts and compounds of this invention. Such processes can be run in a batch, semi-batch or continuous mode. Examples of such processes are well known in the art. A support for the catalyst may be employed, which may be inorganic (such as alumina, magnesium chloride or silica) or organic (such as a polymer or cross-linked polymer). Methods for the preparation of supported catalysts are known in the art. Slurry, suspension, gas phase and high-pressure processes as known to those skilled in the art may also be used with supported catalysts of the invention.

Other additives that are useful in a polymerization reaction may be employed, such as scavengers, promoters, modifiers and/or chain transfer agents, such as hydrogen, aluminum alkyls and/or silanes.

As discussed herein, catalytic performance can be determined a number of different ways, as those of skill in the art will appreciate. Catalytic performance can be determined by the yield of polymer obtained per mole of metal complex, which in some contexts may be considered to be activity. The examples provide data for these comparisons.

As stated herein, a solution process is specified for certain benefits, with the solution process being run at a temperature above 90° C., more specifically at a temperature above 100° C., further more specifically at a temperature above 110° C. and even further more specifically at a temperature above 130° C. Suitable solvents for polymerization are non-coordinating, inert liquids. Examples include straight and branched-chain hydrocarbons such as isobutane, butane, pentane, isopentane, hexane, isohexane, heptane, octane, Isopar-E® and mixtures thereof; cyclic and alicyclic hydrocarbons such as cyclohexane, cycloheptane, methylcyclohexane, methylcycloheptane, and mixtures thereof; perhalogenated hydrocarbons such as perfluorinated $C_{4-10}$ alkanes, chlorobenzene, and aromatic and alkyl substituted aromatic compounds such as benzene, toluene, mesitylene, and xylene. Suitable solvents also include liquid olefins which may act as monomers or comonomers including ethylene, propylene, 1-butene, butadiene, cyclopentene, 1-hexene, 1-pentene, 3-methyl-1-pentene, 4-methyl-1-pentene, 1,4-hexadiene, 1-octene, 1-decene, isobutylene, styrene, divinylbenzene, allylbenzene, and vinyltoluene (including all isomers alone or in admixture). Mixtures of the foregoing are also suitable.

In some embodiments, a solution process is specified for crystalline polypropylene production. The solution process to prepare isotactic polypropylene comprises adding a catalyst and propylene monomer to a reactor and subjecting the contents to polymerization conditions.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. Nos. 5,985,356, 6,030,917 and WO 98/03521, all of which are incorporated herein by reference, generally disclose combinatorial methods. In this regard, the ligands, metal-ligand complexes or compositions may be prepared and/or tested in rapid serial and/or parallel fashion, e.g., in an array format. When prepared in an array format, ligands, metal-ligand complexes or compositions may take the form of an array comprising a plurality of compounds wherein each compound can be characterized by any of the above general formulas (i.e., I, II, III, etc.). An array of ligands may be synthesized using the procedures outlined previously. The array may also be of metal precursor compounds, the metal-ligand complexes or compositions characterized by the previously described formulae and/or description. Typically, each member of the array will have differences so that, for example, a ligand or activator or metal precursor or R group in a first region of the array may be different than the ligand or activator or metal precursor or R group in a second region of the array. Other variables may also differ from region to region in the array.

In such a combinatorial array, typically each of the plurality of compositions or complexes has a different composition or stoichiometry, and typically each composition or complex is at a selected region on a substrate such that each compound is isolated from the other compositions or complexes. This isolation can take many forms, typically depending on the substrate used. If a flat substrate is used, there may simply be sufficient space between regions so that there cannot be interdiffusion between compositions or complexes. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components referred to herein (with components referring to ligands, metal precursors, activators, group 13 reagents, solvents, monomers, supports, etc.). In other embodiments, there are at least 20 compounds, complexes or compositions on or in the substrate each having a different chemical formula. In still other embodiments, there are at least 40 or 90 or 124 compounds, complexes or compositions on or in the substrate each having a different chemical formula. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. Polymerizations can also be performed in a combinatorial fashion, see, e.g., U.S. Pat. Nos. 6,306,658, 6,508,984 and WO 01/98371, each of which is herein incorporated by reference.

EXAMPLES

All air sensitive reactions were performed under a purified argon or nitrogen atmosphere in a Vacuum Atmospheres or MBraun glove box. All solvents used were anhydrous, deoxygenated and purified according to known techniques. All ligands and metal precursors were prepared according to procedures known to those of skill in the art, e.g., under inert atmosphere conditions, etc. Unless otherwise indicated, polymerizations were generally carried out in a parallel pressure reactor, which is described in U.S. Pat. Nos. 6,306,658, 6,455, 316 and 6,489,168, and WO 00/09255, each of which is incorporated herein by reference. The above-described analytical techniques were utilized, generally.

Section 1. Ligand Synthesis

Building blocks used for the synthesis of ligands A1-A35, B1-B6, C1-C27, D1-D3, E2-E24, F1-F12, and G1-G4, are listed in the Building Block Table. Building block BB1 was purchased from Lancaster. Building blocks BB5 and BB7 were purchased from Aldrich. All other building blocks listed in Building Block Table were prepared by Syngene. Aryloximes and arylhyroximidoyl chlorides used for the synthesis of ligands A1-A35 were either available commercially or prepared using techniques known to those of skill in the art (see Liu, et al., *J. Org. Chem.* 1980, 45, 3916-3918). All boronic acids used were commercially available with the exception of 9-anthracenylboronic acid that was prepared as described in Scheme D1. 2,4-Dibromothiazole was purchased from Frontier Scientific. All benzils used for the synthesis of ligands E2-E16 were available commercially. Phenol protecting groups, methoxymethyl ether and methyl ether, were introduced using standard procedures known to those of skill in the art.

Building Block Table

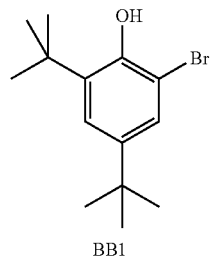

BB1

-continued
Building Block Table
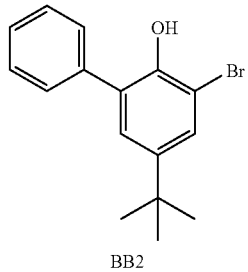
BB2
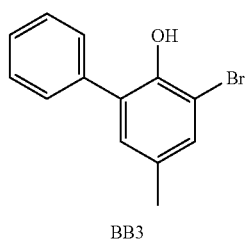
BB3
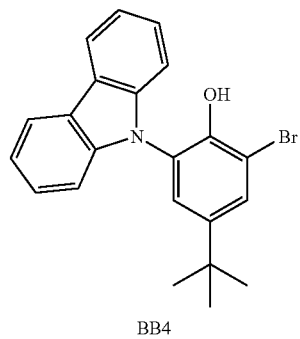
BB4
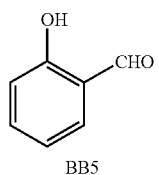
BB5
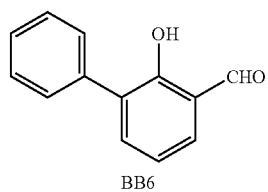
BB6
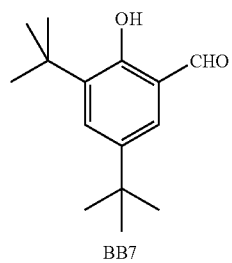
BB7
-continued
Building Block Table
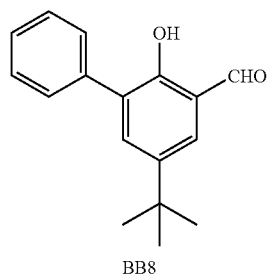
BB8
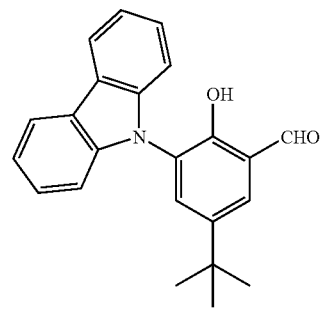
BB9
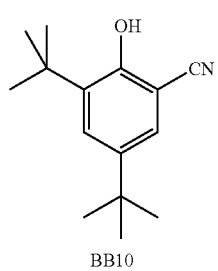
BB10
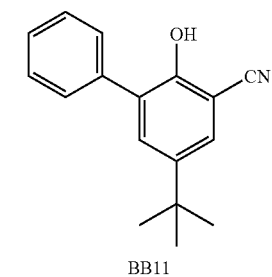
BB11
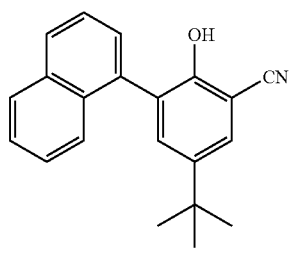
BB12

-continued

Building Block Table

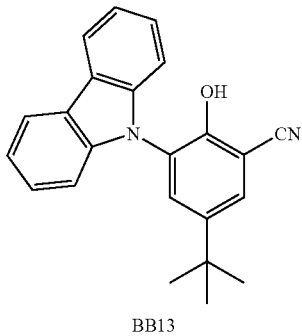

BB13

Section 1A. 3-Aryl Phenol Oxadiazole Ligands

Ligands A12, A14-A19, A21, and A23-A29 were synthesized according to the above procedure in yields ranging from 45-82% with the exception of ligand A29 which was isolated in 26% yield.

Ligand A22 was synthesized using a slightly modified procedure to that described above for ligand A1. A mixture of the oxime (0.90 mmol), cyclohexane (3.0 mL), and N-chlorosuccinimide (0.90 mmol) was first heated to 80° C. for 1 h. After cooling to rt, a solution of BB11 (0.30 mmol) and 2,6-lutidine (0.90 mmol) in cyclohexane (3.0 mL) was added. The reaction was heated back to 80° C. for 18 h. Ligand A22 was isolated in 58% yield.

Ligand A35 was synthesized as described for ligand A1 except an aqueous workup was done prior to chromatography. Cyclohexane was removed by rotary evaporation and the crude reaction mixture was taken up in $Et_2O$. The $Et_2O$ solution was washed twice with $H_2O$, once with brine, and then dried over $Na_2SO_4$. Ligand A35 was isolated in 79% yield.

Scheme A1

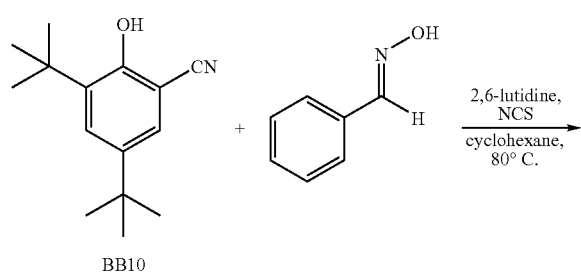

Scheme A2

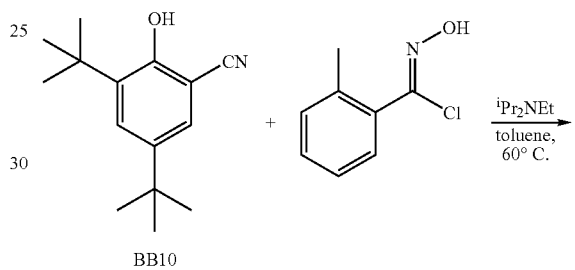

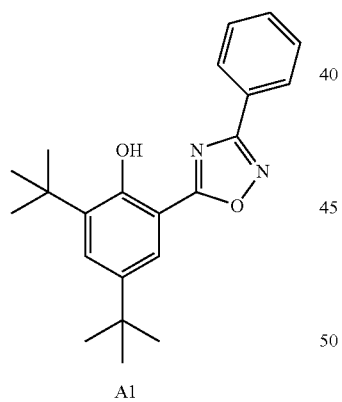

A1

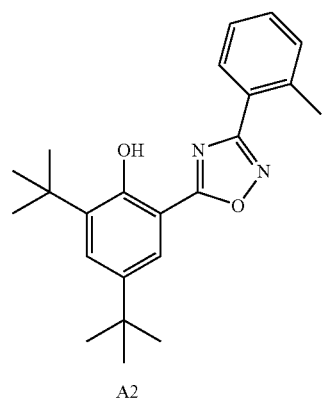

A2

A reaction flask was charged, under $N_2$, with BB10 (46 mg, 0.20 mmol), benzaldehyde oxime (0.066 mL, 0.60 mmol), cyclohexane (4.0 mL), 2,6-lutidine (0.07 mL, 0.60 mmol), and N-chlorosuccinimide (80 mg, 0.60 mmol). The reaction was heated at 80° C. for 18 h. The crude reaction mixture was purified by silica gel chromatography eluting with hexanes/$CH_2C_2$=5/1. Isolated 64 mg, 91% yield, of ligand A1 as a white solid. $^1H$ NMR (300 MHz, $C_6D_6$) δ 1.24 (s, 9H, $^tBu$), 1.64 (s, 9H, $^tBu$), 7.05-7.11 (m, 3H), 7.68 (d, 1H), 7.91 (d, 1H), 7.99 (m, 2H), 11.24 (s, 1H, OH).

A reaction flask was charged, under $N_2$, with BB10 (46 mg, 0.20 mmol), 2-methyl-N-hydroxybenzenecarboximidoyl chloride (51 mg, 0.30 mmol), toluene (2.0 mL), and $^iPr_2NEt$ (0.052 mL, 0.30 mmol). The reaction was heated at 60° C. for 24 h. The crude product mixture was purified by silica gel chromatography eluting with hexanes/$CH_2Cl_2$=10/1. Isolated 59 mg, 81% yield, of ligand A2 as a faint yellow solid. $^1H$ NMR (300 MHz, $C_6D_6$) δ 1.25 (s, 9H, $^tBu$), 1.63 (s, 9H, $^tBu$), 2.59 (s, 3H, $CH_3$), 7.00-7.12 (m, 3H), 7.68 (d, 1H), 7.92 (m, 2H), 11.29 (s, 1H, OH).

Ligands A3-A9 were synthesized as described above for ligand A2 in yields ranging from 49-84%.

Section 1B. 5-Aryl Phenol Oxadiazole Ligands

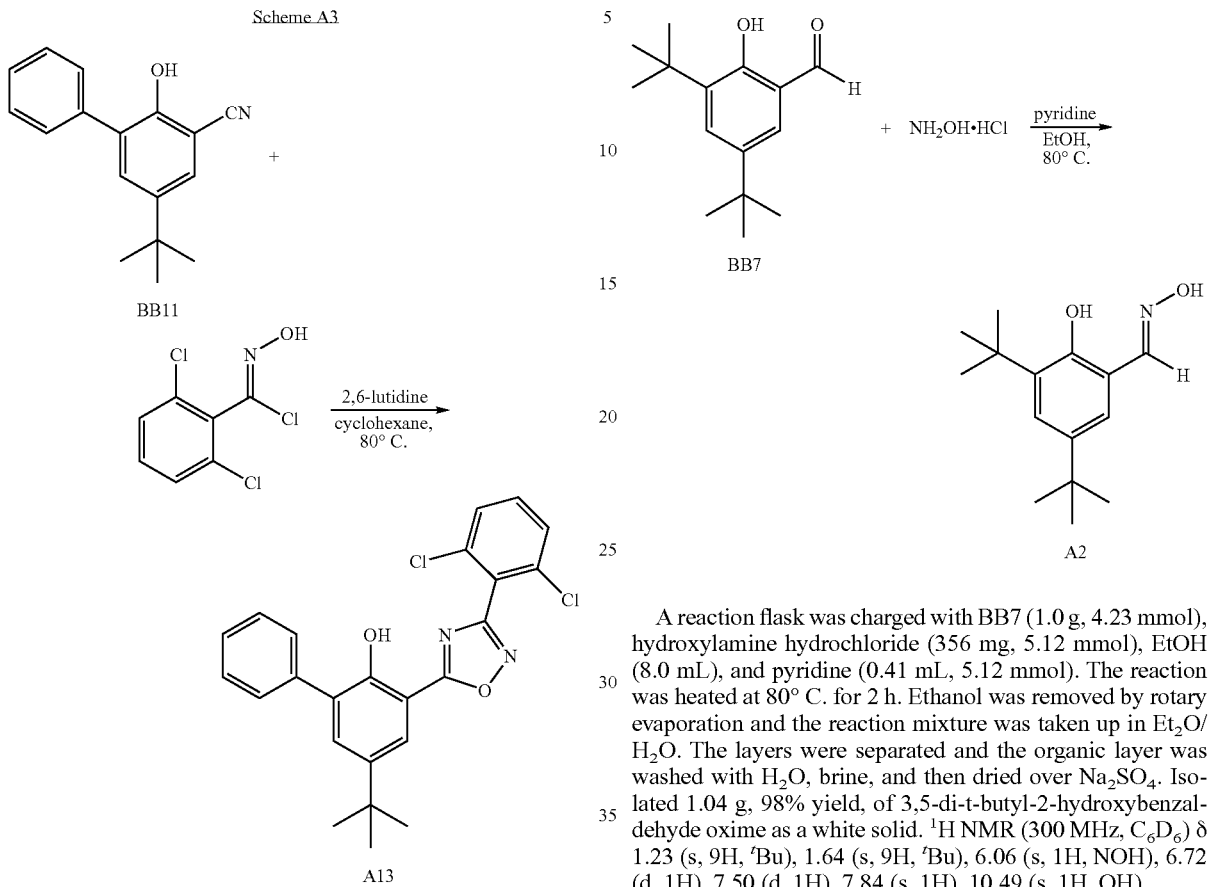

A reaction flask was charged with BB7 (1.0 g, 4.23 mmol), hydroxylamine hydrochloride (356 mg, 5.12 mmol), EtOH (8.0 mL), and pyridine (0.41 mL, 5.12 mmol). The reaction was heated at 80° C. for 2 h. Ethanol was removed by rotary evaporation and the reaction mixture was taken up in Et$_2$O/H$_2$O. The layers were separated and the organic layer was washed with H$_2$O, brine, and then dried over Na$_2$SO$_4$. Isolated 1.04 g, 98% yield, of 3,5-di-t-butyl-2-hydroxybenzaldehyde oxime as a white solid. $^1$H NMR (300 MHz, C$_6$D$_6$) δ 1.23 (s, 9H, $^t$Bu), 1.64 (s, 9H, $^t$Bu), 6.06 (s, 1H, NOH), 6.72 (d, 1H), 7.50 (d, 1H), 7.84 (s, 1H), 10.49 (s, 1H, OH).

A reaction flask was charged, under N$_2$, with BB11 (239 mg, 0.95 mmol), 2,6-dichloro-N-hydroxybenzenecarboximidoyl chloride (642 mg, 2.86 mmol), cyclohexane (19 mL), and 2,6-lutidine (0.33 mL, 2.86 mmol). The reaction was heated at 80° C. for 20 h. The crude reaction mixture was purified by silica gel chromatography eluting with hexanes/EtOAc=20/1. Isolated 373 mg, 89% yield, of ligand A13 as a white solid. $^1$H NMR (300 MHz, C$_6$D$_6$) δ 1.18 (s, 9H, $^t$Bu), 6.40 (dd, 1H), 6.77 (d, 2H), 7.18-7.21 (m, 1H), 7.27-7.33 (m, 2H), 7.58 (d, 1H), 7.69-7.72 (m, 2H), 7.90 (d, 1H), 10.75 (s, 1H, OH).

Ligands A20, and A30-A32 were synthesized as described above for ligand A13. Ligand A20 was isolated in 91% yield, ligand A30 in 87% yield, ligand A31 in 77% yield, and ligand A32 in 47% yield.

Ligands A10 and A11 were synthesized as described for ligand A13 except the reaction temperature was 60° C. instead of 80° C. Ligand A10 was isolated in 93% yield, and ligand A11 in 81% yield.

Ligands A33 and A34 were synthesized as described for ligand A13 except an aqueous workup was done prior to chromatography. Cyclohexane was removed by rotary evaporation and the crude reaction mixture was taken up in CH$_2$Cl$_2$. The CH$_2$Cl$_2$ solution was washed twice with H$_2$O, once with brine, and then dried over Na$_2$SO$_4$. Ligand A33 was isolated in 44% yield and ligand A34 in 62% yield.

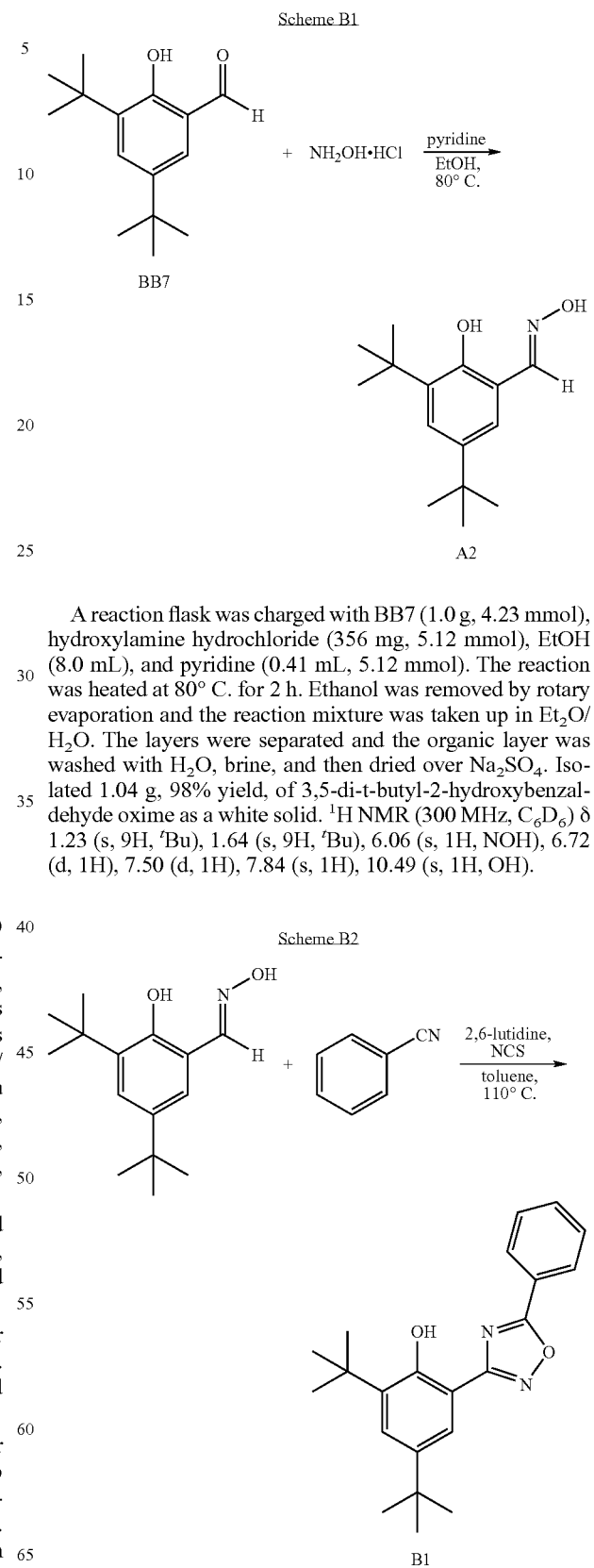

A reaction flask was charged, under $N_2$, with 3,5-di-tert-butyl-2-hydroxybenzaldehyde oxime (50 mg, 0.20 mmol), toluene (5 mL), 2,6-lutidine (0.07 mL, 0.60 mmol), N-chlorosuccinimide (30 mg, 0.22 mmol), and benzonitrile (0.21 mL, 2.0 mmol). The reaction was heated at 110° C. for 18 h. The crude reaction mixture was purified by silica gel chromatography eluting with hexanes/$CH_2Cl_2$=5/1. Isolated 47 mg, 67% yield, of ligand B1 as a white solid. $^1$H NMR (300 MHz, $C_6D_6$) δ 1.35 (s, 9H, $^t$Bu), 1.70 (s, 9H, $^t$Bu), 6.89-7.03 (m, 3H), 7.71 (d, 1H), 7.75-7.78 (m, 2H), 8.42 (d, 1H), 10.35 (s, 1H, OH).

Ligands B2 and B3 were synthesized as described above for ligand B1 in yields of 46% and 52%, respectively.

Ligands B4-B6 were synthesized as described for B1 except 5.0 eq of nitrile was used instead of 10.0 eq. Ligand B4 was isolated in 32% yield, ligand B5 in 42% yield, and ligand B6 in 57% yield.

Section 1C. 4-Aryl Phenol Thiazole Ligands

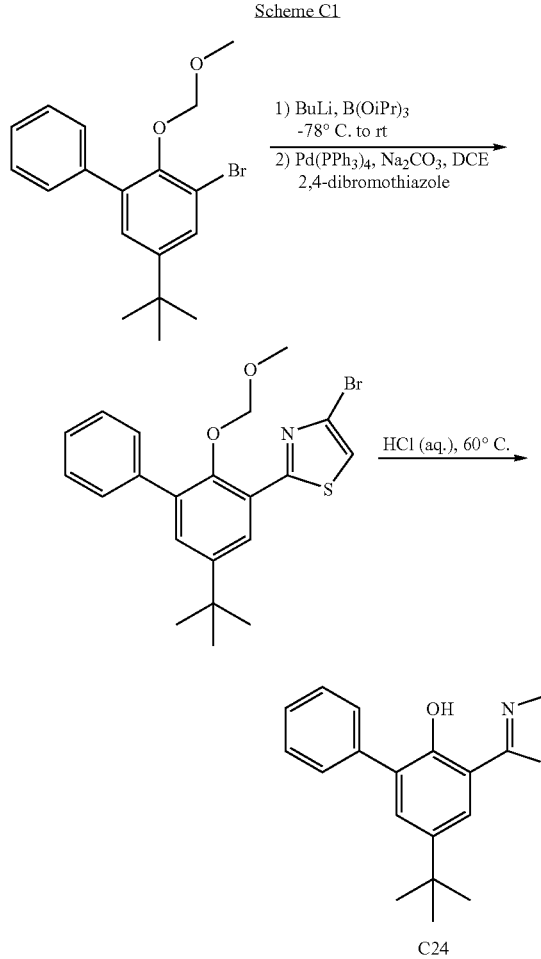

Scheme C1

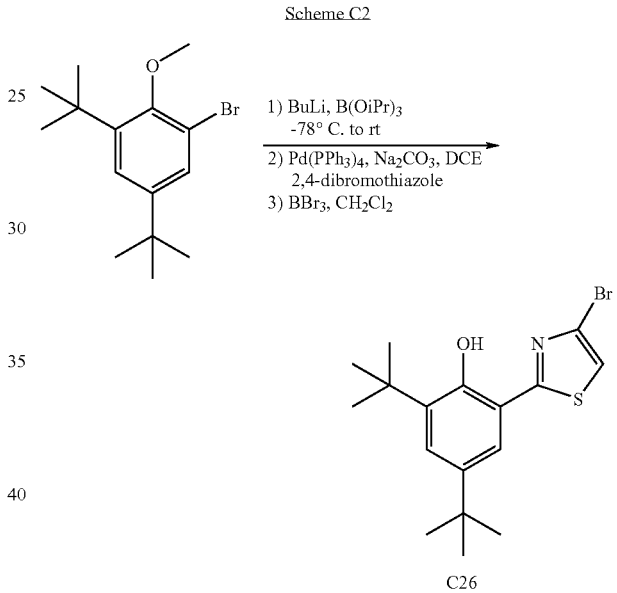

Scheme C2 n-BuLi (4.1 mL, 6.60 mmol, 1.6M in cyclohexane) was added dropwise to a solution of MOM-protected BB2 (1.92 g, 5.5 mmol) in THF (20 mL) at −78° C. under $N_2$. After 30 min. at −78° C., triisopropylborate (1.65 mL, 7.15 mmol) was added and the reaction was warmed to rt. After 1 h at rt, the reaction was quenched with MeOH (2 mL) then concentrated by rotary evaporation. The reaction flask was then charged, under $N_2$, with 2,4-dibromothiazole (972 mg, 4.0 mmol), $Pd(PPh_3)_4$ (318 mg, 5 mol %), $Na_2CO_3$ (2.1 mL, 2.0M solution in $H_2O$), and 1,2-dichloroethane (10 mL). The reaction was heated overnight at 80° C. After cooling to rt, $H_2O$ was added and the layers were separated. The aqueous phase was extracted several times with $CH_2Cl_2$. The combined organic layers were washed with $H_2O$, brine, and then dried over $Na_2SO_4$. Sodium sulfate was removed by filtration and to the organic solution was added conc. HCl (1 mL). The solution was heated to 60° C. and monitored by TLC and GC/MS until deprotection of the phenol was complete (~2 h). The reaction solution was washed with $H_2O$, sat. $NaHCO_3$ (aq.), brine, and then dried over $Na_2SO_4$. The crude product mixture was purified by silica gel chromatography eluting with 3-5% $Et_2O$ in Hexane. Isolated 1.1 g, 71% yield, of C24 as an off-white solid. $^1$H NMR (300 MHz, $CDCl_3$) δ 1.38 (s, 9H, $^t$Bu), 7.19 (s, 1H, CH, thiazole), 7.35-7.50 (m, 4H), 7.57 (d, 1H), 7.62-7.66 (m, 2H), 11.72 (s, 1H, OH).

Ligands C25 and C27 were synthesized as described above for C24 in yields of 79% and 59%, respectively.

n-BuLi (2.4 mL, 3.84 mmol, 1.6M in cyclohexane) was added dropwise to a solution of methyl-protected BB1 (1.0 g, 3.34 mmol) in $Et_2O$ (10 mL) at −78° C. under $N_2$. After 30 min. at −78° C., triisopropylborate (0.88 mL, 3.84 mmol) was added and the reaction was warmed to rt. After 1 h at rt, the reaction was quenched with MeOH (2 mL) then concentrated by rotary evaporation. The reaction flask was then charged, under $N_2$, with 2,4-dibromothiazole (486 mg, 2.0 mmol), $Pd(PPh_3)_4$ (116 mg, 5 mol %), $Na_2CO_3$ (1.1 mL, 2.0M solution in $H_2O$), and toluene (10 mL). The reaction was heated overnight at 90° C. After cooling to rt, $H_2O$ was added and the layers were separated. The aqueous phase was extracted several times with $CH_2Cl_2$. The combined organic layers were washed with $H_2O$, brine, and then dried over $Na_2SO_4$. The crude reaction mixture was dissolved in $CH_2Cl_2$ (5.0 mL) and $BBr_3$ (3.0 mL, 1.0M in $CH_2Cl_2$) was added dropwise at rt. After 1 h, the reaction was quenched with several drops of MeOH, washed with $H_2O$, sat. $NH_4Cl$ (aq.), brine, and then dried over $Na_2SO_4$. The crude product was purified by silica gel chromatography eluting with 1-2% $Et_2O$ in hexanes. Isolated 715 mg, 97% yield, of ligand C26 as a white solid.

Scheme C3

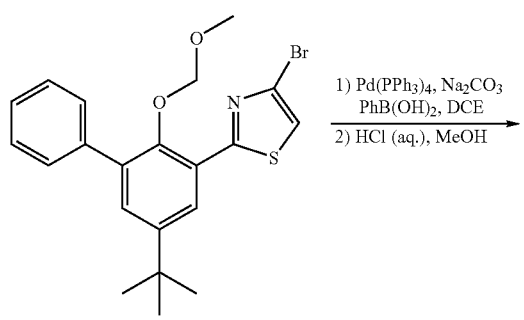

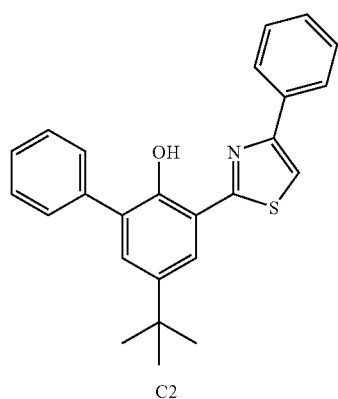

C2

Scheme C4

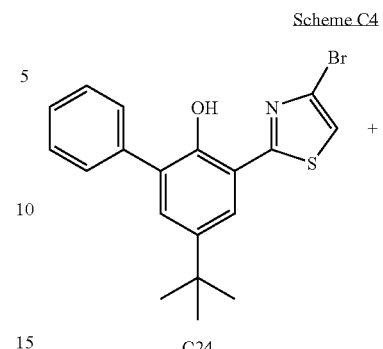

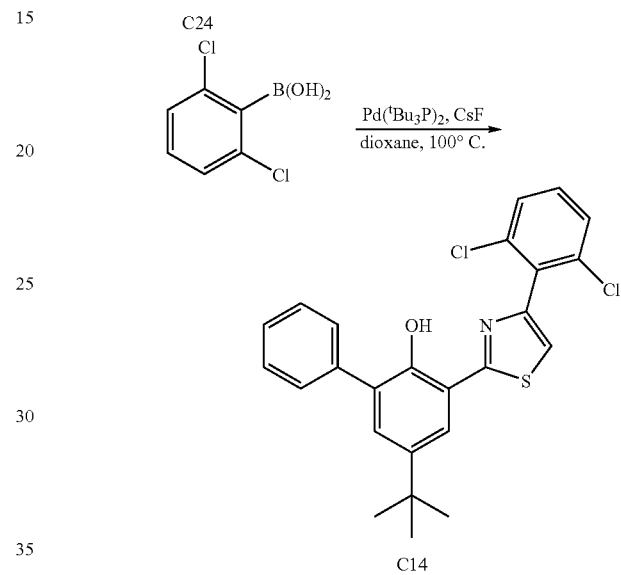

C14

A reaction flask was charged, under $N_2$, with MOM-protected C24 (142 mg, 0.33 mmol), phenylboronic acid (43 mg, 0.35 mmol), $Na_2CO_3$ (0.2 mL, 2.0 M solution in $H_2O$), $Pd(PPh_3)_4$ (20 mg, 5.0 mol %), and 1,2-dichloroethane (4 mL). The reaction was heated at 80° C. for 18 h. Water was added and the layers were separated. The aqueous phase was extracted three times with $CH_2Cl_2$. The combined organic layers were washed with water, brine, and then dried over $Na_2SO_4$. Sodium sulfate was removed by filtration and to the reaction solution was added conc. HCl (aq.) (1.0 mL) and MeOH (1.0 mL). After 2 h at 60° C., the reaction was washed with $H_2O$, sat. $NaHCO_3$ (aq.), brine, and then dried over $Na_2SO_4$. The crude product mixture was purified by silica gel chromatography eluting with 2-5% $Et_2O$ in hexanes. Isolated 57 mg, 45% yield, of ligand C2 as a white solid. $^1H$ NMR (300 MHz, $CDCl_3$) δ 1.39 (s, 9H, $^tBu$), 7.33-7.51 (m, 8H), 7.63-7.68 (m, 3H), 7.86-7.90 (m, 2H), 12.77 (s, 1H, OH).

Ligands C1, C3-C13, C20, and C21 were synthesized as described for C2 in yields ranging from 10-83%.

Ligand C15 was synthesized, in 81% yield, as described for C2 except toluene was used as solvent and the reaction was run at 90° C.

Ligand C16 was synthesized as described for C2 except the phenol was protected as the methyl ether instead of the methoxy methyl ether. Ligand C16 was obtained after deprotection with $BBr_3$ as described for C26. Ligand C16 was isolated in 32% yield.

A reaction flask was charged, under $N_2$, with C24 (74 mg, 0.19 mmol), 2,6-dichlorophenylboronic acid (57 mg, 0.30 mmol), CsF (35 mg, 0.23 mmol), $Pd(^tBu_3P)_2$ (5 mol %), and dioxane (2 mL). The reaction was heated at 100° C. overnight. The crude reaction mixture was purified by silica gel chromatography eluting with 2% $Et_2O$ in hexanes. Isolated 54 mg, 54% yield, of C14 as a light yellow solid. $^1H$ NMR (300 MHz, $CDCl_3$) δ 1.39 (s, 9H, $^tBu$), 7.24-7.45 (m, 8H), 7.62-7.67 (m, 3H), 12.41 (s, 1H, OH).

Ligands C18, C22, and C23 were synthesized as described for C14 in yields of 25%, 50%, and 37%, respectively.

Ligands C17 and C19 were synthesized as described for C14 but using $Pd(PPh_3)_4$, $Na_2CO_3$, and toluene. Yield of C17 was 60% and C19 was 54%.

Scheme C5

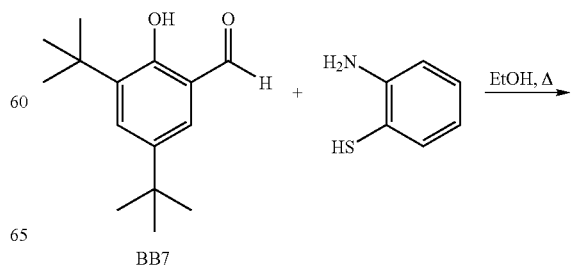

BB7

-continued

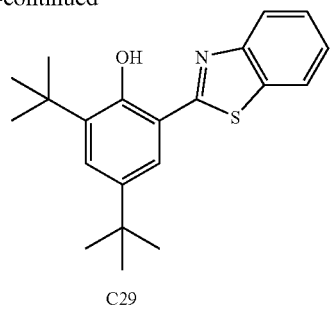

C29

A reaction flask was charged with BB7 (50 mg, 0.21 mmol), 2-aminothiophenol (0.023 mL, 0.21 mmol), and EtOH (2.0 mL). The reaction was heated at reflux for 2 days. The crude product mixture was purified by silica gel chromatography eluting with hexanes/EtOAc=20/1. Isolated 35 mg, 49% yield, of ligand C29 as a light yellow solid. $^1$H NMR (300 MHz, C$_6$D$_6$) δ 1.32 (s, 9H, $^t$Bu), 1.69 (s, 9H, $^t$Bu), 6.90-6.96 (m, 1H), 7.02-7.08 (m, 1H), 7.32 (m, 1H), 7.61-7.66 (m, 3H), 13.40 (s, 1H, OH).

Section 1D. 2-Aryl Phenol Thiazole Ligands

Scheme D1

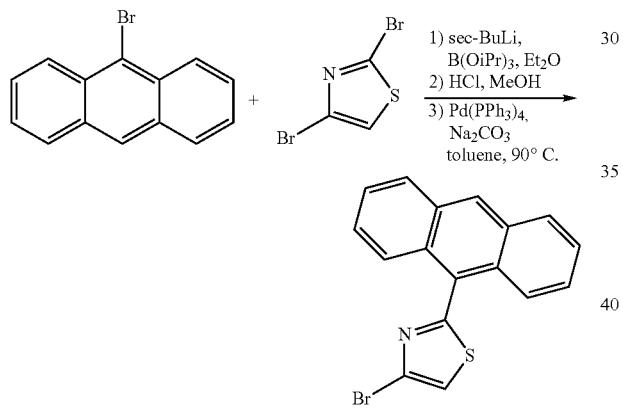

sec-BuLi (4.3 mL, 6.0 mmol, 1.4M solution in cyclohexane) was added dropwise to a solution of 9-bromoanthracene (1.29 g, 5.0 mmol) in Et$_2$O (20 mL) at 0° C. under N$_2$. The reaction was held at 0° C. for 15 minutes then warmed to rt and stirred an additional 45 minutes. Triisopropylborate (1.5 mL, 6.5 mmol) was added and the reaction was stirred at rt for 18 h. Concentrated HCl (1.0 mL) and MeOH (1.0 mL) was added and the reaction was stirred for 30 minutes. The layers were separated and the aqueous phase was extracted three times with CH$_2$Cl$_2$. The combined organic layers were washed with H$_2$O, sat. NaHCO$_3$ (aq.), brine, and then dried over Na$_2$SO$_4$. Filtration and concentration gave 1.05 g of 9-anthraceneboronic acid.

A reaction flask was charged, under N$_2$, with 9-anthraceneboronic acid (220 mg, 1.0 mmol), Pd(PPh$_3$)$_4$ (29 mg, 5.0 mol %), 2,4-dibromothiazole (122 mg, 0.5 mmol), Na$_2$CO$_3$ (0.5 mL, 2.0 M solution in H$_2$O), and toluene (4.0 mL). The reaction was heated at 90° C. for 18 h. After cooling to rt, water was added and the layers were separated. The aqueous phase was extracted three times with CH$_2$Cl$_2$. The combined organic layers were washed with H$_2$O, brine, and then dried over Na$_2$SO$_4$. The crude product mixture was purified by silica gel chromatography eluting with 1% Et$_2$O in hexanes. Isolated 93 mg, 50% yield, of 2-anthracenyl-4-bromothiazole.

Scheme D2

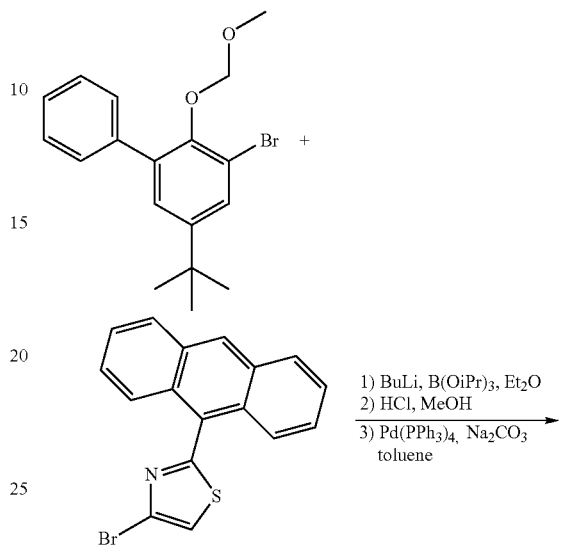

D1 n-BuLi (0.44 mL, 0.7 mmol, 1.6 M solution in cyclohexane) was added dropwise to a solution of MOM-protected BB2 (210 mg, 0.6 mmol) in Et$_2$O (2.0 mL) at −20° C. under N$_2$. After 20 minutes at −20° C., triisopropylborate (0.17 mL, 0.72 mmol) was added and the reaction was warmed to rt and stirred for 1 h. The reaction was quenched with MeOH (1.0 mL) then concentrated by rotary evaporation. The reaction flask was then charged, under N$_2$, with 2-anthracenyl-4-bromothiazole (93 mg, 0.27 mmol), Pd(PPh$_3$)$_4$ (16 mg, 5.0 mol %), Na$_2$CO$_3$ (0.15 mL, 2.0 M solution in H$_2$O), and toluene (2.0 mL). The reaction was heated at 90° C. for 18 h. Water was added, the layers separated, and the aqueous phase extracted three times with CH$_2$Cl$_2$. The combined organic layers were washed with H$_2$O, brine, and then dried over Na$_2$SO$_4$. Sodium sulfate was removed by filtration and to the reaction solution was added concentrated HCl (1.0 mL). The solution was heated at 60° C. for 1 h. The reaction solution was washed with H$_2$O, sat. NaHCO$_3$ (aq.), brine, and then dried over Na$_2$SO$_4$. The crude product mixture was purified by silica gel chromatography eluting with 3-5% Et$_2$O in hexanes. Isolated 32 mg, 24% yield, of ligand D1 as a yellow solid. $^1$H NMR (300 MHz, CDCl$_3$) δ 1.53 (s, 9H, $^t$Bu), 7.26-

7.52 (m, 8H), 7.59 (d, 2H), 7.72 (d, 2H), 7.81 (d, 1H), 8.00 (s, 1H), 8.06 (d, 2H), 8.62 (s, 1H), 11.98 (s, 1H, OH).

Ligands D2 and D3 were synthesized as described above in yields of 52% and 11%, respectively.

Section 1E. Phenol (NH)-Imidazoles

Scheme E1

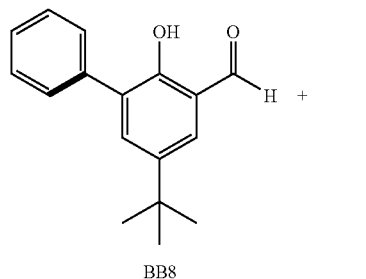

BB8

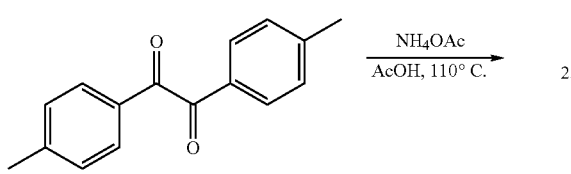

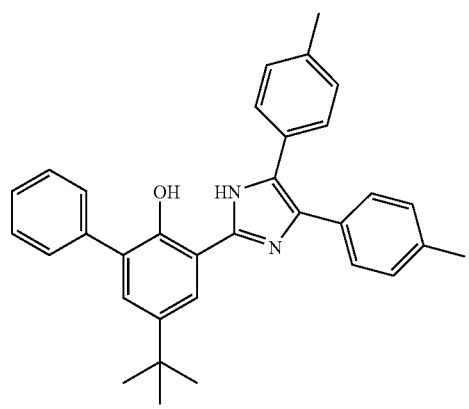

E10

BB8 (200 mg, 0.79 mmol), 4,4'-dimethylbenzil (187 mg, 0.79 mmol), ammonium acetate (485 mg, 6.30 mmol), and glacial acetic acid (4 mL) were combined and heated at 110° C. for 6 h. The reaction was diluted with $CH_2Cl_2$ then washed twice with $H_2O$, twice with sat. $NaHCO_3$ (aq.), once with brine, and dried over $Na_2SO_4$. The crude reaction mixture was purified by silica gel chromatography eluting with hexanes/$CH_2Cl_2$=1/1. Isolated 323 mg, 87% yield, of ligand E10 as a white solid. $^1$H NMR (300 MHz, $C_6D_6$) δ 1.33 (s, 9H, $^t$Bu), 2.07 (s, 3H, $CH_3$), 2.09 (s, 3H, $CH_3$), 6.91 (d, 2H), 6.97 (d, 2H), 7.07 (d, 2H), 7.20-7.25 (m, 2H), 7.34-7.39 (m, 2H), 7.59 (d, 1H), 7.77 (d, 2H), 7.97 (m, 2H), 8.70 (br s, 1H, NH), 13.78 (br s, 1H, OH).

Ligands E2-E9 and E11-E16 were prepared as described above for ligand E10 in yields ranging from 64-88%.

Scheme E2

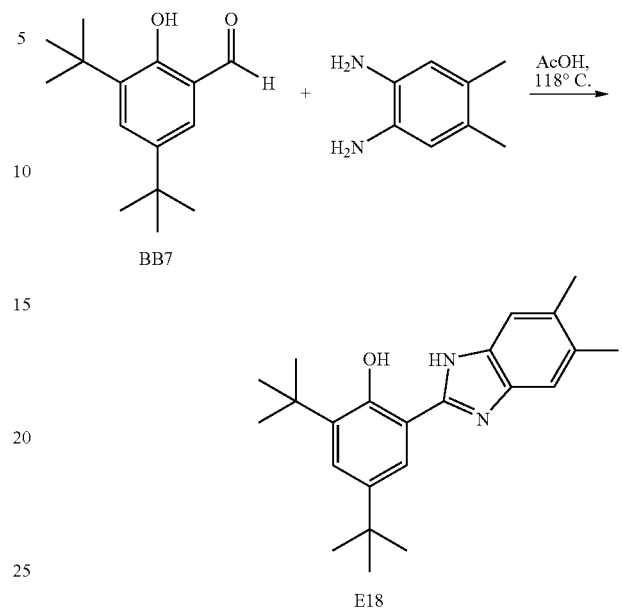

BB7 (59 mg, 0.25 mmol), 4,5-dimethyl-1,2-phenylenediamine (68 mg, 0.50 mmol), and glacial acetic acid (3 mL) were combined and heated at 118° C. for 24 h. The reaction was diluted with $H_2O$ then extracted three times with EtOAc. The combined EtOAc layers were washed once with $H_2O$, twice with sat. $NaHCO_3$ (aq.), once with brine, and then dried over $Na_2SO_4$. The crude product was purified by silica gel chromatography eluting with hexanes/EtOAc=5/1. Isolated 80 mg, 91% yield, of ligand E18 as a light yellow solid. $^1$H NMR (300 MHz, $C_6D_6$) δ 1.39 (s, 9H, $^t$Bu), 1.73 (s, 9H, $^t$Bu), 2.13 (s, 3H, $CH_3$), 2.20 (s, 3H, $CH_3$), 6.72 (s, 1H), 7.12 (d, 1H), 7.47 (s, 1H), 7.64 (d, 1H), 8.21 (br s, 1H, NH), 14.34 (br s, OH).

Ligands E17 and E19-E24 were synthesized as described above for ligand E18 in yields ranging from 61-91% with the exception of ligand E21 which was isolated in 31% yield.

Section 1F. Phenol (NMe)-Imidazoles

Scheme F1

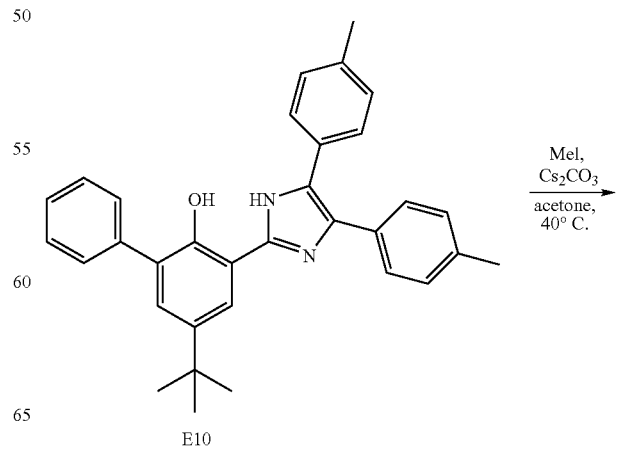

E10

-continued

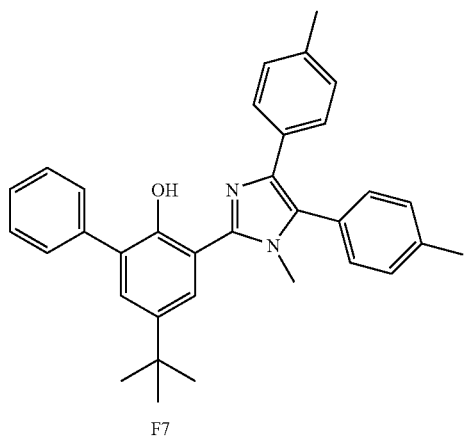

F7

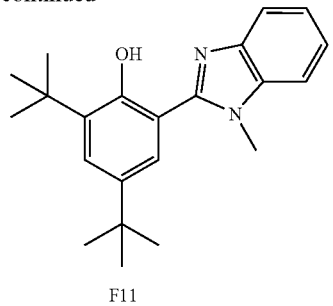

F11

A reaction flask was charged with E10 (173 mg, 0.37 mmol), Cs$_2$CO$_3$ (143 mg, 0.44 mmol), acetone (5 mL), and iodomethane (0.027 mL, 0.43 mmol). The reaction was heated at 40° C. for 24 h. Acetone was removed by rotary evaporation and the crude reaction mixture was taken up in CH$_2$Cl$_2$. The CH$_2$Cl$_2$ solution was washed twice with H$_2$O, once with brine, and then dried over Na$_2$SO$_4$. The crude product mixture was purified by silica gel chromatography eluting with hexanes/EtOAc=20/1 then 10/1. Isolated 122 mg, 66% yield, of ligand F7 as a white solid. $^1$H NMR (300 MHz, C$_6$D$_6$) δ 1.33 (s, 9H, $^t$Bu), 2.05 (s, 3H, CH$_3$), 2.11 (s, 3H, CH$_3$), 2.97 (s, 3H, CH$_3$), 6.93-6.98 (m, 6H), 7.22-7.26 (m, 1H), 7.36-7.42 (m, 2H), 7.45 (d, 1H), 7.61 (d, 1H), 7.73 (d, 2H), 8.01 (d, 2H), 13.70 (br s, 1H, OH).

Ligands F2-F6 and F8-F10 were synthesized as described above for F7 in yields ranging from 50-80%.

Ligand F1 was synthesized as described above for ligand F7 with the exception that K$_2$CO$_3$ was used instead of Cs$_2$CO$_3$. Ligand F1 was isolated in 65% yield.

Scheme F2

FF1

DDQ (2,3-dichloro-5,6-dicyano-1,4-benzoquinone) (86 mg, 0.38 mmol) was added to a solution of imine FF1 (117 mg, 0.35 mmol) in acetonitrile (6 mL) at rt. After 6 h the crude reaction mixture was purified by silica gel chromatography eluting with hexanes/EtOAc=20/1. Isolated 65 mg, 55% yield, of ligand F11 as a white solid. $^1$H NMR (300 MHz, CD$_2$Cl$_2$) δ 1.37 (s, 9H, $^t$Bu), 1.48 (s, 9H, $^t$Bu), 4.00 (s, 3H, CH$_3$), 7.32-7.37 (m, 2H), 7.42-7.46 (m, 2H), 7.55 (d, 1H), 7.71-7.73 (m, 1H), 12.74 (br s, 1H, OH).

F1 was prepared by reacting BB7 with N-methyl-1,2-phenylenediamine using techniques known to those of skill in the art.

Ligand F12 was synthesized in 62% yield as described above for ligand F11.

Section 1G. Phenol Pyrazole Ligands

Scheme G1

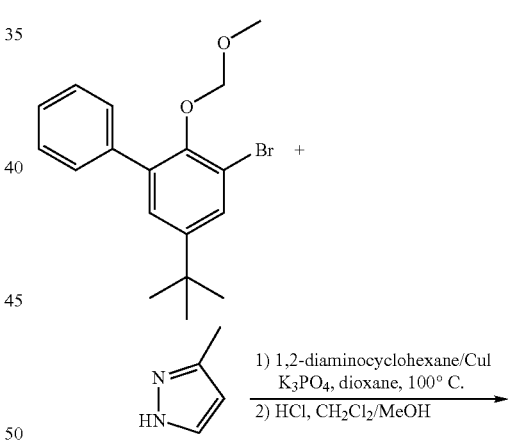

G2

A reaction flask was charged, under N$_2$, with 3-methylpyrazole (49 mg, 0.6 mmol), MOM-protected BB2 (175 mg, 0.50 mmol), CuI (10 mg, 0.05 mmol), K$_3$PO$_4$ (222 mg, 1.05 mmol), (trans)-1,2-diaminocyclohexane (11.0 mg, 0.10 mmol), and dioxane (1.0 mL). The reaction was heated at 100° C. for 20 h. After cooling to rt, the reaction suspension was filtered through a small plug of silica gel washing through with CH$_2$Cl$_2$. The CH$_2$Cl$_2$ solution was washed with H$_2$O, brine, and then dried over Na$_2$SO$_4$. Purified by silica gel chromatography eluting with hexane/Et$_2$O=95/5 to give 27 mg of the MOM-protected ligand. To the MOM-protected ligand, in 2 mL of CH$_2$Cl$_2$/MeOH (1/1), was added 10 drops of conc. HCl. Deprotection was complete after 2 h at 60° C. The reaction was diluted with CH$_2$Cl$_2$ then washed with H$_2$O, sat. NaHCO$_3$ (aq.), brine, and dried over Na$_2$SO$_4$. Purified by passing through a small plug of silica gel using hexanes/Et$_2$O=80/20. Isolated 23 mg, 15% yield, of ligand G2 as an off-white solid. $^1$H NMR (300 MHz, CDCl$_3$) δ 1.36 (s, 9H, $^t$Bu), 2.35 (s, 3H, CH$_3$), 6.27 (d, 1H), 7.23 (d, 1H), 7.30 (d, 1H), 7.34 (m, 1H), 7.44 (m, 2H), 7.64 (m, 2H), 7.93 (d, 1H), 11.73 (s, 1H, OH).

Ligands G1 and G3 were synthesized as described above in isolated yields of 9% and 14%, respectively.

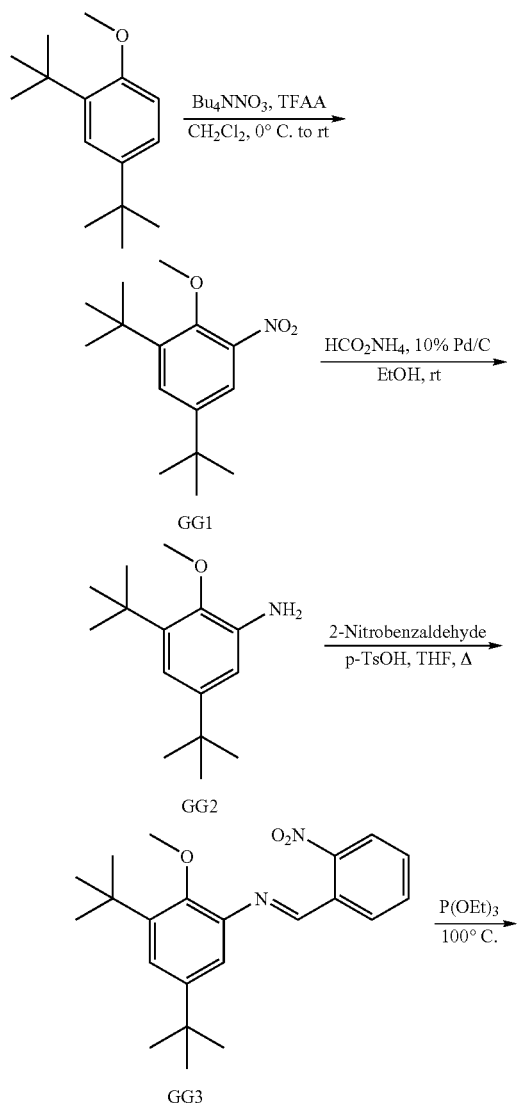

Scheme G2

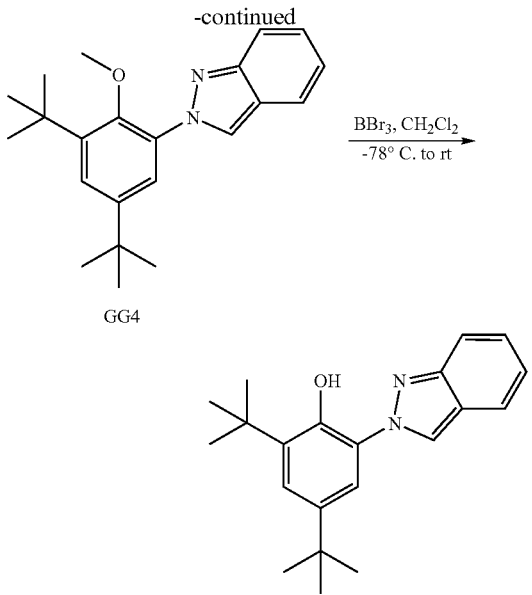

Synthesis of GG1. Trifluoroacetic anhydride (1.35 mL, 9.52 mmol) was added dropwise to a solution of 2,4-di-tert-butylanisole (2.0 g, 9.08 mmol) and tetrabutylammonium nitrate (2.9 g, 9.52 mmol) in CH$_2$Cl$_2$ at 0° C. under N$_2$. The reaction was allowed to warm to rt. After 2 h, the reaction was washed once with H$_2$O, twice with 10% HCl (aq.), once with brine, and then dried over Na$_2$SO$_4$. The crude product mixture was chromatographed on silica gel eluting with hexanes/EtOAc=40/1. Isolated 1.96 g, 81% yield, of GG1 as a yellow solid.

Synthesis GG2. A reaction flask was charged, under N$_2$, with GG1 (133 mg, 0.50 mmol), 10% Pd/C (a couple of small spatula scoops), EtOH (2.0 mL), and ammonium formate (158 mg, 2.50 mmol). After 1 h at rt the reaction was filtered through a pad of Celite and washed through with EtOAc. The EtOAc solution was washed twice with H$_2$O, once with brine, and then dried over Na$_2$SO$_4$. Isolated 110 mg, 93% yield, of GG2 as a white solid. The product was used directly in the next step without further purification.

Synthesis of GG4. GG2 (110 mg, 0.47 mmol), 2-nitrobenzaldehyde (71 mg, 0.47 mmol), and p-TsOH (~10.0 mol %) were combined in THF (10 mL) over 3 Å molecular sieves. The reaction was heated at reflux for 4 h. The sieves were removed by filtration and the reaction solution was concentrated to give imine GG3 as a yellow solid. GG3 was taken up in P(OEt)$_3$ (1 mL) and heated at 100° C. for 18 h. The reaction mixture was purified by silica gel chromatography eluting with hexanes/EtOAc=20/1. Isolated 119 mg, 76% yield, of GG4 as a light yellow powder.

Synthesis of Ligand G4. BBr$_3$ (0.51 mL, 1.0 M in CH$_2$Cl$_2$) was added dropwise to a solution of GG4 (115 mg, 0.34 mmol) in CH$_2$Cl$_2$ (4 mL) at −78° C. under N$_2$. The reaction was warmed slowly to rt and stirred overnight. The reaction was washed with sat. NaHCO$_3$ (aq.), H$_2$O, brine, and then dried over Na$_2$SO$_4$. Purified by silica gel chromatography eluting with hexanes/EtOAc=10/1. Isolated 60 mg, 55% yield, of ligand G4 as a faint yellow solid. $^1$H NMR (300 MHz, C$_6$D$_6$) δ 1.32 (s, 9H, $^t$Bu), 1.68 (s, 9H, $^t$Bu), 6.93 (m, 1H), 7.10 (m, 2H), 7.42 (d, 1H), 7.52 (d, 1H), 7.57 (d, 1H), 7.65 (s, 1H), 12.70 (s, 1H, OH).

Section 2. Primary Screening

Section 2A. General Protocols and Materials

All air sensitive procedures were performed under a purified argon or nitrogen atmosphere in a Vacuum Atmospheres or MBraun glove box. All solvents used were anhydrous, de-oxygenated and purified according to known techniques. All ligands and metal precursors were prepared according to procedures known to those of skill in the art, e.g., under inert atmosphere conditions, etc.

Group 13 reageants were purchased from Strem Chemicals Inc. (Newburyport, Mass.) and Azko Chemical Inc. (Chicago, Ill.). Activators were purchased from Boulder Scientific Company (Mead, Colo.) or prepared according to procedures known to those of skill in the art.

Section 2Bi. 1-Octene Homopolymerization Examples in a 96-well Format

1-Octene homopolymerization reactions were performed in a 96-well format using 8 mm×30 mm tarred glass vials arranged in an 8×12 array within an aluminum block. Reagents were added from stock solutions or slurries to the 8 mm×30 mm vials using a Cavro liquid handling robot driven by library design and/or automation software, such as Library Studio® and Impressionist® software, available from Symyx Technologies, Inc., of Santa Clara, Calif., which is described in European Patent No. 1080435, U.S. Pat. No. 6,507,645, and European Patent No. 1175645. The vials contain parylene coated stir-bars and were weighed prior to their use in screening (described below). Solutions of a parent array of desired ligands were transferred to arrays of glass vials (0.3-0.6 µmol of each ligand) and the solvent was then removed from the ligand array using a nitrogen or argon stream. The resultant ligand array was contacted with a suitable group IV precursor, a group 13 reagent, 100 µl of 1-octene and an activator (or combination of group 13 reagents and activators, from a stock solution). A Teflon sheet and rubber gasket were then placed over the top of the array and an aluminum cover was screwed on the top to seal the array (reactor A). Specific details are described below. The aluminum block reactor (reactor A) has been described in U.S. Pat. No. 6,507,645, which is incorporated by reference herein.

Section 2Bii. Stock Solutions

Solutions of metal precursors were prepared in toluene typically at 10-20 mmol/l: $Ti(CH_2C_6H_5)_4$; $Zr(CH_2C_6H_5)_4$; $Hf(CH_2C_6H_5)_4$; $Ti(N(CH_3)_2)_4$; $Zr(N(CH_3)_2)_4$; $Hf(N(CH_3)_2)_4$; $TiC_2(N(CH_3)_2)_2$.

Solutions of group 13 reagents were prepared in toluene typically at 50-250 mmol/l: $Al(Me)_3$, (TMA); $Al(Et)_3$, (TEA); $Al(^iBu)_3$, (TIBA); PMAO-IP & MMAO-3A. Alumoxanes were supplied by Azko Chemical Inc., Chicago, Ill.

Solutions of activators were prepared in toluene typically at 4-10 mmol/l; $B(C_6F_5)_3$; $[C(C_6H_5)_3]^+[B(C_6F_5)_4]^-$, (TBF20); $[HN(CH_3)_2Ph]+[B(C_6F_5)_4]^-$, (ABF20).

Section 2Biii. In-Situ Preparation and Screening of Ligand-Group IV Compositions Method 1: 75° C. Complexation, Reactor A, 75° C. Screening: the ligand array (0.3-0.6 µmol of each ligand) was first contacted with toluene (ca. 100 µL per well) and then toluene solutions of the desired group IV precursor (15-30 µL per well, 0.3 µmol) were added. The resultant mixtures were stirred for a period of 30-45 minutes at 75° C. The array was then treated with a stock solution of the appropriate group 13 reagent activator (30 µL per well, contact time of ca. 10 min), followed by 100 µl of 1-octene, and finally an activator (or activator mixture, 30-75 µL per well). Immediately a Teflon sheet and rubber gasket were then placed over the top of the array and an aluminum cover was screwed on the top to seal the array (reactor A) and the array was stirred at 75° C. for 1 hour.

Section 2Biv. Product Analysis

After 1 hour the reactor was unsealed and the array was removed. The array of vials was then transferred to a fume hood, and to each vial was quenched by 100-300 µL of methanol. The volatiles were removed by using a nitrogen stream, followed by drying the array over-night in vacuo. The vials were weighed in order to determine the yield of polymer produced. 800 µL of toluene was added to select and the resulting toluene solutions were mechanically agitated for approximately an hour. An aliquot was injected into a rapid-GPC in order to determine Mw. Table 2A presents the results from the 1-octene homopolymerization reactions performed in a 96-well format.

TABLE 2A

Select Polymerization Examples: 1-Octene Homopolymerization

| Example | Ligand | µmol Ligand | Group IV Precursor (0.3 µmol) | mol equivalents of Group 13 Reagent | Group 13 Reagent | mol equivalents of Activation Reagent | Activation Reagents | µmol catalyst | Reactor | mg poly-1-octene produced | Mw (k) |
|---|---|---|---|---|---|---|---|---|---|---|---|
| O1 | E17 | 0.3 | $Hf(CH_2C_6H_5)_4$ | 5 | TIBA | 1 | ABF20 | 0.3 | A | 21 | — |
| O2 | E18 | 0.3 | $Zr(CH_2C_6H_5)_4$ | 5 | TIBA | 1 | ABF20 | 0.3 | A | 12 | — |
| O3 | E19 | 0.3 | $Zr(CH_2C_6H_5)_4$ | 5 | TIBA | 1 | ABF20 | 0.3 | A | 13 | — |
| O4 | E19 | 0.3 | $Hf(CH_2C_6H_5)_4$ | 5 | TIBA | 1 | ABF20 | 0.3 | A | 57 | — |
| O5 | E20 | 0.3 | $Hf(CH_2C_6H_5)_4$ | 5 | TIBA | 1 | ABF20 | 0.3 | A | 31 | — |
| O6 | E23 | 0.3 | $Hf(CH_2C_6H_5)_4$ | 5 | TIBA | 1 | ABF20 | 0.3 | A | 15 | — |
| O7 | E24 | 0.3 | $Hf(NMe_2)_4$ | 15 | TIBA | 1 | ABF20 | 0.3 | A | 11 | — |
| O8 | F11 | 0.3 | $Ti(NMe_2)_4$ | 15 | TIBA | 1 | ABF20 | 0.3 | A | 11 | 126 |

Section 2Ci. Ethylene-Styrene Copolymerization Examples in a 96-Well Format

Ethylene-styrene copolymerization reactions were performed in a 96-well format using 8 mm×30 mm tarred glass vials arranged in an 8×12 array within an aluminum block. Reagents were added from stock solutions or slurries to the 8 mm×30 mm vials using a Cavro liquid handling robot driven by library design and/or automation software, such as Library Studio® and Impressionist® software, available from Symyx Technologies, Inc., of Santa Clara, Calif., which is described in European Patent No. 1080435, U.S. Pat. No. 6,507,645, and European Patent No. 1175645. The vials contain parylene coated stir-bars and were weighed prior to their use in screening (described below). Solutions of a parent array of desired ligands were transferred to arrays of glass vials (0.3-0.6 µmol of each ligand) and the solvent was then removed from the ligand array using a nitrogen or argon stream. The resultant ligand array was contacted with a suitable group IV precursor, a group 13 reagent and an activator (or combination of group 13 reagents and activators, from a stock solution), followed by 20 µl of styrene. The array was sealed with a reactor top capable of delivering gaseous reagent(s) (reactor B) and pressurized with ethylene. Specific details are described below. The HiP reactor (reactor B) is described in U.S. Patent Publication No. 2003-0161763, which is incorporated herein by reference.

Section 2Cii. Stock Solutions

Solutions of metal precursors were prepared in toluene typically at 10-20 mmol/l: $Ti(CH_2C_6H_5)_4$; $Zr(CH_2C_6H_5)_4$; $Hf(CH_2C_6H_5)_4$; $Ti(N(CH_3)_2)_4$; $Zr(N(CH_3)_2)_4$; $Hf(N(CH_3)_2)_4$; $TiCl_2(N(CH_3)_2)_2$.

Solutions of group 13 reagents were prepared in toluene typically at 50-250 mmol/l: $Al(Me)_3$, (TMA); $Al(Et)_3$, (TEA); $Al(^iBu)_3$, (TIBA); PMAO-IP & MMAO-3A. Aluموxanes were supplied by Azko Chemical Inc., Chicago, Ill.

Solutions of activators were prepared in toluene typically at 4-10 mmol/l; $B(C_6F_5)_3$; $[C(C_6H_5)_3]^+[B(C_6F_5)_4]^-$, (TBF20); $[HN(CH_3)_2Ph]+[B(C_6F_5)_4]^-$, (ABF20).

Section 2Ciii. In-Situ Preparation and Screening of Ligand-Group IV Compositions Method 1: 75° C. Complexation, Reactor B, 75° C. Screening: the ligand array (0.3-0.6 µmol of each ligand) was first contacted with toluene (ca. 100 µL per well) and then toluene solutions of the desired group IV precursor (30 µL per well, 0.3 µmol) were added. The resultant mixtures were stirred for a period of 30-45 minutes at 75° C. The array was then treated with a stock solution of the appropriate group 13 reagent activator (30 µL per well, contact time of ca. 10 min), followed by an activator (or activator mixture, 30-75 µL per well, contact time of ≦5 min). 20 µl of styrene was added to each vial, and the array was immediately sealed using a reactor top capable of delivering gaseous reagent(s) (reactor B) and stirred at 75° C. under 50 psi of ethylene for 1 hour.

Section 2Civ. Product Analysis

After 1 hour the reactor was depressurized and the array was removed. The array of vials was then transferred to a fume hood, and to each vial was quenched by 500 µL of acidified methanol. A Teflon sheet and rubber gasket are then placed over the top of the array and an aluminum cover was screwed on the top to seal the array. The array was first mechanically agitated for approximately an hour and then centrifuged at 1500 rpm for 10 minutes. The acidified methanol solution was decanted off. This process was repeated twice more with acidified methanol, followed by three washing rounds using methylethylketone (MEK) to remove soluble polystyrene. The array was then dried over-night in vacuo. The vials were weighed in order to determine the yield of polymer produced. 1,2,4-Trichlorobenzene (TCB) was added vials which met a minimum yield criteria, and the resulting TCB solutions were heated for 2 hours at 140° C. An aliquot of the hot solution was deposited on a wafer, in order to form a thin film. The resultant polymer thin-films were analyzed via a rapid FT-IR method (details in the secondary screening section) to determine total mol % styrene. Table 2B presents the results from the ethylene-styrene copolymerization reactions performed in a 96-well format.

TABLE 2B

Select Polymerization Examples: Ethylene-Styrene Copolymerizations

| Example | Ligand | µmol Ligand | Group IV Precursor (0.3 µmol) | mol equivalents of Group 13 Reagent | Group 13 Reagent | mol equivalents of Activation Reagent | Activation Reagents | µmol catalyst | Reactor | mg polymer produced | mol % total Styrene |
|---|---|---|---|---|---|---|---|---|---|---|---|
| ES1 | A1 | 0.6 | $Zr(CH_2C_6H_5)_4$ | 5 | TIBA | 1 | ABF20 | 0.3 | B | 23 | 1 |
| ES2 | A1 | 0.3 | $Zr(CH_2C_6H_5)_4$ | 5 | TIBA | 1 | ABF20 | 0.3 | B | 9 | 1 |
| ES3 | E3 | 0.3 | $Zr(NMe_2)_4$ | 15 | TIBA | 1 | ABF20 | 0.3 | B | 5 | 1 |
| ES4 | E17 | 0.3 | $Zr(CH_2C_6H_5)_4$ | 5 | TIBA | 1 | ABF20 | 0.3 | B | 34 | 1 |
| ES5 | E18 | 0.3 | $Zr(CH_2C_6H_5)_4$ | 5 | TIBA | 1 | ABF20 | 0.3 | B | 12 | 5 |
| ES6 | E19 | 0.3 | $Zr(CH_2C_6H_5)_4$ | 5 | TIBA | 1 | ABF20 | 0.3 | B | 53 | 2 |
| ES7 | E19 | 0.3 | $Zr(NMe_2)_4$ | 15 | TIBA | 1 | ABF20 | 0.3 | B | 10 | 1 |
| ES8 | E20 | 0.3 | $Zr(CH_2C_6H_5)_4$ | 5 | TIBA | 1 | ABF20 | 0.3 | B | 31 | 1 |
| ES9 | E21 | 0.3 | $Zr(CH_2C_6H_5)_4$ | 5 | TIBA | 1 | ABF20 | 0.3 | B | 25 | 2 |
| ES10 | E22 | 0.3 | $Zr(CH_2C_6H_5)_4$ | 5 | TIBA | 1 | ABF20 | 0.3 | B | 26 | 1 |
| ES11 | E23 | 0.3 | $Zr(CH_2C_6H_5)_4$ | 5 | TIBA | 1 | ABF20 | 0.3 | B | 39 | 6 |
| ES12 | E24 | 0.3 | $Zr(CH_2C_6H_5)_4$ | 5 | TIBA | 1 | ABF20 | 0.3 | B | 5 | 2 |
| ES13 | F11 | 0.3 | $Hf(NMe_2)_4$ | 15 | TIBA | 1 | ABF20 | 0.3 | B | 3 | 2 |

Section 2Di. Propylene Homopolymerization Examples in a 96-Well Format

Propylene homopolymerization reactions were performed in a 96-well format using 8 mm×30 mm tarred glass vials arranged in an 8×12 array within an aluminum block. Reagents were added from stock solutions or slurries to the 8 mm×30 mm vials using a Cavro liquid handling robot driven library design and/or automation software, such as Library Studio® and Impressionist® software, available from Symyx Technologies, Inc., of Santa Clara, Calif., which is described in European Patent No. 1080435, U.S. Pat. No. 6,507,645, and European Patent No. 1175645. The vials contain parylene coated stir-bars and were weighed prior to their use in screening (described below). Solutions of a parent array of desired ligands were transferred to arrays of glass vials (0.3-0.6 µmol of each ligand) and the solvent was then removed from the ligand array using a nitrogen or argon stream. The resultant ligand array under went two possible paths: i) the ligand array was contacted with a suitable group IV precursor, a group 13 reagent and an activator (or combination of group 13 reagents and activators, from a stock solution), sealed with a reactor top capable of delivering gaseous reagent(s) (reactor B) and pressurized with propylene; or ii) the ligand array was contacted with a suitable group IV precursor, a group 13 reagent, pressurized with propylene within a parallel batch reactor with in situ injection capability (reactor C), upon reaching the desired reaction pressure within the reactor, an activator (or combination of group 13 reagents and activators, from a stock solution) was added via in situ injection. Specific details are described below. The HiP reactor (reactor B) is described in U.S. Patent Publication No. 2003-0161763, and the parallel batch reactor (reactor C) is described in WO 04/060550 and U.S. Patent Publication No. 2004/0121448, each of which is incorporated herein by reference.

Section 2Dii. Stock Solutions

Solutions of metal precursors were prepared in toluene typically at 10 mmol/l: $Ti(CH_2C_6H_5)_4$; $Zr(CH_2C_6H_5)_4$; $Hf(CH_2C_6H_5)_4$; $Ti(N(CH_3)_2)_4$; $Zr(N(CH_3)_2)_4$; $Hf(N(CH_3)_2)_4$; $TiCl_2(N(CH_3)_2)_2$. $[Zr(CH_2C_6H_5)_3^+][C_6H_5CH_2B(C_6F_5)_3^-]$ and $[Hf(CH_2C_6H_5)_3^+][C_6H_5CH_2B(C_6F_5)_3^-]$ were generated in situ within the 96 well arrays by addition of 0.3 μmol of $M(CH_2C_6H_5)_4$ followed by 0.3 μmol of $B(C_6F_5)_3$.

Solutions of group 13 reagents were prepared in toluene typically at 50-250 mmol/l: $Al(Me)_3$, (TMA); $Al(Et)_3$, (TEA); $Al(^iBu)_3$, (TIBA); PMAO-IP & MMAO-3A. Alumoxanes were supplied by Azko Chemical Inc., Chicago, Ill.

Solutions of activators were prepared in toluene typically at 4-10 mmol/l; $B(C6F_5)_3$, (BF15); $[C(C_6H_5)_3]^+[B(C_6F_5)_4]^-$, (TBF20); $[HN(CH_3)_2Ph]+[B(C_6F_5)_4]^-$, (ABF20); $[HN(C_6H_{15})_2(\text{-}para\text{-}C_4H_9\text{-}Ph)]+[B(C_6F_5)_4]^-$, (SJBF20). SJBF20+BF15 was prepared before use as a toluene solution.

Section 2Diii. In-Situ Preparation and Screening of Ligand-Group IV Compositions Method 1: 75° C. Complexation, Reactor B, 75° C. Screening: the ligand array (0.3-0.6 μmol of each ligand) was first contacted with toluene (ca. 100 μL per well) and then toluene solutions of the desired group IV precursor (30 μL per well, 0.3 μmol) were added. The resultant mixtures were stirred for a period of 30-45 minutes at 75° C. The array was then treated with a stock solution of the appropriate group 13 reagent activator (30 μL per well, contact time of ca. 10 min), followed by an activator (or activator mixture, 30-75 μL per well, contact time of ≦5 min). The array was sealed using a reactor top capable of delivering gaseous reagent(s) (reactor B) and stirred at 75° C. under 80 psi of propylene for 1 hour.

Method 2: 75° C. Complexation, Reactor C, 75° C. Screening: the ligand array (0.3-0.6 μmol of each ligand) was first contacted with toluene (ca. 100 μL per well) and then toluene solutions of the desired group IV precursor (30 μL per well, 0.3 μmol) were added. The resultant mixtures were stirred for a period of 30-45 minutes at 75° C. The array was then treated with a stock solution of the appropriate group 13 reagent activator (30 μL per well, contact time of ca. 10 min), while aging, the array was inserted into a heated (75° C.) parallel batch reactor with in situ injection capability (reactor C), which was subsequently pressured to 80 psi propylene. Following the ca. 10 minutes of aging (and at 80 psi propylene), an activator (or activator mixture, 30-75 μL per well) was added via in situ injection to the array. Post activation step, the array continued to be stirred while the reactor was at 75° C. under 80 psi of propylene for 1 hour.

Section 2Div. Product Analysis

After 1 hour the reactor was depressurized and the array was removed. The array of vials was then transferred to a fume hood, and to each vial was quenched by added 100-300 uL of methanol. The volatiles were removed by using a nitrogen stream, followed by drying the array over-night in vacuo. The vials were weighed in order to determine the yield of polymer produced. 1,2,4-Trichlorobenzene (TCB) was added vials which met a minimum yield criteria, and the resulting TCB solutions were heated for 2 hours at 140° C. An aliquot of the hot solution was deposited on a wafer, in order to form a thin film. The resultant polymer thin-films were analyzed via a rapid-FT-IR method (details in the secondary screening section) to determine tacticity. Table 2C presents the results from the propylene homopolymerization reactions performed in a 96-well format.

TABLE 2C

Select Polymerization Examples: Propylene Homopolymerizations

| Example | Ligand | μmol Ligand | Group IV Precursor (0.3 μmol) | mol equivalents of Group 13 Reagent | Group 13 Reagent | mol equivalents of Activation Reagent | Activation Reagents | μmol catalyst | Reactor | mg polypropylene produced | IR Indices |
|---|---|---|---|---|---|---|---|---|---|---|---|
| P1  | A3  | 0.6 | $Zr(CH_2C_6H_5)_4$ | 5 | TIBA | 1 + 2 | SJBF20 + BF15 | 0.3 | C | 31  | 0.37 |
| P2  | A3  | 0.3 | $Zr(CH_2C_6H_5)_4$ | 5 | TIBA | 1 + 2 | SJBF20 + BF15 | 0.3 | C | 22  | 0.39 |
| P3  | A5  | 0.3 | $Zr(CH_2C_6H_5)_4$ | 5 | TIBA | 1     | SJBF20        | 0.3 | C | 65  | 0.33 |
| P4  | A5  | 0.6 | $Zr(CH_2C_6H_5)_4$ | 5 | TIBA | 1     | TBF20         | 0.3 | C | 9   | 0.27 |
| P5  | A5  | 0.3 | $Hf(CH_2C_6H_5)_4$ | 5 | TIBA | 1     | SJBF20        | 0.3 | C | 94  | 0.24 |
| P6  | A5  | 0.6 | $Hf(CH_2C_6H_5)_4$ | 5 | TIBA | 1     | SJBF20        | 0.3 | C | 88  | 0.22 |
| P7  | A9  | 0.6 | $Zr(CH_2C_6H_5)_4$ | 5 | TIBA | 1 + 2 | SJBF20 + BF15 | 0.3 | C | 92  | 0.44 |
| P8  | A9  | 0.3 | $Zr(CH_2C_6H_5)_4$ | 5 | TIBA | 1     | SJBF20        | 0.3 | C | 14  | 0.45 |
| P9  | A9  | 0.6 | $Hf(CH_2C_6H_5)_4$ | 5 | TIBA | 1     | TBF20         | 0.3 | C | 91  | 0.2  |
| P10 | A10 | 0.6 | $Zr(CH_2C_6H_5)_4$ | 5 | TIBA | 1 + 2 | SJBF20 + BF15 | 0.3 | C | 11  | 0.58 |
| P11 | A12 | 0.6 | $Zr(CH_2C_6H_5)_4$ | 5 | TIBA | 1     | TBF20         | 0.3 | C | 53  | 0.28 |
| P12 | A12 | 0.3 | $Zr(CH_2C_6H_5)_4$ | 5 | TIBA | 1     | TBF20         | 0.3 | C | 32  | 0.24 |
| P13 | A12 | 0.6 | $Hf(CH_2C_6H_5)_4$ | 5 | TMA  | 1 + 2 | SJBF20 + BF15 | 0.3 | C | 62  | 0.63 |
| P14 | A12 | 0.3 | $Hf(CH_2C_6H_5)_4$ | 5 | TMA  | 1 + 2 | SJBF20 + BF15 | 0.3 | C | 9   | 0.65* |
| P15 | A13 | 0.6 | $Zr(CH_2C_6H_5)_4$ | 5 | TIBA | 1     | TBF20         | 0.3 | C | 235 | 0.21 |
| P16 | A13 | 0.3 | $Zr(CH_2C_6H_5)_4$ | 5 | TIBA | 1     | TBF20         | 0.3 | C | 63  | 0.24 |
| P17 | A13 | 0.6 | $Hf(CH_2C_6H_5)_4$ | 5 | TIBA | 1     | TBF20         | 0.3 | C | 368 | 0.35 |
| P18 | A13 | 0.3 | $Hf(CH_2C_6H_5)_4$ | 5 | TIBA | 1     | TBF20         | 0.3 | C | 35  | 0.44* |
| P19 | A14 | 0.3 | $Zr(CH_2C_6H_5)_4$ | 5 | TMA  | 1 + 2 | SJBF20 + BF15 | 0.3 | C | 55  | 0.3  |
| P20 | A14 | 0.3 | $Hf(CH_2C_6H_5)_4$ | 5 | TMA  | 1 + 2 | SJBF20 + BF15 | 0.3 | C | 78  | 0.71* |
| P21 | A14 | 0.3 | $Hf(CH_2C_6H_5)_4$ | 5 | TMA  | 1     | TBF20         | 0.3 | C | 11  | 0.47* |

TABLE 2C-continued

Select Polymerization Examples: Propylene Homopolymerizations

| Example | Ligand | μmol Ligand | Group IV Precursor (0.3 μmol) | mol equivalents of Group 13 Reagent | Group 13 Reagent | mol equivalents of Activation Reagent | Activation Reagents | μmol catalyst | Reactor | mg polypropylene produced | IR Indices |
|---|---|---|---|---|---|---|---|---|---|---|---|
| P22 | A23 | 0.3 | Zr(CH$_2$C$_6$H$_5$)$_4$ | 5 | TMA | 1 | TBF20 | 0.3 | C | 107 | 0.26 |
| P23 | A23 | 0.6 | Zr(CH$_2$C$_6$H$_5$)$_4$ | 5 | TIBA | 1 | TBF20 | 0.3 | C | 40 | 0.29 |
| P24 | A23 | 0.6 | Hf(CH$_2$C$_6$H$_5$)$_4$ | 5 | PMAO | 1 + 2 | SJBF20 + BF15 | 0.3 | C | 166 | 0.26 |
| P25 | A23 | 0.3 | Hf(CH$_2$C$_6$H$_5$)$_4$ | 5 | PMAO | 1 + 2 | SJBF20 + BF15 | 0.3 | C | 60 | 0.2 |
| P26 | A27 | 0.6 | Zr(CH$_2$C$_6$H$_5$)$_4$ | 5 | TIBA | 1 + 2 | SJBF20 + BF15 | 0.3 | C | 142 | 0.13 |
| P27 | A27 | 0.3 | Zr(CH$_2$C$_6$H$_5$)$_4$ | 5 | TIBA | 1 | SJBF20 | 0.3 | C | 33 | 0.17 |
| P28 | A27 | 0.6 | Hf(CH$_2$C$_6$H$_5$)$_4$ | 5 | TIBA | 1 + 2 | SJBF20 + BF15 | 0.3 | C | 241 | 0.15 |
| P29 | A27 | 0.3 | Hf(CH$_2$C$_6$H$_5$)$_4$ | 5 | PMAO | 1 | SJBF20 | 0.3 | C | 33 | 0.19 |
| P30 | A29 | 0.3 | Zr(CH$_2$C$_6$H$_5$)$_4$ | 5 | TMA | 1 + 2 | SJBF20 + BF15 | 0.3 | C | 10 | 0.34 |
| P31 | A29 | 0.3 | Hf(CH$_2$C$_6$H$_5$)$_4$ | 5 | TIBA | 1 + 2 | SJBF20 + BF15 | 0.3 | C | 22 | 0.25 |
| P32 | A31 | 0.6 | Zr(CH$_2$C$_6$H$_5$)$_4$ | 5 | TIBA | 1 | TBF20 | 0.3 | C | 37 | 0.1 |
| P33 | A31 | 0.6 | Hf(CH$_2$C$_6$H$_5$)$_4$ | 5 | TIBA | 1 | TBF20 | 0.3 | C | 122 | 0.21 |
| P34 | A31 | 0.3 | Hf(CH$_2$C$_6$H$_5$)$_4$ | 5 | PMAO | 1 + 2 | SJBF20 + BF15 | 0.3 | C | 45 | 0.32 |
| P35 | A32 | 0.3 | Zr(CH$_2$C$_6$H$_5$)$_4$ | 5 | TMA | 1 | TBF20 | 0.3 | C | 126 | 0.55* |
| P36 | A32 | 0.3 | Zr(CH$_2$C$_6$H$_5$)$_4$ | 5 | TIBA | 1 | SJBF20 | 0.3 | C | 33 | 0.21 |
| P37 | A32 | 0.3 | Hf(CH$_2$C$_6$H$_5$)$_4$ | 5 | PMAO | 1 | TBF20 | 0.3 | C | 25 | 0.28 |
| P38 | A35 | 0.6 | Zr(CH$_2$C$_6$H$_5$)$_4$ | 5 | TMA | 1 + 2 | SJBF20 + BF15 | 0.3 | C | 8.1 | 0.47 |
| P39 | B1 | 0.3 | Zr(CH$_2$C$_6$H$_5$)$_4$ | 5 | TMA | 1 + 2 | SJBF20 + BF15 | 0.3 | C | 24 | 0.42* |
| P40 | B1 | 0.6 | Zr(CH$_2$C$_6$H$_5$)$_4$ | 5 | TMA | 1 + 2 | SJBF20 + BF15 | 0.3 | C | 16 | 0.41* |
| P41 | B1 | 0.3 | Hf(CH$_2$C$_6$H$_5$)$_4$ | 5 | TIBA | 1 | TBF20 | 0.3 | C | 35 | 0.2 |
| P42 | B2 | 0.3 | Zr(CH$_2$C$_6$H$_5$)$_4$ | 5 | TMA | 1 | TBF20 | 0.3 | C | 53 | 0.27 |
| P43 | B2 | 0.6 | Zr(CH$_2$C$_6$H$_5$)$_4$ | 5 | TMA | 1 | TBF20 | 0.3 | C | 49 | 0.28 |
| P44 | B2 | 0.3 | Hf(CH$_2$C$_6$H$_5$)$_4$ | 5 | TIBA | 1 | TBF20 | 0.3 | C | 45 | 0.23 |
| P45 | B2 | 0.6 | Hf(CH$_2$C$_6$H$_5$)$_4$ | 5 | PMAO | 1 | SJBF20 | 0.3 | C | 12 | 0.41* |
| P46 | B3 | 0.3 | Zr(CH$_2$C$_6$H$_5$)$_4$ | 5 | TMA | 1 + 2 | SJBF20 + BF15 | 0.3 | C | 14 | 0.4* |
| P47 | B4 | 0.3 | Zr(CH$_2$C$_6$H$_5$)$_4$ | 5 | TMA | 1 + 2 | SJBF20 + BF15 | 0.3 | C | 28 | 0.43* |
| P48 | B4 | 0.6 | Zr(CH$_2$C$_6$H$_5$)$_4$ | 5 | TMA | 1 + 2 | SJBF20 + BF15 | 0.3 | C | 23 | 0.4* |
| P49 | B5 | 0.6 | Zr(CH$_2$C$_6$H$_5$)$_4$ | 5 | TMA | 1 | TBF20 | 0.3 | C | 69 | 0.24 |
| P50 | B5 | 0.3 | Zr(CH$_2$C$_6$H$_5$)$_4$ | 5 | TMA | 1 | TBF20 | 0.3 | C | 44 | 0.26 |
| P51 | B5 | 0.3 | Hf(CH$_2$C$_6$H$_5$)$_4$ | 5 | PMAO | 1 | TBF20 | 0.3 | C | 35 | 0.31 |
| P52 | B5 | 0.6 | Hf(CH$_2$C$_6$H$_5$)$_4$ | 5 | PMAO | 1 | TBF20 | 0.3 | C | 20 | 0.4* |
| P53 | B6 | 0.6 | Zr(CH$_2$C$_6$H$_5$)$_4$ | 5 | TMA | 1 | TBF20 | 0.3 | C | 109 | 0.24 |
| P54 | B6 | 0.3 | Zr(CH$_2$C$_6$H$_5$)$_4$ | 5 | TMA | 1 | SJBF20 | 0.3 | C | 62 | 0.27 |
| P55 | B6 | 0.3 | Zr(CH$_2$C$_6$H$_5$)$_4$ | 5 | TIBA | 1 | SJBF20 | 0.3 | C | 8 | 0.4* |
| P56 | B6 | 0.6 | Hf(CH$_2$C$_6$H$_5$)$_4$ | 5 | TMA | 1 | SJBF20 | 0.3 | C | 111 | 0.31 |
| P57 | B6 | 0.3 | Hf(CH$_2$C$_6$H$_5$)$_4$ | 5 | PMAO | 1 | SJBF20 | 0.3 | C | 10 | 0.43* |
| P58 | C6 | 0.3 | Zr(CH$_2$C$_6$H$_5$)$_4$ | 5 | PMAO | 1 | TBF20 | 0.3 | C | 37 | 0.31 |
| P59 | C14 | 0.6 | Zr(CH$_2$C$_6$H$_5$)$_4$ | 5 | TIBA | 1 + 2 | SJBF20 + BF15 | 0.3 | C | 105 | 0.39 |
| P60 | C14 | 0.3 | Zr(CH$_2$C$_6$H$_5$)$_4$ | 5 | TIBA | 1 + 2 | SJBF20 + BF15 | 0.3 | C | 34 | 0.3 |
| P61 | C14 | 0.6 | Hf(CH$_2$C$_6$H$_5$)$_4$ | 5 | TIBA | 1 + 2 | SJBF20 + BF15 | 0.3 | C | 250 | 0.37 |
| P62 | C14 | 0.3 | Hf(CH$_2$C$_6$H$_5$)$_4$ | — | | 1 + 2 | SJBF20 + BF15 | 0.3 | C | 120 | 0.46 |
| P63 | C15 | 0.3 | Zr(CH$_2$C$_6$H$_5$)$_4$ | | — | 1 | SJBF20 | 0.3 | C | 128 | 0.2 |
| P64 | C15 | 0.3 | Zr(CH$_2$C$_6$H$_5$)$_4$ | 5 | PMAO | 1 | SJBF20 | 0.3 | C | 32 | 0.17 |
| P65 | C15 | 0.6 | Hf(CH$_2$C$_6$H$_5$)$_4$ | 5 | TIBA | 1 | SJBF20 | 0.3 | C | 112 | 0.46 |
| P66 | C15 | 0.6 | Hf(CH$_2$C$_6$H$_5$)$_4$ | 5 | TIBA | 1 + 2 | SJBF20 + BF15 | 0.3 | C | 68 | 0.29 |
| P67 | C16 | 0.3 | Zr(CH$_2$C$_6$H$_5$)$_4$ | 5 | TIBA | 1 | TBF20 | 0.3 | C | 107 | 0.35 |
| P68 | C16 | 0.3 | Zr(CH$_3$)$_4$ | 5 | TIBA | 1 | TBF20 | 0.3 | C | 107 | 0.2 |
| P69 | C16 | 0.3 | Ti(CH$_2$C$_6$H$_5$)$_4$ | 5 | PMAO | 1 | TBF20 | 0.3 | C | 62 | 0.1 |
| P70 | C16 | 0.3 | Hf(CH$_2$C$_6$H$_5$)$_4$ | 5 | PMAO | 1 | TBF20 | 0.3 | C | 64 | 0.2 |
| P71 | C17 | 0.3 | Zr(CH$_2$C$_6$H$_5$)$_4$ | 5 | TMA | 1 | TBF20 | 0.3 | C | 34 | 0.2 |
| P72 | C17 | 0.6 | Ti(CH$_2$C$_6$H$_5$)$_4$ | 5 | PMAO | 1 | TBF20 | 0.3 | C | 33 | 0.36 |
| P73 | C18 | 0.3 | Zr(CH$_2$C$_6$H$_5$)$_4$ | 5 | PMAO | 1 | TBF20 | 0.3 | C | 19 | 0.4 |
| P74 | C19 | 0.3 | Zr(CH$_2$C$_6$H$_5$)$_4$ | 5 | TIBA | 1 | SJBF20 | 0.3 | C | 134 | 0.29 |
| P75 | C19 | 0.6 | Zr(CH$_2$C$_6$H$_5$)$_4$ | 5 | TIBA | 1 | SJBF20 | 0.3 | C | 29 | 0.3 |
| P76 | C19 | 0.3 | Zr(CH$_3$)$_4$ | 5 | TIBA | 1 | SJBF20 | 0.3 | C | 169 | 0.28 |
| P77 | C19 | 0.6 | Hf(CH$_2$C$_6$H$_5$)$_4$ | 5 | TIBA | 1 | SJBF20 | 0.3 | C | 112 | 0.31 |
| P78 | C19 | 0.3 | Hf(CH$_2$C$_6$H$_5$)$_4$ | 5 | TIBA | 1 | SJBF20 | 0.3 | C | 95 | 0.24 |
| P79 | C19 | 0.3 | Hf(CH$_3$)$_4$ | 5 | TIBA | 1 | SJBF20 | 0.3 | C | 200 | 0.21 |
| P80 | C20 | 0.3 | Zr(CH$_2$C$_6$H$_5$)$_4$ | 5 | TIBA | 1 | TBF20 | 0.3 | C | 79 | 0.24 |
| P81 | C20 | 0.3 | Zr(CH$_2$C$_6$H$_5$)$_3$$^+$ | 5 | TIBA | 1 | TBF20 | 0.3 | C | 104 | 0.3 |
| P82 | C20 | 0.3 | Hf(CH$_2$C$_6$H$_5$)$_4$ | 5 | TIBA | 1 | TBF20 | 0.3 | C | 56 | 0.23 |
| P83 | C29 | 0.3 | Zr(CH$_2$C$_6$H$_5$)$_4$ | 5 | PMAO | 1 | TBF20 | 0.3 | C | 34 | 0.36 |
| P84 | C29 | 0.6 | Zr(CH$_2$C$_6$H$_5$)$_3$$^+$ | 5 | PMAO | 1 | TBF20 | 0.3 | C | 11 | 0.49* |
| P85 | C29 | 0.6 | Hf(CH$_2$C$_6$H$_5$)$_4$ | 5 | PMAO | 1 | TBF20 | 0.3 | C | 21 | 0.21 |
| P86 | D1 | 0.3 | Zr(CH$_2$C$_6$H$_5$)$_4$ | | — | 1 + 2 | SJBF20 + BF15 | 0.3 | C | 59 | 0.23 |
| P87 | D1 | 0.6 | Zr(CH$_2$C$_6$H$_5$)$_4$ | 5 | TMA | 1 + 2 | SJBF20 + BF15 | 0.3 | C | 10 | 0.26 |
| P88 | D1 | 0.3 | Hf(CH$_2$C$_6$H$_5$)$_4$ | | — | 1 + 2 | SJBF20 + BF15 | 0.3 | C | 29 | 0.21 |
| P89 | D2 | 0.3 | Zr(CH$_2$C$_6$H$_5$)$_4$ | | — | 1 | TBF20 | 0.3 | C | 78 | 0.23 |
| P90 | D2 | 0.6 | Zr(CH$_2$C$_6$H$_5$)$_4$ | 5 | TIBA | 1 + 2 | SJBF20 + BF15 | 0.3 | C | 16 | 0.22 |
| P91 | D2 | 0.3 | Hf(CH$_2$C$_6$H$_5$)$_4$ | 5 | TIBA | 1 | TBF20 | 0.3 | C | 50 | 0.19 |
| P92 | D2 | 0.6 | Hf(CH$_2$C$_6$H$_5$)$_4$ | 5 | TIBA | 1 | TBF20 | 0.3 | C | 33 | 0.23 |
| P93 | E1 | 0.3 | Hf(CH$_2$C$_6$H$_5$)$_4$ | 5 | PMAO | 1 | ABF20 | 0.3 | B | 15 | 0.2 |

TABLE 2C-continued

Select Polymerization Examples: Propylene Homopolymerizations

| Example | Ligand | µmol Ligand | Group IV Precursor (0.3 µmol) | mol equivalents of Group 13 Reagent | Group 13 Reagent | mol equivalents of Activation Reagent | Activation Reagents | µmol catalyst | Reactor | mg polypropylene produced | IR Indices |
|---|---|---|---|---|---|---|---|---|---|---|---|
| P94 | E4 | 0.6 | Hf(CH$_2$C$_6$H$_5$)$_4$ | 5 | TIBA | 1 | TBF20 | 0.3 | C | 33 | 0.22 |
| P95 | E4 | 0.3 | Hf(CH$_2$C$_6$H$_5$)$_4$ | 5 | TIBA | 1 | TBF20 | 0.3 | C | 102 | 0.25 |
| P96 | E4 | 0.3 | Zr(CH$_2$C$_6$H$_5$)$_4$ | 5 | TMA | 1 | TBF20 | 0.3 | C | 27 | 0.23 |
| P97 | E6 | 0.3 | Zr(CH$_2$C$_6$H$_5$)$_4$ | 5 | TIBA | 1 | TBF20 | 0.3 | C | 18 | 0.27 |
| P98 | E7 | 0.6 | Hf(CH$_2$C$_6$H$_5$)$_4$ | 5 | TIBA | 1 | TBF20 | 0.3 | C | 35 | 0.18 |
| P99 | E7 | 0.3 | Hf(CH$_2$C$_6$H$_5$)$_4$ | 5 | TIBA | 1 | TBF20 | 0.3 | C | 91 | 0.26 |
| P100 | E7 | 0.3 | Zr(CH$_2$C$_6$H$_5$)$_4$ | 5 | TMA | 1 | TBF20 | 0.3 | C | 38 | 0.26 |
| P101 | E7 | 0.6 | Zr(CH$_2$C$_6$H$_5$)$_4$ | 5 | TIBA | 1 | TBF20 | 0.3 | C | 51 | 0.22 |
| P102 | E10 | 0.3 | Zr(CH$_2$C$_6$H$_5$)$_3$$^+$ | 5 | TIBA | 1 | TBF20 | 0.3 | C | 10 | 0.18 |
| P103 | E15 | 0.3 | Zr(CH$_2$C$_6$H$_5$)$_3$$^+$ | 5 | PMAO | 1 | TBF20 | 0.3 | C | 12 | 0.22 |
| P104 | E17 | 0.3 | Zr(CH$_2$C$_6$H$_5$)$_4$ | 5 | TIBA | 1 | ABF20 | 0.3 | B | 8 | 0.26 |
| P105 | E18 | 0.3 | Zr(CH$_2$C$_6$H$_5$)$_4$ | 5 | TIBA | 1 | ABF20 | 0.3 | B | 9 | 0.34 |
| P106 | E23 | 0.3 | Hf(CH$_2$C$_6$H$_5$)$_4$ | 5 | TIBA | 1 | ABF20 | 0.3 | B | 8 | 0.32 |
| P107 | F1 | 0.3 | Zr(CH$_2$C$_6$H$_5$)$_4$ | 5 | TIBA | 1 | TBF20 | 0.3 | C | 35 | 0.34 |
| P108 | F1 | 0.3 | Zr(CH$_2$C$_6$H$_5$)$_4$ | 5 | TIBA | 1 | SJBF20 | 0.3 | C | 16 | 0.34 |
| P109 | F1 | 0.3 | Hf(CH$_2$C$_6$H$_5$)$_4$ | 5 | TIBA | 1 | TBF20 | 0.3 | C | 27 | 0.24 |
| P110 | F2 | 0.3 | Zr(CH$_2$C$_6$H$_5$)$_4$ | 5 | PMAO | 1 | SJBF20 | 0.3 | C | 42 | 0.28 |
| P111 | F2 | 0.6 | Zr(CH$_2$C$_6$H$_5$)$_4$ | 5 | TIBA | 1 | TBF20 | 0.3 | C | 10 | 0.32 |
| P112 | F2 | 0.3 | Hf(CH$_2$C$_6$H$_5$)$_4$ | 5 | PMAO | 1 | TBF20 | 0.3 | C | 81 | 0.23 |
| P113 | F3 | 0.3 | Zr(CH$_2$C$_6$H$_5$)$_4$ | 5 | TIBA | 1 + 2 | SJBF20 + BF15 | 0.3 | C | 11 | 0.29 |
| P114 | F4 | 0.3 | Zr(CH$_2$C$_6$H$_5$)$_4$ | 5 | TIBA | 1 | TBF20 | 0.3 | C | 112 | 0.24 |
| P115 | F4 | 0.6 | Zr(CH$_2$C$_6$H$_5$)$_4$ | 5 | TIBA | 1 | TBF20 | 0.3 | C | 49 | 0.27 |
| P116 | F4 | 0.3 | Hf(CH$_2$C$_6$H$_5$)$_4$ | 5 | TIBA | 1 | TBF20 | 0.3 | C | 124 | 0.23 |
| P117 | F4 | 0.6 | Hf(CH$_2$C$_6$H$_5$)$_4$ | 5 | TIBA | 1 | TBF20 | 0.3 | C | 11 | 0.24 |
| P118 | F5 | 0.6 | Zr(CH$_2$C$_6$H$_5$)$_4$ | 5 | TMA | 1 + 2 | SJBF20 + BF15 | 0.3 | C | 24 | 0.47 |
| P119 | F5 | 0.3 | Zr(CH$_2$C$_6$H$_5$)$_4$ | 5 | TMA | 1 | TBF20 | 0.3 | C | 14 | 0.42 |
| P120 | F5 | 0.3 | Hf(CH$_2$C$_6$H$_5$)$_4$ | 5 | TMA | 1 + 2 | SJBF20 + BF15 | 0.3 | C | 36 | 0.63 |
| P121 | F5 | 0.3 | Hf(CH$_2$C$_6$H$_5$)$_4$ | 5 | PMAO | 1 + 2 | SJBF20 + BF15 | 0.3 | C | 22 | 0.43 |
| P122 | F5 | 0.3 | Hf(CH$_2$C$_6$H$_5$)$_4$ | 5 | TMA | 1 | SJBF20 | 0.3 | C | 20 | 0.72 |
| P123 | F7 | 0.3 | Zr(CH$_2$C$_6$H$_5$)$_4$ | 5 | PMAO | 1 | TBF20 | 0.3 | C | 21 | 0.24 |
| P124 | F9 | 0.3 | Zr(CH$_2$C$_6$H$_5$)$_4$ | 5 | PMAO | 1 | TBF20 | 0.3 | C | 36 | 0.18 |
| P125 | F10 | 0.3 | Zr(CH$_2$C$_6$H$_5$)$_4$ | 5 | PMAO | 1 | TBF20 | 0.3 | C | 32 | 0.24 |
| P126 | F10 | 0.3 | Hf(CH$_2$C$_6$H$_5$)$_4$ | 5 | TIBA | 1 | TBF20 | 0.3 | C | 30 | 0.18 |
| P127 | G1 | 0.3 | Zr(CH$_2$C$_6$H$_5$)$_3$$^+$ | 5 | PMAO | 1 | TBF20 | 0.3 | C | 22 | 0.2 |

*= end groups visible with FT-IR spectrum

Section 3. Secondary Screening

Additional General Analytical Procedures:

High temperature Size Exclusion Chromatography was performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407, and 6,294,388 each of which is incorporated herein by reference. In the current apparatus, a series of two 30 cm×7.5 mm linear columns in used, with both columns containing PLgel 10 um, MixB (available from Polymer Labs). The GPC system was calibrated using narrow polystyrene standards. Unless otherwise indicated, the system was operated at an eluent flow rate of 1.5 mL/min and an oven temperature of 160° C.; o-dichlorobenzene was used as the eluent; the polymer samples were dissolved 1,2,4-trichlorobenzene at a concentration of about 5 mg/mL; 200 µL of a polymer solution were injected into the system; and the concentration of the polymer in the eluent was monitored using an evaporative light scattering detector. All of the molecular weight results obtained are relative to linear polystyrene standards.

Differential Scanning Calorimetry (DSC) measurements were performed on a TA instrument DSC 2920 to determine the melting point of polymers. 10-30 mg of polymer were despoited as a 200 mg/mL solutions in 1,2,4-trichlorobenzene into an Aluminium substrate and dried. The sample was dried under vacuum for 4 hours at 185° C.; afterwards the sample was allowed to cool to room temperature ("RT") overnight while under vacuum. The sample was heated to 300° C. at a rate of 10° C./min and data were collected during that heating period. Reported are the peak maxima of the melting transition. In case of multiple peaks in the transition, multiple melting temperatures are reported, ("#/#").

Section 3A. Propylene Polymerizations using metal-ligand compositions: A total of 23 separate polymerization reactions were performed as follows.

Section 3Ai. Preparation of the Polymerization Reactor Prior to Injection of Catalyst Composition Method A: A pre-weighed glass vial insert and disposable stirring paddle were fitted to each reaction vessel of the reactor. The reactor was then closed, 0.200 mL of a 0.05 M solution of Modified Methylaluminoxane 3A (from Azko Chemical Inc., Chicago, Ill.) ("MMAO") in toluene and 3.8 mL of toluene were injected into each pressure reaction vessel through a valve. The temperature was then set to the appropriate setting (with specific temperatures for each polymerization being listed in Table 3A and Table 3B, below), and the stirring speed was set to 800 rpm unless otherwise noted. The mixture was exposed to propylene at 100 psi pressure. A propylene pressure of 100 psi in the pressure cell and the temperature setting were maintained, using computer control, until the end of the polymerization experiment.

Section 3Aii. In Situ Preparation of Metal-Ligand Compositions

The following methods were employed to prepare the metal-ligand compositions as indicated in Table 3A and Table 3C. Method ZA: 24 μL of the ligand solution (25 mM in 1,2-dichloroethane) was dispensed in a 1 mL glass vial followed by the removal of solvent. To the 1 mL glass vial containing the ligand was added toluene (50 μL) followed by the addition of an equimolar amount of metal precursor solution (10 mM in toluene) to form the metal-ligand composition solution. The reaction mixture was heated at 75° C. for 35 min. Method ZB: Similar to Method ZA except that 60 μl of the ligand solution (10 mM in 1,2-dichloroethane) was dispensed in the 1 mL glass vial. Method ZC: 48 μl of the ligand solution (25 mM in 1,2-dichloroethane) was dispensed in a 1 mL glass vial followed by the removal of solvent. To the 1 mL glass vial containing the ligand was added toluene (50 μL) followed by the addition of 0.5 mol equivalents of metal precursor solution (10 mM in toluene) to form the metal-ligand composition solution. The reaction mixture was heated at 75° C. for 35 min. Method ZD: Similar to Method ZC except that 120 μL of the ligand solution (10 mM in 1,2-dichloroethane) was dispensed in the 1 mL glass vial. Method ZE: Similar to Method ZC except that 60 μL of toluene (instead of 50 μL) was added to the 1 mL glass vial containing the ligand prior to the addition of the metal precursor and the reaction mixture was kept at ambient temperature prior to screening. Method ZF: 40 μL of the ligand solution (25 mM in toluene) was dispensed in a 1 mL glass vial followed by the removal of solvent. To the 1 mL glass vial containing the ligand was added toluene (100 μL) followed by the addition of an equimolar amount of the metal precursor solution (10 mM in toluene) to form the metal-ligand composition solution. The reaction mixture was kept at ambient temperature prior to screening. Method ZG: 80 μL of the ligand solution (25 mM in toluene) was dispensed in a 1 mL glass vial followed by the removal of solvent. To the 1 mL glass vial containing the ligand was added toluene (100 μL) followed by the addition of 0.5 mol equivalents of metal precursor solution (10 mM in toluene) to form the metal-ligand composition solution. The reaction mixture was kept at ambient temperature prior to screening. Method ZH: 48 μL of the ligand solution (25 mM in toluene) was dispensed in a 1 mL glass vial followed by the removal of solvent. To the 1 mL glass vial containing the ligand was added toluene (60 μL) followed by the addition of 0.5 mol equivalents of the metal precursor solution (10 mM in toluene) to form the metal-ligand composition solution. The reaction mixture was heated at 75° C. for 45 min. Method ZI: Similar to Method ZH except that 40 μL (instead of 50 μL) of toluene was added to the 1 mL glass vial prior to the addition of the metal precursor and the reaction mixture was kept at ambient temperature prior to screening: Method ZJ: 24 μL of the ligand solution (25 mM in 1,2-dichloroethane) was dispensed in a 1 mL glass vial followed by the removal of solvent. To the 1 mL glass vial containing the ligand was added toluene (40 μL) followed by the addition of an equimolar amount of metal precursor solution (10 mM in toluene) to form the metal-ligand composition solution. The reaction mixture was heated at 75° C. for 45 min. Method ZK: Similar to Method ZJ except that 24 μL of the ligand solution (25 mM in toluene) was dispensed in the 1 mL glass vial. Method ZL: Similar to ZH except that 96 μL of the ligand solution (25 mM in toluene) was dispensed in the 1 mL glass vial. Method ZM: Similar to Method ZJ except that 48 μL of the ligand solution (25 mM in toluene) was dispensed in the 1 mL glass vial. Method ZN: 40 μL of the ligand solution (25 mM in toluene) was dispensed in a 1 mL glass vial followed by the removal of solvent. To the 1 mL glass vial containing the ligand was added toluene (100 μL) followed by the addition of 0.5 mol equivalents of the metal precursor solution (10 mM in toluene) to form the metal-ligand composition solution. The reaction mixture was kept at ambient temperature for over 1 h prior to screening. Method ZO: Similar to method ZN except that 100 μL of the ligand solution (10 mM in toluene) was dispensed into the 1 mL glass vial. Method ZP: Similar to Method ZN except that 60 μL (instead of 100 μL) of toluene was added to the 1 mL glass vial prior to the addition of metal precursor. Method ZQ: 20 μL of the ligand solution (25 mM in toluene) was dispensed in a 1 mL glass vial followed by the removal of solvent. To the 1 mL glass vial containing the ligand was added toluene (40 μL) followed by the addition of an equimolar amount of the metal precursor (5 mM in toluene) to form the metal-ligand composition solution. The reaction mixture was heated at 70° C. for 1 h. Method ZR: Similar to Method ZQ except that a 25 mM ligand solution in 1,2-dichloroethane was used.

Section 3Aiii. Preparation of the Group 13 Reagent and Activator Stock Solutions.

The "activator solution" is a solution of N,N'-dimethylanilinium tetrakis (pentafluorophenyl) borate ("ABF$_{20}$") in toluene or a solution of a 1:2 (molar ratio) mixture of N,N'-dimethylanilinium tetrakis (pentafluorophenyl) borate ("ABF$_{20}$") and tris(pentafluorophenyl)borane ("BF$_{15}$") in toluene (the mixture is abbreviated as "ABF$_{20}$/BF$_{15}$", also as "ABC"). The identity and molarity of this solution is indicated in the "activation method" of the individual example described below. The ABF$_{20}$ and ABC solutions are heated to approximately 85° C. to dissolve the reagent. The "group 13 reagent" solution is either a solution of trimethylaluminum ("TMA"), triisobutylaluminium ("TIBA") or a solution of nonhydrolytic polymethylaluminoxane (Akzo Nobel PMAO-IP, referred to below as "PMAO", available from Akzo Nobel Polymer Chemicals, Chicago, Ill., USA), all "group 13 reagent" solutions were in toluene. The molarity of the solutions used is indicated in the "activation method" of the individual example described below.

Section 3Aiv. Activation Methods and Injection of Solutions into the Pressure Reactor Vessel The following methods were employed to activate and inject the metal-ligand compositions for the examples in Tables 3A and 3C: Method AAAA: To the 1 mL glass vial containing the metal-ligand composition, the appropriate amount of the group 13 reagent solution as a 50 mM solution, containing the indicated equivalents of group 13 reagent (per metal precursor) in the specific example, was added. After about 11 minutes, 1.1 mol equivalents (per metal precursor) of the activator solution (2.5 mM) was added to the 15 mL vial and the reaction mixture was mixed. Approximately 30 seconds later, a fraction of the 1 mL vial contents corresponding to the indicated "catalyst amount injected", based on micromoles (μmol) of metal precursor, was injected into the pre-pressurized reaction vessel and was followed immediately by injection of toluene to bring the total volume injected to 0.8 mL. Method BBBB: To the 1 mL glass vial containing the metal-ligand composition, the appropriate amount of the group 13 reagent solution as a 50 mM solution, containing the indicated equivalents group 13 reagent (per metal precursor) in the specific example, was added. After about 11 minutes, 1.1 mol equivalents (per metal precursor) of the "activator solution" (2.5 mM) was added to the 1 mL vial followed by an immediate addition of 750 μL of toluene. The contents of the 1 mL vial were mixed. Approximately 30 seconds later, a fraction of the 1 mL vial contents corresponding to the indicated "catalyst amount injected", based on micromoles (μmol) of metal precursor, was injected into the pre-pressurized reaction vessel and was followed immediately by injection of toluene to bring the total volume injected to 0.5 mL. Method CCCC: Similar to Method AAAA except that the activator solution was a toluene solution of the mixture of ABF$_{20}$ and BF$_{15}$ (2.5 mM ABF$_{20}$/5 mM BF$_{15}$) and a total of 3.3 mol equivalents (per metal precursor) was used. Method DDDD: Similar to method AAAA except that 200 mM of group 13 reagent solution and 5 mM activator solution were used (instead of 50 mM and 2.5 mM respectively) and the total volume injected was 1.0 mL (instead of 0.8 mL). Method EEEE: Similar to Method DDDD except that a total of 3.3 mol equivalents (per metal precursor) of the activator (5 mM ABF$_{20}$/10 mM BF$_{15}$) was used. Method FFFF: Similar to method BBBB except that a total of 3.3 mol equivalents (per metal precursor) of the activator (2.5 mM ABF$_{20}$/5.0 mM BF$_{15}$) was used and 400 µL of toluene was added to the 1 mL vial immediately after the activator. Method GGGG: Similar to method AAAA except that a total of 3.3 mol equivalents (per metal precursor) of the activator solution (2.5 mM ABF$_{20}$/5.0 mM BF$_{15}$) was used and the total volume injected to the reaction vessel was 0.5 mL (instead of 0.8 mL). Method HHHH: To the 1 mL glass vial containing the metal-ligand composition, the appropriate amount of the group 13 reagent solution as a 50 mM solution, containing the indicated equivalents group 13 reagent (per metal precursor) in the specific example, was added. After 45 seconds, a total of 3.3 mol equivalents (per metal precursor) of the activator solution (2.5 mM ABF$_{20}$/5 mM BF$_{15}$) was added and the reaction mixture was mixed. Approximately 90 seconds later a fraction of the total 1 mL vial contents containing the indicated "catalyst amount injected", based on micromoles (µmol) of metal precursor, was injected into the pre-pressurized reaction vessel and was followed immediately by injection of toluene to bring the total volume injected to 0.500 mL. Method IIII: Similar to method AAAA except that the total volume injected was 0.5 mL (instead of 0.8 mL). Method JJJJ: Similar to Method HHHH except that 200 mM of group 13 reagent solution and 5 mM ABF$_{20}$/10 mM BF$_{15}$ were used and the total volume injected to the pre-pressurized reaction vessel was 0.8 mL. Method KKKK: To the 1 mL glass vial containing the metal-ligand composition, the appropriate amount of the group 13 reagent solution as a 50 mM solution, containing the indicated equivalents of group 13 reagent (per metal precursor) in the specific example, was added followed by an immediate addition of 300 µL of toluene. After 45 seconds, 1.1 mol equivalents (per metal precursor) of the activator solution (2.5 mM) was added to the 1 mL vial followed by an immediate addition of another 300 µL of toluene and the reaction mixture was mixed. Approximately 90 seconds later a fraction of the total 1 mL vial contents containing the indicated "catalyst amount injected", based on micromoles (µmol) of metal precursor, was injected into the pre-pressurized reaction vessel and was followed immediately by injection of toluene to increase the total volume injected to 0.500 mL. Method LLLL: Similar to Method HHHH except that 1.1 mol equivalents of activator solution (2.5 mM) was used. Method MMMM: Similar to Method AAAA except that the total volume injected to the pre-pressurized reaction vessel was 0.5 mL. Method NNNN: Similar to method AAAA except that the total volume injected was 1.0 mL (instead of 0.8 mL).

Section 3Av. Polymerization

The polymerization reaction was allowed to continue for 60-1800 seconds, during which time the temperature and pressure were maintained at their pre-set levels by computer control. The specific polymerization times for each polymerization are shown in Table 3A. After the reaction time elapsed, the reaction was quenched by addition of an overpressure of carbon dioxide sent to the reactor. The polymerization times were the lesser of the maximum desired polymerization time or the time taken for a predetermined amount of monomer gas to be consumed in the polymerization reaction.

Section 3Avi. Product Work Up: Propylene Polymerizations

After the polymerization reaction, the glass vial insert, containing the polymer product and solvent, was removed from the pressure cell and removed from the inert atmosphere dry box. The volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above, to determine the molecular weight of the polymer produced, and by FTIR spectroscopy to determine the crystallinity index. The melting point of selected samples was measured by DSC, as described above.

Section 3B. Propylene Polymerizations using isolated complexes:

A total of 5 separate polymerization reactions were performed as follows. (Table 3B)

Section 3Bi. Preparation of the Polymerization Reactor Prior to Injection of Catalyst Composition The polymerization reactor was prepared in the manner described in Section 3Ai, method A.

Section 3Bii. Preparation of the Group 13 Reagent and Activator Stock Solutions

The "activator solution" is either a solution of N,N'-dimethylanilinium tetrakis (pentafluorophenyl) borate ("ABF$_{20}$") in toluene or a solution of trityl tetrakis (pentafluorophenyl) borate ("TBF$_{20}$") in toluene. The "ABF$_{20}$" solution is heated to approximately 85° C. to dissolve the reagent. The "TBF$_{20}$" solution is at ambient temperature. The molarity is indicated in the "activation method" of the individual example described below. The "group 13 reagent solution" is either a solution of trimethylaluminium ("TMA") or a solution of tri-isobutyl aluminium ("TIBA"). The molarity of the solutions used is indicated in the "activation method" of the individual example described below.

Section 3Biii. Activation Method and Injection of Solutions into the Pressure Reactor Vessel The following method was employed to activate and inject the isolated complexes as indicated in Table 3B. Method AA: 40 µL of a 50 mM solution of the group 13 reagent was dispensed into a 1 mL vial. 80 µL of complex solution (5 mM in toluene) containing 0.4 µmol metal complex was added. After about 12 min, 176 µL of the activator solution in toluene (2.5 mM) was added to the 1 mL vial and the contents of the 1 mL vial were mixed. Approximately 70 seconds later a fraction of the total 1 mL vial contents containing the indicated "catalyst amount injected" in Table 3B, based on micromoles (µmol) of metal complex, was injected into the pre-pressurized reaction vessel and was followed immediately by injection of toluene to increase the total volume injected to 0.500 mL.

Section 3Biv. Polymerization

The polymerization reaction was allowed to continue for 60-1800 seconds, during which time the temperature and pressure were maintained at their pre-set levels by computer control. The specific polymerization times for each polymerization are shown in Table 3B. After the reaction time elapsed, the reaction was quenched by addition of an overpressure of carbon dioxide sent to the reactor. The polymerization times were the lesser of the maximum desired polymerization time or the time taken for a predetermined amount of monomer gas to be consumed in the polymerization reaction.

Section 3Bv. Product Work Up: Propylene Polymerizations

After the polymerization reaction, the glass vial insert, containing the polymer product and solvent, was removed from the pressure cell and removed from the inert atmosphere dry box. The volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by rapid GPC, as described above, to determine the molecular weight of the polymer produced, and by FTIR spectroscopy to determine the crystallinity index.

Section 3C. Ethylene-1-Octene Copolymerizations Using Metal-Ligand Compositions

A total of 29 separate ethylene-1-octene polymerization reactions were performed as follows. (Table 3C)

Section 3Ci. Preparation of the Polymerization Reactor Prior to Injection of Catalyst Composition Method B: A pre-weighed glass vial insert and disposable stirring paddle were fitted to each reaction vessel of the reactor. The reactor was then closed, 0.200 mL of a 0.05 M solution of Modified Methylaluminoxane 3A (from Azko Chemical Inc., Chicago, Ill.) ("MMAO") in toluene, 0.400 mL of octene and 4.4 mL of toluene were injected into each pressure reaction vessel through a valve. The temperature was then set to the appropriate setting (with specific temperatures for each polymerization being listed in Table 3C and Table 3D, below), and the stirring speed was set to 800 rpm unless otherwise noted. The mixture was exposed to ethylene at 100 psi pressure. An ethylene pressure of 100 psi in the pressure cell and the temperature setting were maintained, using computer control, until the end of the polymerization experiment.

Method C: Method C is similar to method B except that 0.200 mL of a 0.05 M solution of PMAO in toluene was injected (instead of MMAO).

Section 3Cii. Preparation of Metal-Ligand Compositions

The metal-ligand compositions were prepared as described in Section 3Aii, above.

Section 3Ciii. Activation Methods and Injection of Solutions into the Pressure Reactor Vessel The methods used for activating and injecting the catalyst into the reactor are described in Section 3Aiv above.

Section 3Civ. Polymerization

The polymerization reaction was allowed to continue for 60-1800 seconds, during which time the temperature and pressure were maintained at their pre-set levels by computer control. The specific times for each polymerization are shown in Table 3C. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Section 3Cv. Product Work Up: ethylene/1-octene Copolymerizations

After the polymerization reaction, the glass vial insert, containing the polymer product and solvent, was removed from the pressure cell and removed from the inert atmosphere dry box. The volatile components were removed using a centrifuge vacuum evaporator. After substantial evaporation of the volatile components, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and FTIR spectroscopy to determine the comonomer incorporation. Results are presented in Table 3C.

Section 3D. Ethylene-1-Octene Copolymerizations Using Isolated Complexes

A total of 33 separate ethylene-1-octene polymerization reactions were performed as follows. (Table 3D)

Section 3Di. Preparation of the Polymerization Reactor Prior to Injection of Catalyst Composition The reactor was prepared as described in Methods B and C, above. In some examples hydrogen (as a mixture with nitrogen) was added; the amount added is noted in Table 3D. An ethylene pressure of 100 psi in the pressure cell and the temperature setting were maintained, using computer control, until the end of the polymerization experiment.

Section 3Dii. Preparation of the Group 13 Reagent and Activator Stock Solutions

The "activator solution" is either a 2.5 mM solution of N,N'-dimethylanilinium tetrakis (pentafluorophenyl) borate ("$ABF_{20}$") in toluene or a 400 mM solution of Modified Methylaluminoxane-3A (Azko) ("MMAO") in toluene. The "$ABF_{20}$" solution is heated to approximately 85° C. to dissolve the reagent. The "MMAO" solution is at ambient temperature. The group 13 reagent solution is either a solution of triisobutylaluminium or modified methalumoxane-3A ("MMAO") in toluene. The molarity of the group 13 reagent is noted below and the molar equivalents is noted in Table 3D.

Section 3Diii. Activation Methods and Injection of Solutions into the Pressure Reactor Vessel Method AAA: 75 μL of a 20 mM solution of the group 13 reagent was dispensed into a 1 mL vial. 60 μL of complex solution (5 mM in toluene) containing 0.3 μmol metal complex was added. After about 45 seconds, 132 μL of the activator solution in toluene (2.5 mM) was added to the 1 mL vial followed by an immediate addition of 700 μL of toluene and the contents of the 1 mL vial were mixed. Approximately 80 seconds later a fraction of the total 1 mL vial contents containing the indicated "catalyst amount injected" in 3D, based on micromoles (μmol) of metal complex, was injected into the pre-pressurized reaction vessel and was followed immediately by injection of toluene to increase the total volume injected to 0.500 mL. Method BBB: Similar to Method AAA, except that 340 μL of toluene (instead of 700 μL) was added to the 1 mL vial immediately after the activator. Method CCC: Similar to Method BBB, except that 150 μL of a 400 mM activator solution was used. Method DDD: Similar to Method CCC, except that 150 μL of a 400 mM group 13 reagent solution was added to the 1 mL vial prior to the addition of the metal complex and 700 μL (instead of 340 μL) of toluene was added to the 1 mL vial immediately after the activator. Method EEE: Similar to Method DDD except that 340 μL of toluene was added to the 1 mL vial immediately after the activator. Method FFF Similar to Method AAA, except that 340 μL (instead of 700 μL) of toluene was added to the 1 mL vial immediately after the activator. Method GGG Similar to Method CCC except that 700 μL (instead of 340 μL) of toluene was added immediately after the activator. Method HHH: 50 μL of a 20 mM solution of the group 13 reagent was dispensed into a 1 mL vial. 50 μL of complex solution (4 mM in toluene) containing 0.2 μmol metal complex was added. After about 12 min, 88 μL of the activator solution in toluene (2.5 mM) was added to the 1 mL vial immediately followed by the addition of 800 μL of toluene and the contents of the 1 mL vial were mixed. Approximately 70 seconds later a fraction of the total 1 mL vial contents containing the indicated "catalyst amount injected" in Table 3D, based on micromoles (μmol) of metal complex, was injected into the pre-pressurized reaction vessel and was followed immediately by injection of toluene to increase the total volume injected to 0.500 mL. Method III: Similar to Method HHH except that 50 μL of the activator solution (400 mM) was used. Method JJJ: Similar to Method AAA except that 300 μL of toluene was added immediately after the activator. Method KKK: Similar to Method JJJ except that no toluene was added after the activator. Method LLL. Similar to Method JJJ except that only 450 μL of toluene (not "activator") was added to the 1 mL vial after the complex ("catalyst precursor" was activated inside the reaction vessel). Method MMM: Similar to Method LLL except that 150 μL of toluene was added after complex. Method NNN: 40 μL of a 50 mM solution of the group 13 reagent was dispensed into a 1 mL vial. 80 μL of complex solution (5 mM in toluene) containing 0.4 μmol metal complex was added. After about 12 min, 176 μL of the activator solution in toluene (2.5 mM) was added to the 1 mL vial immediately followed by 800 μL of toluene and the contents of the 1 mL vial were mixed. Approximately 70 seconds later a fraction of the total 1 mL vial contents containing the indicated "catalyst amount injected" in Table 3D, based on micromoles (μmol) of metal complex, was injected into the pre-pressurized reaction vessel and was followed immediately by injection of toluene to increase the total volume injected to 0.500 mL. Method OOO: 40 μL of a 50 mM solution of the group 13 reagent was dispensed into a 1 mL vial. 80 μL of complex solution (5 mM in toluene) containing 0.4 μmol metal complex was added. After about 12 min, 1000 μL of toluene was added and the contents of the 1 mL vial were mixed. Approximately 70 seconds later a fraction of the total 1 mL vial contents containing the indicated "catalyst amount injected" in Table 3D, based on micromoles (μmol) of metal complex, was injected into the pre-pressurized reaction vessel and was followed immediately by injection of toluene to increase the total volume injected to 0.500 mL. Method PPP: Similar to Method OOO except that 500 μL of toluene was added to the 1 mL vial prior to the final mixing.

Section 3Div. Polymerization

The polymerization reaction was allowed to continue for 60-600 seconds, during which time the temperature and pressure were maintained at their pre-set levels by computer control. The specific times for each polymerization are shown in Table 3D. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Section 3Dv. Product Work Up: ethylene/1-octene Copolymerizations

After the polymerization reaction, the glass vial insert, containing the polymer product and solvent, was removed from the pressure cell and removed from the inert atmosphere dry box. The volatile components were removed using a centrifuge vacuum evaporator. After substantial evaporation of the volatile components, the vial contents were dried thoroughly by evaporation at elevated temperature under reduced pressure. The vial was then weighed to determine the yield of polymer product. The polymer product was then analyzed by rapid GPC, as described above to determine the molecular weight of the polymer produced, and FTIR spectroscopy to determine the comonomer incorporation. Results are presented in Table 3D.

Section 3E: Styrene Polymerizations in 12-Well Format

Section 3Ei: Stock Solutions: Solutions of metal precursors were prepared in toluene typically at 10-20 mmol/l: $Ti(CH_2C_6H_5)_4$; $Zr(CH_2C_6H_5)_4$; $Hf(CH_2C_6H_5)_4$; $Ti(N(CH_3)_2)_4$; $Zr(N(CH_3)_2)_4$; $Hf(N(CH_3)_2)_4$; $TiCl_2(N(CH_3)_2)_2$; $[Ti(CH_2C_6H_5)_3^+][C_6H_5CH_2B(C_6F_5)_3^-]$; $[Zr(CH_2C_6H_5)_3^+][C_6H_5CH_2B(C_6F_5)_3^-]$ and $[Hf(CH_2C_6H_5)_3^+][C_6H_5CH_2B(C_6F_5)_3^-]$ were generated in situ within the 12 well arrays by addition of $M(CH_2C_6H_5)_4$ followed by 1 equivalent of $B(C_6F_5)_3$. Solutions of group 13 reagents were prepared in toluene typically at 50-250 mmol/l: $Al(Me)_3$, (TMA); $Al(Et)_3$, (TEA); $Al(^iBu)_3$, (TIBA); PMAO-IP & MMAO-3A. Alumoxanes were supplied by Azko Chemical Inc., Chicago, Ill. Solutions of activators were prepared in toluene typically at 4-10 mmol/l, except MAO's (0.5-1 mol/l); $B(C_6F_5)_3$; $[C(C_6H_5)_3]^+[B(C_6F_5)_4]^-$, (TBF20); $[HN(CH_3)_2Ph]+[B(C_6F_5)_4]^-$, (ABF20); $[HN(C_6H_{13})_2(-para-C_4H_9-Ph)]+[B(C_6F_5)_4]^-$, (SJBF20); $[HN(C_{10}H_{21})_2(-para-C_4H_9-Ph)]+[B(C_6F_5)_4]^-$, (SJ2BF20); PMAO-IP and MMAO-3A.

Section 3Eii: Reactor Set-up: Organized in 4×3 arrays within an aluminum block, pre-mix catalyst solutions were prepared 8*30 mm vials (containing parylene coated stirbars) using a pipette or liquid handling robot driven by software (available from Symyx Technologies, Inc., Santa Clara and described within EP 1080435, U.S. Pat. No. 6,507,645, and EP 1175645). The pre-mix catalyst solutions contain toluene; one or two ligands (0.3-1.5 μmol); a specified group IV metal precursor; a group 13 reagent; and an activator (or combination of group 13 reagents and activators, from a stock solution). Aliquots of pre-mix catalyst solutions were transferred to 15 mL tarred glass vials containing Teflon coated stir bars; styrene; solvent; and a group 13 scavenger. The 15 mL vials were housed in a large aluminum block (4×3 array reactor) mounted on a heater pre-set at the desired polymerization temperature with pot-magnet stirring (each vial has dedicated stirring). Each vial was sealed during the allotted experiment time with a Teflon coated septa seated within a latched Al cover. The reactor was a parallel reactor with quenching capability.

Section 3Eiii: Polymerization conditions: Seven different processing conditions were used for these polymerizations, with the conditions being presented in Table 3E by reference to the method number. Method 1: In-situ Complexation; 1 ligand species per well; 25° C. complexation, 105° C. reaction temperature; ca. 4 mL total volume per well: The ligand array (1.0-2.0 μmol of each ligand) was first contacted with toluene (ca. 100 µL per well) and then toluene solutions of the desired group IV precursor (15-60 µL per well, 0.5-1.0 µmol) were added. The resultant mixtures were stirred for a period of 45-60 minutes at 25° C. within an A1 block (pre-mix array). Individual vials were then treated with a stock solution of the appropriate group 13 reagent activator (30-60 µL per well, contact time of ca. 10 min, 25° C.), followed by an activator (or activator mixture, 30-75 µL per well, contact time of ca. 2 min, 25° C.). Individual aliquots of the solutions contained within the pre-mix array were transferred to 15 mL tarred glass vials containing Teflon coated stir bars; 2.0 mL of styrene, 2.0 ml toluene and a group 13 scavenger (10 µmol). The vials were housed within a reactor, with its heater pre-set at 105° C. temperature; and it stirrer set at 300-800 rpm. 2-25 minutes post addition of the catalyst solutions, the vials were removed from the reactor; placed into a RT A1 block; and 3 mL of cold toluene was injected into each well. The 15 mL vials were then removed from the glove box and transferred to a fume hood to be quenched with 5 mL of methanol. Method 2: In-situ Complexation: 1 ligand species per well, 75° C. complexation, 105° C. reaction temperature: ca. 4 mL total volume per well: The ligand array (1.0-2.0 µmol of each ligand) was first contacted with toluene (ca. 100 µL per well) and then toluene solutions of the desired group TV precursor (15-60 µL per well, 0.5-1.0 µmol) were added. The resultant mixtures were stirred for a period of 45 minutes at 75° C. within an A1 block (pre-mix array). The pre-mix array was allowed to cool to RT (ca. 25° C.). Individual vials were then treated with a stock solution of the appropriate group 13 reagent activator (30-60 µL per well, contact time of ca. 10 min, 25° C.), followed by an activator (or activator mixture, 30-75 µL per well, contact time of ca. 2 min, 25° C.). Individual aliquots of the solutions contained within the pre-mix array were transferred to 15 mL tarred glass vials containing Teflon coated stir bars; 2.0 mL of styrene, 2.0 ml toluene and a group 13 scavenger (10 µmol). The vials were housed within a reactor, with its heater pre-set at 105° C. temperature; and it stirrer set at 300-800 rpm. 2-25 minutes post addition of the catalyst solutions, the vials were removed from the reactor; placed into a RT A1 block; and 3 mL of cold toluene was injected into each well. The 15 mL vials were then removed from the glove box and transferred to a fume hood to be quenched with 5 mL of methanol. Method 3: In-situ Complexation: 2 ligand species per well; 25° C. complexation, 105° C. reaction temperature: ca. 4 mL total volume per well: The ligand array (0.75 µmol of each ligand 1) was first contacted with toluene (ca. 100 µL per well) and then toluene solutions of the desired group IV precursor (50 µL per well, 0.75 µmol) were added. The resultant mixtures were stirred (at 25° C.) within an A1 block (pre-mix array). After 30 minutes an equal equivalent of a second ligand was added to each well (ligand 2-0.75 µmol), and the resultant mixtures were stirrer for an additional 30 minutes. Individual vials were then treated with a stock solution of the appropriate group 13 reagent activator (30-60 µL per well, contact time of ca. 10 min, 25° C.), followed by an activator (or activator mixture, 30-75 µL per well, contact time of ca. 2 min, 25° C.). Individual aliquots of the solutions contained within the pre-mix array were transferred to 15 mL tarred glass vials con- taining Teflon coated stir bars; 2.0 mL of styrene, 2.0 ml toluene and a group 13 scavenger (10 µmol). The vials were housed within a reactor, with its heater pre-set at 105° C. temperature; and it stirrer set at 300-800 rpm. 2-25 minutes post addition of the catalyst solutions, the vials were removed from the reactor; placed into a RT A1 block; and 3 mL of cold toluene was injected into each well. The 15 mL vials were then removed from the glove box and transferred to a fume hood to be quenched with 5 mL of methanol. Method 4: In-situ Complexation; 1 ligand species per well; 25° C. com- plexation, 125° C. reaction temperature; ca. 4 mL total vol- ume per well: Procedure equivalent to Method 1 except: 1) reactor temperature equals 125° C.; 2) and 2.0 mL ethylben- zene instead of 2.0 mL toluene as solvent within 15 mL vial. Method 5: In-situ Complexation; 1 ligand species per well: 75° C. complexation. 125° C. reaction temperature: ca. 4 mL total volume per well: Procedure equivalent to Method 2 except: 1) reactor temperature equals 125° C.; 2) and 2.0 mL ethylbenzene instead of 2.0 mL toluene as solvent within 15 mL vial. Method 6: In-situ Complexation: 2 ligand species per well; 25° C. complexation, 125° C. reaction temperature: ca. 4 mL total volume per well: Procedure equivalent to Method 3 except: 1) reactor temperature equals 125° C.; 2) and 2.0 mL ethylbenzene instead of 2.0 mL toluene as solvent within 15 mL vial. Method 7: In-situ Complexation: 2 ligand species per well: 25° C. complexation. 125° C. reaction tem- perature: ca. 4 mL total volume per well: The ligand array (0.75 µmol of each ligand I & 0.75 µmol of each ligand 2) was first contacted with toluene (ca. 100 µL per well) and then toluene solutions of the desired group IV precursor (50 µL per well, 0.75 µmol) were added. The resultant mixtures were stirred (at 25° C.) within an A1 block (pre-mix array). Indi- vidual vials were then treated with a stock solution of the appropriate group 13 reagent activator (30-60 µL per well, contact time of ca. 10 min, 25° C.), followed by an activator (or activator mixture, 30-75 µL per well, contact time of ca. 2 min, 25° C.). Individual aliquots of the solutions contained within the pre-mix array were transferred to 15 mL tarred glass vials containing Teflon coated stir bars; 2.0 mL of sty- rene, 2.0 ml toluene and a group 13 scavenger (10 µmol). The vials were housed within a reactor, with its heater pre-set at 105° C. temperature; and it stirrer set at 300-800 rpm. 2-25 minutes post addition of the catalyst solutions, the vials were removed from the reactor; placed into a RT A1 block; and 3 mL of cold toluene was injected into each well. The 15 mL vials were then removed from the glove box and transferred to a fume hood to be quenched with 5 mL of methanol.

Section 3Eiv: Product Analysis: Post methanol quench, the array was dried over-night in vacuo to remove the liquid phase, followed by 2-4 hour drying cycles within a vacuum oven set at 130° C. The vials were weighed via an automated weigh station, to constant weight. 1,2,4-Trichlorobenzene (TCB) was added vials which met a minimum yield criteria, and the resulting TCB solutions were heated for 2 hours at 160° C. An aliquot of the hot solution was injected into a rapid HT-GPC in order to determine Mw and PDI. Table 3E present representative results from the styrene homopolymerization reactions performed in a 12-well format.

Section 3F: Slurry ethylene-1-octene Copolymerizations

Section 3Fi: Preparation of the slurry polymerization reac- tor: The slurry parallel pressure reactor is described in U.S. Pat. No. 6,759,014, which is incorporated herein by refer- ence. A pre-weighed glass vial insert and disposable stirring paddle were fitted to each reaction vessel of the reactor. The reactor was then closed, 0.200 mL of a 0.02 M solution of tri-n-octylaluminum (Sigma-Aldrich) ("TNOA") in heptane, 0.125 mL of 1-octene and 4 mL of heptane were injected into each pressure reaction vessel through a valve. The temperature was then set to 85° C., the stirring speed was set to 800 rpm, and the mixture was exposed to 120 psi ethylene. In some cases hydrogen (as a mixture with nitrogen) was added; the amount added is noted in Table 3F. An ethylene pressure of 120 psi in the pressure cell and the temperature setting were maintained, using computer control, until the end of the polymerization experiment.

Section 3Fii Preparation of supported catalyst S-M2: 12 mg of MAO supported on silica (4.5 mmol Al/g silica provided by Univation Technologies, "SMAO") was vortexed at 1200 rpm in 2.909 mL of dodecane (4 mg/mL slurry concentration). 91 μL of a 0.025 M toluene solution of catalyst M2 is added to the vortexing SMAO slurry and allowed to vortex at room temperature or 50° C. (support temperature noted in Table 3F) for approximately 2 hour before diluting with an additional 3 mL of dodecane (final slurry concentration: 2 mg/mL; catalyst loading: 19 umol/g). The diluted catalyst slurries were then vortexed at 1200 rpm at room temperature for 1-3 hours prior to injection into the pressure reactor vessel.

Section 3Fiii Injection of supported catalyst slurries into the slurry pressure reactor vessel: Supported catalysts were vortexed at 1200 rpm throughout the experiment and during syringe aspiration prior to delivery of the catalyst to the reactor. A 90-100 uL buffer of heptane followed by 100-150 μL of the supported catalyst were injected into the pre-pressurized reaction vessel and were followed immediately by injection of heptane to increase the total volume injected to 0.600 mL.

Section 3Fiv Polymerization: The polymerization reaction was allowed to continue for 300-600 seconds, during which time the temperature and pressure were maintained at their pre-set levels by computer control. The specific times for each polymerization are shown in Table 3F. The polymerization times were the lesser of the maximum desired polymerization time or the time taken for a predetermined amount of monomer gas to be consumed in the polymerization reaction. After the reaction time elapsed, the reaction was quenched by addition of an overpressure of carbon dioxide sent to the reactor.

Section 3Fv Product work up: After the polymerization reaction, the glass vial insert, containing the polymer product and solvent, was removed from the pressure cell and removed from the inert atmosphere dry box, and the volatile components were removed using a centrifuge vacuum evaporator. After most of the volatile components had evaporated, the vial contents were dried thoroughly by evaporation at elevated temperature under reduced pressure. The vial was then weighed to determine the yield of polymer product. The polymer product was then analyzed by Rapid GPC, to determine the molecular weight of the polymer produced, and by FTIR spectroscopy to determine the mole percent octene incorporated in the polymer as described above.

TABLE 3A

Select Examples of Propylene Homopolymerization with in situ prepared Metal-Ligand Compositions

| Example | Metal Precursors | Ligand | Ligand to Metal Ratio | Complexation Method | Reactor Prep. Method | Activation/ Injection Method | Polymerization Temp(C.) | Group 13 Reagent and mole Equivalent Alkyl |
|---|---|---|---|---|---|---|---|---|
| PP1 | Hf(CH$_2$C$_6$H$_5$)$_4$ | A5 | 1 | ZA | A | AAAA | 75 | 5 TMA |
| PP2 | Hf(CH$_2$C$_6$H$_5$)$_4$ | A14 | 1 | ZB | A | AAAA | 75 | 5 TMA |
| PP3 | Hf(CH$_2$C$_6$H$_5$)$_4$ | A13 | 2 | ZC | A | BBBB | 75 | 5 TIBA |
| PP4 | Hf(CH$_2$C$_6$H$_5$)$_4$ | A13 | 2 | ZC | A | CCCC | 75 | 5 TMA |
| PP5 | Hf(CH$_2$C$_6$H$_5$)$_4$ | A13 | 2 | ZE | A | BBBB | 75 | 5 TIBA |
| PP6 | Zr(CH$_2$C$_6$H$_5$)$_4$ | A13 | 2 | ZE | A | BBBB | 75 | 5 TMA |
| PP7 | Zr(CH$_2$C$_6$H$_5$)$_4$ | A13 | 2 | ZE | A | BBBB | 75 | 5 TIBA |
| PP8 | Hf(CH$_2$C$_6$H$_5$)$_4$ | A14 | 2 | ZD | A | AAAA | 75 | 5 TMA |
| PP9 | Zr(CH$_2$C$_6$H$_5$)$_4$ | A5 | 2 | ZE | A | AAAA | 75 | 5 TIBA |
| PP10 | Hf(CH$_2$C$_6$H$_5$)$_4$ | A5 | 2 | ZE | A | AAAA | 75 | 5 TIBA |
| PP11 | Zr(CH$_2$C$_6$H$_5$)$_4$ | A3 | 1 | ZF | A | DDDD | 75 | 5 TIBA |
| PP12 | Zr(CH$_2$C$_6$H$_5$)$_4$ | A12 | 1 | ZF | A | DDDD | 75 | 5 TIBA |
| PP13 | Zr(CH$_2$C$_6$H$_5$)$_4$ | A12 | 2 | ZG | A | EEEE | 75 | 5 TIBA |
| PP14 | Hf(CH$_2$C$_6$H$_5$)$_4$ | A12 | 2 | ZG | A | DDDD | 75 | 5 TIBA |
| PP15 | Zr(CH$_2$C$_6$H$_5$)$_4$ | A27 | 2 | ZH | A | FFFF | 75 | 5 TIBA |
| PP16 | Hf(CH$_2$C$_6$H$_5$)$_4$ | A27 | 2 | ZH | A | GGGG | 75 | 5 TIBA |
| PP17 | Hf(CH$_2$C$_6$H$_5$)$_4$ | A23 | 2 | ZH | A | GGGG | 75 | 5 PMAO |
| PP18 | Zr(CH$_2$C$_6$H$_5$)$_4$ | C19 | 2 | ZI | A | HHHH | 75 | 5 TIBA |
| PP19 | Zr(CH$_2$C$_6$H$_5$)$_4$ | C15 | 1 | ZJ | A | IIII | 75 | a |
| PP20 | Zr(CH$_2$C$_6$H$_5$)$_4$ | C20 | 1 | ZK | A | IIII | 75 | 5 TIBA |
| PP21 | Hf(CH$_2$C$_6$H$_5$)$_4$ | C19 | 2 | ZI | A | HHHH | 75 | 5 TIBA |

TABLE 3A-continued

Select Examples of Propylene Homopolymerization with in situ prepared Metal-Ligand Compositions

| | | | | | | | | | |
|---|---|---|---|---|---|---|---|---|---|
| PP22 | Hf(CH$_2$C$_6$H$_5$)$_4$ | F5 | 2 | ZL | A | JJJJ | | 75 | 5 TMA |
| PP23 | Hf(CH$_2$C$_6$H$_5$)$_4$ | F5 | 1 | ZM | A | JJJJ | | 75 | 5 TMA |

| Example | Activator | μmol Catalyst Injected | Polymerization Time(s) | Activity (g polymer/ min * mmol) | Mw (k) | PDI (Mw/Mn) | Crystallinity Index | M.p. (deg. C.) |
|---|---|---|---|---|---|---|---|---|
| PP1 | 1.1 ABF20 | 0.24 | 870 | 28 | 751 | 5.7 | 0.22 | nd |
| PP2 | 1.1 ABF20 | 0.24 | 1346 | 17 | 114 | 4.8 | 0.21 | 77/153 |
| PP3 | 1.1 ABF20 | 0.02 | 62 | 11659 | 3 | 1.8 | 0.46* | nd |
| PP4 | 3.3 ABC | 0.24 | 61 | 2181 | 3 | 1.9 | 0.34* | nd |
| PP5 | 1.1 ABF20 | 0.02 | 61 | 12786 | 4 | 1.3 | 0.48* | nd |
| PP6 | 1.1 ABF20 | 0.02 | 60 | 6290 | 2 | 1.1 | 0.27* | nd |
| PP7 | 1.1 ABF20 | 0.02 | 61 | 7041 | 2 | 1.1 | 0.25* | nd |
| PP8 | 1.1 ABF20 | 0.24 | 1800 | 6 | 40 | 8 | 0.38 | 129/152 |
| PP9 | 1.1 ABF20 | 0.36 | 189 | 150 | 177 | 1.9 | 0.27 | nd |
| PP10 | 1.1 ABF20 | 0.36 | 1159 | 19 | 534 | 2.1 | 0.26 | nd |
| PP11 | 1.1 ABF20 | 0.75 | 307 | 22 | 179 | 2.4 | 0.30 | nd |
| PP12 | 1.1 ABF20 | 0.75 | 416 | 19 | 80 | 1.8 | 0.20 | nd |
| PP13 | 3.3 ABC | 0.75 | 156 | 64 | 83/2 | 1.6/1.1 | 0.30 | nd |
| PP14 | 1.1 ABF20 | 0.75 | 1310 | 7 | 9 | 1.5 | 0.52 | nd |
| PP15 | 3.3 ABC | 0.03 | 89 | 735 | 1 | 1.1 | 0.14* | nd |
| PP16 | 3.3 ABC | 0.1 | 66 | 1816 | 2 | 1.2 | 0.19* | nd |
| PP17 | 3.3 ABC | 0.1 | 355 | 201 | 2 | 1.2 | 0.25* | nd |
| PP18 | 3.3 ABC | 0.1 | 155 | 838 | 109 | 1.6 | 0.43 | nd |
| PP19 | 1.1 ABF20 | 0.2 | 285 | 146 | 77 | 1.6 | 0.26 | nd |
| PP20 | 1.1 ABF20 | 0.2 | 226 | 231 | 56 | 1.5 | 0.36 | nd |
| PP21 | 3.3 ABC | 0.1 | 416 | 268 | 119 | 1.7 | 0.20 | nd |
| PP22 | 3.3 ABC | 0.9 | 1800 | 1 | 1108 | 1.6 | 0.78 | 154 |
| PP23 | 3.3 ABC | 0.9 | 1800 | 1 | 353 | 5.3 | 0.59 | 125/151 | a = no group 13 reagent was added to the 1 mL vial (toluene was used to replace the group 13 reagent).
*= end groups visible with FT-IR spectrum

TABLE 3B

Select Examples of Propylene Homopolymerization with Isolated Complexes

| Example | Isolated Complex | Reactor Prep. Method | Activation/ Injection Method | Polymerization Temp(C.) | Group 13 Reagent and mole Equivalent Alkyl | Activator | μmol Catalyst Injected | Polymerization Time (s) | Activity (g polymer/ min * mmol) | Mw (k) | PDI (Mw/Mn) | Crystallinity Index |
|---|---|---|---|---|---|---|---|---|---|---|---|---|
| PP24 | M1 | A | AA | 75 | 5 TIBA | 1.1 TBF20 | 0.02 | 106 | 3725 | 4 | 1.3 | 0.51* |
| PP25 | M1 | A | AA | 75 | 5 TIBA | 1.1 ABF20 | 0.02 | 71 | 7781 | 4 | 1.3 | 0.43* |
| PP26 | M1 | A | AA | 75 | 5 TMA | 1.1 ABF20 | 0.02 | 148 | 2161 | 4 | 1.3 | 0.50* |
| PP27 | M5 | A | AA | 75 | 5 TIBA | 1.1 TBF20 | 0.25 | 65 | 732 | 4 | 1.3 | 0.51* |
| PP28 | M5 | A | AA | 75 | 5 TIBA | 1.1 ABF20 | 0.1 | 102 | 555 | 3 | 1.2 | 0.42* |

*= end groups visible with FT-IR spectrum

TABLE 3C

Select Examples of Ethylene-1-Octene Copolymerization with in situ prepared Metal-Ligand Compositions

| Example | Ligand | Metal Precursors | Ligand to Metal Ratio | Complexation Method | Reactor Prep. Method | Activation/ Injection Method | Polymerization Temp (C.) | Group 13 Reagent and mole Equivalent Alkyl | Activator | μmol Catalyst Injected | Polymerization Time(s) | Activity (g polymer/ min * mmol) | Mw (k) | PDI (Mw/Mn) | mol % Octene by FTIR |
|---|---|---|---|---|---|---|---|---|---|---|---|---|---|---|---|
| EO1 | A13 | Zr(CH$_2$C$_6$H$_5$)$_4$ | 2 | ZN | B | KKKK | 100 | 5 TMA | 1.1 ABF20 | 0.02 | 61 | 13153 | 16 | 1.7 | 9 |
| EO2 | A13 | Zr(CH$_2$C$_6$H$_5$)$_4$ | 2 | ZN | B | KKKK | 100 | 5 TIBA | 1.1 ABF20 | 0.02 | 61 | 12099 | 13 | 1.6 | 9 |
| EO3 | A13 | Hf(CH$_2$C$_6$H$_5$)$_4$ | 2 | ZN | B | KKKK | 100 | 5 TMA | 1.1 ABF20 | 0.02 | 61 | 11072 | 78 | 1.6 | 9 |
| EO4 | A13 | Hf(CH$_2$C$_6$H$_5$)$_4$ | 2 | ZN | B | KKKK | 100 | 5 TIBA | 1.1 ABF20 | 0.02 | 68 | 6238 | 117 | 1.5 | 6 |
| EO5 | A27 | Zr(CH$_2$C$_6$H$_5$)$_4$ | 2 | ZN | B | KKKK | 100 | 5 TMA | 1.1 ABF20 | 0.02 | 61 | 8201 | 12 | 1.6 | 5 |
| EO6 | A27 | Zr(CH$_2$C$_6$H$_5$)$_4$ | 2 | ZN | B | KKKK | 100 | 5 TIBA | 1.1 ABF20 | 0.02 | 61 | 9567 | 12 | 1.6 | 5 |
| EO7 | A27 | Hf(CH$_2$C$_6$H$_5$)$_4$ | 2 | ZN | B | KKKK | 100 | 5 TMA | 1.1 ABF20 | 0.02 | 61 | 7475 | 64 | 1.6 | 4 |
| EO8 | A27 | Hf(CH$_2$C$_6$H$_5$)$_4$ | 2 | ZN | B | KKKK | 100 | 5 TIBA | 1.1 ABF20 | 0.02 | 61 | 6518 | 64 | 1.6 | 4 |
| EO9 | A12 | Zr(CH$_2$C$_6$H$_5$)$_4$ | 2 | ZN | B | LLLL | 100 | 5 TMA | 1.1 ABF20 | 0.05 | 120 | 960 | 49 | 1.5 | 2 |
| EO10 | A12 | Hf(CH$_2$C$_6$H$_5$)$_4$ | 2 | ZN | B | KKKK | 100 | 5 TIBA | 1.1 ABF20 | 0.02 | 1356 | 186 | 286 | 1.5 | 3 |
| EO11 | A23 | Zr(CH$_2$C$_6$H$_5$)$_4$ | 2 | ZN | B | KKKK | 100 | 5 TIBA | 1.1 ABF20 | 0.02 | 1801 | 101 | | 1.7 | lowC8 |
| EO12 | A14 | Zr(CH$_2$C$_6$H$_5$)$_4$ | 2 | ZO | B | KKKK | 100 | 5 TIBA | 1.1 ABF20 | 0.02 | 102 | 3338 | 28 | 2.5 | 2 |
| EO13 | A14 | Zr(CH$_2$C$_6$H$_5$)$_4$ | 2 | ZO | B | KKKK | 100 | 5 TIBA | 1.1 ABF20 | 0.02 | 105 | 3280 | 29 | 2.7 | 2 |
| EO14 | C14 | Zr(CH$_2$C$_6$H$_5$)$_4$ | 2 | ZP | B | MMMM | 100 | 5 TIBA | 1.1 TBF20 | 0.1 | 61 | 1679 | 29 | 2 | 3 |
| EO15 | C14 | Zr(CH$_2$C$_6$H$_5$)$_4$ | 2 | ZP | B | MMMM | 100 | 5 TIBA | 1.1 ABF20 | 0.067 | 64 | 2018 | 81 | 1.7 | 3 |
| EO16 | C14 | Hf(CH$_2$C$_6$H$_5$)$_4$ | 2 | ZP | B | MMMM | 100 | 5 TIBA | 1.1 TBF20 | 0.067 | 61 | 2374 | 101 | 1.8 | 4 |
| EO17 | C14 | Hf(CH$_2$C$_6$H$_5$)$_4$ | 2 | ZP | B | MMMM | 100 | 5 TIBA | 1.1 TBF20 | 0.067 | 62 | 1969 | 53 | 1.7 | 3 |
| EO18 | C15 | Zr(CH$_2$C$_6$H$_5$)$_4$ | 2 | ZP | B | MMMM | 100 | 5 TIBA | 1.1 ABF20 | 0.2 | 415 | 81 | 66 | 1.8 | 10 |
| EO19 | C15 | Hf(CH$_2$C$_6$H$_5$)$_4$ | 2 | ZP | B | MMMM | 100 | 5 TIBA | 1.1 ABF20 | 0.2 | 477 | 84 | 57 | 1.8 | 12 |
| EO20 | C19 | Zr(CH$_2$C$_6$H$_5$)$_4$ | 2 | ZP | B | MMMM | 100 | 5 TIBA | 1.1 ABF20 | 0.1 | 99 | 1155 | 93 | 1.6 | 12 |
| EO21 | C19 | Zr(CH$_2$C$_6$H$_5$)$_4$ | 2 | ZP | B | MMMM | 100 | 5 TIBA | 1.1 TBF20 | 0.067 | 123 | 1297 | 84 | 1.9 | 11 |
| EO22 | C19 | Hf(CH$_2$C$_6$H$_5$)$_4$ | 2 | ZP | B | GGGG | 100 | 5 TIBA | 3.3 ABC | 0.1 | 277 | 298 | 99 | 1.8 | 14 |
| EO23 | C19 | Hf(CH$_2$C$_6$H$_5$)$_4$ | 2 | ZP | B | MMMM | 100 | 5 TIBA | 1.1 ABF20 | 0.067 | 258 | 472 | 175 | 1.8 | 12 |
| EO24 | E4 | Zr(CH$_2$C$_6$H$_5$)$_4$ | 1 | ZQ | B | NNNN | 100 | 5 TIBA | 1.1 ABF20 | 0.15 | 480 | 79 | 170 | 1.8 | 10 |
| EO25 | E7 | Zr(CH$_2$C$_6$H$_5$)$_4$ | 1 | ZR | B | NNNN | 100 | 5 TIBA | 1.1 TBF20 | 0.15 | 868 | 41 | 189 | 3.69 | 5 |
| EO26 | E7 | Hf(CH$_2$C$_6$H$_5$)$_4$ | 1 | ZR | B | NNNN | 100 | 5 TIBA | 1.1 TBF20 | 0.15 | 1801 | 19 | 262 | 9.09 | 5 |
| EO27 | F4 | Zr(CH$_2$C$_6$H$_5$)$_4$ | 1 | ZQ | B | NNNN | 100 | 5 TIBA | 1.1 TBF20 | 0.15 | 274 | 131 | 152 | 9.02 | 4 |
| EO28 | F2 | Zr(CH$_2$C$_6$H$_5$)$_4$ | 1 | ZQ | B | NNNN | 100 | 5 TIBA | 1.1 TBF20 | 0.15 | 229 | 214 | 191 | 5.37 | 5 |
| EO29 | F2 | Hf(CH$_2$C$_6$H$_5$)$_4$ | 1 | ZQ | B | NNNN | 100 | 5 TIBA | 1.1 TBF20 | 0.15 | 389 | 113 | 334 | 4.09 | 7 |
| | | | | | | | | | | | | | 42 | 1.67 | |

TABLE 3D

Select Examples of Ethylene-1-octene Copolymerization with Isolated Complexes

| Example | Isolated Complex | Reactor prep. Method | Activation and Injection Method | Polymerization Temp(C.) | Group 13 Reagent and mole Equivalent Alkyl | Activator | μmol Catalyst Injected | H2 added (psi) | Polymerization Time(s) | Activity (g polymer/ min * mmol) | Mw (k) | PDI (Mw/Mn) | mol % Octene by FTIR |
|---|---|---|---|---|---|---|---|---|---|---|---|---|---|
| EO30 | M1 | B | AAA | 100 | 5 TIBA | 1.1 ABF20 | 0.01 | 4 | 163 | 3570 | 174 | 1.7 | 3 |
| EO31 | M1 | B | BBB | 100 | 5 TIBA | 1.1 ABF20 | 0.015 | 0 | 61 | 10082 | 154 | 1.8 | 6 |
| EO32 | M1 | B | CCC | 100 | 5 TIBA | 200 MMAO | 0.015 | 0 | 102 | 4578 | 170 | 1.8 | 4 |
| EO33 | M1 | B | DDD | 100 | 200 MMAO | 200 MMAO | 0.01 | 4 | 167 | 3099 | 161 | 2.5 | 3 |
| EO34 | M1 | B | EEE | 100 | 200 MMAO | 200 MMAO | 0.015 | 0 | 84 | 5735 | 155 | 1.8 | 3 |
| EO35 | M2 | B | AAA | 100 | 5 TIBA | 1.1 ABF20 | 0.01 | 4 | 70 | 10291 | 15 | 1.6 | 6 |
| EO36 | M2 | B | FFF | 130 | 5 TIBA | 1.1 ABF20 | 0.015 | 0 | 80 | 7960 | 17 | 1.6 | 6 |
| EO37 | M2 | B | AAA | 100 | 5 TIBA | 1.1 ABF20 | 0.01 | 4 | 61 | 19878 | 26 | 1.8 | 7 |
| EO38 | M2 | B | GGG | 100 | 5 TIBA | 200 MMAO | 0.01 | 4 | 119 | 4927 | 15 | 1.6 | 4 |
| EO39 | M2 | B | GGG | 100 | 5 TIBA | 200 MMAO | 0.01 | 0 | 61 | 16725 | 27 | 1.8 | 4 |
| EO40 | M2 | B | DDD | 100 | 200 MMAO | 200 MMAO | 0.01 | 0 | 61 | 15624 | 24 | 1.8 | 4 |
| EO41 | M4 | B | AAA | 100 | 5 TIBA | 1.1 ABF20 | 0.01 | 4 | 454 | 1141 | 35 | 2.1 | 2 |
| EO42 | M4 | B | FFF | 130 | 5 TIBA | 1.1 ABF20 | 0.015 | 0 | 901 | 197 | 39 | 2 | 2 |
| EO43 | M4 | B | BBB | 100 | 5 TIBA | 1.1 ABF20 | 0.015 | 0 | 123 | 3659 | 15 | 2 | low C8 |
| EO44 | M4 | B | EEE | 100 | 200 MMAO | 200 MMAO | 0.015 | 0 | 125 | 3512 | 22 | 2 | 3 |
| EO45 | M6 | C | HHH | 100 | 5 TIBA | 1.1 ABF20 | 0.011 | 4 | 61 | 8370 | 2 | 1.1 | 6[a] |
| EO46 | M6 | C | HHH | 130 | 5 TIBA | 1.1 ABF20 | 0.016 | 0 | 61 | 5969 | 2 | 1.1 | 8[a] |
| EO47 | M6 | C | III | 100 | 5 MMAO | 100 MMAO | 0.013 | 0 | 61 | 5712 | 2 | 1.1 | 5[a] |
| EO48 | M9 | C | JJJ | 100 | 5 TIBA | 1.1 ABF20 | 0.02 | 4 | 95 | 3707 | 70 | 2.6 | 3 |
| EO49 | M9 | C | KKK | 100 | 5 TIBA | 1.1 ABF20 | 0.015 | 0 | 135 | 3327 | 152 | 2 | 3 |
| EO50 | M9 | C | LLL | 100 | 5 MMAO | b | 0.02 | 4 | 83 | 4392 | 50 | 2.3 | 3 |
| EO51 | M9 | C | MMM | 130 | 5 MMAO | b | 0.1 | 0 | 68 | 1282 | 23 | 2.3 | 3 |
| EO52 | M10 | C | JJJ | 100 | 5 TIBA | 1.1 ABF20 | 0.02 | 4 | 62 | 6174 | 20 | 2.5 | 3 |
| EO53 | M10 | C | KKK | 130 | 5 TIBA | 1.1 ABF20 | 0.047 | 0 | 124 | 1489 | 49 | 2.5 | 4 |
| EO54 | M10 | C | KKK | 100 | 5 TIBA | 1.1 ABF20 | 0.015 | 0 | 114 | 4589 | 151 | 2.2 | 3 |
| EO55 | M10 | C | LLL | 100 | 5 MMAO | b | 0.02 | 4 | 74 | 5992 | 19 | 2.7 | 3 |
| EO56 | M11 | C | NNN | 100 | 5 TIBA | 1.1 ABF20 | 0.02 | 0 | 274 | 1072 | 308 | 1.5 | 3 |
| EO57 | M11 | C | OOO | 100 | 5 MMAO | b | 0.02 | 4 | 154 | 2005 | 74 | 3 | 3 |
| EO58 | M12 | C | NNN | 100 | 5 TIBA | 1.1 ABF20 | 0.02 | 4 | 177 | 1639 | 46 | 3.8 | 5 |
| EO59 | M12 | C | NNN | 100 | 5 TIBA | 1.1 ABF20 | 0.02 | 0 | 154 | 2147 | 256 | 1.5 | 3 |
| EO60 | M12 | C | OOO | 100 | 5 MMAO | b | 0.02 | 4 | 162 | 1783 | 31 | 2.5 | 2 |
| EO61 | M12 | C | PPP | 130 | 5 MMAO | b | 0.04 | 0 | 462 | 369 | 3 | 1.1 | 3 |
| EO62 | M12 | C | OOO | 100 | 5 MMAO | a | 0.02 | 0 | 152 | 2199 | 267 | 1.5 | 3 | a = significant chain end contribution;
b = no activator was added to the 1 mL glass vial, "catalyst" was activated inside the reaction vessel.

TABLE 3E

Select In-Situ Preparation of Ligand-Group IV Compositions - Styrene Polymerization Results

| Example | method | reaction temperature (°C.) | reaction time (min) | mol equ. of group 13 reagent* | group 13 reagent | mol equ. of activator* | activator | metal precursor | mol equ. of ligand 1* | ligand 1 | mol equ. of ligand 2* | ligand 2' | umol of catalyst | corrected yield (mg) | conversion (mg PS/mg of Sty) * 100 | activity (mg PS/(umol cat * min)) | Mw (k) | PDI | Tacticity (% mm) |
|---|---|---|---|---|---|---|---|---|---|---|---|---|---|---|---|---|---|---|---|
| PS1 | 1 | 105 | 5 | 5 | TIBA | 1 | SJ2BF20 | Zr(CH₂C₆H₅)₄ | 2 | A13 | | | 0.5 | 1246 | 69 | 498 | 127 | 2.3 | |
| PS2 | 1 | 105 | 5 | 5 | PMAO_IP | 1 | SJ2BF20 | Zr(CH₂C₆H₅)₄ | 2 | A13 | | | 0.5 | 515 | 28 | 206 | 113 | 2.5 | |
| PS3 | 3 | 105 | 5 | 5 | TIBA | 1 | SJ2BF20 | Zr(CH₂C₆H₅)₄ | 1 | A13 | | | 0.25 | 1168 | 64 | 934 | 402 | 1.8 | |
| PS4 | 3 | 105 | 5 | 5 | TIBA | 1 | SJ2BF20 | Zr(CH₂C₆H₅)₄ | 1 | A13 | 1 | TRI** | 0.25 | 593 | 33 | 474 | 105 | 2.4 | |
| PS5 | 3 | 105 | 5 | 5 | PMAO_IP | 1 | SJ2BF20 | Zr(CH₂C₆H₅)₄ | 1 | A13 | 1 | A34 | 0.25 | 598 | 33 | 478 | 57 | 1.7 | |
| PS6 | 3 | 105 | 5 | 5 | TIBA | 1 | SJ2BF20 | Zr(CH₂C₆H₅)₄ | 1 | A13 | 1 | B2 | 0.25 | 111 | 6 | 89 | 119 | 2.9 | |
| PS7 | 3 | 105 | 5 | 5 | PMAO_IP | 1 | SJ2BF20 | Zr(CH₂C₆H₅)₄ | 1 | A13 | 1 | A34 | 0.5 | 231 | 13 | 92 | 132 | 2.2 | |
| PS8 | 4 | 125 | 5 | 5 | TIBA | 1 | SJ2BF20 | Zr(CH₂C₆H₅)₄ | 2 | A13 | 1 | B2 | 0.5 | 469 | 26 | 187 | 29 | 1.9 | |
| PS9 | 4 | 125 | 5 | 5 | PMAO_IP | 1 | SJ2BF20 | Zr(CH₂C₆H₅)₄ | 2 | A13 | | | 0.445 | 191 | 11 | 86 | 45 | 3.5 | |
| PS10 | 6 | 125 | 5 | 5 | TIBA | 1 | SJ2BF20 | Zr(CH₂C₆H₅)₄ | 1 | A13 | 1 | TRI | 0.125 | 527 | 29 | 844 | 304 | 2.2 | |
| PS11 | 6 | 125 | 5 | 5 | PMAO_IP | 1 | SJ2BF20 | Zr(CH₂C₆H₅)₄ | 1 | A13 | 1 | TRI | 0.0625 | 467 | 26 | 1494 | 280 | 2.2 | 88 |
| PS12 | 6 | 125 | 5 | 5 | TIBA | 1 | SJ2BF20 | Zr(CH₂C₆H₅)₄ | 1 | A13 | 1 | TRI | 0.125 | 1544 | 85 | 2471 | 294 | 2.7 | |
| PS13 | 7 | 125 | 5 | 5 | PMAO_IP | 1 | SJ2BF20 | Zr(CH₂C₆H₅)₄ | 1 | A13 | 1 | TRI | 0.125 | 1589 | 88 | 2542 | 216 | 2.4 | |
| PS14 | 1 | 105 | 15 | 5 | TIBA | 1 | SJ2BF20 | Zr(CH₂C₆H₅)₄ | 2 | B2 | | | 0.5 | 312 | 17 | 42 | 125 | 1.8 | |
| PS15 | 1 | 105 | 15 | 5 | TIBA | 1 | SJ2BF20 | Zr(CH₂C₆H₅)₄ | 2 | B2 | | | 0.5 | 235 | 13 | 31 | 90 | 1.8 | |
| PS16 | 4 | 125 | 5 | 5 | TIBA | 1 | SJ2BF20 | Zr(CH₂C₆H₅)₄ | 1 | B2 | | | 0.6675 | 244 | 13 | 73 | 123 | 2.8 | |
| PS17 | 4 | 125 | 5 | 5 | PMAO_IP | 1 | SJ2BF20 | Zr(CH₂C₆H₅)₄ | 2 | B2 | | | 0.6675 | 211 | 12 | 63 | 118 | 2.1 | |
| PS18 | 6 | 125 | 5 | 5 | TIBA | 1 | SJ2BF20 | Zr(CH₂C₆H₅)₄ | 1 | B2 | 1 | TRI | 0.125 | 233 | 13 | 373 | 416 | 2.9 | |
| PS19 | 6 | 125 | 5 | 5 | PMAO_IP | 1 | SJ2BF20 | Zr(CH₂C₆H₅)₄ | 1 | B2 | 1 | TRI | 0.125 | 317 | 17 | 506 | 231 | 2.0 | |
| PS20 | 7 | 125 | 5 | 5 | PMAO_IP | 1 | SJ2BF20 | Zr(CH₂C₆H₅)₄ | 1 | B2 | 1 | TRI | 0.25 | 659 | 36 | 527 | 190 | 2.0 | |
| PS21 | 1 | 105 | 5 | 5 | PMAO_IP | 1 | SJ2BF20 | Zr(CH₂C₆H₅)₄ | 2 | A34 | | | 0.125 | 1053 | 58 | 1685 | 76 | 1.7 | |
| PS22 | 1 | 105 | 5 | 5 | TIBA | 1 | SJ2BF20 | Zr(CH₂C₆H₅)₄ | 2 | A34 | | | 0.125 | 1018 | 56 | 1629 | 69 | 1.7 | |
| PS23 | 4 | 125 | 5 | 5 | PMAO_IP | 1 | SJ2BF20 | Zr(CH₂C₆H₅)₄ | 2 | A34 | | | 0.1125 | 386 | 21 | 687 | 52 | 1.9 | |
| PS24 | 4 | 125 | 5 | 5 | TIBA | 1 | SJ2BF20 | Zr(CH₂C₆H₅)₄ | 2 | A34 | | | 0.125 | 813 | 45 | 1300 | 50 | 1.8 | |
| PS25 | 6 | 125 | 5 | 5 | TIBA | 1 | SJ2BF20 | Zr(CH₂C₆H₅)₄ | 1 | A34 | 1 | TRI | 0.125 | 126 | 7 | 202 | 1483 | 4.3 | |
| PS26 | 6 | 125 | 5 | 5 | PMAO_IP | 1 | SJ2BF20 | Zr(CH₂C₆H₅)₄ | 1 | A34 | 1 | TRI | 0.25 | 322 | 18 | 258 | 423 | 3.0 | |
| PS27 | 7 | 125 | 5 | 5 | PMAO_IP | 1 | SJ2BF20 | Zr(CH₂C₆H₅)₄ | 1 | A34 | 1 | TRI | 0.25 | 460 | 25 | 368 | 259 | 2.2 | |
| PS28 | 2 | 105 | 5 | 5 | PMAO_IP | 1 | SJ2BF20 | Zr(CH₂C₆H₅)₄ | 2 | B12 | | | 0.25 | 496 | 27 | 396 | 501 | 1.8 | |
| PS29 | 2 | 125 | 5 | 5 | PMAO_IP | 1 | BF15 | Zr(CH₂C₆H₅)₄ | 2 | B12 | | | 0.125 | 210 | 12 | 336 | 481 | 1.7 | |
| PS30 | 5 | 125 | 5 | 5 | PMAO_IP | 1 | BF15 | Zr(CH₂C₆H₅)₄ | 2 | B12 | | | 0.125 | 208 | 11 | 332 | 211 | 1.6 | |

TABLE 3E-continued

Select In-Situ Preparation of Ligand-Group IV Compositions - Styrene Polymerization Results

| Example | method | reaction temperature (° C.) | reaction time (min) | mol equ. of group 13 reagent* | group 13 reagent | mol equ. of activator* | activator | metal precursor | mol equ. of ligand 1* | ligand 1 | mol equ. of ligand 2* | ligand 2' | umol of catalyst | corrected yield (mg) | conversion (mg PS/mg of Sty) * 100 | activity (mg PS/(umol cat * min)) | Mw (k) | PDI | Tacticity (% mm) |
|---|---|---|---|---|---|---|---|---|---|---|---|---|---|---|---|---|---|---|---|
| PS31 | 5 | 125 | 5 | 5 | PMAO_IP | 1 | SJ2BF20 | Zr(CH₂C₆H₅)₄ | 2 | B12 | | | 0.125 | 314 | 17 | 502 | 207 | 1.6 | 80 |
| PS17 | 4 | 125 | 5 | 5 | PMAO_IP | 1 | SJ2BF20 | Zr(CH₂C₆H₅)₄ | 2 | B2 | | | 0.6675 | 211 | 12 | 63 | 118 | 2.1 | |
| PS18 | 6 | 125 | 5 | 5 | TIBA | 1 | SJ2BF20 | Zr(CH₂C₆H₅)₄ | 1 | B2 | 1 | TRI | 0.125 | 233 | 13 | 373 | 416 | 2.9 | |
| PS19 | 6 | 125 | 5 | 5 | PMAO_IP | 1 | SJ2BF20 | Zr(CH₂C₆H₅)₄ | 1 | B2 | 1 | TRI | 0.125 | 317 | 17 | 506 | 231 | 2.0 | |
| PS20 | 7 | 125 | 5 | 5 | PMAO_IP | 1 | SJ2BF20 | Zr(CH₂C₆H₅)₄ | 1 | B2 | 1 | TRI | 0.25 | 659 | 36 | 527 | 190 | 2.0 | |
| PS21 | 1 | 105 | 5 | 5 | PMAO_IP | 1 | SJ2BF20 | Zr(CH₂C₆H₅)₄ | 2 | A34 | | | 0.125 | 1053 | 58 | 1685 | 76 | 1.7 | |
| PS22 | 1 | 105 | 5 | 5 | TIBA | 1 | SJ2BF20 | Zr(CH₂C₆H₅)₄ | 2 | A34 | | | 0.125 | 1018 | 56 | 1629 | 69 | 1.7 | |
| PS23 | 4 | 125 | 5 | 5 | PMAO_IP | 1 | SJ2BF20 | Zr(CH₂C₆H₅)₄ | 2 | A34 | | | 0.1125 | 386 | 21 | 687 | 52 | 1.9 | |
| PS24 | 4 | 125 | 5 | 5 | TIBA | 1 | SJ2BF20 | Zr(CH₂C₆H₅)₄ | 2 | A34 | | | 0.125 | 813 | 45 | 1300 | 50 | 1.8 | |
| PS25 | 6 | 125 | 5 | 5 | TIBA | 1 | SJ2BF20 | Zr(CH₂C₆H₅)₄ | 1 | A34 | 1 | TRI | 0.125 | 126 | 7 | 202 | 1483 | 4.3 | |
| PS26 | 6 | 125 | 5 | 5 | PMAO_IP | 1 | SJ2BF20 | Zr(CH₂C₆H₅)₄ | 1 | A34 | 1 | TRI | 0.25 | 322 | 18 | 258 | 423 | 3.0 | |
| PS27 | 7 | 125 | 5 | 5 | PMAO_IP | 1 | SJ2BF20 | Zr(CH₂C₆H₅)₄ | 1 | A34 | 1 | TRI | 0.25 | 460 | 25 | 368 | 259 | 2.2 | |
| PS28 | 2 | 105 | 5 | 5 | PMAO_IP | 1 | SJ2BF20 | Zr(CH₂C₆H₅)₄ | 2 | B12 | | | 0.25 | 496 | 27 | 396 | 501 | 1.8 | |
| PS29 | 2 | 105 | 5 | 5 | PMAO_IP | 1 | BF15 | Zr(CH₂C₆H₅)₄ | 2 | B12 | | | 0.125 | 210 | 12 | 336 | 481 | 1.7 | |
| PS30 | 5 | 125 | 5 | 5 | PMAO_IP | 1 | BF15 | Zr(CH₂C₆H₅)₄ | 2 | B12 | | | 0.125 | 208 | 11 | 332 | 211 | 1.6 | |
| PS31 | 5 | 125 | 5 | 5 | PMAO_IP | 1 | SJ2BF20 | Zr(CH₂C₆H₅)₄ | 2 | B12 | | | 0.125 | 314 | 17 | 502 | 207 | 1.6 | 80 |

TABLE 3F

Select Examples of Slurry Ethylene-1-Octene Copolymerization with Supported Catalysts

| Example | Isolated Complex | Polymer-ization Temp(C.) | Support Temp(C.) | mg Catalyst Injected | μmol Catalyst Injected | H2 added (psi) | Polymerization Time(s) | Activity (g polymer/ min * mmol) | Slurry Activity (g polymer/g catalyst * hr) | Mw (k) | PDI (Mw/Mn) | mol % Octene by FTIR |
|---|---|---|---|---|---|---|---|---|---|---|---|---|
| S-EO1 | S-M2 | 85 | RT | 0.3 | 0.0057 | 4 | 605 | 1905 | 2172 | 53 | 2.3 | 1.4 |
| S-EO2 | S-M2 | 85 | RT | 0.2 | 0.0038 | 0 | 375 | 4813 | 5486 | 58 | 2.5 | 1.3 |
| S-EO3 | S-M2 | 85 | 50 | 0.3 | 0.0057 | 4 | 320 | 3816 | 4350 | 40 | 2.4 | 2.5 |
| S-EO4 | S-M2 | 85 | 50 | 0.2 | 0.0038 | 0 | 309 | 5979 | 6816 | 76 | 3.3 | 1.3 |

Section 4. Synthesis of Phenol Heterocycle Complexes M1-M12

In the following sections, "Me" refers to methyl, "'Bu" refers to tert-butyl, "Bz" refers to benzyl, "Ar" refers to aromatic, "Ph" refers to phenyl, "An" refers to anthracenyl, "2,6Cl$_2$Ph" refers to 2,6-dichlorophenyl, "Cbz" refers to carbazole and "PT" refers to phenol thiazole. Unless otherwise noted, all manipulations were conducted under an atmosphere of dry, deoxygenated argon in a Vacuum Atmospheres or MBraun glovebox. MBz$_4$ (M=Hf, Zr) were purchased from Strem Chemicals, Inc. in Newburyport, Mass., U.S.A. Pentane and toluene were sparged with nitrogen and passed though columns of activated Al$_2$O$_3$ and CU-0226S (Engelhart; a commercially available oxygen scavenger). Anhydrous benzene-d$_6$ was purchased from Cambridge Isotopes, degassed and stored over 4 Å molecular sieves under Ar. All other reagents were purchased from Aldrich in the highest available purity and used without further purification.

NMR spectra were recorded on a Bruker 300 MHz spectrometer. $^1$H chemical shifts were referenced relative to residual protio solvent peaks. Due to the large number of aromatic substituents and the complexity of the spectra in the 6.5-8.5 ppm region, the peaks corresponding to the hydrogens on the aromatic rings are generally not assigned and are denoted as "ArH" in the lists of NMR data.

Complexes used in polymerization screening are shown below:

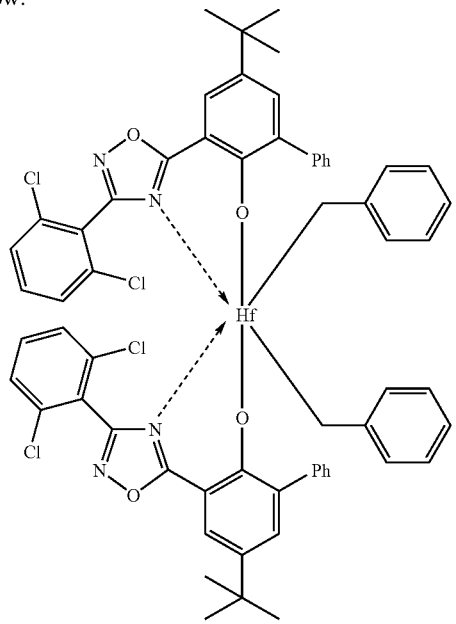

M1

-continued

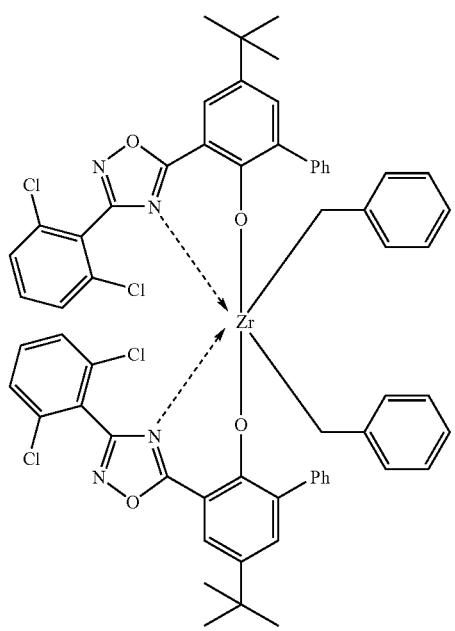

M2

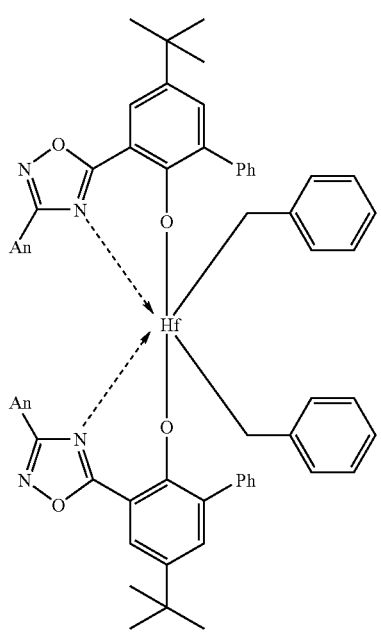

M3

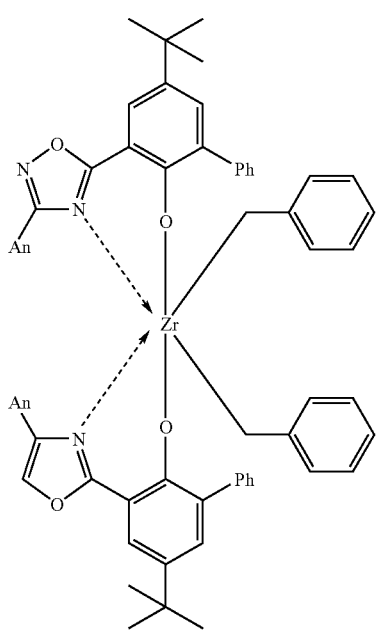
M4
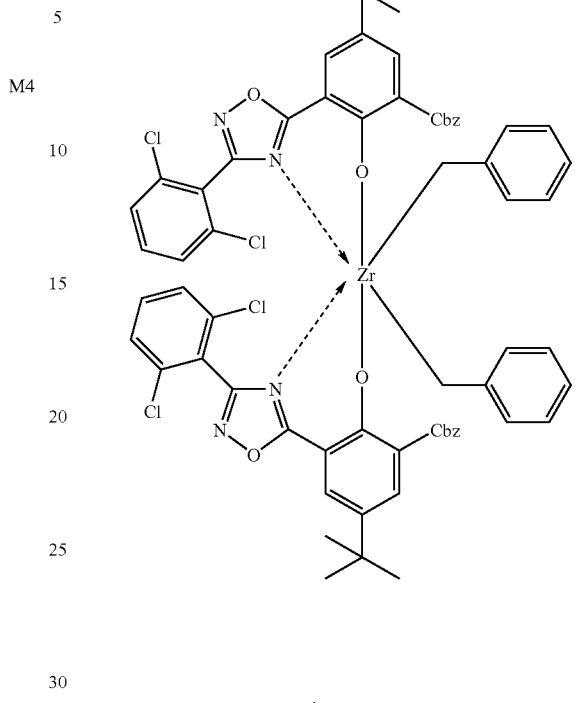
M6
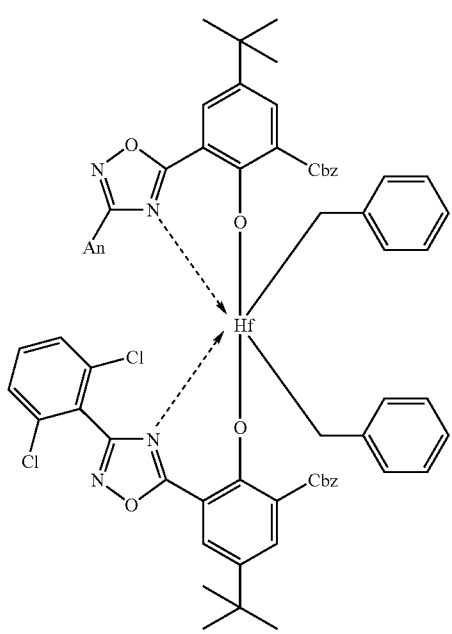
M5
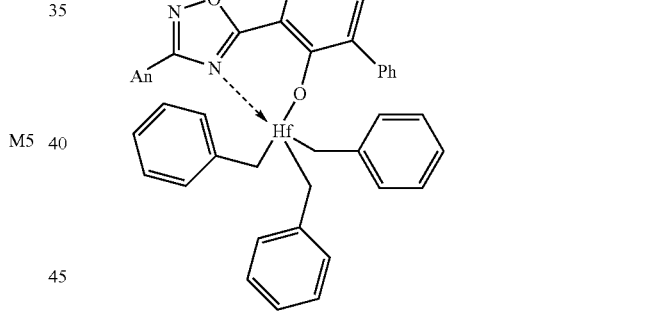
M7
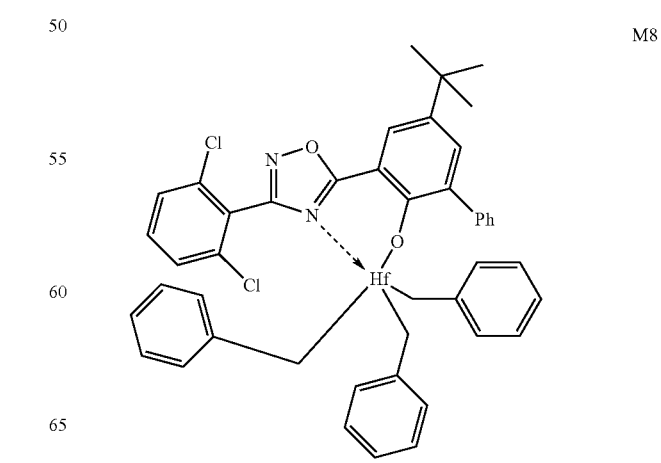
M8

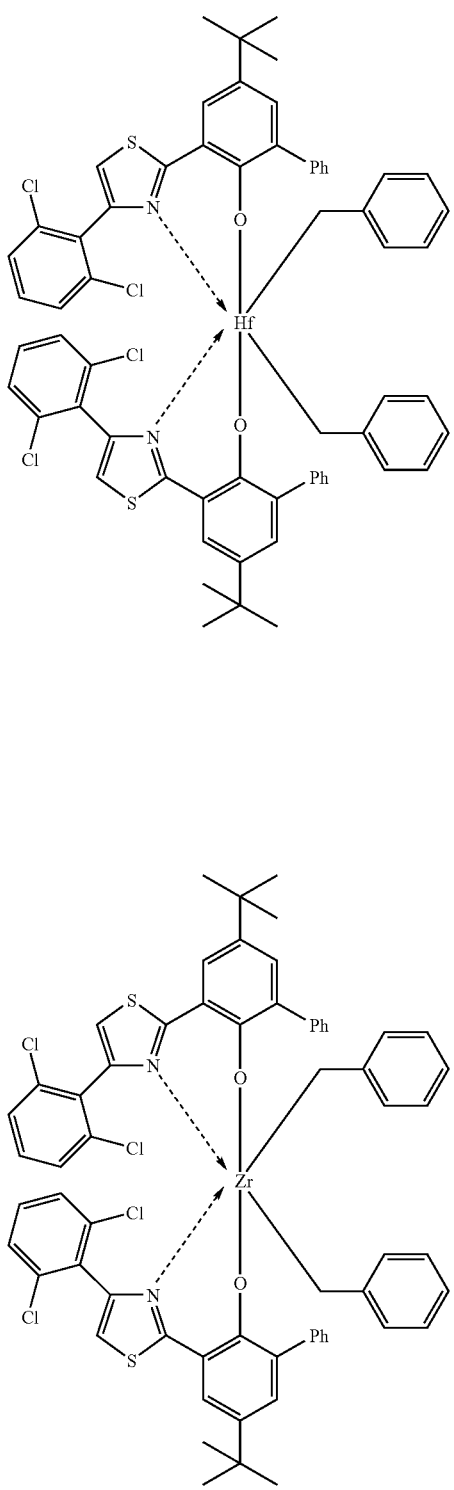

M9

M10

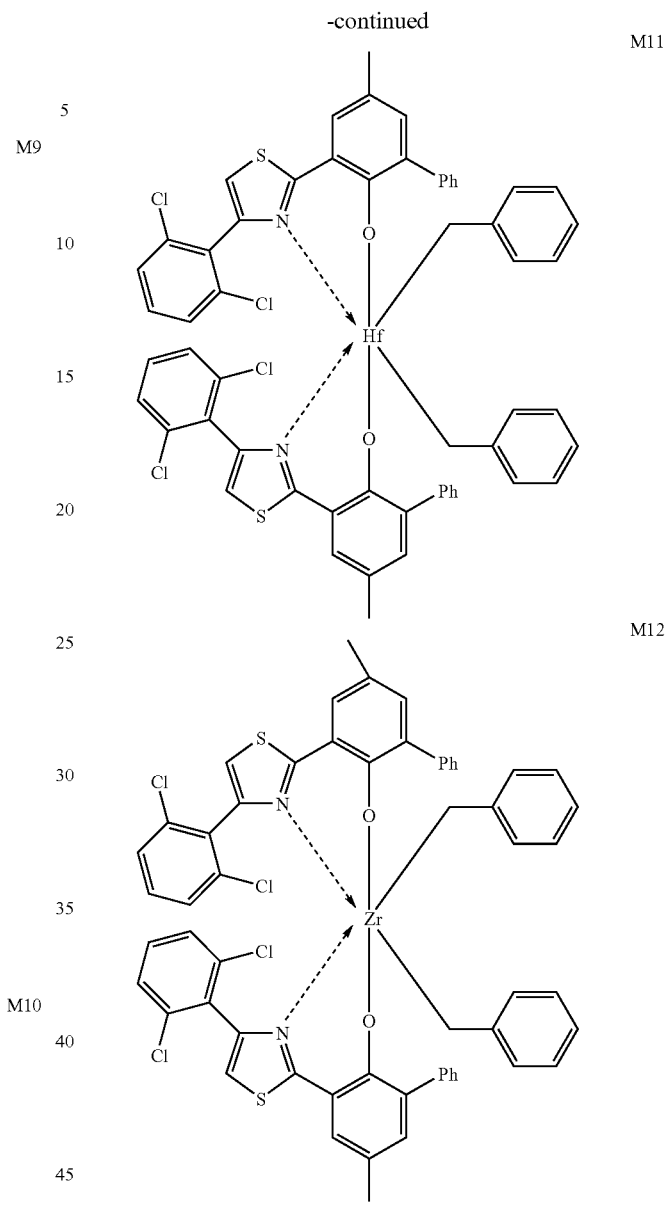

M11

M12

Section 4A. Synthesis of Phenol Oxadiazole Hf Complex [A13]$_2$HfBz$_2$ (M1):

A toluene solution of HfBz$_4$ (140 mg, 0.26 mmol, 3 mL) was added dropwise to a toluene solution of phenol oxadiazole A13 (227 mg, 0.52 mmol, 15 mL). The mixture was stirred for 1 h at room temperature. The volatiles were removed and the resulting residue was washed with pentane and dried under vacuum, yielding a yellow solid product (303 mg, 94%). $^1$H NMR (C$_6$D$_6$, RT) δ 8.0 (d, 2H, ArH), 7.55 (d, 4H, ArH), 7.42 (d, 2H, ArH), 7.34 (t, 4H, ArH), 7.21 (t, 2H, ArH), 6.8-6.7 (m, 8H, ArH), 6.53 (d/d, 2H, ArH), 6.45 (t, 2H, ArH), 6.22 9 (d/d, 2H, ArH), 6.05 (t, 2H, ArH), 2.47 (d, 2H, HfCH$_2$), 2.31 (d, 2H, HfCH$_2$), 1.23 (s, 18H, CMe$_3$).

Section 4B. Synthesis of Phenol Oxadiazole Zr Complex [A13]$_2$ZrBz$_2$ (M2):

A toluene solution of ZrBz$_4$ (104 mg, 0.23 mmol, 4 mL) was added dropwise to a toluene solution of phenol oxadiazole A13 (200 mg, 0.46 mmol, 12 mL). The mixture was stirred for 1 h at room temperature. The volatiles were removed and the resulting residue was washed with pentane and dried under vacuum (190 mg, 73%). $^1$H NMR (C$_6$D$_6$, RT)

δ 8.18 (d, 2H, ArH), 7.56 (d, 4H, o-Ph), 7.50-7.28 (m, 6H, ArH), 7.20 (t, 2H, ArH), 6.7-6.5 (m, 8H, ArH), 6.4-6.2 (m, 6H, ArH), 6.02 (t, 2H, p-Ph), 2.17 (d, 2H, ZrCH$_2$), 1.55 (d, 2H, ZrCH$_2$), 1.24 (s, 18H, CMe$_3$).

Section 4C. Synthesis of Phenol Oxadiazole Hf Complex [A14]$_2$HfBZ$_2$ (M3):

A toluene solution of HfBz$_4$ (24 mg, 0.044 mmol, 3 mL) was added to a toluene solution of phenol oxadiazole A14 (41 mg, 0.088 mmol, 3 mL). The mixture was stirred for 35 min at room temperature and the titled complex formed quantitatively as determined by $^1$H NMR. The volatiles were removed and a yellow solid product was obtained which was used for polymerization screening without further purification. $^1$H NMR (C$_6$D$_6$, RT) δ 7.9 (d, 2H, ArH), 7.8 (s, 2H, ArH), 7.71 (d, 2H, ArH), 7.48 (d, 2H, ArH), 7.47-7.39 (m, ArH), 7.38 (d, 2H, ArH), 7.35-6.8 (m, 12H, ArH, partially overlap with solvent signal), 6.56 (m, 8H, ArH), 6.39 (t, 2H, ArH), 6.25 (d, 4H), 1.77 (d, 2H, HfCH$_2$), 1.46 (d, 2H, HfCH$_2$), 1.37 (s, 18H, CMe$_3$).

Section 4D. Synthesis of Phenol Oxadiazole Zr Complex [A14]$_2$ZrBz$_2$ (M4):

A C$_6$D$_6$ solution of ZrBz$_4$ (10 mg, 0.022 mmol, 1 mL) was added to a C$_6$D$_6$ solution of phenol oxadiazole A14 (21 mg, 0.044 mmol, 1 mL). The mixture was stirred for ~4.5 h at room temperature and the titled complex formed quantitatively as determined by $^1$H NMR. The volatiles were removed and the solid product was washed with pentane and dried (12 mg, 45%). $^1$H NMR (C$_6$D$_6$, RT) δ 8.03 (d, 2H, ArH), 7.95 (d, 2H, ArH), 7.84 (s, 2H, ArH), 7.6-6.8 (m, ArH, partially overlap with solvent signal), 6.60-6.35 (m, 6H, ArH), 6.30 (d, 4H, ArH), 5.82 (d, 4H, ArH), 1.66 (d, 2H, ZrCH$_2$), 1.37 (s, 18H, CMe$_3$), 0.92 (d, 2H, ZrCH$_2$).

Section 4E. Synthesis of Phenol Oxadiazole Hf Complex [A13][A14]HfBZ$_2$ (M5):

A benzene-d$_6$ solution of phenol oxadiazole A14 (9.3 mg, 0.02 mmol, 0.5 mL) and a benzene-d$_6$ solution of HfBz$_4$ (10.9 mg, 0.02 mmol, 0.5 mL). The mixture was stirred briefly and a benzene-d$_6$ solution of phenol oxadiazole A13 (8.9 mg, 0.02 mmol, 0.5 mL) was added. The mixture was stirred for 10 min and the desired product [A13][A14]Hfz$_2$ (M5) formed almost quantitatively as determined by $^1$H NMR. The reaction mixture was dried and the residue product was used for polymerization screening without further purification. $^1$H NMR (C$_6$D$_6$, RT) δ 8.8-6 (m, ArH), 2.23 (d, 1H, HfCH$_2$), 2.0 (d, 1H, HfCH$_2$), 1.92 (d, 1H, HfCH$_2$), 1.78 (d, HfCH$_2$), 1.30 (s, 9H, CMe$_3$), 1.28 (s, 9H, C Me$_3$). (1287-17a-1H)

Section 4F. Synthesis of Phenol Oxadiazole Zr Complex [A31]$_2$ZrBz$_2$ (M6):

A toluene solution of ZrBz$_4$ (35 mg, 0.078 mmol, 2 mL) was added dropwise to a toluene solution of phenol oxadiazole A31 (82 mg, 0.155 mmol, 4 mL). The mixture was stirred for 1 h at room temperature. The mixture was concentrated until almost to dryness and pentane (0.5 mL) was added. The mixture was stored at –35 C for 12 h and an orange solid product was obtained which was then washed with pentane and dried under vacuum. (78 mg, 76%). $^1$H NMR (C$_6$D$_6$, 50° C.) δ 8.22 (D, 2H, ArH), 7.99 (D, 4H, ArH), 7.45 (Br s, 2H, ArH), 7.35-7.06 (m, ArH, partially overlap with solvent signal), 7.01 (t, 4H, ArH), 6.93 (d, 4H, ArH), 6.83 (d, 4H, ArH), 6.6-6.3 (m, 8H, ArH), 5.80 (d, 4H, ArH), 1.74 (br s, 4H, ZrCH$_2$), 1.17 (s, 18H, CMe$_3$).

Section 4G. Synthesis of Phenol Oxadiazole Hf Complex [A14]HfBz$_3$ (M7):

A benzene-d$_6$ solution of phenol oxadiazole A14 (16 mg, 0.035 mmol, 0.6 mL) was added to a benzene-d$_6$ solution of HfBz$_4$ (19.7 mg, 0.036 mmol, 0.6 mL). The titled complex formed quantitatively within 5 min as determined by $^1$H NMR. The volatiles were removed and the resulting product was used for polymerization without further purification. $^1$H NMR (C$_6$D$_6$, RT) δ 8.21 (br s, 1H, ArH), 8.18 (d, 1H, ArH), 7.79 (d, 2H, ArH), 7.7-7.6 (m, 3H, ArH), 7.45 (d, 2H, ArH), 7.3 (t, 2H, ArH), 7.2-6.9 (m, ArH, partially overlap with solvent signal), 6.85 (t, 6H, m-Ph), 6.67 (t, 3H, p-Ph), 6.14 (d, 6H, o-Ph), 1.62 (s, 6H, HfCH$_2$), 1.3 (s, 9H, CMe$_3$).

Section 4H. Synthesis of Phenol Oxadiazole Hf Complex [A13]HfBz$_3$ (M8):

A benzene-d$_6$ solution of phenol oxadiazole A13 (14 mg, 0.032 mmol., 0.6 mL) was added to a benzene-d$_6$ solution of HfBz$_4$ (18 mg, 0.032 mmol, 0.6 mL). The titled complex formed quantitatively within 5 min as determined by $^1$H NMR. The volatiles were removed and the resulting product was used for polymerization screening without further purification. $^1$H NMR (C$_6$D$_6$, RT) δ 7.93 (d, 1H, ArH), 7.55 (d, 1H, ArH), 7.45 (d, 2H, ArH), 7.3 (t, 2H, ArH), 7.25-6.99 (m, ArH, partially overlap with solvent signal), 6.94 (t, 6H, m-Ph), 6.71 (d, 2H, ArH), 6.65 (t, p-Ph), 6.58 (d, 6H, o-Ph), 6.45-6.20 (m, 2H, ArH), 2.2 (s, 6H, HfCH$_2$), 1.2 (s, 9H, CMe$_3$).

Section 4I. Synthesis of Phenol Thiazole Hf Complex [C14]$_2$HfBz$_2$ (M9):

A toluene solution of HfBz$_4$ (120 mg, 0.22 mmol, 6 mL) was added dropwise to a toluene solution of phenol thiazole C14 (200 mg, 0.44 mmol, 8 mL). The mixture was stirred for 40 min at room temperature. The volatiles were removed and the residue was washed with pentane and dried, yielding a yellow solid product (281 mg, 94%). $^1$H NMR (C$_6$D$_6$, RT) δ 7.72 (d, 4H, ArH), 7.65 (d, 2H, ArH), 7.5-7.3 (m, 6H, ArH), 7.21 (t, 2H, ArH), 6.9-6.7 (m, 8H, ArH), 6.63 (d/d, 2H, ArH), 6.55-6.40 (m, 4H, ArH), 6.17 (t, 2H, p-Ph), 6.02 (s, 2H, thiazole), 2.62 (d, 2H, HfCH$_2$), 2.52 (d, HfCH$_2$), 1.36 (s, 18H, CMe$_3$).

Section 4J. Synthesis of Phenol Thiazole Zr Complex [C14]$_2$ZrBz$_2$ (M10):

A toluene solution of ZrBz$_4$ (103 mg, 0.23 mmol, 6 mL) was added dropwise to a toluene solution of phenol thiazole C14 (206 mg, 0.45 mmol, 8 mL). The mixture was stirred for 1 h at room temperature. The volatiles were removed to almost dryness and pentane was added. The mixture was kept at –35° C. for 1 h, an orange solid product was collected and dried (265 mg, 99%). $^1$H NMR (C$_6$D$_6$, RT) δ 7.78 (d, 4H, ArH), 7.72 (d, 2H, ArH), 7.45-7.33 (m, 6H, ArH), 7.22 (t, 2H, ArH), 6.8-6.4 (m, 14H, ArH), 6.17 (t, 2H, ArH), 6.07 (s, 2H, thiazole), 2.63 (d, 2H, ZrCH$_2$), 2.53 (2H, ZrCH$_2$), 1.36 (s, 18H, CMe$_3$).

Section 4K. Synthesis of Phenol Thiazole Hf Complex [C23]$_2$HfBz$_2$ (M11):

A toluene solution of HfBz$_4$ (37 mg, 0.069 mmol, 1.5 mL) was added dropwise to a toluene slurry of phenol thiazole C23 (57 mg, 0.14 mmol, 1.5 mL). The mixture was stirred for 50 min at room temperature. The volatiles were removed and the residue was washed with pentane and dried, yellow solid product was obtained (67 mg, 83%). $^1$H NMR (C$_6$D$_6$, RT) δ 7.67 (d, 4H, ArH), 7.38 (t+d, 6H, ArH), 7.20 (t, 2H, ArH), 7.06 (d, 2H, ArH), 6.95-6.75 (m, 8H, ArH), 6.65-6.40 (m, 6H, ArH), 6.16 (t, 2H, ArH), 6.03 (s, 2H, 2 thiazole), 2.63 (d, 2H, HfCH$_2$), 2.46 (d, 2H, HfCH$_2$), 2.18 (s, 6H, ArMe).

Section 4L. Synthesis of Phenol Thiazole Zr Complex [C23]$_2$ZrBz$_2$ (M12):

A toluene solution of ZrBz$_4$ (25 mg, 0.054 mmol, 1 mL) was added dropwise to a toluene solution of phenol thiazole C23 (44 mg, 0.11 mmol, 1.4 mL). The mixture was stirred for 1 h at room temperature. The volatiles were removed and the residue was washed with pentane and dried, light orange solid product was collected (49 mg, 83%). $^1$H NMR (C$_6$D$_6$, RT) δ 7.71 (d, 4H, ArH), 7.44 (br s, 2H, ArH), 7.38 (t, 4H, ArH), 7.21 (t, 2H, ArH), 7.06 (d, 2H, ArH), 6.82 (t, 4H, ArH), 6.7 (d, 4H, ArH), 6.68-6.40 (m, 6H), 6.15 (t, 2H, ArH), 6.08 (s, 2H, thiazole), 2.63 (d/d, 4H, ZrCH$_2$), 2.18 (s, 6H, ArMe).

Although the present invention has been described with reference to preferred embodiments, persons skilled in the art will recognize that changes may be made in form and detail without departing from the spirit and scope of the invention.

What is claimed is:

1. A compound that is a metal ligand complex characterized by the general formula:

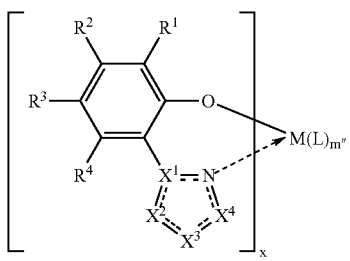

wherein each $R^1$, $R^2$, $R^3$, $R^4$, $R^5$, $R^6$, $R^7$ are the same or different and are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the proviso that $R^1$ may not be hydrogen, and optionally two or more of $R^1$, $R^2$, $R^3$ and $R^4$ may be joined to form a fused ring system having up to 50 atoms, not counting hydrogen atoms;

$X^1$ is C, $X^2$ is O, S, N or $CR^5$, $X^3$ is O, S, N or $CR^6$, and $X^4$ is $CR^7$, provided that the heteroatom containing ring system is heteroaromatic, and provided that when $X^2$ is S, $R^7$ is aryl;

wherein M is a metal selected from the group consisting of groups 3 through 6 of the periodic table elements and lanthanides;

wherein each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof;

x is 2, the complex being a bis-ligand complex comprising a first phenol-heterocycle ligand and a second phenol-heterocycle ligand, wherein the first and second phenol-heterocycle ligands are different from the other; and m" is 0, 1, 2, 3, or 4.

2. The compound of claim 1, wherein the metal ligand complex is characterized by a formula selected from the group consisting of

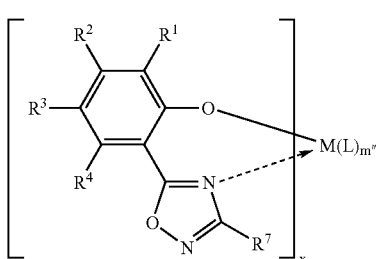

(VIIa)

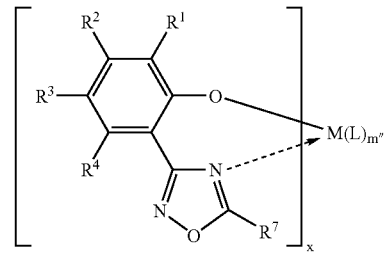

(VIIb)

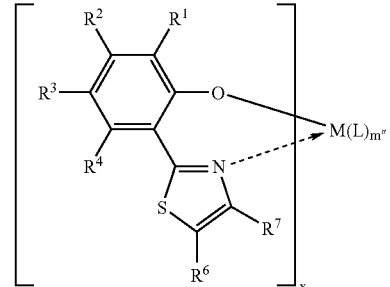

(VIId)

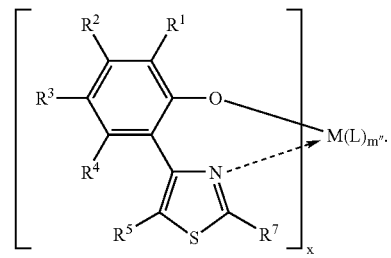

(VIIe)

3. The compound of either of claims 1 or 2, wherein $R^1$ is selected from the group consisting of optionally substituted alkyl, heteroalkyl, aryl and heteroaryl.

4. The compound of either of claims 1 or 2, wherein $R^7$ is selected from the group consisting of optionally substituted alkyl, heteroalkyl, aryl and heteroaryl.

5. The compound of claim 4, wherein $R^1$ is selected from the group consisting of t-butyl, naphthyl, substituted naphthyl, N-carbazolyl, substituted N-carbazolyl, phenyl and substituted phenyl and $R^7$ is selected from the group consisting of substituted phenyl and anthracenyl.

6. A metal-ligand complex that is characterized by the general formula:

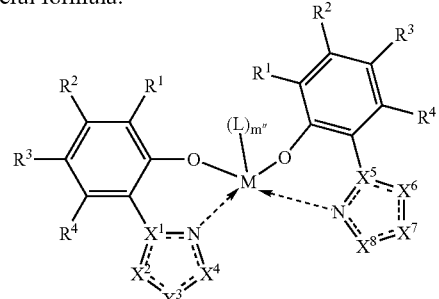

wherein each $R^1$, $R^2$, $R^3$, $R^4$, $R^5$, $R^6$, $R^7$ are the same or different and are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the proviso that $R^1$ may not be hydrogen, optionally two or more of $R^1$, $R^2$, $R^3$ and $R^4$ on the same ring in the formula may be joined to form a fused ring system having up to 50 atoms, not counting hydrogen atoms, and optionally two or more of $R^5$, $R^6$ and $R^7$ on the same ring in the formula may be joined to form a fused ring system having up to 50 atoms, not counting hydrogen atoms;

$X^1$ is N or C, $X^2$ is O, S, $N(R^5)_{n'}$ or $CR^5$, $X^3$ is O, S, $N(R^6)_{n''}$ or $CR^6$, $X^4$ is O, S, $N(R^7)_{n'''}$ or $CR^7$, wherein each n', n", and n'" are each independently 0 or 1, provided that the heteroatom containing ring system is heteroaromatic;

$X^5$ is N or C, $X^6$ is O, S, $N(R^5)_{n'}$ or $CR^5$, $X^7$ is O, S, $N(R^6)_{n''}$ or $CR^6$, $X^8$ is O, S, $N(R^7)_{n'''}$ or $CR^7$, wherein each n', n", and n'" are each independently 0 or 1, provided that the heteroatom containing ring system is heteroaromatic;

further provided that the atoms in the $X^1$, $X^2$, $X^3$, $X^4$, N ring are different from the atoms in the $X^5$, $X^6$, $X^7$, $X^8$, N ring in the selection of the C, N, O or S atom, such that at least, either $X^1$ and $X^5$ are different or $X^2$ and $X^6$ are different or $X^3$ and $X^7$ are different or $X^4$ and $X^8$ are different;

wherein M is a metal selected from the group consisting of groups 3 through 6 of the periodic table elements and lanthanides;

wherein each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof; and m" is 0, 1, 2, or 3.

7. A metal ligand complex characterized by the general formula:

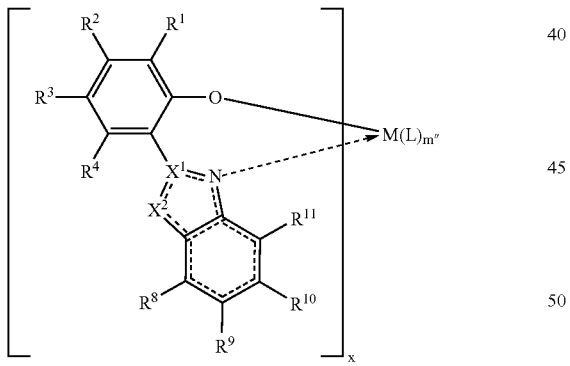

wherein $R^1$, $R^2$, $R^3$, $R^4$, $R^5$, $R^8$, $R^9$, $R^{10}$ and $R^{11}$ are independently selected from the group consisting of hydrogen, alkyl, substituted alkyl, cycloalkyl, substituted cycloalkyl, heteroalkyl, substituted heteroalkyl, heterocycloalkyl, substituted heterocycloalkyl, aryl, substituted aryl, heteroaryl, substituted heteroaryl, alkoxy, aryloxy, halo, silyl, boryl, phosphino, amino, thioalkyl, thioaryl, nitro, and combinations thereof, with the proviso that $R^1$ may not be hydrogen, optionally two or more of $R^1$, $R^2$, $R^3$ and $R^4$ may be joined to form a fused ring system having up to 50 atoms, not counting hydrogen atoms, and optionally two or more of $R^8$, $R^9$, $R^{10}$ and $R^{11}$ may be joined to form a fused ring system having up to 50 atoms, not counting hydrogen atoms;

$X^1$ is N or C, $X^2$ is O, S, $N(R^5)_{n'}$ or $CR^5$, wherein n' is 0 or 1, provided that the heteroatom containing ring system is heteroaromatic, provided $X^1$ and $X^2$ are not both N;

wherein M is a metal selected from the group consisting of groups 3 through 6 of the periodic table of elements and lanthanides;

wherein each L is independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof;

x is 2, forming a bis-ligand complex comprising a first phenol-heterocycle ligand and a second phenol-heterocycle ligand, wherein the first and second phenol-heterocycle ligands are different from the other; and, m" is 0, 1, 2, 3, or 4.

8. The complex of claim 7, wherein the complex is characterized by a formula selected from the group consisting of:

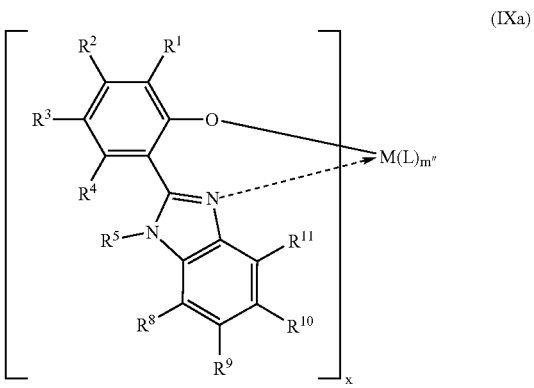

(IXa)

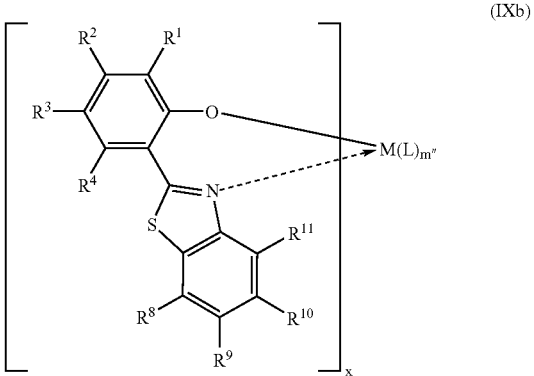

(IXb)

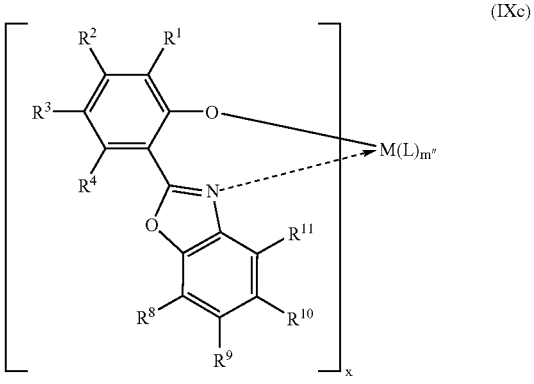

(IXc)

-continued
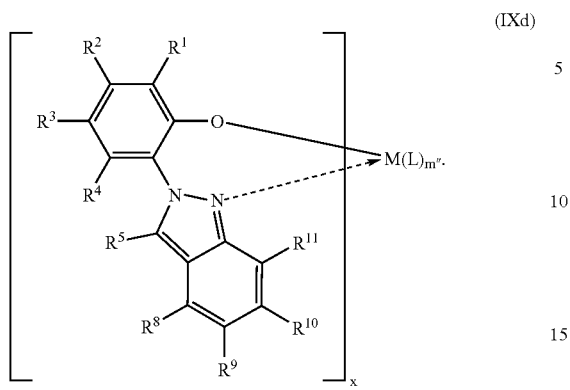
(IXd)
9. The complex of either of claims 7 or 8, wherein $R^1$ is selected from the group consisting of optionally substituted alkyl, heteroalkyl, aryl, and heteroaryl.
10. The complex of any of claims 1, 2, 7 or 8 wherein M is either Zr, Hf or Ti.
* * * * *